United States Patent
Xu et al.

(10) Patent No.: US 12,195,449 B2
(45) Date of Patent: Jan. 14, 2025

(54) 3-[(1H-PYRAZOL-R-YL)OXY]PYRAZIN-2-AMINE COMPOUNDS AS HPK1 INHIBITOR AND USE THEREOF

(71) Applicant: BeiGene, Ltd., Grand Cayman (KY)

(72) Inventors: Sanjia Xu, Beijing (CN); Jing Li, Beijing (CN); Zhiwei Wang, Beijing (CN)

(73) Assignee: BeiGene, Ltd., Grand Cayman (KY)

( * ) Notice: Subject to any disclaimer, the term of this patent is extended or adjusted under 35 U.S.C. 154(b) by 0 days.

(21) Appl. No.: 18/650,207

(22) Filed: Apr. 30, 2024

(65) Prior Publication Data
US 2024/0317714 A1    Sep. 26, 2024

Related U.S. Application Data

(63) Continuation of application No. 18/029,177, filed as application No. PCT/CN2021/121562 on Sep. 29, 2021.

(30) Foreign Application Priority Data

| Sep. 30, 2020 | (WO) | PCT/CN2020/119171 |
| Dec. 21, 2020 | (WO) | PCT/CN2020/135968 |
| Feb. 20, 2021 | (WO) | PCT/CN2021/076993 |
| Aug. 23, 2021 | (WO) | PCT/CN2021/113967 |

(51) Int. Cl.
| C07D 401/14 | (2006.01) |
| A61P 35/00  | (2006.01) |
| C07D 405/14 | (2006.01) |
| C07D 413/14 | (2006.01) |
| C07D 491/107| (2006.01) |

(52) U.S. Cl.
CPC ........... *C07D 401/14* (2013.01); *A61P 35/00* (2018.01); *C07D 405/14* (2013.01); *C07D 413/14* (2013.01); *C07D 491/107* (2013.01)

(58) Field of Classification Search
CPC .. C07D 401/14; C07D 405/14; C07D 413/14; C07D 491/107; A61P 35/00
See application file for complete search history.

(56) References Cited

U.S. PATENT DOCUMENTS

| 10,501,474 B2 | 12/2019 | Sampson et al. |
| 2007/0087988 A1 | 4/2007 | Sawasdikosol |
| 2023/0373963 A1 | 11/2023 | Xu et al. |

FOREIGN PATENT DOCUMENTS

| CN | 107922431 A | 4/2018 | |
| TW | 202115025 A | 4/2021 | |
| WO | 2008124849 A2 | 10/2008 | |
| WO | WO-2016161145 A1 * | 10/2016 | ............. A61P 35/00 |
| WO | 2018049152 A1 | 3/2018 | |
| WO | 2018049191 A1 | 3/2018 | |
| WO | 2018049200 A1 | 3/2018 | |
| WO | 2018049214 A1 | 3/2018 | |
| WO | 2019238067 A1 | 12/2019 | |
| WO | 2020103896 A1 | 5/2020 | |
| WO | 2020206588 A1 | 10/2020 | |
| WO | 2021032148 | 2/2021 | |

OTHER PUBLICATIONS

International Search Report issued Jan. 6, 2022 in PCT/CN2021/121562.
Written Opinion issued Jan. 6, 2022 in PCT/CN2021/121562.
Extended European Search Report mailed Sep. 27, 2024 in connection with European Pat. App. No. 21874503.2 (8 pages).
Hu et al., 1996, "Human HPK1, a novel human hematopoietic progenitor kinase that activates the JNK/SAPK kinase cascade", Genes Dev, 10(18): 2251-64.
Liou, J et al., "HPK1 is activated by lymphocyte antigen receptors and negatively regulates AP-1," Immunity, Apr. 2000, 12(4): 399-408.
Wang et al., 1997, "Activation of the hematopoietic progenitor kinase-1 (HPK1)-dependent, stress-activated c-Jun N-terminal kinase (JNK) pathway by transforming growth factor beta (TGF-beta)-activated kinase (TAK1), a kinase mediator of TGF beta signal transduction", J Biol Chem, 272 (36): 22771-5.
Zhou et al., 1999, "Hematopoietic progenitor kinase 1 is a component of transforming growth factor beta-induced c-Jun N-terminal kinase signaling cascade", J Biol Chem, 274(19): 13133-8.
Ikegami et al., 2001, "The expression of prostaglandin E receptors EP2 and EP4 and their different regulation by lipopolysaccharide in C3H/HeN peritoneal macrophages", J Immunol, 166 (7): 4689-96.

(Continued)

*Primary Examiner* — Joseph K McKane
*Assistant Examiner* — Meghan C Heasley
(74) *Attorney, Agent, or Firm* — McNeill PLLC

(57) ABSTRACT

Disclosed herein is 3-[(1H-pyrazol-4-yl)oxy]pyrazin-2-amine compounds of Formula (I), or a stereoisomer thereof, or a pharmaceutically acceptable salt thereof, and pharmaceutical compositions comprising thereof. Also disclosed is a method of modulating, e.g., inhibiting or treating HPK1 related disorders or diseases including cancer by using the compound disclosed herein

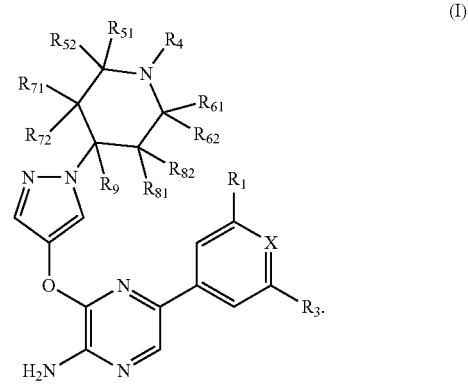

17 Claims, No Drawings

(56) References Cited

OTHER PUBLICATIONS

Sawasdikosol, S. et al., "HPK1 as a novel target for cancer immunotherapy," Immunol Res., Dec. 2012, vol. 54, No. 1-3, pp. 262-265.

Batliwalla et al., 2005, "Microarray analyses of peripheral blood cells identifies unique gene expression signature in psoriatic arthritis", Mol Med, 11 (1-12): 21-9.

Alzabin, S. et al., "Hematopoietic progenitor kinase 1 is a critical component of prostaglandin E2-mediated suppression of the anti-tumor immune response," Cancer Immunol Immunother, Mar. 2010, 59(3):419-429.

* cited by examiner

3-[(1H-PYRAZOL-R-YL)OXY]PYRAZIN-2-AMINE COMPOUNDS AS HPK1 INHIBITOR AND USE THEREOF

CROSS-REFERENCE TO RELATED APPLICATIONS

This application is a continuation of U.S. application Ser. No. 18/029,177, which is a U.S. National Stage Application under 35 U.S.C. § 371 of International Application No. PCT/CN2021/121562, filed Sep. 29, 2021, which claims priority to Patent Application Nos. PCT/CN2020/119171, filed Sep. 30, 2020, PCT/CN2020/135968, filed Dec. 11, 2020, PCT/CN2021/076993, filed Feb. 20, 2021, and PCT/CN2021/113967, filed Aug. 23, 2021, the disclosures of each of which are hereby incorporated by reference in their entireties.

FIELD OF THE INVENTION

The disclosure herein provides 3-[(1H-pyrazol-4-yl)oxy]pyrazin-2-amine compounds as well as their compositions and methods of use. The compounds disclosed herein modulate, e.g., inhibit, hematopoietic progenitor kinase 1 (HPK1) activity and are useful in the treatment of various diseases including cancer.

BACKGROUND OF THE INVENTION

HPK1 is a member of MAP4Ks family, which includes MAP4K1/HPK1, MAP4K2/GCK, MAP4K3/GLK, MAP4K4/HGK, MAP4K5/KHS, MAP4K6/MINK [Hu. M. C., et al., *Genes Dev.* 1996. 10: pp. 2251-64]. HPK1 regulates diverse functions of various immune cells and its kinase activity has been shown to be induced upon activation of T cell receptors (TCR) [Liou J. et al., *Immunity.* 2000. 12 (4): pp. 399-408], B cell receptors (BCR) [Liou J., et al., *Immunity.* 2000. 12 (4): pp. 399-408], transforming growth factor receptor (TGF-βR) [Wang, W., et al., *Biol Chem.* 1997.272 (36): pp. 22771-5; Zhou. G., et al., *J Biol Chem.* 1999. 274 (19): pp. 13133-8], and Gs-coupled PGE2 receptors (EP2 and EP4) [Ikegami. R., et al., *J Immunol.* 2001. 166 (7): pp. 4689-96]. Overexpression of HPK1 suppresses TCR-induced activation of AP-1-dependent gene transcription in a kinase-dependent manner, suggesting that HPK1 is required to inhibit the Erk MAPK pathway [Liou J. et al., *Immunity.* 2000. 12 (4): pp. 399-408] and this blockage is thought to be the inhibitory mechanism that negatively regulates TCR-induced IL-2 gene transcription [S Sawasdikosol., et al., *Immunol Res,* 2012. 54: pp. 262-265].

In vitro HPK1−/− T cells have a lower TCR activation threshold, proliferate robustly, produce enhanced amounts of Th1 cytokines, the HPK1−/− mice experience more severe autoimmune symptoms [S. Sawasdikosol., el al., *Immunol* Res, 2012. 54: pp. 262-265]. In human, HPK1 was downregulated in peripheral blood mononuclear cells of psoriatic arthritis patients or T cells of systemic lupus erythematosus (SLE) patients [Bathiwalla F M. et al., *Mol Med.* 2005. 11 (1-12): pp. 21-9], which indicated that attenuation of HPK1 activity may contribute to autoimmunity in patients. Furthermore, HPK1 may also control antitumor immunity via T cell-dependent mechanisms. In the PGE2-producing Lewis lung carcinoma tumor model, the tumors developed more slowly in HPK1 knockout mice as compared to wild-type mice [US patent application No. 2007/0087988]. HPK1 deficient T cells were more effective in controlling tumor growth and metastasis than wild-type T cells [Alzabin. S., et al., *Cancer Immunol immunother,* 2010. 59 (3): pp. 419-29]. Similarly, BMDCs from HPK1 knockout mice were more efficient to mount a T cell response to eradicate Lewis lung carcinoma as compared to wild-type BMDCs [Alzabin. S., el al., *J Immunol.* 2009. 182 (10): pp. 6187-94]. In all, HPK1 may be a good target for enhancing antitumor immunity.

As HPK1 modulators, WO2016205942 discloses benzoimidazoles. WO2018049152A1 discloses pyrazolopyrimidines, WO2018049191A1 discloses pyrazolopyridones, and WO2008124849, WO2018049200A1 and WO2018049214A1 disclose pyrazolopyridines. WO2019238067 and WO2020103896 disclose pyrrolopyridines.

However, there is a need to provide new HPK1 kinase inhibitors useful in treating cancer.

SUMMARY OF THE INVENTION

In the first aspect, disclosed herein are aminopyrazine compounds of Formula (I), and the methods of use. The first embodiment comprises the following aspects:

Aspect 1: A compound of Formula (I)

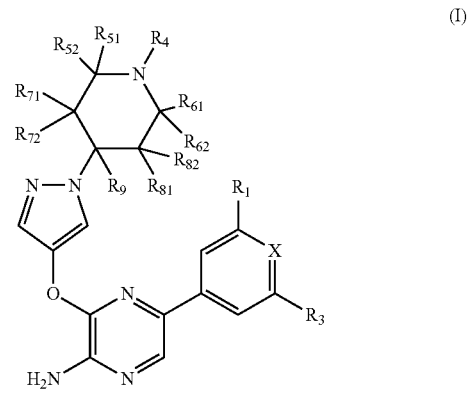

or a pharmaceutically acceptable salt thereof, or a stereoisomer thereof, wherein X is N or $CR_2$, wherein $R_2$ is selected from hydrogen, —$C_{1-8}$alkyl, —$C_{2-8}$alkynyl, halogen, cycloalkyl, aryl, heterocyclyl, heteroaryl, —$NR^cR^d$, —$OR^d$, —$(CR^aR^b)_n$—$R^d$, —$(CR^aR^b)$~-$NR^cR^d$, —$(CR^aR^b)_n$—$CONR^cR^d$, —$CONR^c$—$(CR^aR^b)_n$—$R^d$, —$(CR^aR^b)_n$—$NR^cCOR^d$, —$NR^c$—$CO$—$(CR^aR^b)_n$—$R^d$, —$(CR^aR^b)_n$—$SO_2$—$NR^cR^d$, —$(CR^aR^b)_n$—$NR^c$—$SO_2$—$R^d$, —$SO_2$—$NR^c$—$(CR^aR^b)_n$—$R^d$, —$(CR^aR^b)_n$-$NR^c$—$CS$—$NR^dR^e$, or —$(CR^aR^b)_n$—$NR^c$—$CO$—$NR^cR$ each of said —$C_{1-8}$alkyl, cycloalkyl, aryl, heterocyclyl or heteroaryl is optionally substituted with at least one $R^f$;

$R_1$ and $R_3$ are each independently selected from hydrogen, —$C_{1-8}$alkyl, halogen, cycloalkyl, aryl, heterocyclyl, heteroaryl, —$NR^cR^d$, —$OR^d$, —$SiR^aR^bR$, —$(CR^aR^b)_n$ —$R^d$, —$(CR^aR^b)_n$—$NR^cR^d$, —$(CR^aR^b)_n$—$CONR^cR^d$, —$CONR^c$—$(CR^aR^b)_n$—$R^d$, —$(CR^aR^b)_n$—$NR^cCOR^d$, —$NR^c$—$CO$—$(CR^aR^b)_n$—$R^d$, —$(CR^aR^b)_n$—$SO_2$—$NR^cR^d$, —$(CR^aR^b)_n$—$NR^c$—$SO_2$—$R^d$, —$SO_2$—$NR^c$—$(CR^aR^b)_n$—$R^d$, or —$(CR^aR^b)_n$—$NR^c$—$CO$—$NR^dR^e$, wherein each of said —$C_{1-8}$alkyl, cycloalkyl, aryl, heterocyclyl or heteroaryl is optionally substituted with at least one $R^f$;

$R_4$ is selected from hydrogen, —$C_{1-8}$alkyl, cycloalkyl, heterocyclyl (such as monocyclic heterocyclyl) comprising one, two or three heteroatoms independently selected from nitrogen, oxygen or sulfur as ring member(s), wherein each of said —$C_{1-8}$alkyl, cycloalkyl or heterocyclyl are optionally substituted with $R^f$;

each $R^f$ is independently selected from oxo, halogen, —$C_{1-8}$alkyl, hydroxy. —$NR^{1c}R^{1d}$, —$C_{1-8}$, alkoxy, or heterocyclyl, said heterocyclyl or —$C_{1-8}$alkyl is optionally substituted with at least one $R^g$, wherein $R^{1c}$ and $R^{1d}$ are each independently hydrogen or —$C_{1-8}$ alkyl:

$R_{51}$, $R_{52}$, $R_{61}$, $R_{62}$, $R_{71}$, $R_{72}$, $R_{81}$, $R_{82}$ and $R_9$ are each independently selected from hydrogen, halogen, —$C_{1-8}$ alkyl, or —$C_{1-8}$alkoxy; or ($R_{51}$ and $R_{61}$), ($R_{51}$ and $R_{62}$), ($R_{52}$ and $R_{61}$) or ($R_{52}$ and $R_{62}$), together with the atoms to which they are attached, form a 7- to 12-membered bridged heterocyclyl wherein the bridge contains 1-6 atoms selected from carbon, oxygen, nitrogen or sulfur;

$R^1$ and $R_6$ are each independently hydrogen, —$C_{1-8}$alkyl or heterocyclyl; or $R^a$ and $R^b$, together with the carbon atom to which they are attached, form a 3- to 6-membered ring comprising 0, 1 or 2 heteroatoms selected from nitrogen, oxygen or optionally oxidized sulfur as the ring member(s);

$R^c$, $R^d$ and $R^e$ are each independently hydrogen. —$C_{1-8}$ alkyl, aryl, CN, hydroxyl, —$C_{1-8}$ alkoxy, cycloalkyl, heterocyclyl, heteroaryl or —$NR^{1c}R^{1d}$, wherein each of said —$C_{1-8}$alkyl, cycloalkyl, aryl, heterocyclyl or heteroaryl is optionally substituted with at least one $R^g$, wherein $R^{1c}$ and $R^{1d}$ are each independently hydrogen or —$C_{1-8}$alkyl;

each $R^g$ is independently selected from oxo, hydroxy, halogen, haloalkyl (preferably $CF_3$), —$C_{1-8}$alkyl, —$C_{1-8}$alkoxy, cycloalkyl or heterocyclyl; and n is each independently 0, 1, 2, 3 or 4.

In some embodiments. $R^a$ and $R^b$, together with the carbon atom to which they are attached, form a 3- to 6-membered carbon ring, selected from cyclopropyl, cyclobutyl, cyclopentyl, or cyclohexyl. In some embodiments, ($R_{51}$ and $R_{61}$), ($R_{51}$ and $R_{62}$), ($R_{52}$ and $R_{61}$) or ($R_{52}$ and $R_{62}$), together with the atoms to which they are attached, form a 7- to 12-membered bridged heterocyclyl wherein the bridge contains 1-6 or 1-4 or 1-2 carbon atoms. In some embodiments. ($R_{51}$ and $R_{61}$), ($R_{51}$ and $R_{62}$), ($R_{52}$ and $R_{61}$) or ($R_{52}$ and $R_{62}$), together with the atoms to which they are attached, form a 7- to 12-membered bridged heterocyclyl wherein the bridge contains 1-6 or 1-4 or 1-2 atoms selected from carbon, oxygen or nitrogen.

In some embodiments, $R_4$ is a deuterated $C_{1-8}$alkyl group.

In some embodiments, disclosed here is a compound of Formula (I)

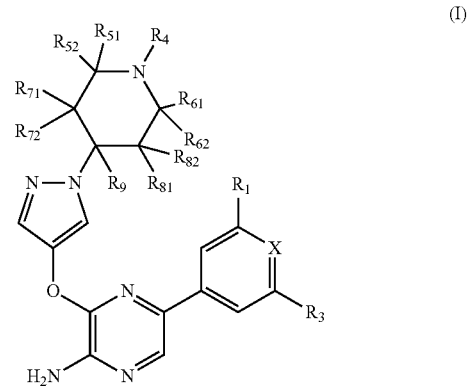

(I)

or a pharmaceutically acceptable salt thereof, or a stereoisomer thereof,
wherein
X is N or $CR_2$, wherein $R_2$ is selected from hydrogen, —$C_{1-8}$alkyl, —$C_{2-8}$alkynyl, halogen, cycloalkyl, aryl, heterocyclyl, heteroaryl, —$NR^cR^d$, —$OR^d$, —$(CR^aR^b)_n$—$R^d$, —$(CRaR^b)_n$—$NR^cR^d$, —$(CRaR^b)_n$—$CONR^cR^d$, —$CONR^c$—$(CR^aR^b)_n$—$R^d$, —$(CRaR^b)_n$—$NR^cCOR^d$, —$NR^c$—$CO$—$(CR^aR^b)_n$—$R^d$, —$(CR^aR^b)_n$—$SO_2$—$NR^cR^d$, —$(CR^aR^b)_n$—$NR^c$—$SO_2$—$R^d$, —$SO_2$—$NR^c$—$(CR^aR^b)_n$—$R^d$, —$(CRaR^b)_n$—$NR^c$—$CS$—$NR^dR^e$, or —$(CR^aR^b)_n$—$NR^c$—$CO$—$NR^dR$ each of said —$C_{1-8}$alkyl, cycloalkyl, aryl, heterocyclyl or heteroaryl is optionally substituted with at least one $R^f$;

$R_1$ and $R_3$ are each independently selected from hydrogen, —$C_{1-8}$alkyl, halogen, cycloalkyl, aryl, heterocyclyl, heteroaryl, —$NR^cR^d$, —$OR^d$, —$(CR^aR^b)_n$—$R^1$, —$(CR^aR^b)_n$—$NR^cR^d$, —$(CRaR^b)_n$—$CONR^cR^d$, —$CONR^c$—$(CRaR^b)_n$—$R^d$, —$(CRaR^b)_n$—$NR^cCOR^d$, —$NR^c$—$CO$—$(CR^aR^b)_n$—$R^d$, —$(CR^aR^b)_n$—$SO_2$—$NR^aR^d$, —$(CR^aR^b)_n$—$NR^c$—$SO_2R$, —$NR$—$(CR^cR)_n$—$R$, or —$(CR^aR^b)_n$—$NR^c$—$CO$—$NR^dR^e$, wherein each of said —$C_{1-8}$alkyl, cycloalkyl, aryl, heterocyclyl or heteroaryl is optionally substituted with at least one $R^f$;

$R_4$ is selected from hydrogen, —$C_{1-8}$alkyl, cycloalkyl, heterocyclyl (such as monocyclic heterocyclyl) comprising one, two or three heteroatoms independently selected from nitrogen, oxygen or sulfur as ring member(s), wherein each of said —$C_{1-8}$alkyl, cycloalkyl or heterocyclyl are optionally substituted with $R^f$;

each $R^f$ is independently selected from oxo, halogen, —$C_{1-8}$alkyl, hydroxy, —$C_{1-8}$alkoxy, or heterocyclyl, said heterocyclyl or —$C_{1-8}$alkyl is optionally substituted with at least one $R^g$;

$R_{51}$, $R_{52}$, $R_{61}$, $R_{62}$, $R_{71}$, $R_{72}$, $Ru_{81}$, $R_{82}$ and $R_9$ are each independently selected from hydrogen, halogen, —$C_{1-8}$ alkyl, or —$C_{1-8}$alkoxy; or ($R_{51}$ and $R_{61}$), ($R_{51}$ and $R_{62}$), ($R_{52}$ and $R_{61}$) or ($R_{52}$ and $R_{62}$), together with the atoms to which they are attached, form a 7- to 12-membered bridged heterocyclyl wherein the bridge contains 1-6 atoms selected from carbon, oxygen, nitrogen or sulfur;

$R^a$ and $R^b$ are each independently hydrogen, —$C_{1-8}$alkyl or heterocyclyl; or $R^a$ and $R^b$, together with the carbon atom to which they are attached, form a 3- to 6-membered ring comprising 0, 1 or 2 heteroatoms selected from nitrogen, oxygen or optionally oxidized sulfur as the ring member(s);

$R^c$, $R^d$ and $R^e$ are each independently hydrogen, —$C_{1-8}$alkyl, aryl. CN, hydroxyl, —$C_{1-8}$alkoxy, cycloalkyl, heterocyclyl, or —$NR^{1c}R^{1d}$, wherein each of said —$C_{1-8}$alkyl, cycloalkyl, aryl or heterocyclyl is optionally substituted with at least one $R^g$, wherein $R^{1c}$ and $R^{1d}$ are each independently hydrogen or —$C_{1-8}$alkyl;

each $R^g$ is independently selected from oxo, hydroxy, halogen, —$C_{1-8}$alkyl, —$C_{1-8}$alkoxy, or heterocyclyl; and n is each independently 0, 1, 2, 3 or 4.

In some embodiments, $R^a$ and $R^b$, together with the carbon atom to which they are attached, form a 3- to 6-membered carbon ring, selected from cyclopropyl, cyclobutyl, cyclopentyl, or cyclohexyl. In some embodiments, ($R_{51}$ and $R_{61}$), ($R_{51}$ and $R_{62}$), ($R_{52}$ and $R_{61}$) or ($R_{52}$ and $R_{62}$), together with the atoms to which they are attached, form a 7- to 12-membered bridged heterocyclyl wherein the bridge contains 1-6 or 1-4 or 1-2 carbon atoms. In some embodiments. ($R_{51}$ and $R_6$), ($R_{51}$ and $R_{62}$), ($R_{52}$ and $R_{61}$) or ($R_{52}$ and $R_{62}$), together with the atoms to which they are attached, form a 7- to 12-membered bridged heterocyclyl wherein the bridge contains 1-6 or 1-4 or 1-2 atoms selected from carbon, oxygen or nitrogen.

Aspect 2: The compound according to aspect 1, wherein

X is N or $CR_2$, wherein $R_2$ is selected from hydrogen, —$C_{1-8}$alkyl, —$C_{2-8}$alkynyl, $C_{3-7}$ cycloalkyl, aryl, 5- to 6-membered heteroaryl comprising one, two or three heteroatoms independently selected from nitrogen, oxygen or optionally oxidized sulfur as the ring member(s), 3- to 7-membered heterocyclyl comprising one, two or three heteroatoms independently selected from nitrogen, oxygen or optionally oxidized sulfur as the ring member(s), —$NR^cR^d$, —$(CR^aR^b)_n$-$R^d$, —$(CR^aR^b)_n$—$NR^cR^d$, —$(CR^aR^b)$, —$CONR^cR^d$, —$CONR^c$, —$(CR^aR^b)_n$—$R^d$, —$(CR^aR^b)_n$—$NR^c$—$COR^d$, —$(CR^aR^b)_n$—$SO_2$—$NR^cR^d$, —$(CR^aR^b)_n$—$NRO^c$—$CO$—$NR^dR^c$, —$(CR^aR^b)_n$—$NR^c$—$CS$—$NR^dR^e$, $(CRR)_n$—$NR$—$SO_2$—$R^d$ or —$(CR^aR^b)$, —$NR^c$—$CO$—$NR^dR^c$; each of said —$C_{1-8}$alkyl, $C_{3-7}$cycloalkyl, aryl, 3- to 7-membered heterocyclyl or 5- to 6-membered heteroaryl is optionally substituted with at least one $R^f$;

$R_1$ is selected from hydrogen. —$C_{1-8}$alkyl, halogen, $C_{3-7}$cycloalkyl, 5- to 6-membered heteroaryl, 3- to 7-membered heterocyclyl comprising one, two or three heteroatoms independently selected from nitrogen, oxygen or optionally oxidized sulfur as the ring member(s), —$NR^cR^d$, or —$OR^d$; each of said —$C_{1-8}$alkyl, $C_{3-7}$cycloalkyl, 5- to 6-membered heteroaryl, or 3- to 7-membered heterocyclyl is optionally substituted with at least one $R^f$;

$R_3$ is selected from hydrogen, —$C_{1-8}$alkyl, $C_{3-7}$cycloalkyl, 3- to 7-membered heterocyclyl comprising one, two or three heteroatoms independently selected from nitrogen, oxygen, silicon or optionally oxidized sulfur as the ring member(s), —$(CR^aR^b)_n$—$NR^cR^d$, —$(CR^aR^b)_n$—$CONR^cR^d$, —$SiR^aR^bR^c$, —$(CR^aR^b)_n$—$NR^cCOR^d$, —$CONR^c$—$(CR^aR^b)_n$—$R^d$, —$(CR_2R^b)$, —$SO_2$—$NR^cR^d$, —$SO_2$—$NR^c$, —$(CR^aR^b)_n$—$R^d$, —$(CR^aR^b)_n$, —$NR^c$—$SO_2$—$R^d$. —$(CR^aR^b)_n$—$NR^C$—$CO$—$NR^dR^c$, or —$(CR^aR^b)_n$—$NR^cR^d$, wherein said —$C_{1-8}$alkyl, $C_{3-7}$cycloalkyl, 3- to 7-membered heterocyclyl is optionally substituted with at least one $R^f$;

$R_4$ is selected from hydrogen, —$C_{1-8}$alkyl, $C_{3-7}$cycloalkyl, 3- to 7-membered heterocyclyl comprising one, two or three heteroatoms independently selected from nitrogen, oxygen or optionally oxidized sulfur as the ring member(s); each said —$C_{1-8}$alkyl, $C_{3-7}$cycloalkyl or 3- to 7-membered heterocyclyl are optionally substituted with $R^f$;

each $R^f$ is independently selected from oxo, halogen, hydroxy, —$NR^{1c}R^{1d}$, —$C_{1-8}$alkyl, —$C_{1-8}$alkoxy, 3- to 7-membered heterocyclyl; said heterocyclyl or —$C_{1-8}$alkyl is optionally substituted with at least one $R^g$, wherein $R^{1c}$ and $R^{1d}$ are each independently hydrogen or —$C_{1-8}$alkyl;

$R_{51}$, $R_{52}$, $R_{61}$, $R_{62}$, $R_{71}$, $R_{72}$, $R_{81}$ and $R_{82}$ are each independently selected from hydrogen, halogen, —$C_{1-8}$ alkyl, or —$C_{1-8}$alkoxy, or ($R_{51}$ and $R_{61}$), ($R_{51}$ and $R_{62}$), ($R_{52}$ and $R_{61}$) or ($R_{52}$ and $R_{62}$), together with the atoms to which they are attached, form a 7- to 12-membered bridged heterocyclyl wherein the bridge contains 1-6 atoms selected from carbon, oxygen, nitrogen or sulfur;

$R^a$ and $R^b$ are each independently hydrogen, —$C_{1-8}$alkyl or heterocyclyl; or $R^a$ and $R^b$, together with the carbon atom to which they are attached, form a 3- to 6-membered ring comprising 0, 1 or 2 heteroatoms selected from nitrogen, oxygen or optionally oxidized sulfur as the ring member(s);

$R^c$, $R^d$ and $R^e$ are each independently hydrogen, —$C_{1-8}$ alkyl, 5- to 6 membered heteroaryl, aryl, CN, hydroxyl, —$C_{1-8}$alkoxy, $C_{3-7}$cycloalkyl, 3- to 7-membered heterocyclyl comprising one, two or three heteroatoms independently selected from nitrogen, oxygen or optionally oxidized sulfur, or —$NR^{1c}R^{1d}$; each said —$C_{1-8}$alkyl, 5- to 6 membered heteroaryl, $C_{3-7}$cycloalkyl, aryl or 3- to 7-membered heterocyclyl is optionally substituted with at least one $R^g$; wherein $R^{1c}$ and $R^{1d}$ are each independently hydrogen or —$C_{1-8}$alkyl; each $R^g$ is independently selected from oxo, hydroxy, halogen, —$C_{1-8}$alkyl, —$C_{1-8}$alkoxy, or 3- to 7-membered heterocyclyl, and n is each independently 0, 1, 2, 3 or 4.

In some embodiments, $R_4$ is 3- to 7-membered monocyclic heterocyclyl. In some embodiments, ($R_{51}$ and $R_{61}$), ($R_{52}$ and $R_{62}$), ($R_{52}$ and $R_{61}$) or ($R_{52}$ and $R_{62}$), together with the atoms to which they are attached, form a 7- to 12-membered bridged heterocyclyl wherein the bridge contains 1-6 or 1-4 or 1-2 atoms selected from carbon or oxygen.

In some embodiments, X is N or $CR_2$, wherein $R_2$ is selected from hydrogen, halogen. —$C_{1-8}$alkyl, —$C_{2-8}$alkynyl, $C_{3-7}$cycloalkyl, aryl, 5- to 6-membered heteroaryl comprising one, two or three heteroatoms independently selected from nitrogen, oxygen or optionally oxidized sulfur as the ring member(s), 3- to 7-membered heterocyclyl comprising one, two or three heteroatoms independently selected from nitrogen, oxygen or optionally oxidized sulfur as the ring member(s), —$NR^cR^d$, —$(CR^aR^b)_n$—$R^d$, —$(CR^aR^b)_n$—$NR^c$ $R^d$, —$(CR^aR^b)_n$—$CONR^cR^d$, —$CONR^c$, —$(CR^aR^b)_n$—$R^d$, —$(CR^aR^b)_n$—$NR^cCOR^d$, —$(CR^aR^b)_n$—$SO_2$—$NR^cR^d$, —$(CR^aR^b)_n$—$NR$—$CO$—$NR^cR^c$, —$(CR^aR^b)_n$—$NR^c$—$CS$—$NR^dR^c$ or —$(CR^aR^b)$~—$NR^c$—$SO_2$—$R^d$; each of said —$C_{1-8}$alkyl, $C_{3-7}$cycloalkyl, aryl, 3- to 7-membered heterocyclyl or 5- to 6-membered heteroaryl is optionally substituted with at least one $R^f$;

$R_1$ is selected from hydrogen, —$C_{1-8}$alkyl, halogen, $C_{3-7}$cycloalkyl, 3- to 7-membered heterocyclyl comprising one, two or three heteroatoms independently selected from nitrogen, oxygen or optionally oxidized sulfur as the ring member(s), —$NR^cR^d$, or —$OR^d$; each of said —$C_{1-8}$ alkyl, $C_{3-7}$cycloalkyl, 3- to 7-membered heterocyclyl is optionally substituted with at least one $R^f$;

R$_3$ is selected from hydrogen, —C$_{1-8}$alkyl, —(CR$^a$R$^b$)$_n$—CONR$^c$R$^d$, —(CR$^a$R$^b$)$_n$—NR$^c$COR$^d$, —CONR$^c$—(CR$^a$R$^b$)$_n$—R$^d$, —(CR$^a$R$^b$)$_n$—SO$_2$—NR$^c$R$^d$, —SO$_2$—NR$^c$—(CR$^a$R$^b$), —R$^d$, —(CR$_2$R$^b$)$_n$—NR$^c$—SO$_2$—R$^d$, —(CR$^a$R$^b$)$_n$—NR$^c$—CO—NR$^d$R$^c$, or —(CR$^a$R$^b$)$_n$—NR$^c$R$^d$, wherein said —C$_{1-8}$alkyl is optionally substituted with at least one R;

R$_4$ is selected from hydrogen, —C$_{1-8}$alkyl, C$_{3-7}$cycloalkyl, 3- to 7-membered heterocyclyl comprising one, two or three heteroatoms independently selected from nitrogen, oxygen or optionally oxidized sulfur as the ring member(s); each said —C$_{1-8}$alkyl, C$_{3-7}$cycloalkyl or 3- to 7-membered heterocyclyl are optionally substituted with R$^f$;

each R$^f$ is independently selected from oxo, halogen, hydroxy, —C$_{1-8}$alkyl, —C$_{1-8}$alkoxy, 3- to 7-membered heterocyclyl; said heterocyclyl or —C$_{1-8}$alkyl is optionally substituted with at least one R$^g$;

R$_{51}$, R$_{52}$, R$_{61}$, R$_{62}$, R$_{71}$, R$_{72}$, R$_{81}$ and R$_{82}$ are each independently selected from hydrogen, halogen, —C$_{1-8}$alkyl, or —C$_{1-8}$alkoxy; or (R$_{51}$ and R$_{61}$), (R$_{51}$ and R$_{62}$), (R$_{52}$ and R$_{61}$) or (R$_{51}$ and R$_{62}$), together with the atoms to which they are attached, form a 7- to 12-membered bridged heterocyclyl wherein the bridge contains 1-6 atoms selected from carbon, oxygen, nitrogen or sulfur;

R$^a$ and R$^b$ are each independently hydrogen, —C$_{1-8}$alkyl or heterocyclyl; or R$^a$ and R$^b$, together with the carbon atom to which they are attached, form a 3- to 6-membered ring comprising 0, 1 or 2 heteroatoms selected from nitrogen, oxygen or optionally oxidized sulfur as the ring member(s);

R$^c$, R$^d$ and R$^e$ are each independently hydrogen, —C$_{1-8}$ alkyl, aryl, CN, hydroxyl, —C$_{1-8}$alkoxy, C$_{3-7}$ cycloalkyl, 3- to 7-membered heterocyclyl comprising one, two or three heteroatoms independently selected from nitrogen, oxygen or optionally oxidized sulfur, or —NR$^{1c}$R$^{1d}$; each said —C$_{1-8}$alkyl, C$_{3-7}$cycloalkyl, aryl or 3- to 7-membered heterocyclyl is optionally substituted with at least one R$^g$; wherein R$^{1c}$ and R$^{1d}$ are each independently hydrogen or —C$_{1-8}$alkyl; each R$^g$ is independently selected from oxo, hydroxy, halogen, —C$_{1-8}$alkyl, —C$_{1-8}$alkoxy, or 3- to 7-membered heterocyclyl; and n is each independently 0, 1, 2, 3 or 4.

In some embodiments, R$_4$ is 3- to 7-membered monocyclic heterocyclyl. In some embodiments, (R$_{51}$ and R$_{61}$), (R$_{51}$ and R$_{62}$), (R$_{52}$ and R$_{61}$) or (R$_{52}$ and R$_{62}$), together with the atoms to which they are attached, form a 7- to 12-membered bridged heterocyclyl wherein the bridge contains 1-6 or 1-4 or 1-2 atoms selected from carbon or oxygen.

Aspect 3: The compound according to aspects 1 or 2, wherein

R$_1$ is selected from halogen, —NR$^c$R$^d$, or —OR$^c$, —C$_{1-4}$alkyl, C$_{3-8}$cycloalkyl, 4- to 6-membered C-linked heterocyclyl comprising one to three heteroatoms selected from nitrogen, oxygen, silicon or sulfur, 4- to 6-membered Si-linked heterocyclyl comprising 0, 1 or 2 additional heteroatoms selected from nitrogen, oxygen, or sulfur, 5-, 6- or 7-membered N-linked heterocyclyl comprising 0, 1 or 2 additional heteroatoms selected from nitrogen, oxygen or optionally oxidized sulfur as ring member(s), or 5- to 6-membered heteroaryl; wherein each of said —C$_{1-4}$alkyl, C$_{3-6}$cycloalkyl, 4- to 6-membered C-linked heterocyclyl, 4- to 6-membered Si-linked heterocyclyl or 5-, 6- or 7-membered N-linked heterocyclyl or 5- to 6-membered heteroaryl is optionally substituted with at least one substituent selected from halogen, hydroxy, oxo, —NH(C$_{1-4}$alkyl) or —C$_{1-4}$alkyl; R$^c$ and R$^d$ are each independently hydrogen or —C$_{1-4}$alkyl.

In some embodiments, said —C$_{1-4}$alkyl or C$_{3-6}$cycloalkyl is optionally substituted with at least one halogen or hydroxyl; and/or said 4- to 6-membered C-linked heterocyclyl or 4- to 6-membered Si-linked heterocyclyl, said heterocyclyl is optionally substituted with at least one halogen, hydroxyl. —NH(CH$_3$) or oxo; and/or said 5-, 6- or 7-membered N-linked heterocyclyl is optionally substituted with —C$_{1-4}$alkyl (preferably methyl); and/or said 5- to 6-membered heteroaryl is optionally substituted with —C$_{1-4}$alkyl (preferably methyl). Preferably, the 5- to 6-membered N-linked heterocyclyl is pyrrolidinyl, piperidinyl, piperazinyl, morpholino, or morpholinyl, each of which is optionally substituted with halogen, hydroxy or —C$_{1-4}$alkyl. Preferably, the 4- to 6-membered C-linked heterocyclyl is tetrahydrofuranyl, pyrrolidin-2-yl or pyrrolidin-3-yl, oxetanyl, or tetrahydropyranyl, each of which is optionally substituted with halogen, hydroxy, oxo, —NH(C$_{1-4}$alkyl) or —C$_{1-4}$alkyl. Preferably, the 4- to 6-membered Si-linked heterocyclyl is siletanyl or silolanyl, each of which is optionally substituted with hydroxy.

In some embodiments, R$_1$ is selected from halogen, —NR$^c$R$^d$, or —OR$^c$, —C$_{1-4}$alkyl, C$_{3-5}$ cycloalkyl, or 5-, 6- or 7-membered N-linked heterocyclyl comprising 0, 1 or 2 additional heteroatoms selected from nitrogen, oxygen or optionally oxidized sulfur as ring member(s), wherein each of said —C$_{1-4}$alkyl, C$_{3-6}$cycloalkyl or 5-, 6- or 7-membered N-linked heterocyclyl is optionally substituted with at least one substituent selected from halogen or —C$_{1-4}$ alkyl; R$^f$ and R$^d$ are each independently hydrogen or —C$_{1-4}$alkyl.

In some embodiments, said —C$_{1-4}$alkyl is optionally substituted with at least one halogen, and/or said 5- to 6-membered N-linked heterocyclyl is optionally substituted with —C$_{1-4}$alkyl (preferably methyl). Preferably, the 5- to 6-membered N-linked heterocyclyl is pyrrolidinyl, piperidinyl, piperazinyl, morpholino, or morpholinyl, each of which is optionally substituted with halogen or —C$_{1-4}$alkyl.

Aspect 4: The compound according to any one of aspects 1-3, wherein

R$_1$ is selected from hydrogen, methyl, tert-butyl, ethyl, n-propyl, iso-propyl, cyclopropyl, 2-methylpropyl, butyl, pentyl, hexyl, chloro, fluoro, methoxy, —CHF$_2$, —NHCH$_3$, —N(C$_2$H$_5$)$_2$, —OCH(CH$_3$)$_2$, —S(O)$_2$—NHCH$_3$, —Si(CH$_3$)$_2$OH, —Si(C$_2$H$_5$)$_2$OH, —CH(CH$_3$)$_2$OH, —CH$_2$OCH$_3$,

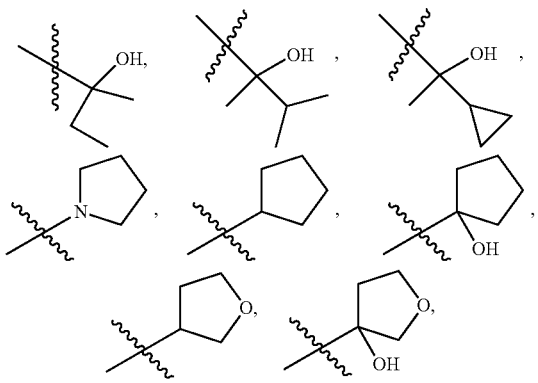

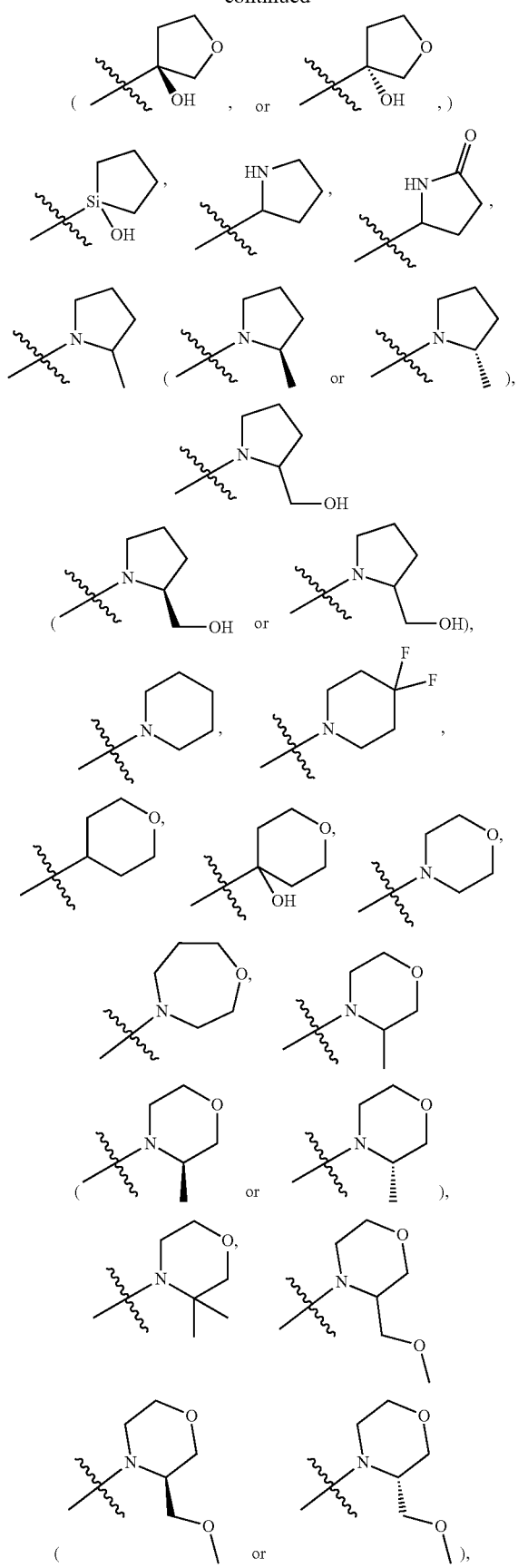

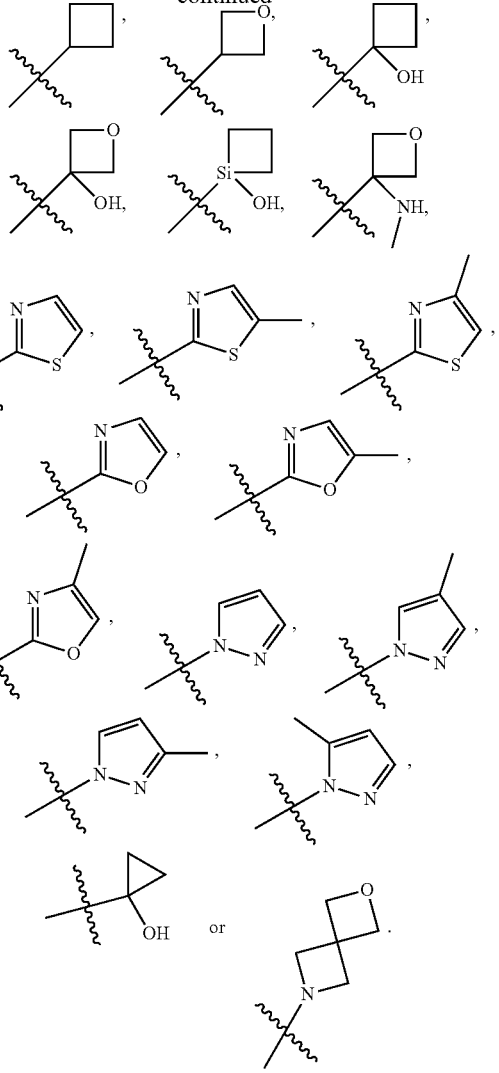

In some embodiments, Rr is selected from hydrogen, methyl, tert-butyl, ethyl, n-propyl, iso-propyl, 2-methylpropyl, butyl, pentyl, hexyl, chloro, fluoro, methoxy, —CHF$_2$, —NHCH$_3$, —N(C$_2$H$_5$)$_2$, —OCH(CH$_3$)$_2$, Aspect 5: The compound according to any one of aspects 1-4, wherein
X is —CR$_2$, wherein R$_2$ is selected from hydrogen, —C$_{1-4}$alkyl, aryl, 5- to 6-membered heteroaryl comprising one, two or three heteroatoms independently selected from nitrogen, oxygen or optionally oxidized sulfur, 3- to 7-membered heterocyclyl comprising one, two or three heteroatoms independently selected from nitrogen, oxygen or optionally oxidized sulfur, —(CH$_2$)$_n$—, —CONHR$^d$, —CONH—(CH$_2$)$_n$—R$^d$, —CONH—R$^d$, —(CH$_2$)$_n$—NHR$^d$, —(CH$_2$)$_n$—NHCOR$^d$, —(CH$_2$)$_n$—R$^d$, —SO$_2$—NH—(CH$_2$)$_n$—R$^d$, —(CH$_2$)$_n$—SO$_2$—NHR$^d$, (CH$_2$)—NH—CO—NRR, (CH$_2$)$_n$—NH—CS—NR$^d$R$^e$, or —(CH$_2$)$_n$—NH—SO$_2$—R$^d$; wherein each of said aryl, 5- to 6-membered heteroaryl or 3- to 7-membered heterocyclyl is optionally substituted with at least one selected from —C$_{1-4}$alkyl or oxo; and n is 1 or 2;

R$^d$ and R$^e$ each is independently selected from hydrogen, hydroxyl, —C$_{1-4}$alkyl, phenyl, —C$_{1-4}$ alkoxy, C$_{3-6}$ cycloalkyl, aryl, 5- to 6-membered heterocyclyl, 5- to 6-membered heteroaryl or —NR$^{1c}$R$^{1d}$, wherein each of said —C$_{1-4}$alkyl, C$_{3-6}$ cycloalkyl, aryl, 5- to 6-membered heteroaryl or 5- to 6-membered heterocyclyl is optionally substituted with at least one halogen, CF$_3$, —C$_{1-4}$alkyl or oxo;

R$^{1c}$ and R$^{1d}$ are each independently hydrogen or —C$_{1-4}$ alkyl.

In some embodiments, R$^d$ is 5- to 6-membered monocyclic heterocyclyl comprising one or two heteroatoms selected from oxygen, nitrogen, silicon or optionally oxidized sulfur, and optionally substituted with halogen or —C$_{1-4}$alkyl. In further embodiments, R$^d$ is pyrrolidinyl, piperidinyl, piperazinyl, morpholino, morpholinyl, or tetrahydropyranyl.

In some embodiments, R$^d$ is 5- to 6-membered heteroaryl comprising one or two or three heteroatoms selected from oxygen, nitrogen or sulfur, and optionally substituted with at least one halogen and/or —C$_{1-4}$alkyl. In further embodiments, R$^d$ is

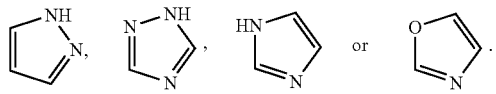

Aspect 6: The compound according to aspect 5, wherein R$_2$ is selected from hydrogen, hydroxyl, methyl, halogen,

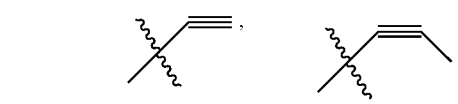

—CONHCH$_3$, —CONHOCH$_3$,

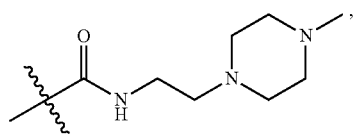

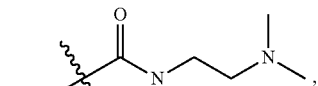

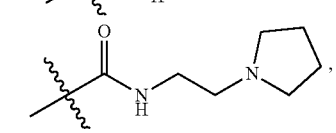

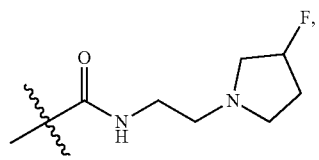

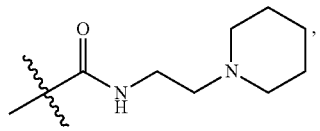

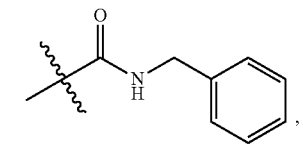

—SO$_2$NHCH$_3$, —CH$_2$NHCONHCH$_3$, —CH$_2$NHCSNH-CH$_3$, —CH$_2$NHCOCH$_3$, —CH$_2$NHSO$_2$CH$_3$, —CH$_2$NHCONHC$_2$H$_5$,

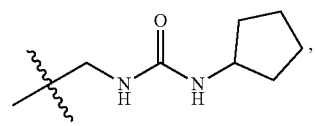 [SMILES: *CNC(=O)NC1CCCC1]

—C$_2$H$_4$NHSO$_2$CH$_3$, —CH$_2$SO$_2$NHCH$_3$, —CH$_2$NHCH$_2$CF$_3$, —CH$_2$NHCONHCH$_2$CF$_3$, —CH$_2$NHCONHC(CH$_3$)$_3$, —CH$_2$NHCOCN(CH$_3$)$_2$,

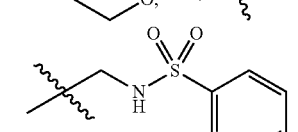

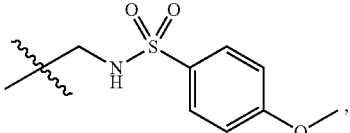

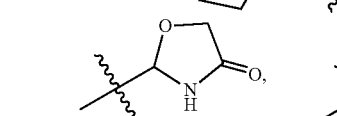

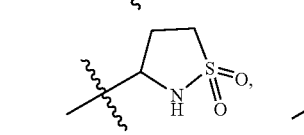

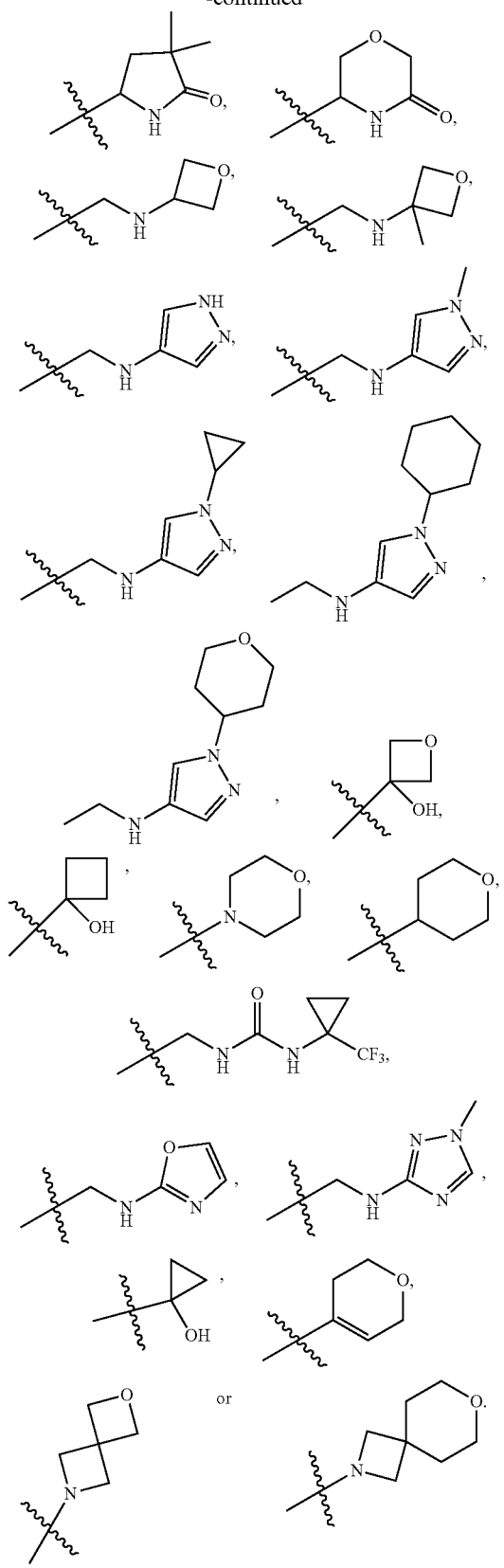
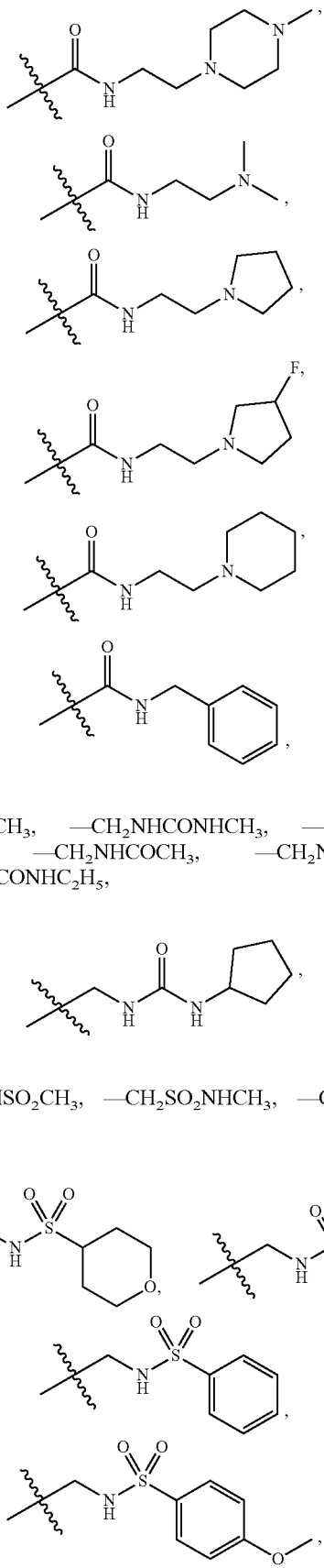
In some embodiments, $R_2$ is selected from hydrogen, hydroxyl, methyl, —CONHCH₃, —CONHOCH₃, -continued

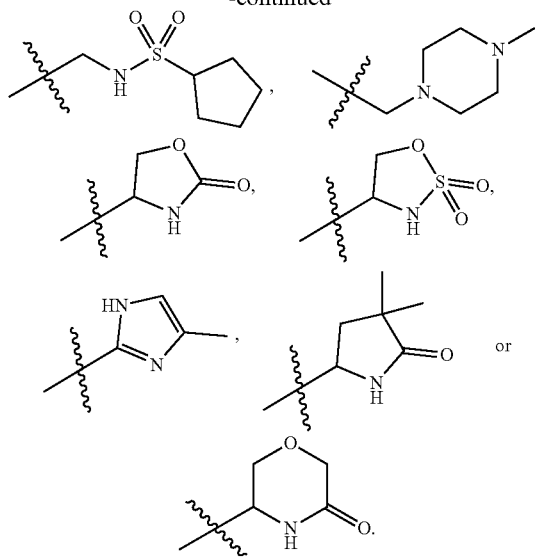

Aspect 7: The compound according to any one of aspects 1 to 6, wherein $R_3$ is selected from hydrogen, —$C_{1-4}$alkyl, $C_{3-6}$cycloalkyl, 4- to 6-membered heterocyclyl comprising one to three heteroatoms selected from nitrogen, oxygen, silicon or sulfur, —(CH$_2$)$_n$—CONHR$^d$, —CONH—(CH$_2$)$_n$—R$^d$, —CONH—R$^d$, —(CH$_2$)$_n$, —NHCOR$^d$, —SO$_2$—NH—(CH$_2$)$_n$—R$^d$, —(CH$_2$)$_n$—SO$_2$—NHR$^d$, —(CH$_2$)$_n$—NH—CO—NR$^d$R$^e$, —(CH$_2$)$_n$—NH—SO$_2$—R$^d$, —Si$^a$R$^b$R$^c$,

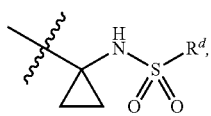

or 5- to 6-membered heteroaryl, wherein said —$C_{1-4}$alkyl, $C_{3-6}$cycloalkyl, 4- to 6-membered heterocyclyl or 5- to 6-membered heteroaryl is optionally substituted with —$C_{1-4}$alkyl, halogen, oxo or hydroxy;

n is 0, 1 or 2;

$R^d$ and $R^e$ each is independently selected from hydrogen, —$C_{1-4}$alkyl, phenyl, —$C_{1-4}$alkoxy, CN, $C_{3-6}$cycloalkyl, 5- to 6-membered heterocyclyl, or —NR$^{1c}$R$^{1d}$, wherein each said —$C_{1-4}$alkyl, $C_{3-6}$cycloalkyl, aryl or 5- to 6-membered heterocyclyl is optionally substituted with at least one of —$C_{1-4}$alkyl, halogen or oxo; and $R^{1c}$ and $R^{1d}$ are each independently hydrogen or —$C_{1-4}$alkyl.

In some embodiments. $C_{3-6}$cycloalkyl is selected from cyclopropyl, cyclobutyl, cyclopentyl or cyclohexyl.

In some embodiments, 4- to 6-membered heterocyclyl is selected from oxetanyl, tetrahydrofuranyl, tetrahydropyranyl, siletanyl, pyrrolidinyl, piperidinyl, azetidinyl, silolanyl, morpholinyl, or oxazolidinyl.

In some embodiments, $R_3$ is selected from hydrogen, —$C_{1-4}$alkyl, —(CH$_2$)$_n$—CONHR$^d$, —CONH—(CH$_2$)$_n$—R$^d$, —CONH—R$^d$, —(CH$_2$)$_n$—NHCOR$^d$, —SO$_2$—NH—(CH$_2$)$_n$—R$^d$, —(CH$_2$)$_n$—SO$_2$—NHR$^d$, —(CH$_2$)$_n$—NH—CO—NR$^d$R$^e$, —(CH$_2$)$_n$—NH—SO$_2$—R$^d$, or

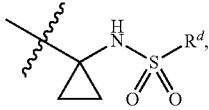

wherein said —$C_{1-4}$alkyl is optionally substituted with halogen or hydroxy;

n is 0, 1 or 2;

$R^d$ and $R^e$ each is independently selected from hydrogen, —$C_{1-4}$alkyl, phenyl, —$C_{1-4}$alkoxy, CN, $C_{3-6}$cycloalkyl, 5- to 6-membered heterocyclyl, or —NR$^{1c}$R$^{1d}$, wherein each said —$C_{1-4}$alkyl, $C_{3-6}$cycloalkyl, aryl or 5- to 6-membered heterocyclyl is optionally substituted with at least one of —$C_{1-4}$alkyl, halogen or oxo; and $R^{1c}$ and $R^{1d}$ are each independently hydrogen or —$C_{1-4}$alkyl.

In some embodiments, 5- to 6-membered heteroaryl is selected from

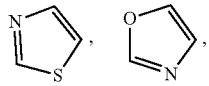

or

Aspect 8. The compound according to Aspect 7, wherein $R_3$ is selected from methyl, ethyl, propyl, cyclopropyl, —CH(OH)CH$_3$, —C(OH)(CH$_3$)$_2$, —SO$_2$NHCH$_3$, —SO$_2$NH$_2$, —SO$_2$NHC$_2$H$_5$, —CH(OH)CF$_3$, —C(OH)(CF$_3$)$_2$, —C(OH)(CH$_3$)$_2$, Si(CH$_3$)$_2$OH, —Si(C$_2$H$_5$)$_2$OH, —CH$_2$NHCH$_3$,

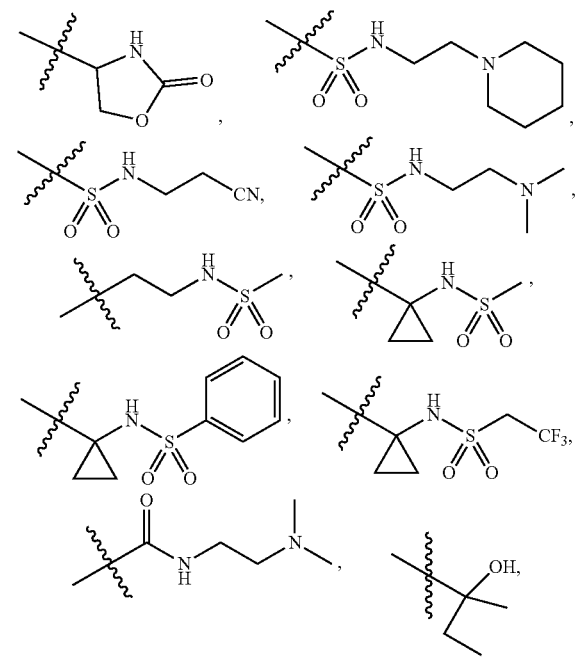

-continued
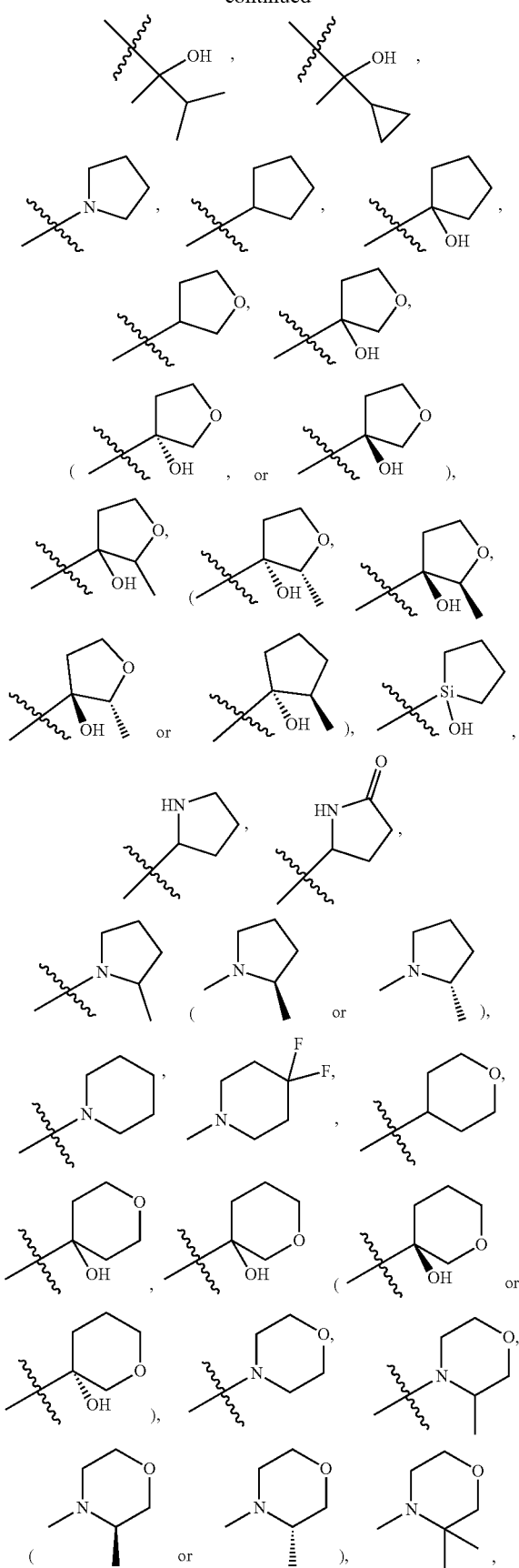
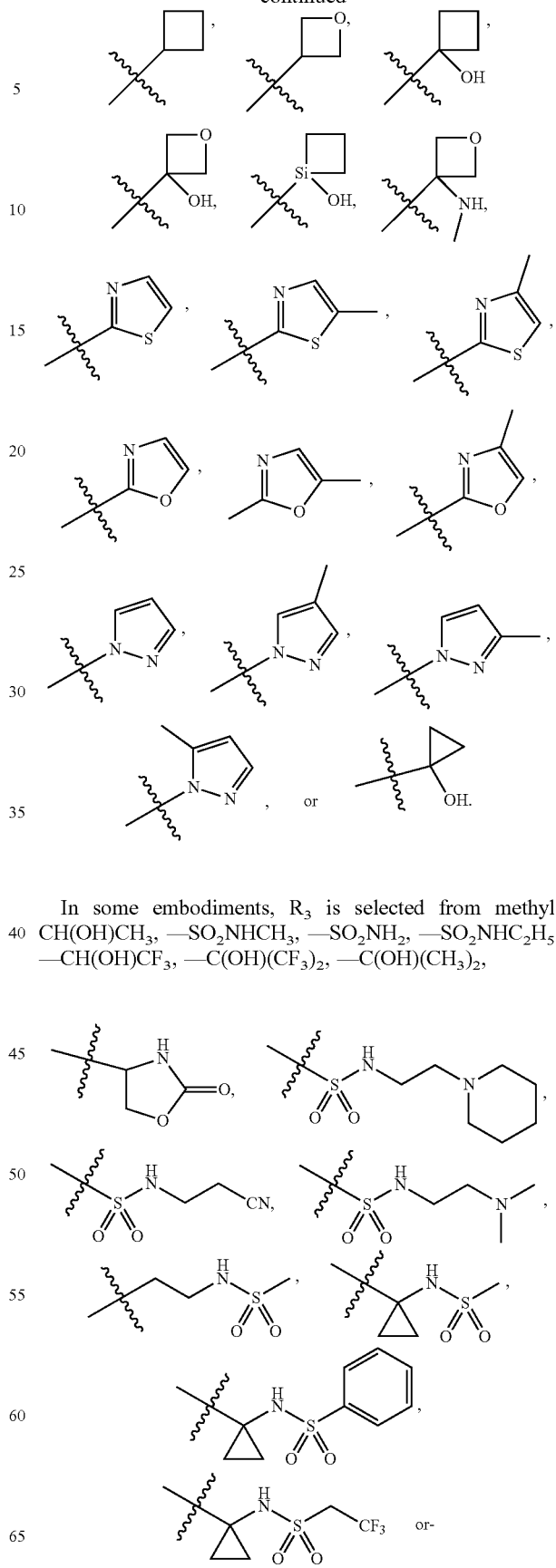
In some embodiments, $R_3$ is selected from methyl, $CH(OH)CH_3$, $-SO_2NHCH_3$, $-SO_2NH_2$, $-SO_2NHC_2H_5$, $-CH(OH)CF_3$, $-C(OH)(CF_3)_2$, $-C(OH)(CH_3)_2$, -continued

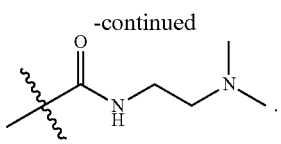

Aspect 9: The compound according to any one of aspects 1 to 8, wherein $R_4$ is selected from $C_{3-6}$cycloalkyl, or —$C_{1-4}$alkyl optionally substituted with 4- to 6-membered monocyclic heterocyclyl.

In some embodiments, $R_4$ is a deuterated $C_{1-4}$alkyl group.
Aspect 10: The compound according to any one of aspects 1 to 9, wherein
$R_4$ is selected from methyl, ethyl, isopropyl, cyclopropyl, or

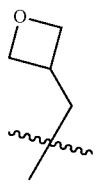 [SMILES: *CC1COC1]

(oxetan-3-ylmethyl).
In some embodiments, $R_4$ is $CD_3$ or $-CD_2CD_3$.
Aspect 11: The compound according to any one of aspects 1 to 10, wherein $R_{51}$, $R_{52}$, $R_{61}$, and $R_{62}$ are hydrogen.
Aspect 12: The compound according to any one of aspects 1 to 11, wherein $R_{51}$ and $R_6$, together with the atoms to which they are attached, form an 8-membered bridged heterocyclyl wherein the bridge contains two carbon atoms (i.e., —$CH_2$—$CH_2$—); and $R_{52}$ and $R^a$ are hydrogen.
Aspect 13: The compound according to any one of aspects 1 to 12, wherein $R_{71}$, $R_{72}$, $R_{81}$, $R_{82}$ and $R_9$ are hydrogen.
Aspect 14: The compound according to any one of aspects 1 to 13, which is Formula (II),

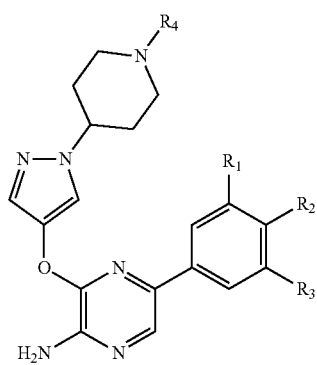

(II)

wherein $R_1$, $R_2$, $R_3$ and $R_4$ are defined as herein in Aspects 1-13.

In some embodiments, $R_1$ is 3- to 7-membered heterocyclyl comprising one, two or three heteroatoms independently selected from nitrogen, oxygen or optionally oxidized sulfur as the ring member(s).

In some embodiments, $R_1$ is 3-,4-,5-,6- or 7-membered heterocyclyl selected from pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxothiomorpholinyl, oxazolidinyl, or oxazolidin-4-yl;

wherein 3-,4-,5-,6- or 7-membered heterocyclyl is optionally substituted with at least one (preferably 1, 2, 3 or 4) substituent(s) selected from halogen, hydroxy, oxo, —NH($C_{1-4}$alkyl) or —$C_{1-8}$alkyl.

Preferably, 3- to 7-membered heterocyclyl is 5-, 6- or 7-membered N-linked heterocyclyl comprising 0, 1 or 2 additional heteroatoms selected from nitrogen, oxygen or optionally oxidized sulfur as ring member(s).

In some embodiments, $R_1$ is selected from hydrogen, methyl, tert-butyl, ethyl, n-propyl, iso-propyl, cyclopropyl, 2-methylpropyl, butyl, pentyl, hexyl, chloro, fluoro, methoxy, —$CHF_2$, —$NHCH_3$, —$N(C_2H_5)_2$, —$OCH(CH_3)_2$, —$S(O)_2$—$NHCH_3$, —$Si(CH_3)_2OH$, —$Si(C_2H_5)_2OH$, —$CH(CH_3)_2OH$, —$CH_2OCH_3$,

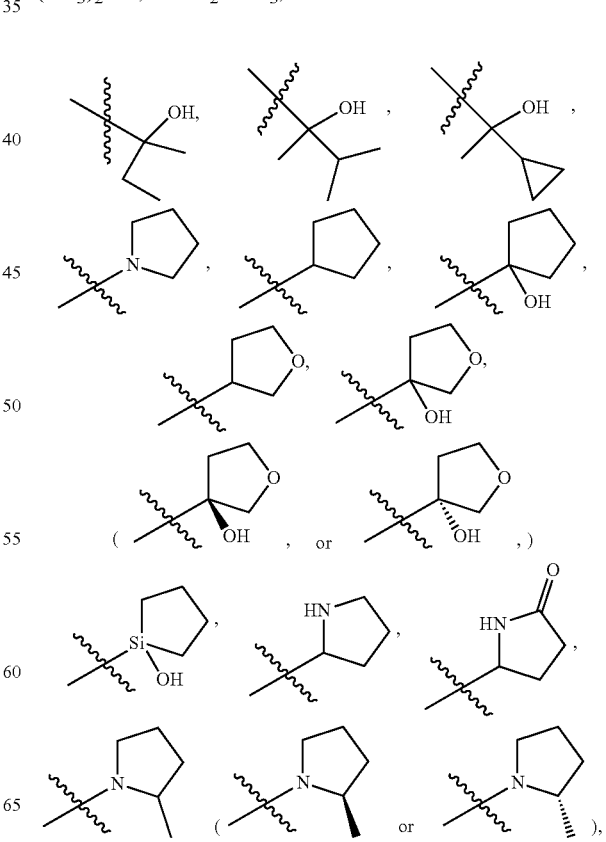

-continued
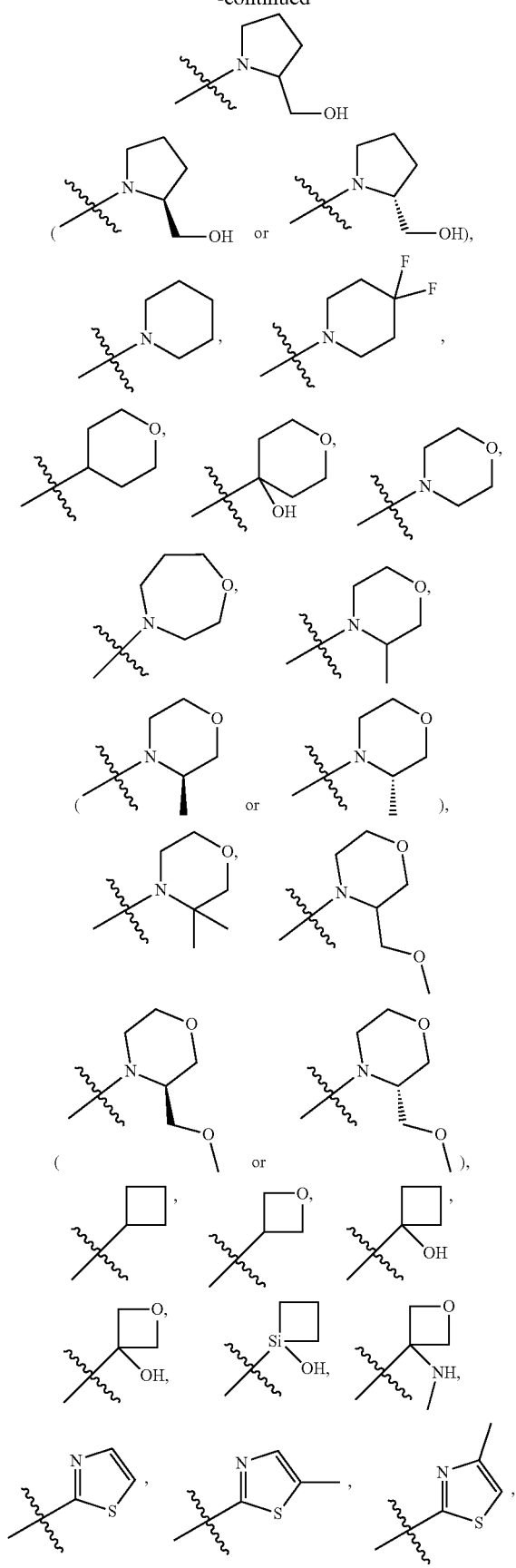
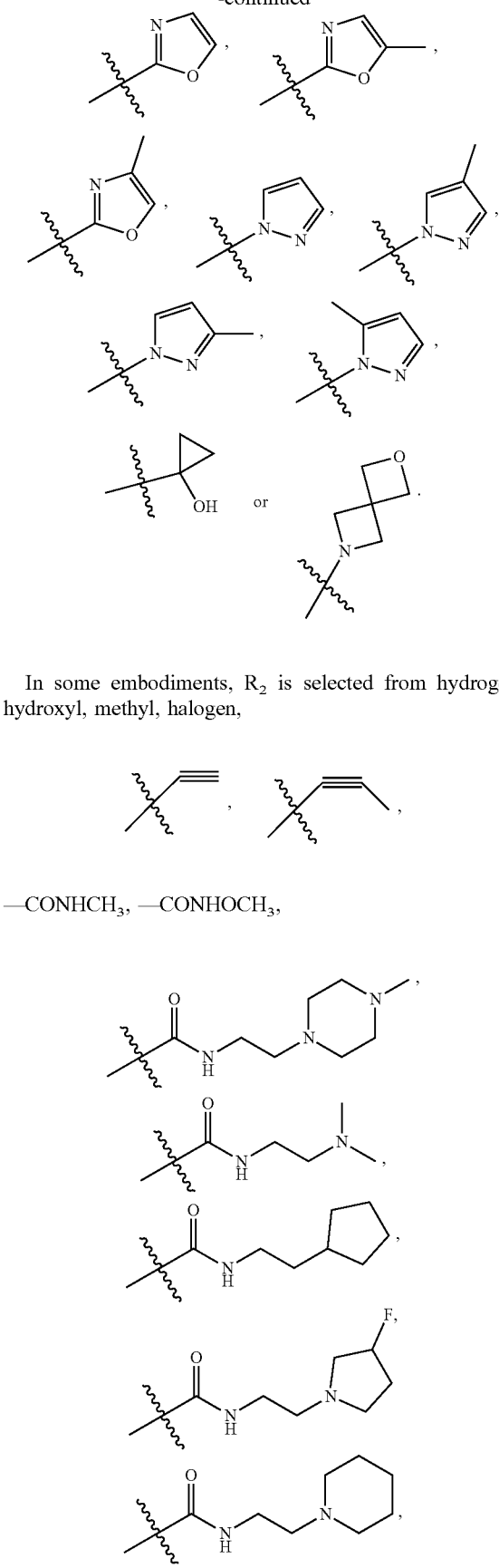
In some embodiments, $R_2$ is selected from hydrogen, hydroxyl, methyl, halogen,
—CONHCH$_3$, —CONHOCH$_3$,

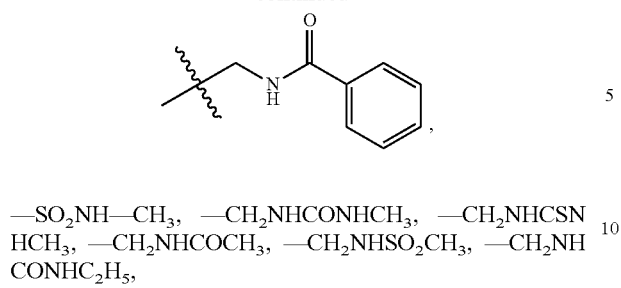

—SO$_2$NH—CH$_3$, —CH$_2$NHCONHCH$_3$, —CH$_2$NHCSN HCH$_3$, —CH$_2$NHCOCH$_3$, —CH$_2$NHSO$_2$CH$_3$, —CH$_2$NH CONHC$_2$H$_5$,

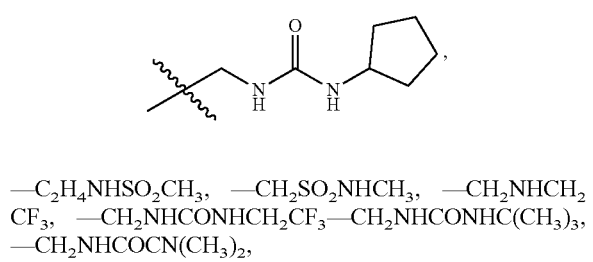

—C$_2$H$_4$NHSO$_2$CH$_3$, —CH$_2$SO$_2$NHCH$_3$, —CH$_2$NHCH$_2$ CF$_3$, —CH$_2$NHCONHCH$_2$CF$_3$—CH$_2$NHCONHC(CH$_3$)$_3$, —CH$_2$NHCOCN(CH$_3$)$_2$,

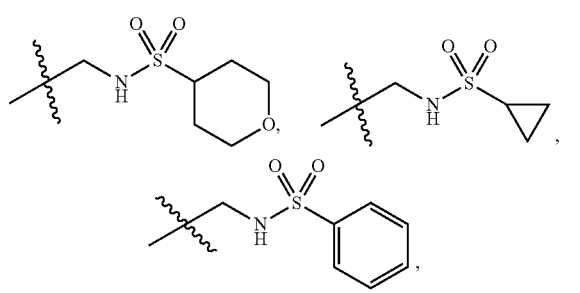

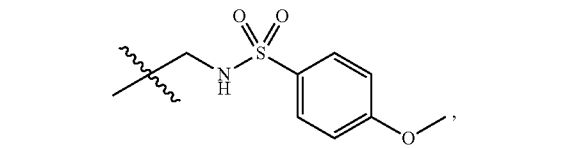

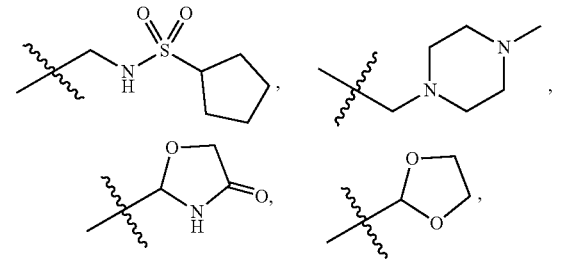

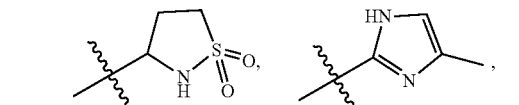

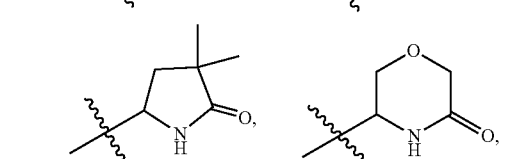

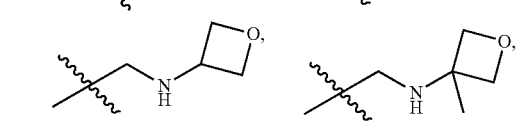

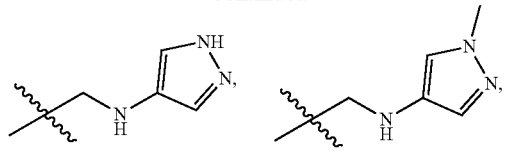

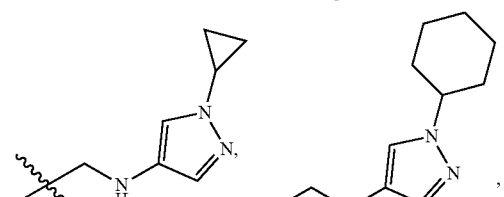

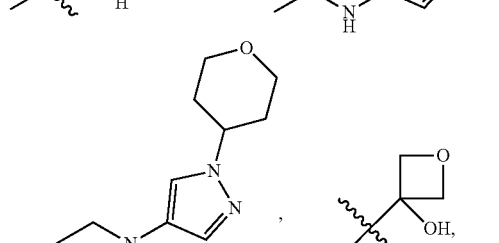

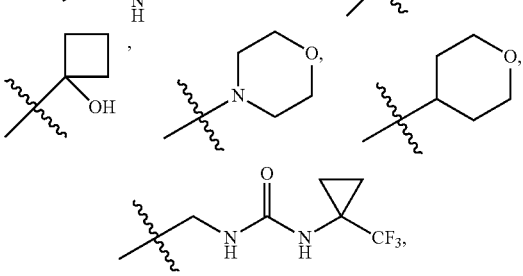

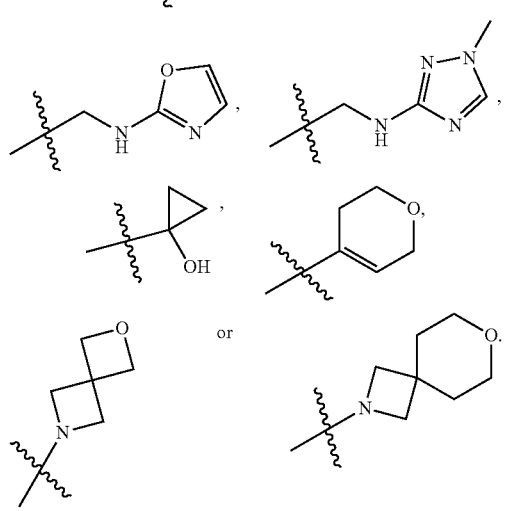

In some embodiments, R$_3$ is selected from hydrogen, —C$_{1-4}$alkyl, C$_{3-6}$cycloalkyl, 4- to 6-membered heterocyclyl comprising one to three heteroatoms selected from nitrogen, oxygen, silicon or sulfur, wherein said 4- to 6-membered heterocyclyl is optionally substituted with 1, 2, 3 or 4 substitutes selected from —C$_{1-4}$alkyl, halogen, oxo or hydroxy.

In some embodiments, R$_3$ is selected from methyl, ethyl, propyl, cyclopropyl, —CH(OH)CH$_3$, —C(OH)(CH$_3$)$_2$, —SO$_2$NHCH$_3$, —SO$_2$NH$_2$, —SO$_2$NHC$_2$H$_5$, —CH(OH) CF$_3$, —C(OH)(CF$_3$)$_2$, —C(OH)(CH$_3$)$_2$, Si(CH$_3$)$_2$OH, —Si (C$_2$H$_5$)$_2$OH, —CH$_2$NHCH$_3$,

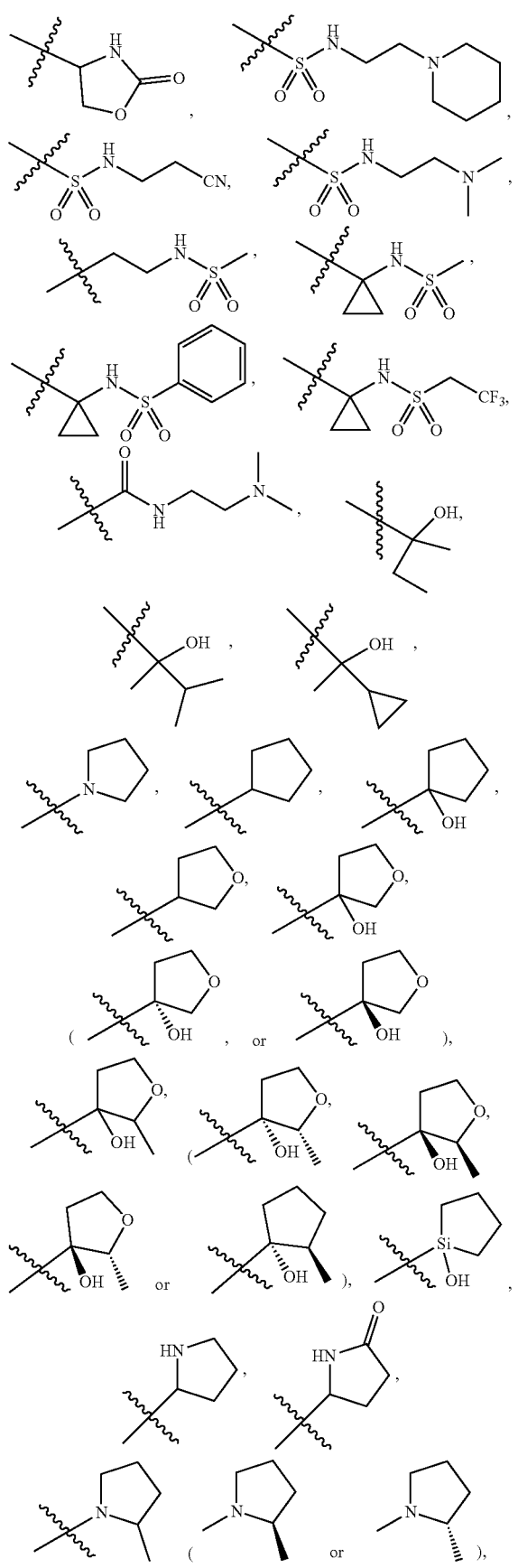
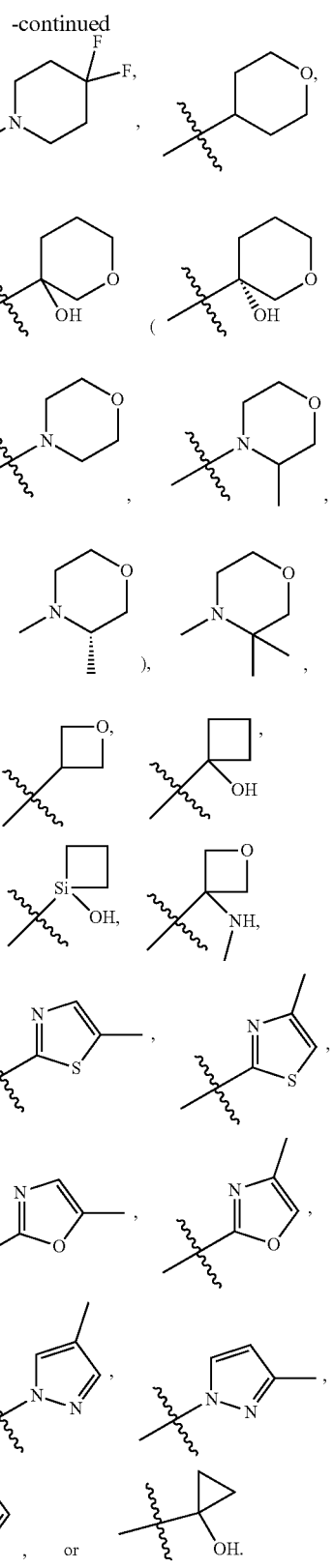
In some embodiments, $R_4$ is selected from $C_{3-6}$cycloalkyl, or —$C_{1-4}$alkyl optionally substituted with 4- to 6-membered monocyclic heterocyclyl.

| Aspect 15: A compound selected from |
|---|
| 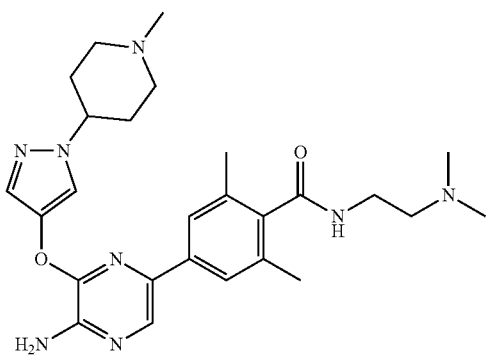 A1 |
| 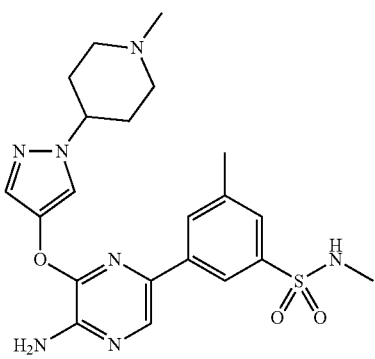 A2 |
| 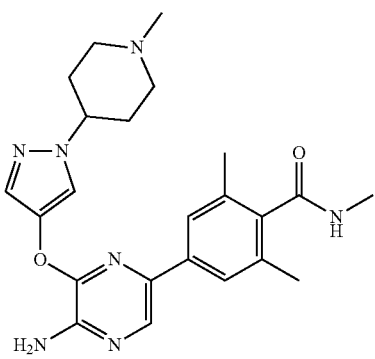 A3 |
| 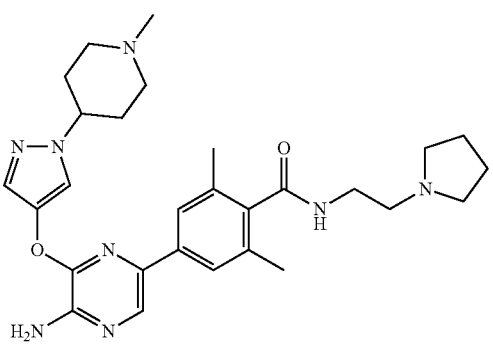 A4 |
-continued
| Aspect 15: A compound selected from |
|---|
| 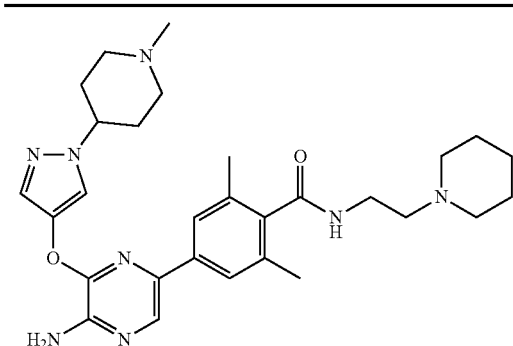 A5 |
| 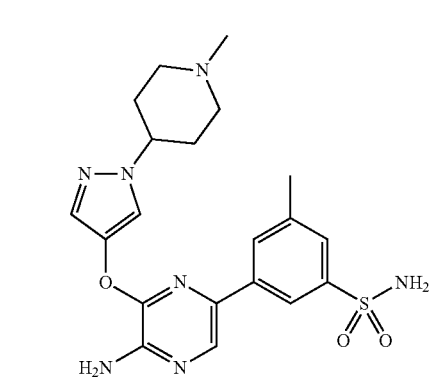 A6 |
| 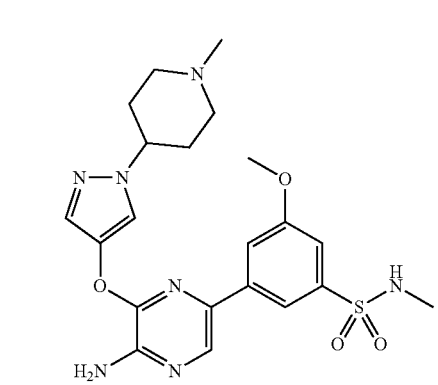 A7 |
| 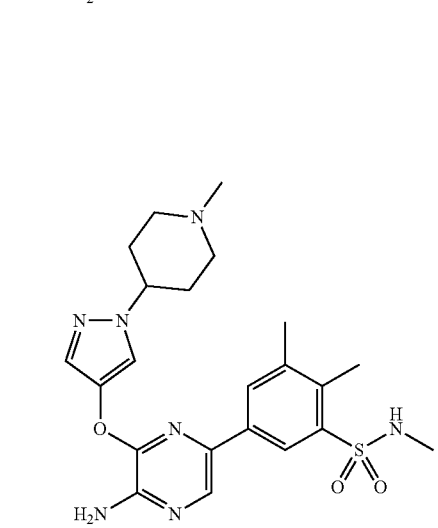 A8 |

Aspect 15: A compound selected from
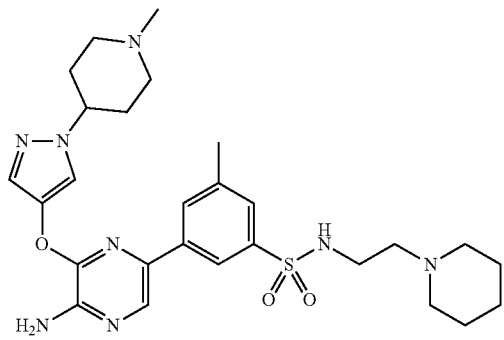 [SMILES: Cc1cc(-c2cnc(N)c(Oc3cnn(C4CCN(C)CC4)c3)n2)cc(S(=O)(=O)NCCN2CCCCC2)c1] A9
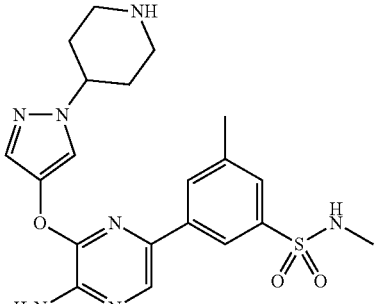 A13
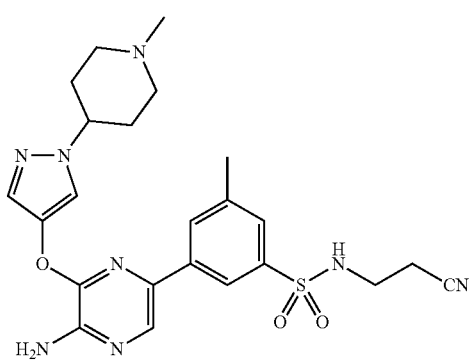 [SMILES: Cc1cc(-c2cnc(N)c(Oc3cnn(C4CCN(C)CC4)c3)n2)cc(S(=O)(=O)NCCC#N)c1] A10
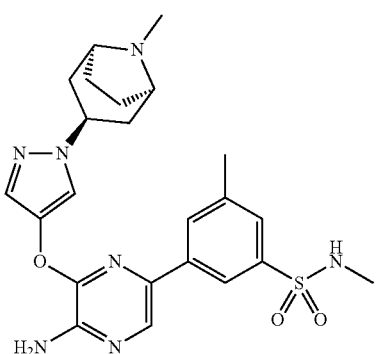 A14
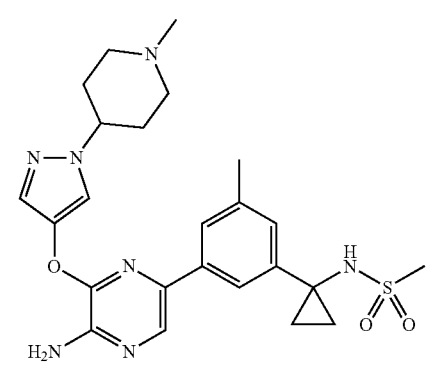 [SMILES: Cc1cc(-c2cnc(N)c(Oc3cnn(C4CCN(C)CC4)c3)n2)cc(C2(NS(C)(=O)=O)CC2)c1] A11
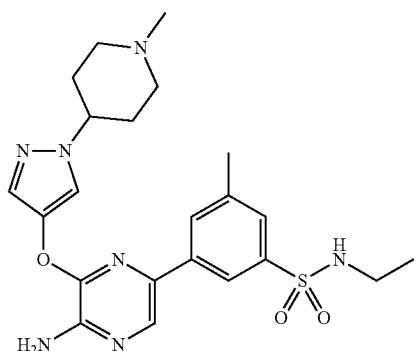 A15
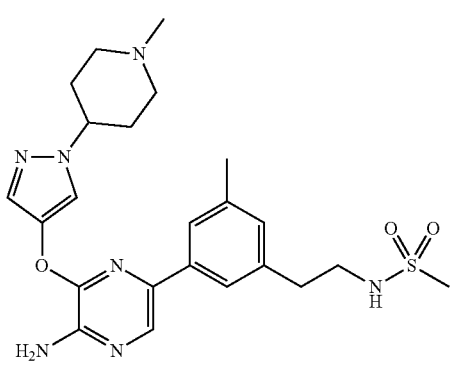 [SMILES: Cc1cc(CCNS(C)(=O)=O)cc(-c2cnc(N)c(Oc3cnn(C4CCN(C)CC4)c3)n2)c1] A12
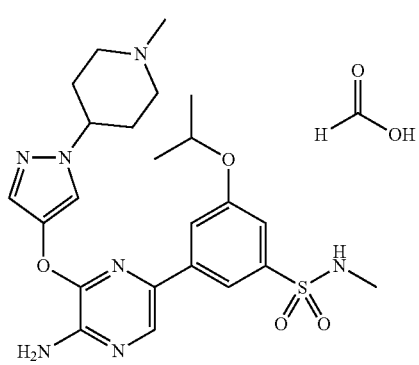 [SMILES: CNS(=O)(=O)c1cc(OC(C)C)cc(-c2cnc(N)c(Oc3cnn(C4CCN(C)CC4)c3)n2)c1 ; O=CO] A16

Aspect 15: A compound selected from
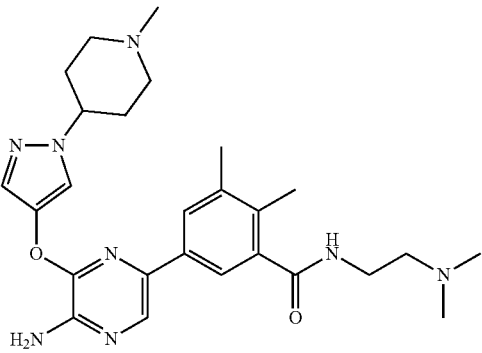 [SMILES: Cc1cc(-c2cnc(N)c(Oc3cnn(C4CCN(C)CC4)c3)n2)cc(C(=O)NCCN(C)C)c1C] A17
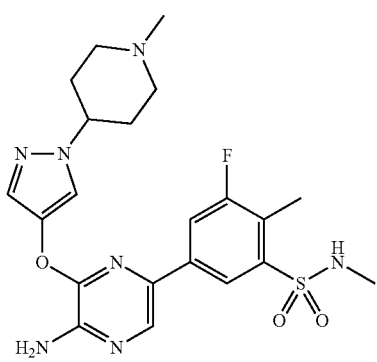 A18
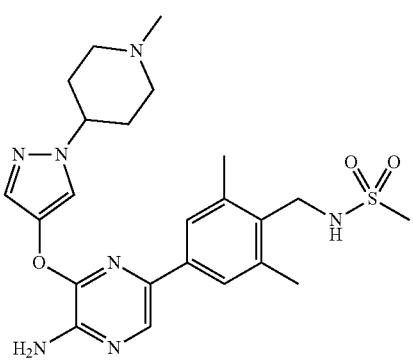 [SMILES: Cc1cc(-c2cnc(N)c(Oc3cnn(C4CCN(C)CC4)c3)n2)cc(C)c1CNS(C)(=O)=O] A19
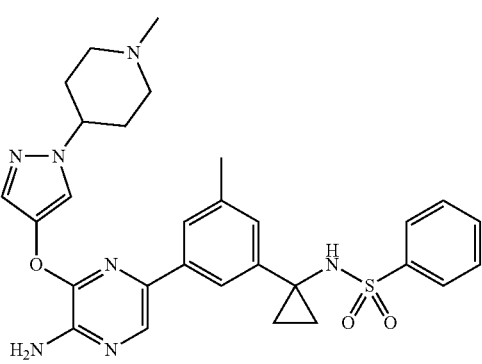 [SMILES: Cc1cc(-c2cnc(N)c(Oc3cnn(C4CCN(C)CC4)c3)n2)cc(C2(NS(=O)(=O)c3ccccc3)CC2)c1] A20
Aspect 15: A compound selected from
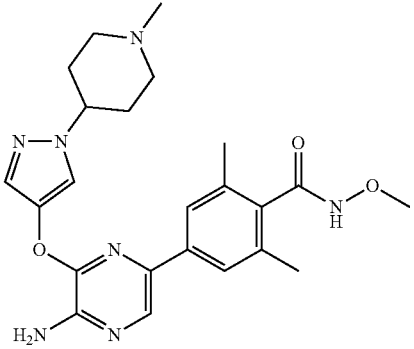 [SMILES: CONC(=O)c1c(C)cc(-c2cnc(N)c(Oc3cnn(C4CCN(C)CC4)c3)n2)cc1C] A21
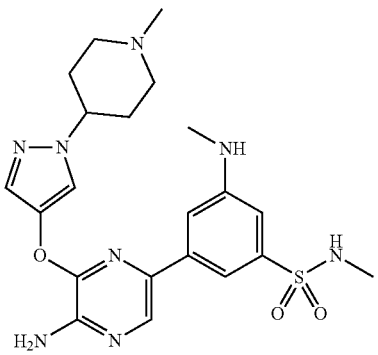 A22
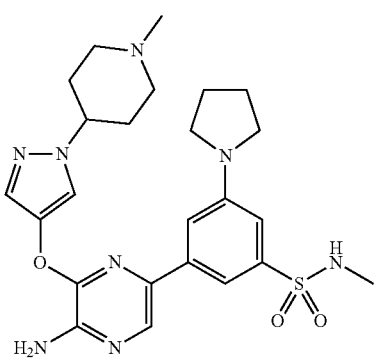 [SMILES: CNS(=O)(=O)c1cc(-c2cnc(N)c(Oc3cnn(C4CCN(C)CC4)c3)n2)cc(N2CCCC2)c1] A23
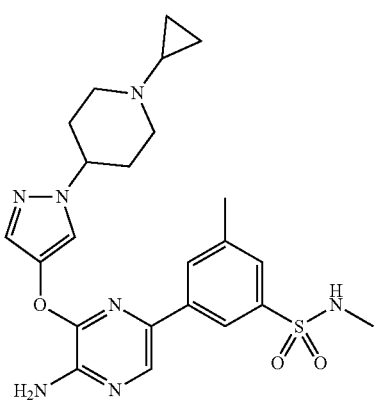 [SMILES: CNS(=O)(=O)c1cc(C)cc(-c2cnc(N)c(Oc3cnn(C4CCN(C5CC5)CC4)c3)n2)c1] A24

| Aspect 15: A compound selected from | Aspect 15: A compound selected from |
|---|---|
| 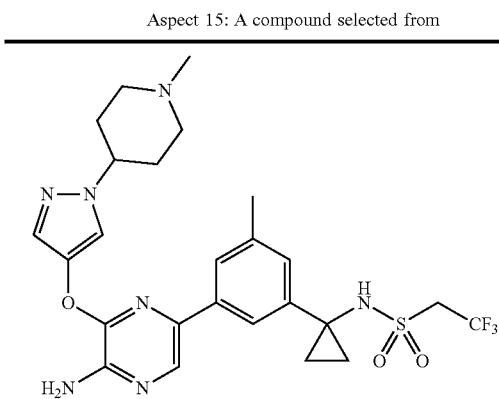 A25 | 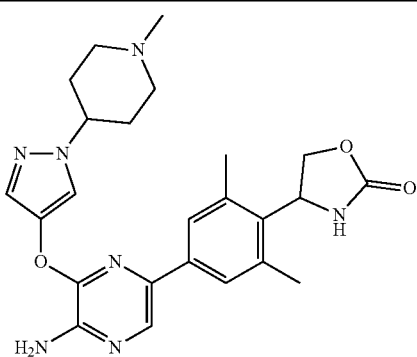 A29 |
| 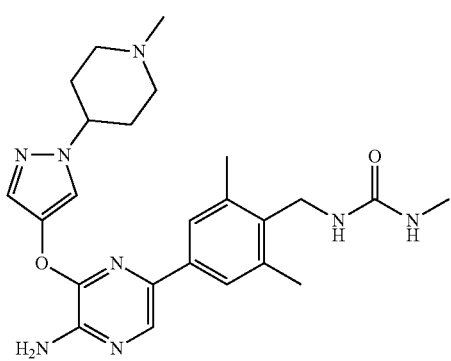 A26 | 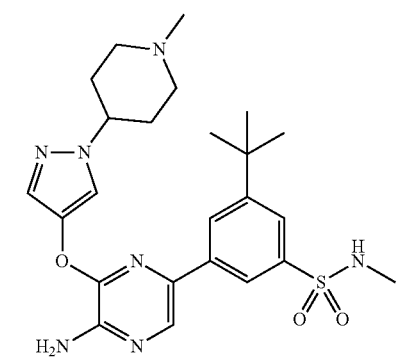 A30 |
| 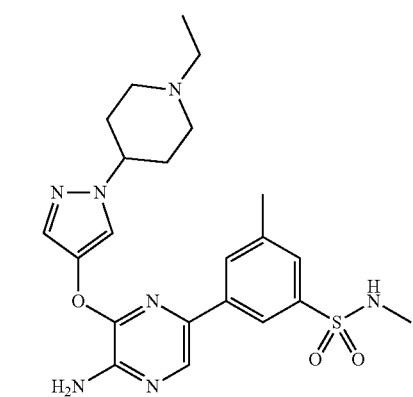 A27 | 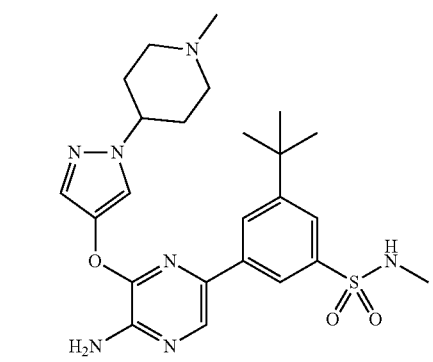 A31 |
| 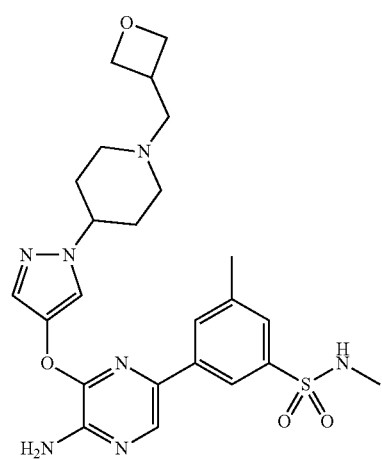 A28 | 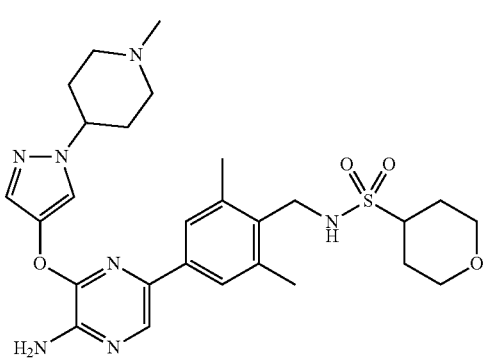 A32 |

Aspect 15: A compound selected from
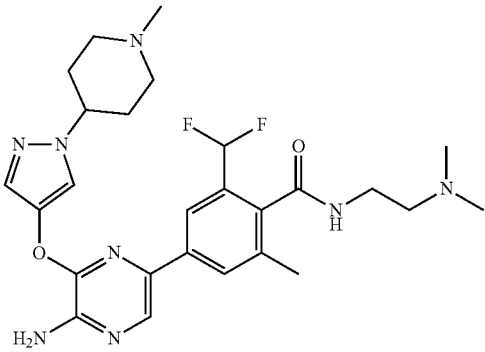 [SMILES: Cc1cc(-c2cnc(N)c(Oc3cnn(C4CCN(C)CC4)c3)n2)cc(C(F)F)c1C(=O)NCCN(C)C]
A33
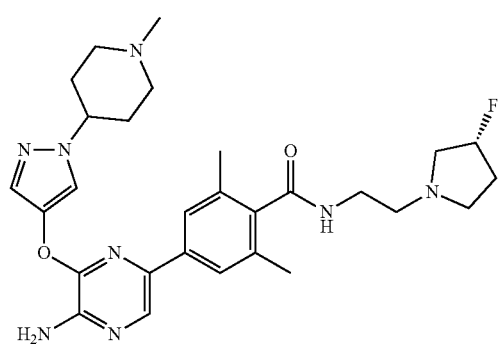 [SMILES: Cc1cc(-c2cnc(N)c(Oc3cnn(C4CCN(C)CC4)c3)n2)cc(C)c1C(=O)NCCN1CC[C@@H](F)C1]
A34
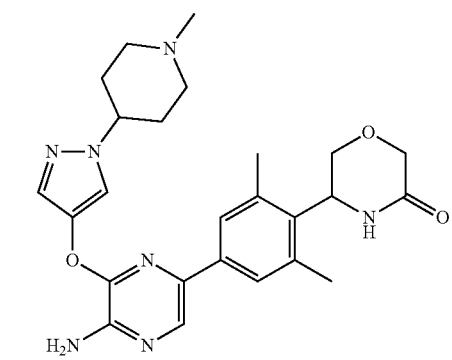 [SMILES: Cc1cc(-c2cnc(N)c(Oc3cnn(C4CCN(C)CC4)c3)n2)cc(C)c1C1COCC(=O)N1]
A35
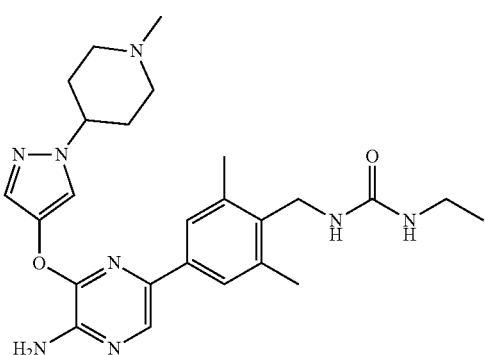
A36
Aspect 15: A compound selected from
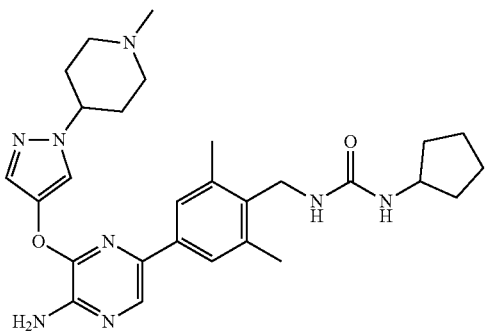 [SMILES: Cc1cc(-c2cnc(N)c(Oc3cnn(C4CCN(C)CC4)c3)n2)cc(C)c1CNC(=O)NC1CCCC1]
A37
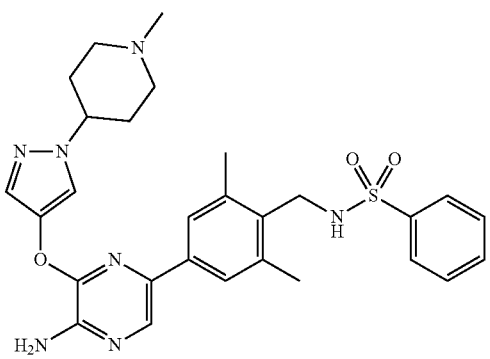 [SMILES: Cc1cc(-c2cnc(N)c(Oc3cnn(C4CCN(C)CC4)c3)n2)cc(C)c1CNS(=O)(=O)c1ccccc1]
A38
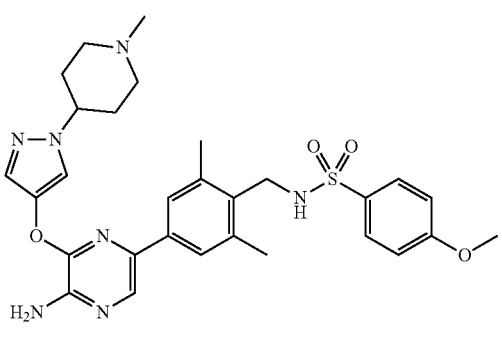 [SMILES: COc1ccc(S(=O)(=O)NCc2c(C)cc(-c3cnc(N)c(Oc4cnn(C5CCN(C)CC5)c4)n3)cc2C)cc1]
A39
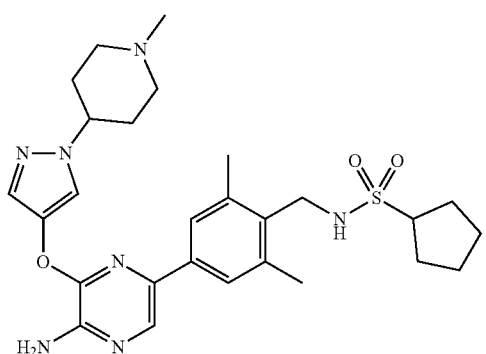
A40

| Aspect 15: A compound selected from | Aspect 15: A compound selected from |
|---|---|
| 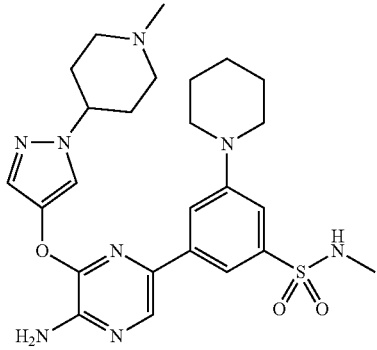 A41 | 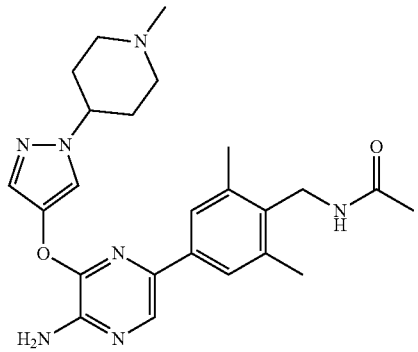 A45 |
| 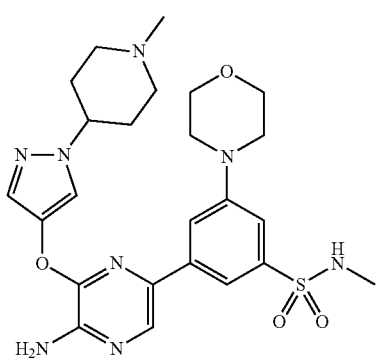 A42 | 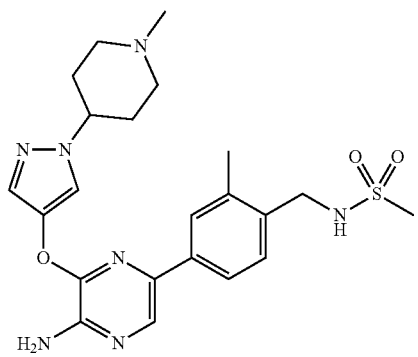 A46 |
| 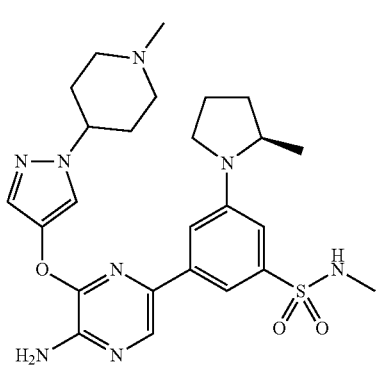 A43 | 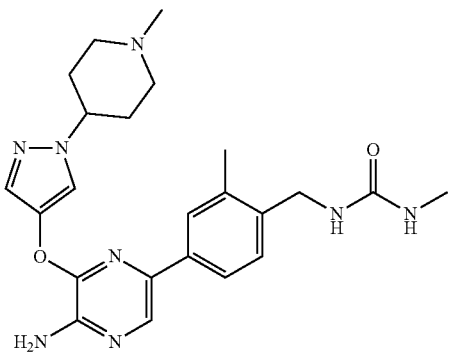 A47 |
| 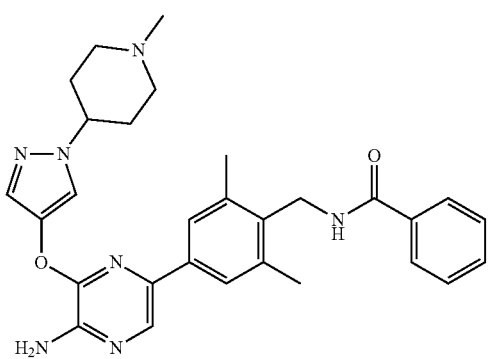 A44 | 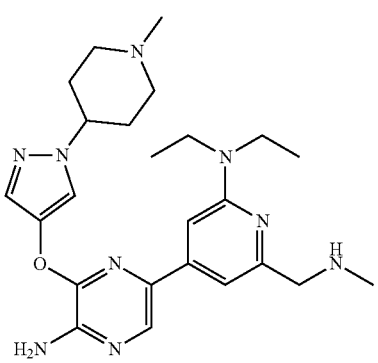 B1 |

| Aspect 15: A compound selected from | Aspect 15: A compound selected from |
|---|---|
| 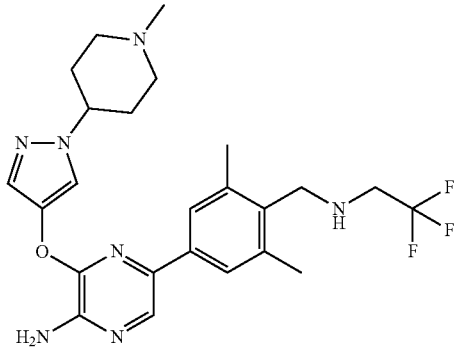 A48 | 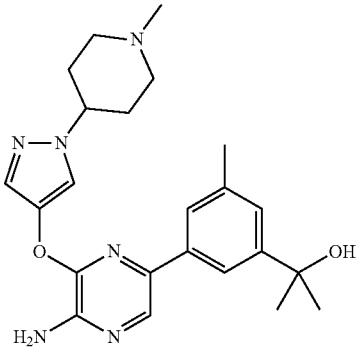 A52 |
| 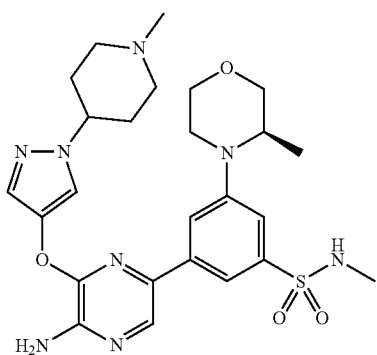 A49 | 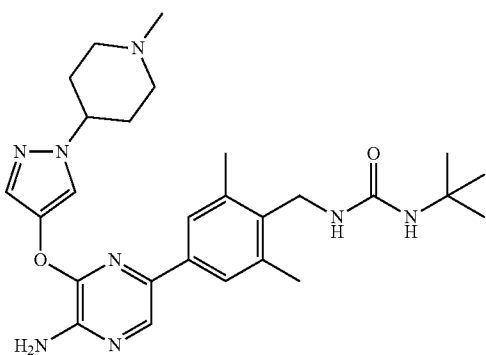 A53 |
| 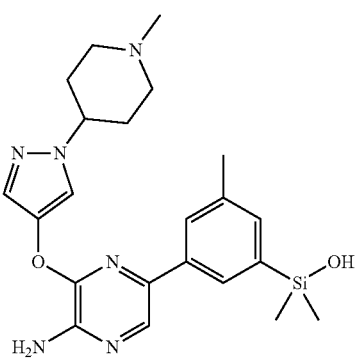 A50 | 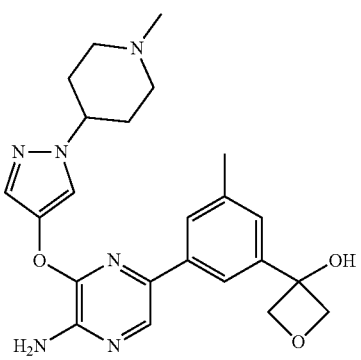 A54 |
| 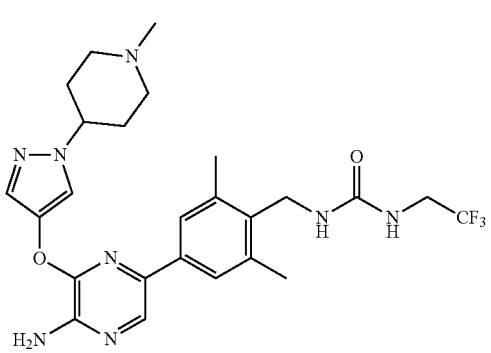 A51 | 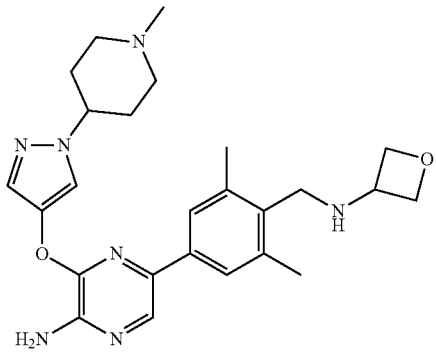 A55 |

Aspect 15: A compound selected from
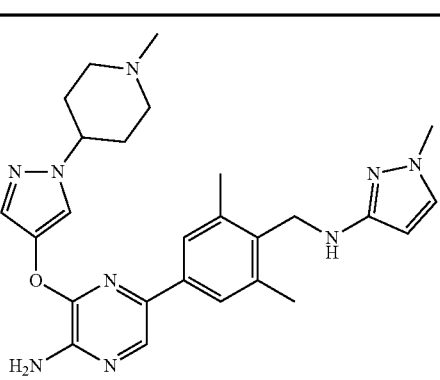 A56
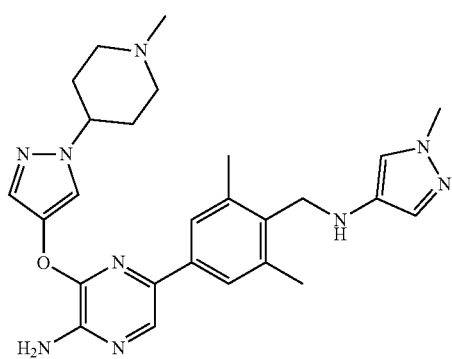 [SMILES: Cc1cc(-c2cnc(N)c(Oc3cnn(C4CCN(C)CC4)c3)n2)cc(C)c1CNc1cnn(C)c1] A57
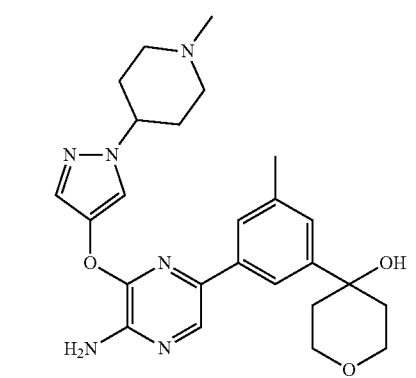 [SMILES: Cc1cc(-c2cnc(N)c(Oc3cnn(C4CCN(C)CC4)c3)n2)cc(C2(O)CCOCC2)c1] A58
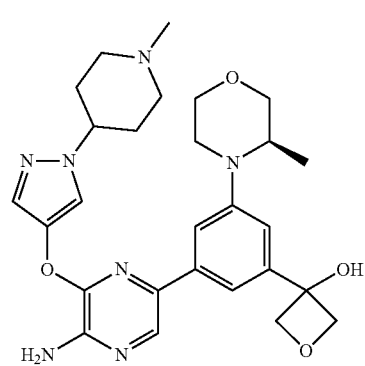 A59
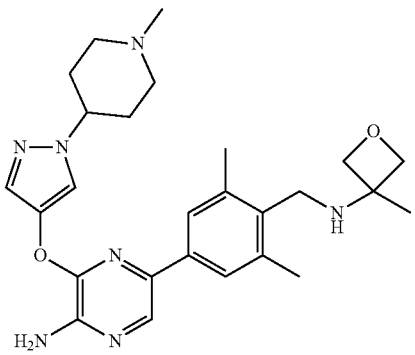 [SMILES: Cc1cc(-c2cnc(N)c(Oc3cnn(C4CCN(C)CC4)c3)n2)cc(C)c1CNC1(C)COC1] A60
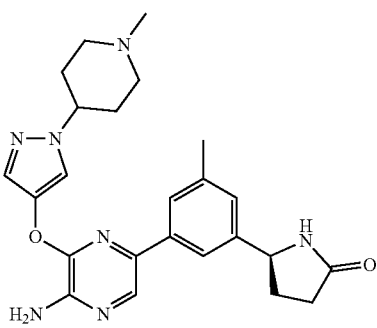 A61A & A61B
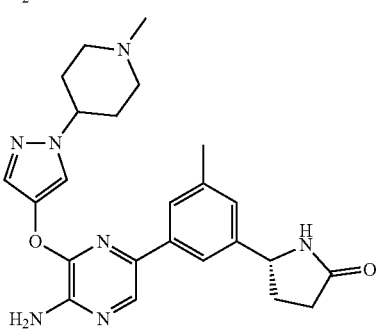
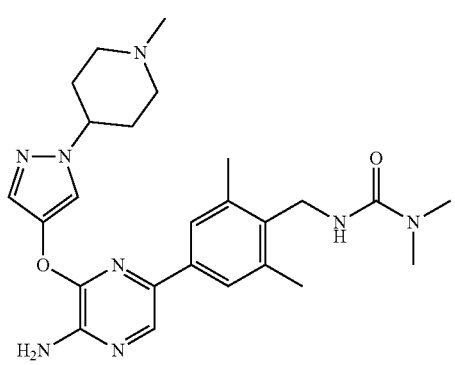 [SMILES: Cc1cc(-c2cnc(N)c(Oc3cnn(C4CCN(C)CC4)c3)n2)cc(C)c1CNC(=O)N(C)C] A62

| Aspect 15: A compound selected from | Aspect 15: A compound selected from |
|---|---|
| 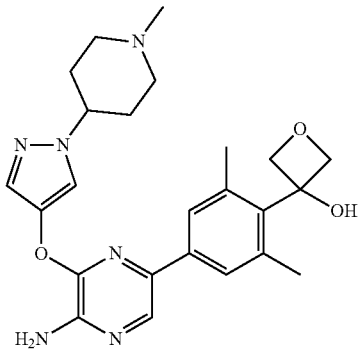 A63 | 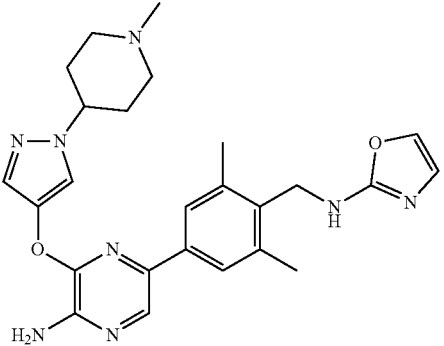 A67 |
| 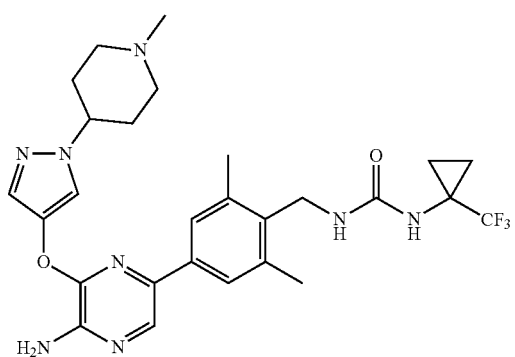 A64 | 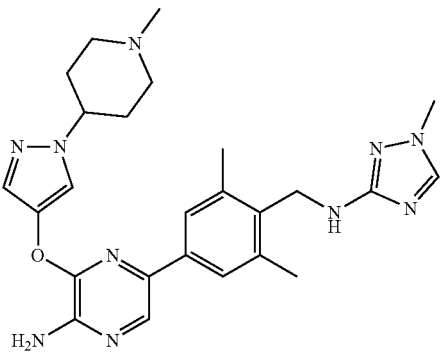 A68 |
| 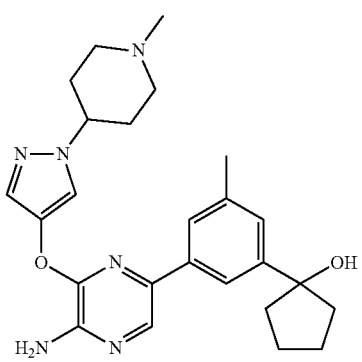 A65 | 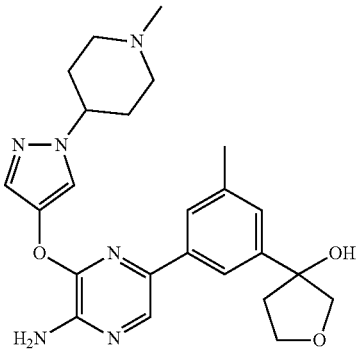 A69 |
| 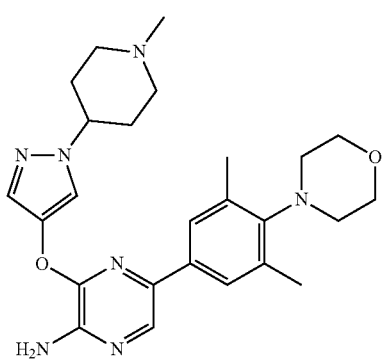 A66 | 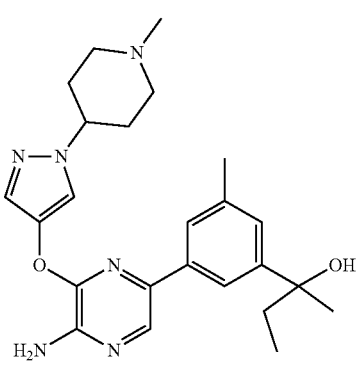 A70 |

| Aspect 15: A compound selected from | Aspect 15: A compound selected from |
|---|---|
| 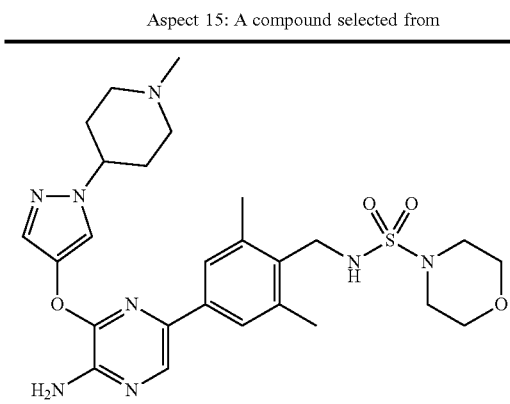 A71 | 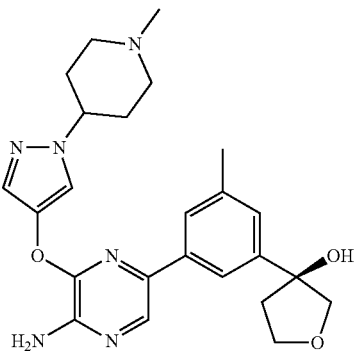 A74A |
| 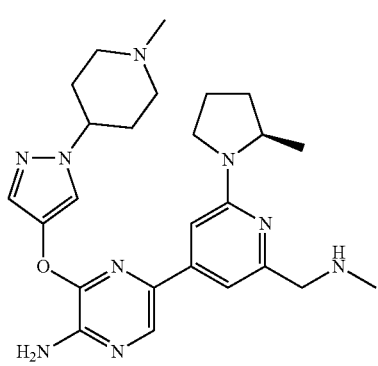 B2 | 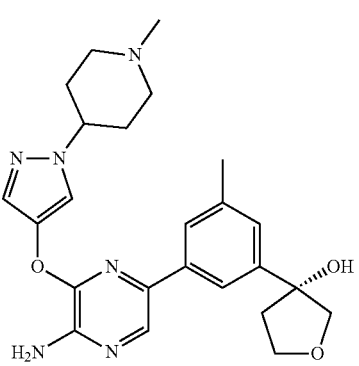 A74B |
| 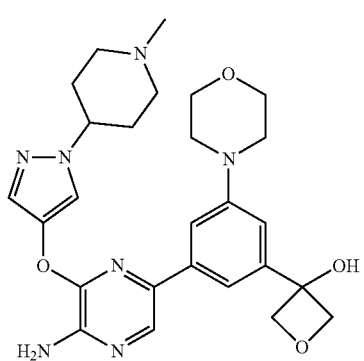 A72 | 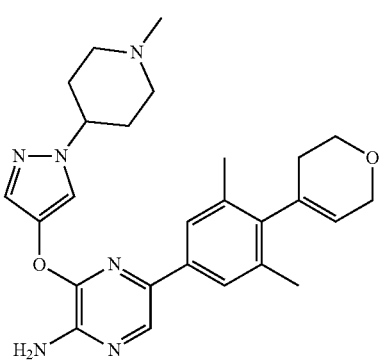 A75 |
| 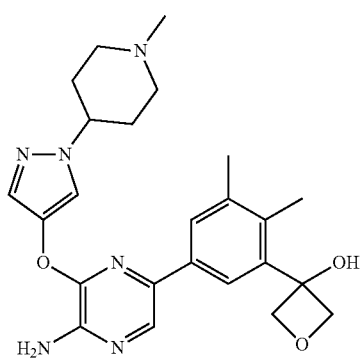 A73 | 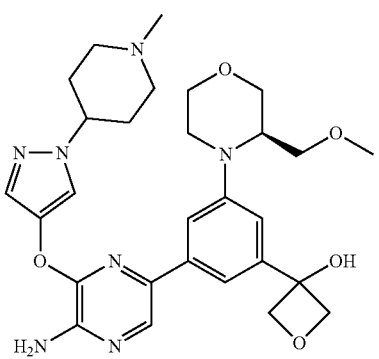 A76 |

| Aspect 15: A compound selected from | Aspect 15: A compound selected from |
|---|---|
| 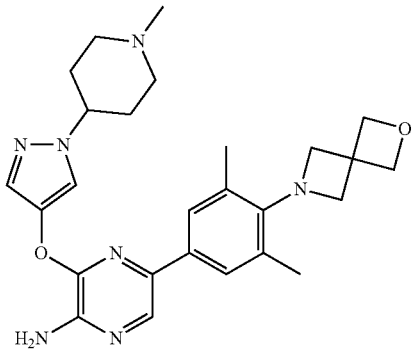 A77 | 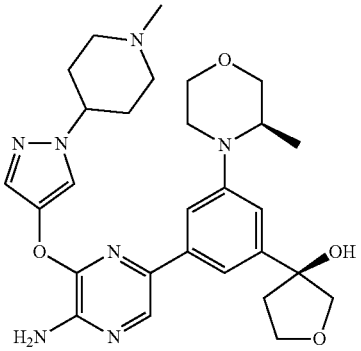 A80A |
| 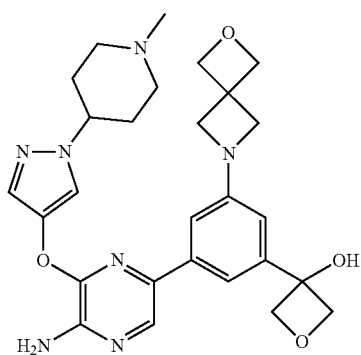 A78 | 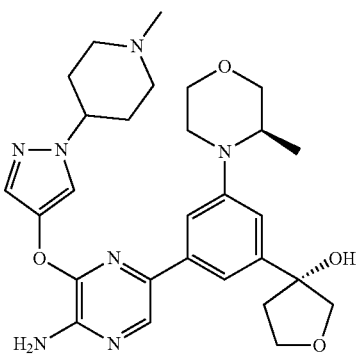 A80B |
| 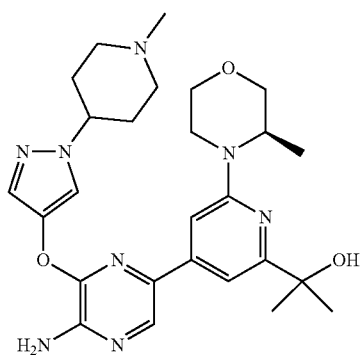 B3 | 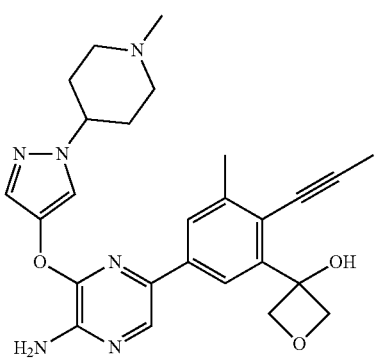 A81 |
| 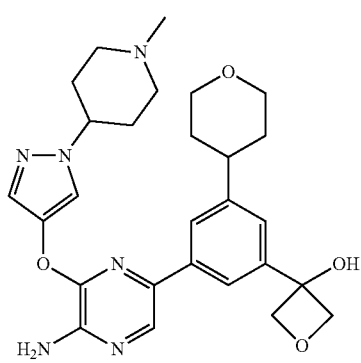 A79 | 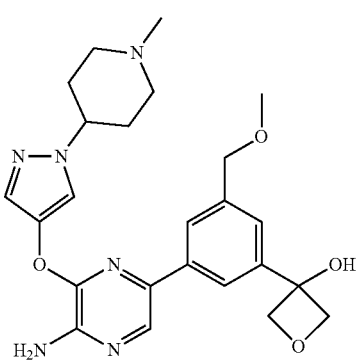 A82 |

| Aspect 15: A compound selected from | Aspect 15: A compound selected from |
|---|---|
| 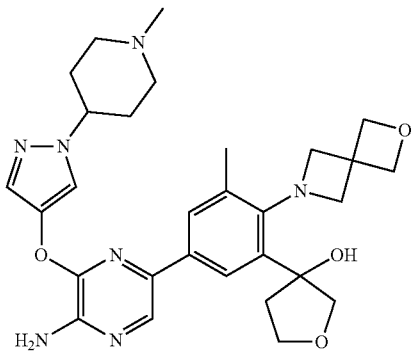 A83 | 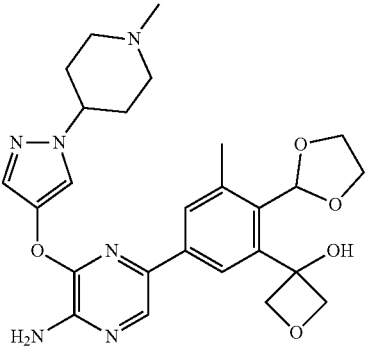 A87 |
| 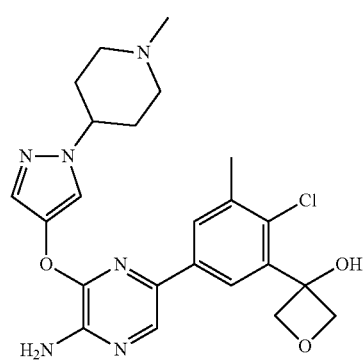 A84 | 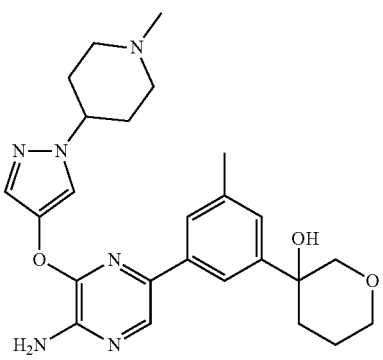 A88 |
| 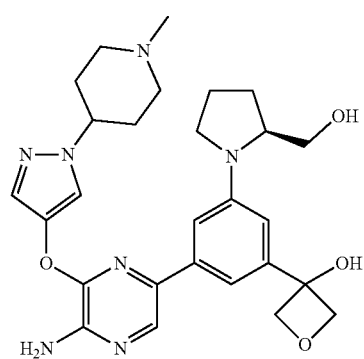 A85 | 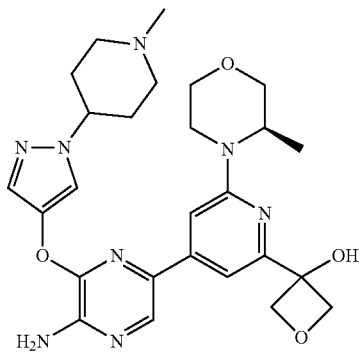 B4 |
| 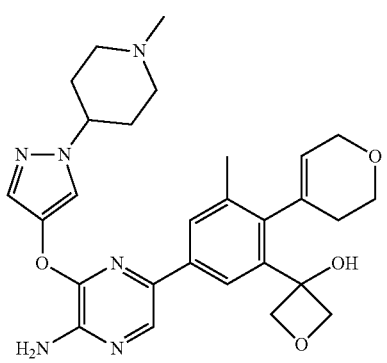 A86 | 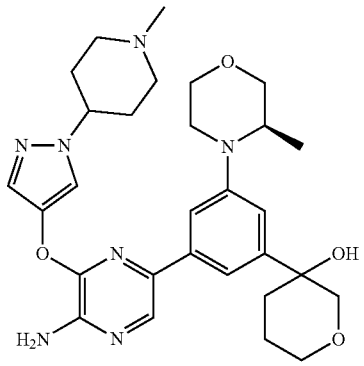 A89 |

51
-continued
| Aspect 15: A compound selected from |
|---|
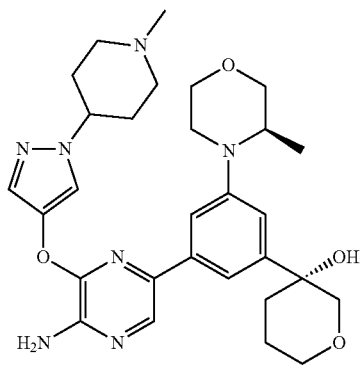 A90A & A90B
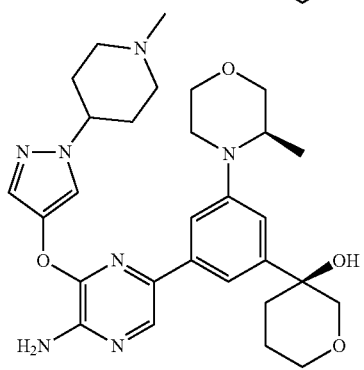 A91
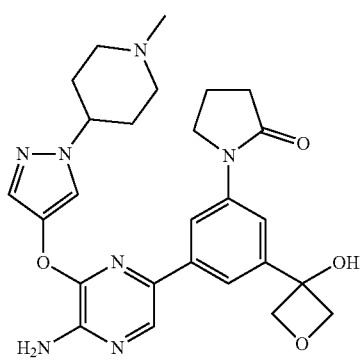 [SMILES: CN1CCC(n2cc(Oc3nc(-c4cc(N5CCCC5=O)cc(C5(O)COC5)c4)cnc3N)cn2)CC1] A92
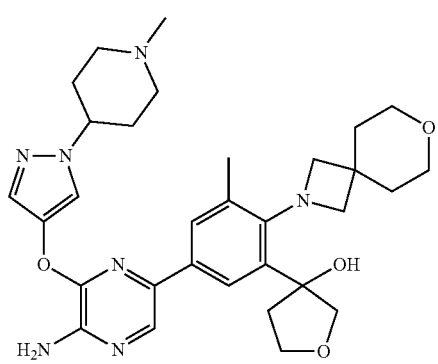 [SMILES: Cc1cc(-c2cnc(N)c(Oc3cnn(C4CCN(C)CC4)c3)n2)cc(C2(O)CCOC2)c1N1CC2(CCOCC2)C1]
52
-continued
| Aspect 15: A compound selected from |
|---|
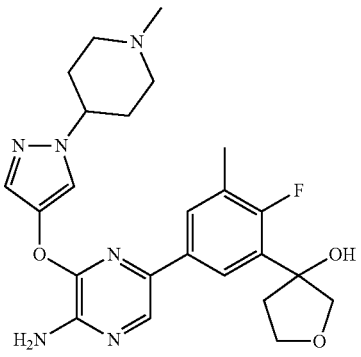 [SMILES: Cc1cc(-c2cnc(N)c(Oc3cnn(C4CCN(C)CC4)c3)n2)cc(C2(O)CCOC2)c1F] A93
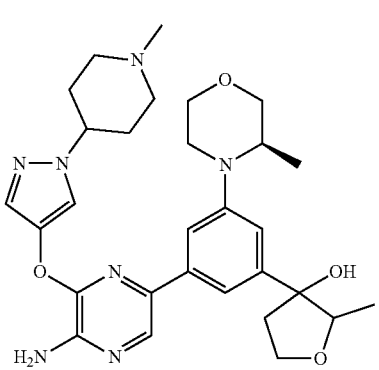 [SMILES: CC1OCCC1(O)c1cc(-c2cnc(N)c(Oc3cnn(C4CCN(C)CC4)c3)n2)cc(N2CCOC[C@H]2C)c1] A94
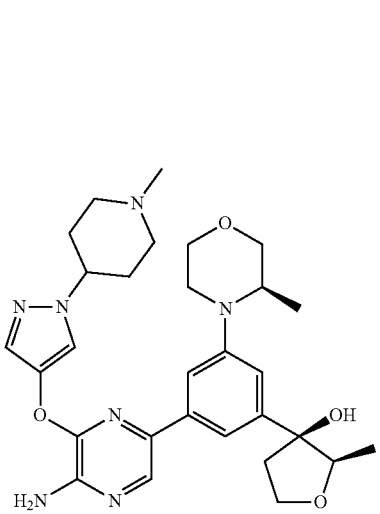 A95A & A95B

| Aspect 15: A compound selected from | Aspect 15: A compound selected from |
|---|---|
| 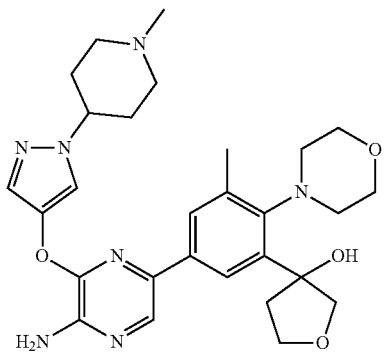 A96 | 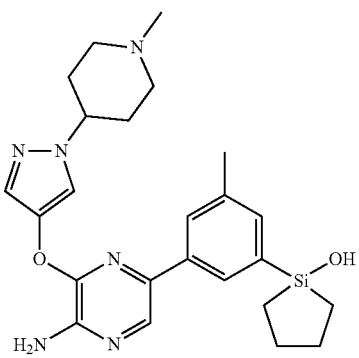 [SMILES: Cc1cc(-c2cnc(N)c(Oc3cnn(C4CCN(C)CC4)c3)n2)cc([Si]2(O)CCCC2)c1] |
| 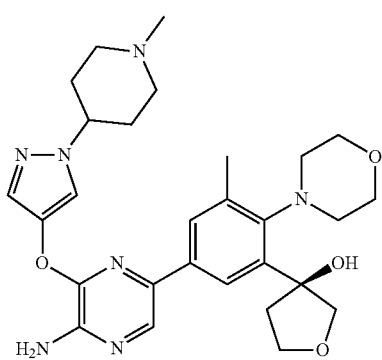 A97A & A97B | 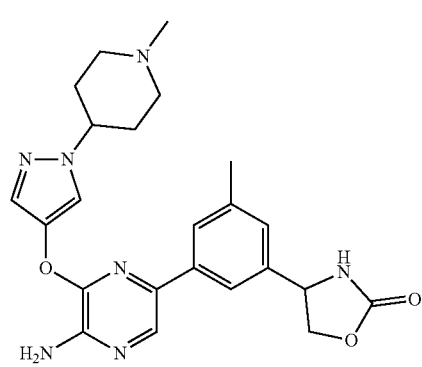 [SMILES: Cc1cc(-c2cnc(N)c(Oc3cnn(C4CCN(C)CC4)c3)n2)cc(C2COC(=O)N2)c1] |
| 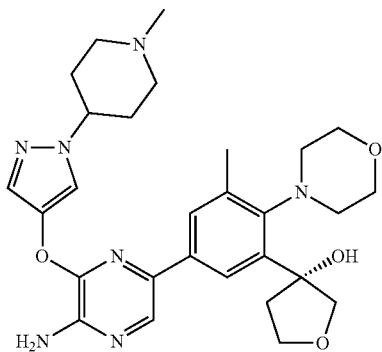 | 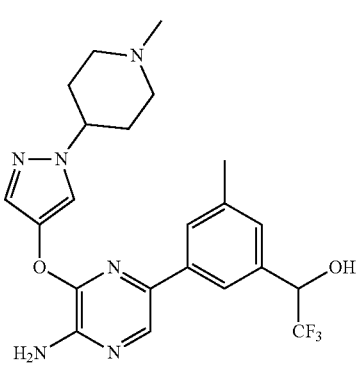 [SMILES: Cc1cc(-c2cnc(N)c(Oc3cnn(C4CCN(C)CC4)c3)n2)cc(C(O)C(F)(F)F)c1] |
| 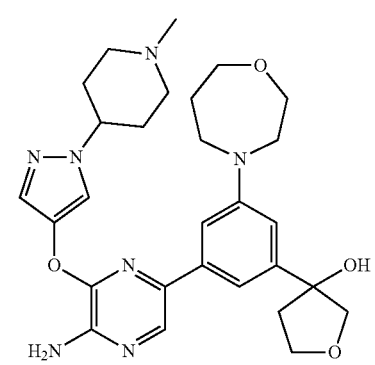 | 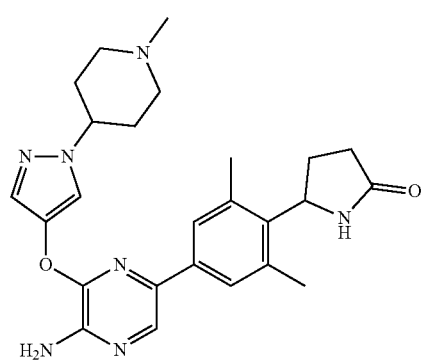 [SMILES: Cc1cc(-c2cnc(N)c(Oc3cnn(C4CCN(C)CC4)c3)n2)cc(C)c1C1CCC(=O)N1] A98 |

| Aspect 15: A compound selected from | Aspect 15: A compound selected from |
|---|---|
| 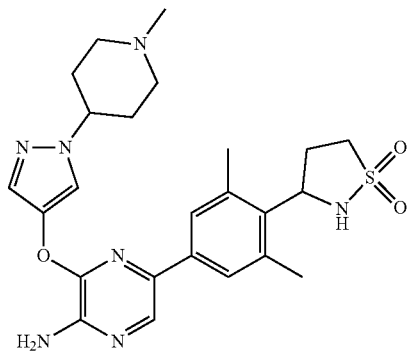 [SMILES: Cc1cc(-c2cnc(N)c(Oc3cnn(C4CCN(C)CC4)c3)n2)cc(C)c1C1CCS(=O)(=O)N1] | 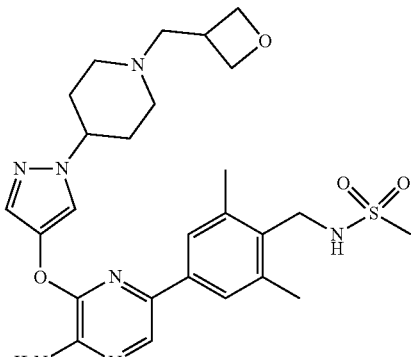 |
| 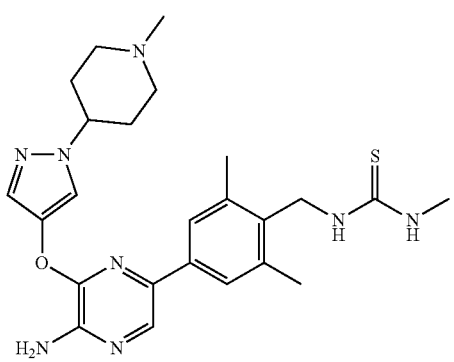 [SMILES: CNC(=S)NCc1c(C)cc(-c2cnc(N)c(Oc3cnn(C4CCN(C)CC4)c3)n2)cc1C] | 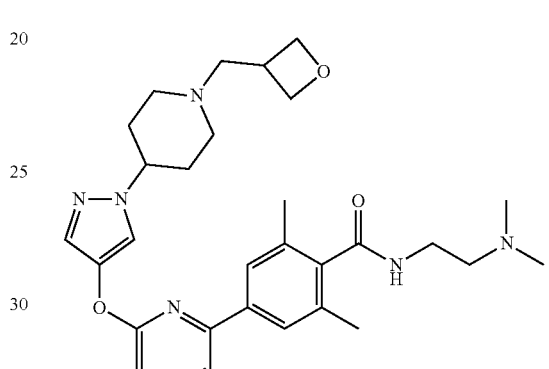 |
| 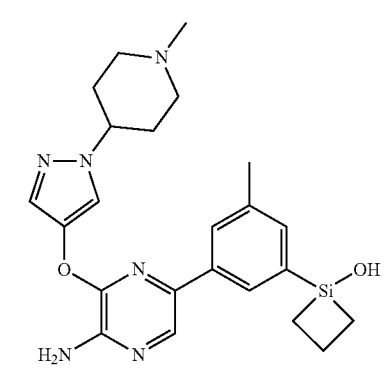 [SMILES: Cc1cc(-c2cnc(N)c(Oc3cnn(C4CCN(C)CC4)c3)n2)cc([Si]2(O)CCC2)c1] | 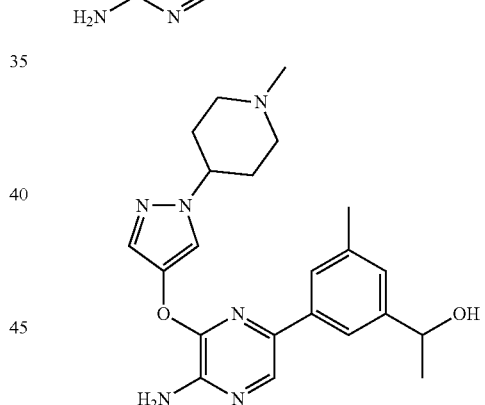 |
| 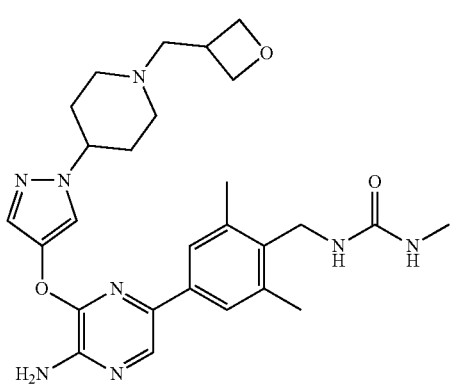 [SMILES: CNC(=O)NCc1c(C)cc(-c2cnc(N)c(Oc3cnn(C4CCN(CC5COC5)CC4)c3)n2)cc1C] | 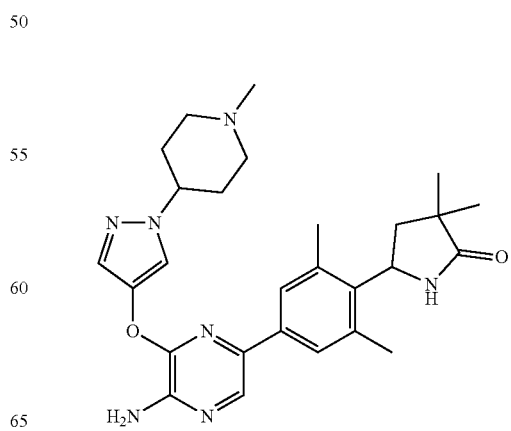 |

| 57 | 58 |
|---|---|
| -continued | -continued |
| Aspect 15: A compound selected from | Aspect 15: A compound selected from |
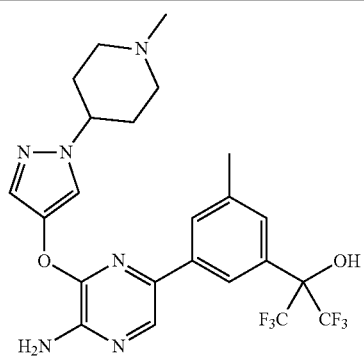 [SMILES: Cc1cc(-c2cnc(N)c(Oc3cnn(C4CCN(C)CC4)c3)n2)cc(C(O)(C(F)(F)F)C(F)(F)F)c1]
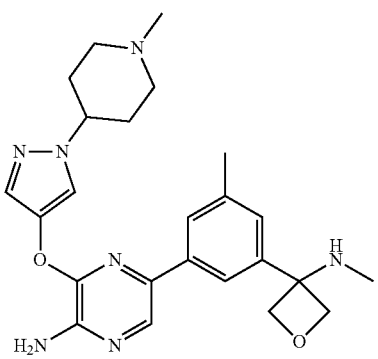 [SMILES: CNC1(c2cc(C)cc(-c3cnc(N)c(Oc4cnn(C5CCN(C)CC5)c4)n3)c2)COC1]
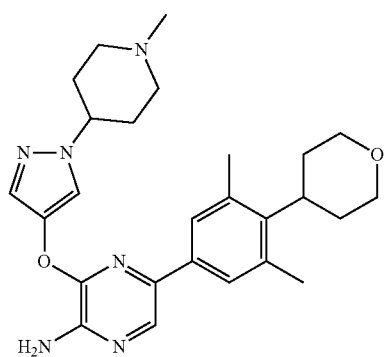
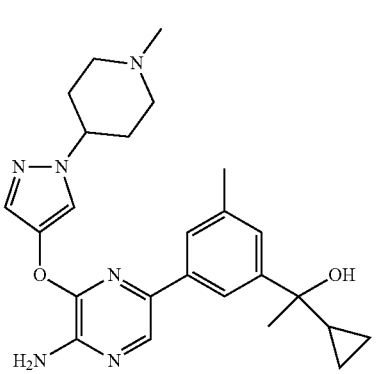 [SMILES: Cc1cc(-c2cnc(N)c(Oc3cnn(C4CCN(C)CC4)c3)n2)cc(C(C)(O)C2CC2)c1]
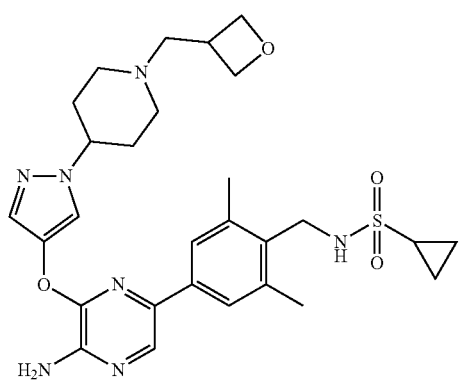
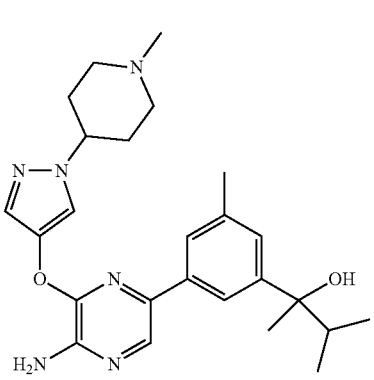 [SMILES: Cc1cc(-c2cnc(N)c(Oc3cnn(C4CCN(C)CC4)c3)n2)cc(C(C)(O)C(C)C)c1]
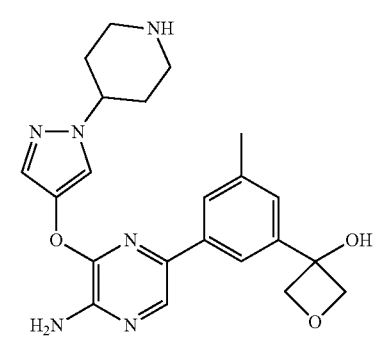
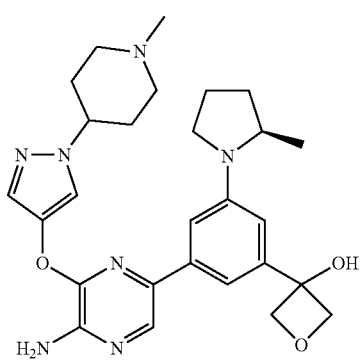 [SMILES: C[C@@H]1CCCN1c1cc(-c2cnc(N)c(Oc3cnn(C4CCN(C)CC4)c3)n2)cc(C2(O)COC2)c1]

| Aspect 15: A compound selected from | Aspect 15: A compound selected from |
|---|---|
| 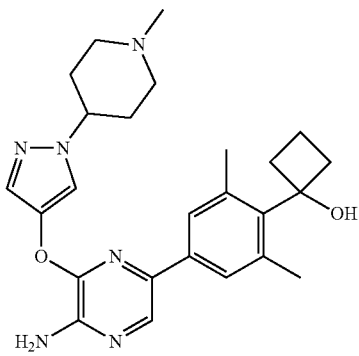 [SMILES: Cc1cc(-c2cnc(N)c(Oc3cnn(C4CCN(C)CC4)c3)n2)cc(C)c1C1(O)CCC1] | 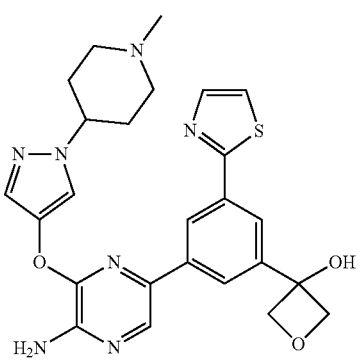 |
| 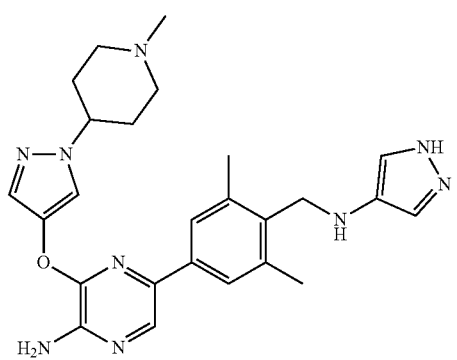 [SMILES: Cc1cc(-c2cnc(N)c(Oc3cnn(C4CCN(C)CC4)c3)n2)cc(C)c1CNc1cn[nH]c1] | 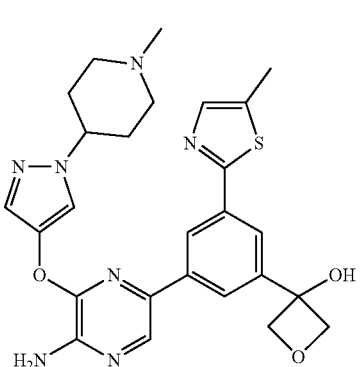 |
| 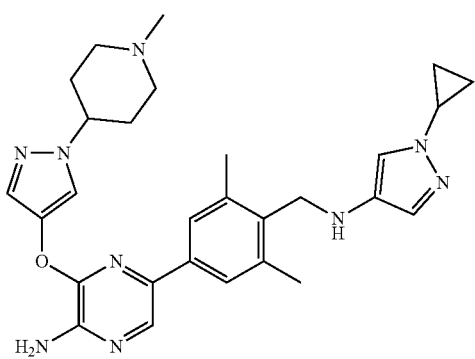 [SMILES: Cc1cc(-c2cnc(N)c(Oc3cnn(C4CCN(C)CC4)c3)n2)cc(C)c1CNc1cnn(C2CC2)c1] | 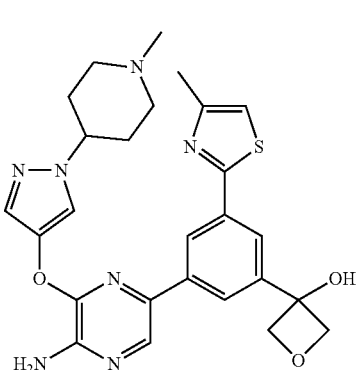 |
| 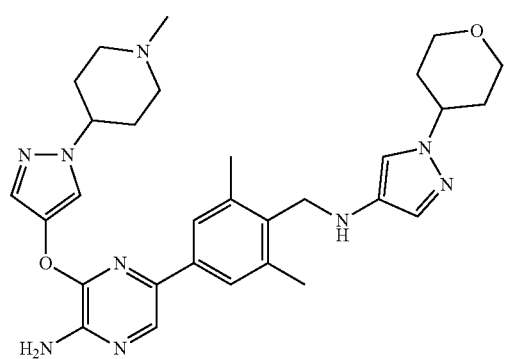 [SMILES: Cc1cc(-c2cnc(N)c(Oc3cnn(C4CCN(C)CC4)c3)n2)cc(C)c1CNc1cnn(C2CCOCC2)c1] | 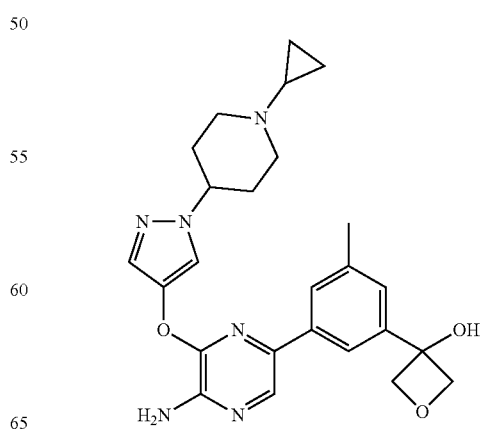 |

| 61 -continued | 62 -continued |
|---|---|
| Aspect 15: A compound selected from | Aspect 15: A compound selected from |
| 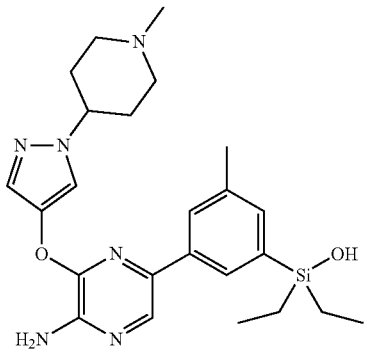 [SMILES: CC[Si](O)(CC)c1cc(C)cc(-c2cnc(N)c(Oc3cnn(C4CCN(C)CC4)c3)n2)c1] | 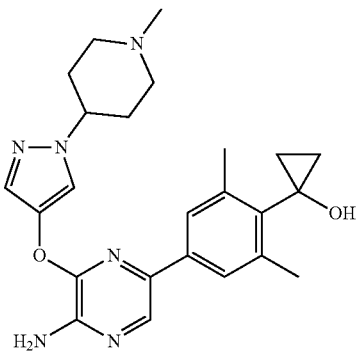 |
| 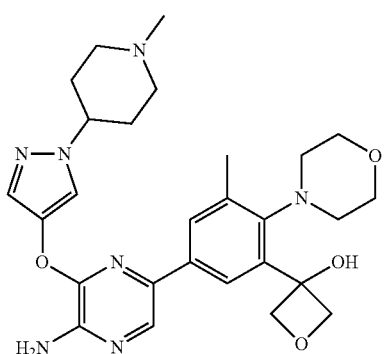 | 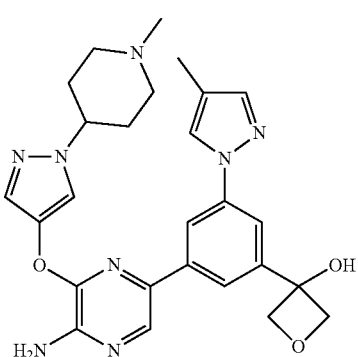 |
| 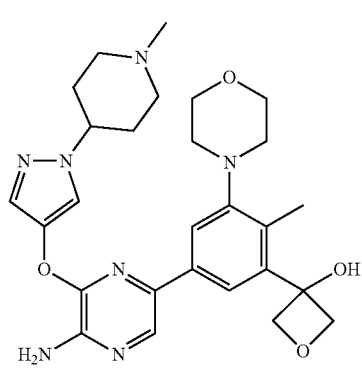 [SMILES: Cc1c(N2CCOCC2)cc(-c2cnc(N)c(Oc3cnn(C4CCN(C)CC4)c3)n2)cc1C1(O)COC1] | 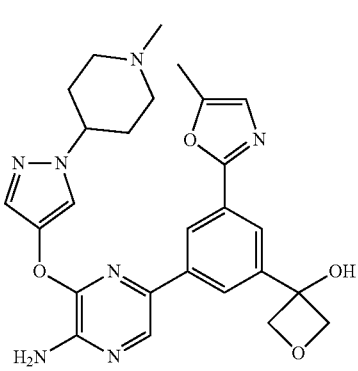 |
| 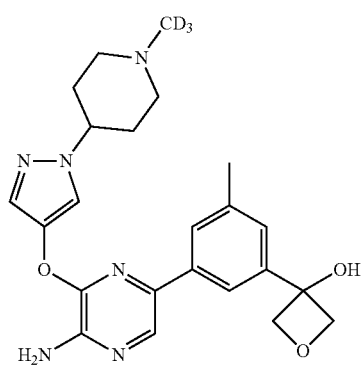 [SMILES: [2H]C([2H])([2H])N1CCC(n2cc(Oc3nc(-c4cc(C)cc(C5(O)COC5)c4)cnc3N)cn2)CC1] | 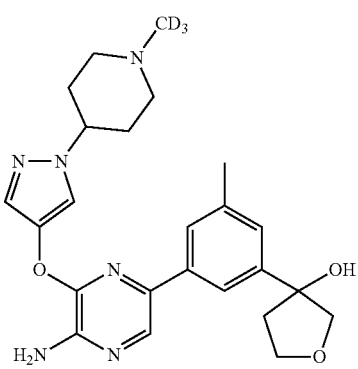 [SMILES: [2H]C([2H])([2H])N1CCC(n2cc(Oc3nc(-c4cc(C)cc(C5(O)CCOC5)c4)cnc3N)cn2)CC1] |

| Aspect 15: A compound selected from | Aspect 15: A compound selected from |
|---|---|
| 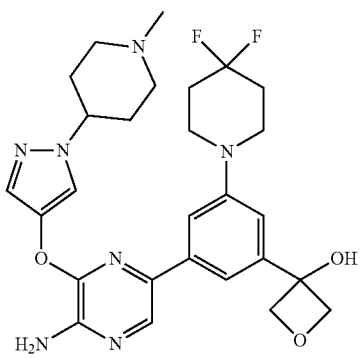 [SMILES: CN1CCC(n2cc(Oc3nc(-c4cc(N5CCC(F)(F)CC5)cc(C5(O)COC5)c4)cnc3N)cn2)CC1] | 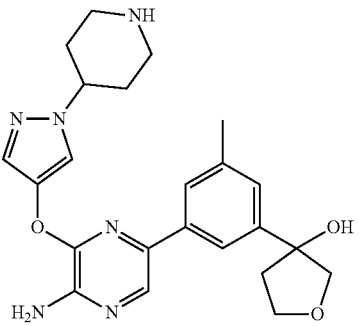 |
| 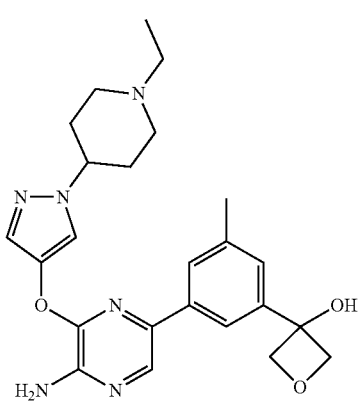 [SMILES: CCN1CCC(n2cc(Oc3nc(-c4cc(C)cc(C5(O)COC5)c4)cnc3N)cn2)CC1] | 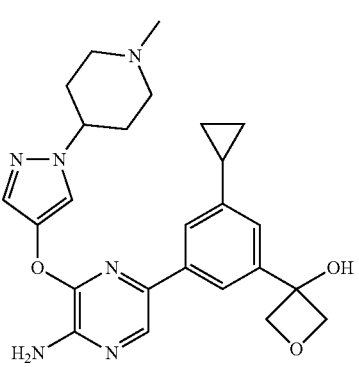 |
| 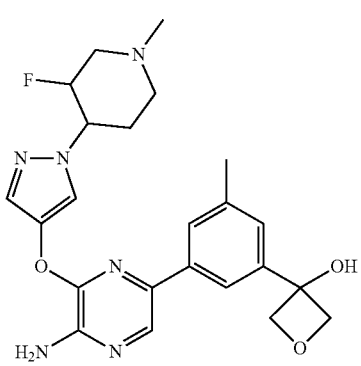 [SMILES: Cc1cc(-c2cnc(N)c(Oc3cnn(C4CCN(C)CC4F)c3)n2)cc(C2(O)COC2)c1] | 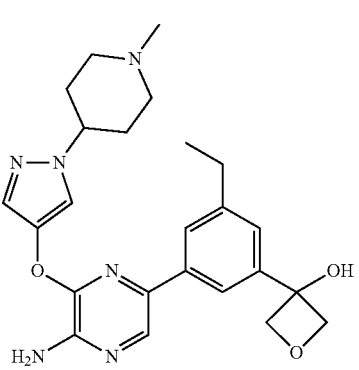 |
| 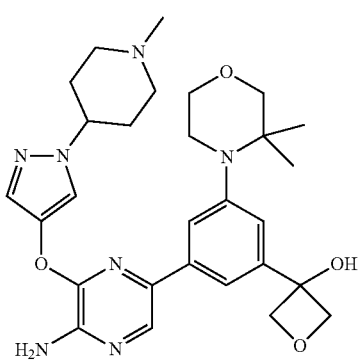 [SMILES: CN1CCC(n2cc(Oc3nc(-c4cc(N5CCOCC5(C)C)cc(C5(O)COC5)c4)cnc3N)cn2)CC1] | 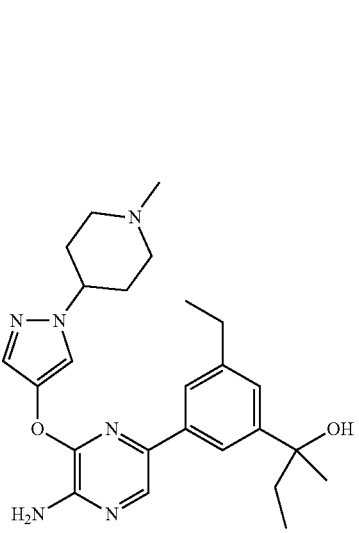 [SMILES: CCc1cc(-c2cnc(N)c(Oc3cnn(C4CCN(C)CC4)c3)n2)cc(C(C)(O)CC)c1] |

| Aspect 15: A compound selected from | Aspect 15: A compound selected from |
|---|---|
| 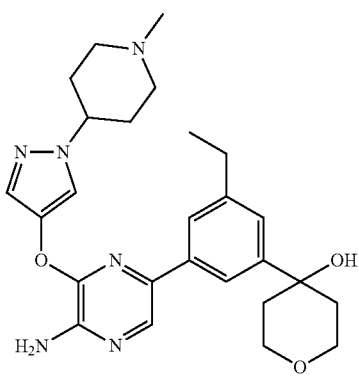 [SMILES: CCc1cc(-c2cnc(N)c(Oc3cnn(C4CCN(C)CC4)c3)n2)cc(C2(O)CCOCC2)c1] | 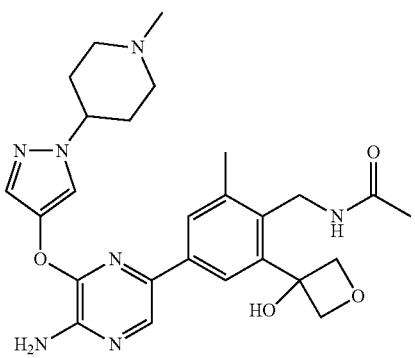 |
| 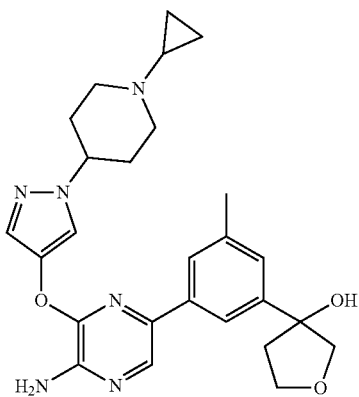 [SMILES: Cc1cc(-c2cnc(N)c(Oc3cnn(C4CCN(C5CC5)CC4)c3)n2)cc(C2(O)CCOC2)c1] | 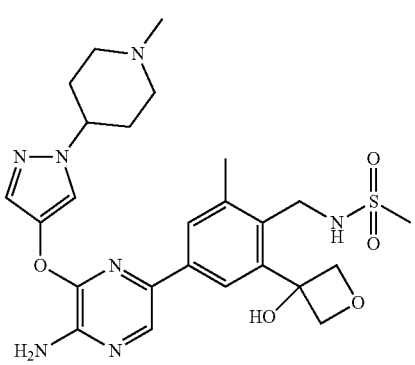 |
| 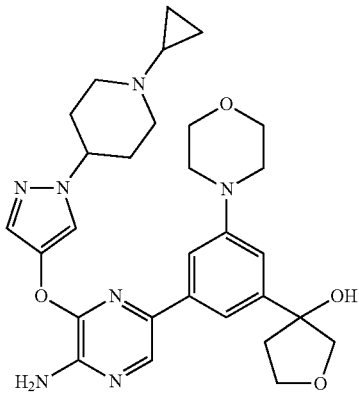 [SMILES: Nc1ncc(-c2cc(N3CCOCC3)cc(C3(O)CCOC3)c2)nc1Oc1cnn(C2CCN(C3CC3)CC2)c1] | 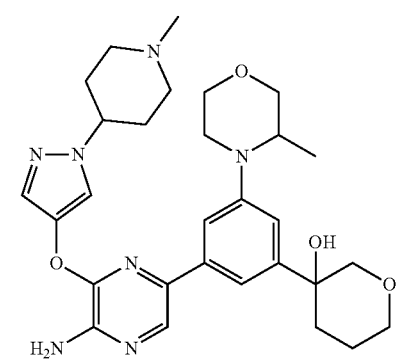 |
| 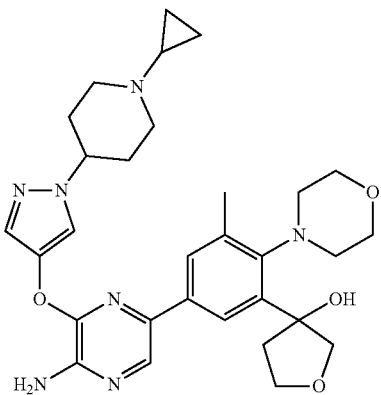 [SMILES: Cc1cc(-c2cnc(N)c(Oc3cnn(C4CCN(C5CC5)CC4)c3)n2)cc(C2(O)CCOC2)c1N1CCOCC1] | 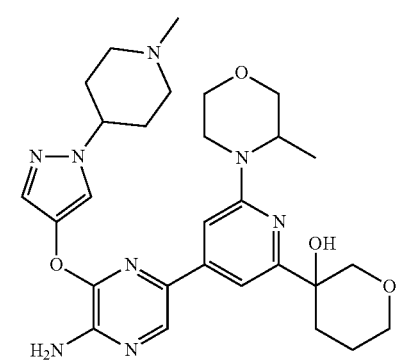 [SMILES: CC1COCCN1c1cc(-c2cnc(N)c(Oc3cnn(C4CCN(C)CC4)c3)n2)cc(C2(O)CCCOC2)c1] |

Aspect 15: A compound selected from

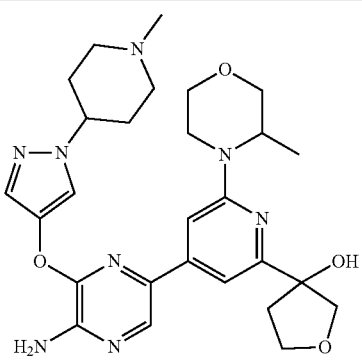 [SMILES: CC1COCCN1c1cc(-c2cnc(N)c(Oc3cnn(C4CCN(C)CC4)c3)n2)cc(C2(O)CCOC2)n1]

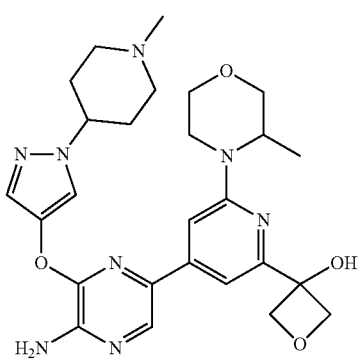 [SMILES: CC1COCCN1c1cc(-c2cnc(N)c(Oc3cnn(C4CCN(C)CC4)c3)n2)cc(C2(O)COC2)n1]

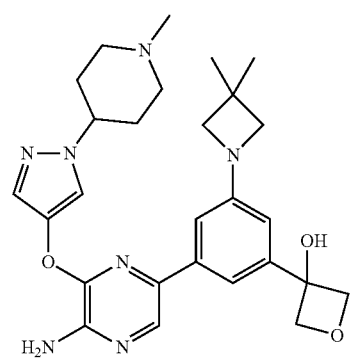 [SMILES: CN1CCC(n2cc(Oc3nc(-c4cc(N5CC(C)(C)C5)cc(C5(O)COC5)c4)cnc3N)cn2)CC1]

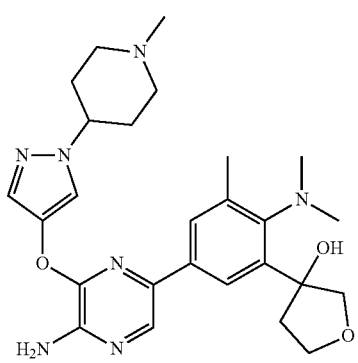 [SMILES: Cc1cc(-c2cnc(N)c(Oc3cnn(C4CCN(C)CC4)c3)n2)cc(C2(O)CCOC2)c1N(C)C]

Aspect 15: A compound selected from

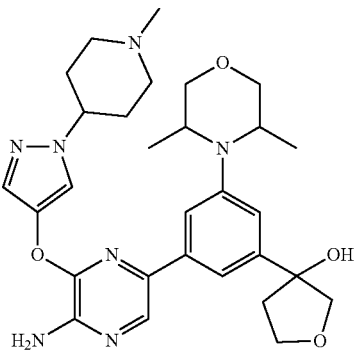 [SMILES: CC1COCC(C)N1c1cc(-c2cnc(N)c(Oc3cnn(C4CCN(C)CC4)c3)n2)cc(C2(O)CCOC2)c1]

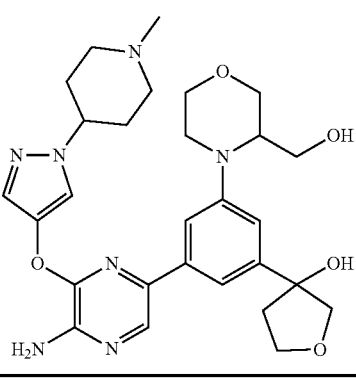

or a pharmaceutically acceptable salt thereof, or a stereoisomer thereof.

In the second aspect, disclosed herein is a pharmaceutical composition comprising the compound disclosed herein, or a pharmaceutically acceptable salt thereof, and at least one pharmaceutically acceptable carrier or excipient.

In the third aspect, disclosed herein is a method of inhibiting HPK1 activity, which comprises administering to an individual the compound disclosed herein, or a pharmaceutically acceptable salt thereof, including the compound of formula (I) or the specific compounds exemplified herein.

In the fourth aspect, disclosed herein is a method of treating a disease or disorder in a patient comprising administering to the patient a therapeutically effective amount of the compound disclosed herein, or a pharmaceutically acceptable salt thereof as an HPK1 kinase inhibitor, wherein the compound disclosed herein includes the compound of formula (I) or the specific compounds exemplified herein. In some embodiments, the disease or disorder is is associated with inhibition of HPK1 interaction. Preferably, the disease or disorder is cancer.

DETAILED DESCRIPTION OF THE INVENTION

The following terms have the indicated meaning throughout the specification:

Unless specifically defined elsewhere in this document, all other technical and scientific terms used herein have the meaning commonly understood by one of ordinary skill in the art to which this invention belongs.

The following terms have the indicated meanings throughout the specification:

As used herein, including the appended claims, the singular forms of words such as "a". "an", and "the", include their corresponding plural references unless the context clearly indicates otherwise.

The term "or" is used to mean, and is used interchangeably with, the term "and/or" unless the context clearly dictates otherwise.

The term "alkyl" refers to a hydrocarbon group selected from linear and branched, saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "propyl" refers to 1-propyl or n-propyl ("n-Pr"), 2-propyl or isopropyl ("i-Pr").

The term "butyl" refers to 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu").

The term "pentyl" refers to 1-pentyl, 2-pentyl, 3-pentyl, 2-methyl-2-butyl, 3-methyl-2-butyl, 3-methyl-1-butyl, 2-methyl-1-butyl.

The term "hexyl" refers to 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

The term "halogen" refers to fluoro (F), chloro (Cl), bromo (Br) and iodo (I).

The term "haloalkyl" refers to an alkyl group in which one or more hydrogen is/are replaced by one or more halogen atoms such as fluoro, chloro, bromo, and iodo. Examples of the haloalkyl include halo$C_{1-8}$alkyl, halo$C_{1-6}$alkyl or halo $C_{1-4}$alkyl, but not limited to —$CF_3$, —$CH_2Cl$, —$CH_2CF_3$, —$CHCl_2$, —$CF_3$, and the like.

The term "alkenyl" refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C=C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "cycloalkyl" refers to a hydrocarbon group selected from saturated cyclic hydrocarbon groups, comprising monocyclic and polycyclic (e.g., bicyclic and tricyclic) groups.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, Examples of the saturated monocyclic cycloalkyl group. e.g., $C_{3-8}$cycloalkyl, include, but not limited to cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6]ring systems, or as a bridged bicyclic ring selected from bicyclo[2,2,1] heptane, bicyclo[2,2,2]octane, and bicyclo[3,2,2]nonane. Further Examples of the bicyclic cycloalkyl groups include those arranged as a bicyclic ring selected from [5,6] and [6,6] ring systems.

The term "fused cycloalkyl" refers to a bicyclic cycloalkyl group as defined herein which is saturated and is formed by two or more rings sharing two adjacent atoms.

The term "bridged cycloalkyl" refers to a cyclic structure which contains carbon atoms and is formed by two rings sharing two atoms which are not adjacent to each other. The term "7 to 12 membered bridged cycloalkyl" refers to a cyclic structure which contains 7 to 12 carbon atoms and is formed by two rings sharing two atoms which are not adjacent to each other.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, 1-cyclopent-1-enyl, 1-cyclopent-2-enyl, 1-cyclopent-3-enyl, 1-cyclohex-1-enyl, 1-cyclohex-2-enyl, 1-cyclohex-3-enyl, cyclohexadienyl, preferably cyclohexenyl.

The term "fused cycloalkenyl" refers to a bicyclic cycloalkyl group as defined herein which contain at least one double bond and is formed by two or more rings sharing two adjacent atoms.

The term "cycloalkynyl" refers to non-aromatic cycloalkyl groups of from 5 to 10 carbon atoms having single or multiple rings and having at least one triple bond.

The term "fused cycloalkynyl" refers to a bicyclic cycloalkyl group as defined herein which contains at least one triple bond and is formed by two or more rings sharing two adjacent atoms.

Examples of fused cycloalkyl, fused cycloalkenyl, or fused cycloalkynyl include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$cycloalkenyl, 2,3-dihydro-1H-indenyl, 1H-indenyl, 1, 2, 3,4-tetralyl, 1,4-dihydronaphthyl, etc. Preferred embodiments are 8 to 9 membered fused ring, which refer to cyclic structures containing 8 to 9 ring atoms within the above examples.

The term "aryl" used alone or in combination with other terms refers to a group selected from:
  a) 5- and 6-membered carbocyclic aromatic rings, e.g., phenyl;
  b) bicyclic ring systems such as 7 to 12 membered bicyclic ring systems, wherein at least one ring is carbocyclic and aromatic, e.g., naphthyl and indanyl; and, c) tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" refers to a bicyclic aryl ring as defined herein. The typical bicyclic fused aryl is naphthalene.

The term "heteroaryl" refers to a group selected from:
a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
b) 7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

Specifically, the term "bicyclic fused heteroaryl" refers to a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

Representative examples of bicyclic fused heteroaryl include, but not limited to, the following groups benzisoxazolyl, benzodiazolyl, benzofuranyl, benzofurazanyl, benzofuryl, benzoimidazolyl, benzoisothiazolyl, benzothiadiazolyl, benzothiazolyl, benzothienyl, benzothiophenyl, benzotriazolyl, benzoxadiazolyl, benzoxazolyl, furopyridinyl, furopyrrolyl, imidazopyridinyl, imidazopyridyl, imidazothiazolyl, indazolyl, indolizinyl, indolyl, isobenzofuryl, isoindolyl, isoquinolinyl (or isoquinolyl), naphthyridinyl, phthalazinyl, pteridinyl, purinyl, pyrazinopyridazinyl, pyrazolopyridinyl, pyrazolopyrimidinyl, pyrazolopyridyl, pyrazolotriazinyl, pyridazolopyridyl, pyrrolopyridinyl, quinazolinyl, quinolinyl (or quinolyl), quinoxalinvl, thiazolopyridyl, thienopyrazinyl, thienopyrazolyl, thienopyridyl, thienopyrrolyl, thienothienyl, or triazolopyridyl.

The term a "benzo fused heteroaryl" is a bicyclic fused heteroaryl in which a 5- to 7-membered (preferably, 5- or 6-membered) monocyclic heteroaryl ring as defined herein fused to a benzene ring.

The terms "aromatic heterocyclic ring" and "heteroaryl" are used interchangeably throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is an 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), and indazolyl (such as 1H-indazol-5-yl).

"Heterocyclyl", "heterocycle" or "heterocyclic" are interchangeable and refer to a non-aromatic heterocyclyl group comprising one or more heteroatoms selected from nitrogen, oxygen, silicon or optionally oxidized sulfur as ring members, with the remaining ring members being carbon, including monocyclic, fused ring, i.e., containing monocyclic heterocyclyl, and fused heterocyclic groups, bridged heterocyclic groups or spiro heterocyclic groups.

The term "optionally oxidized sulfur" used herein refers to S, SO or $SO_2$.

The term "monocyclic heterocyclyl" refers to monocyclic groups in which at least one ring member (e.g., 1-3 heteroatoms, 1 or 2 heteroatom(s)) is a heteroatom selected from nitrogen, oxygen, silicon or optionally oxidized sulfur. A heterocycle may be saturated or partially saturated (i.e., not forming a completely conjugated pi-electron system).

Exemplary monocyclic 4 to 9-membered heterocyclyl groups include, but not limited to, pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, oxazolidinyl, or oxazolidin-4-yl.

The term "fused heterocyclyl" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but the fused heterocyclic group does not have a completely conjugated pi-electron system. Preferably, a fused heterocyclyl is 6 to 14-membered, and more preferably 7 to 12-membered, or 7- to 10-membered. According to the number of membered rings, a fused heterocyclyl is divided into bicyclic, tricyclic, tetracyclic, or polycyclic fused heterocyclyl. The group can be attached to the remainder of the molecule through either ring.

Specifically, the term "bicyclic fused heterocyclyl" refers to a 7 to 12-membered, preferably 7- to 10-membered, more preferably 9- or 10-membered fused heterocyclyl as defined herein comprising two fused rings and comprising 1 to 4 heteroatoms selected from nitrogen, oxygen or optionally oxidized sulfur as ring members. Typically, a bicyclic fused heterocyclyl is 5-membered/5-membered, 5-membered/6-membered, 6-membered/6-membered, or 6-membered/7-membered bicyclic fused heterocyclyl. Representative examples of (bicyclic) fused heterocycles include, but not limited to, the following groups octahydrocyclopenta[c]pyrrole, octahydropyrrolo[3,4-c]pyrrolyl, octahydroisoindolyl, isoindolinyl, octahydro-benzo[b][1,4]dioxin, indolinyl, isoindolinyl, benzopyranyl, dihydrothiazolopyrimidinyl, tetrahydroquinolyl, tetrahydroisoquinolyl (or tetrahydroisoquinolinyl), dihydrobenzofuranyl, dihydrobenzoxazinyl, dihydrobenzoimidazolyl, tetrahydrobenzothienyl, tetrahydrobenzofuranyl, benzodioxolyl, benzodioxonyl, chromanyl, chromenyl, octahydrochromenyl, dihydrobenzodioxynyl, dihydrobenzoxezinyl, dihydrobenzodioxepinyl, dihydrothienodioxynyl, dihydrobenzooxazepinyl, tetrahydrobenzooxazepinyl, dihydrobenzoazepinyl, tetrahydrobenzoazepinyl, isochromanyl, chromanyl, or tetrahydropyrazolopyrimidinyl (e.g., 4,5,6,7-tetrahydropyrazolo[1,5-a]pyrimidin-3-yl).

The term a "benzo fused heterocyclyl" is a bicyclic fused heterocyclyl in which a monocyclic 4 to 9-membered heterocyclyl as defined herein (preferably 5- or 6-membered) fused to a benzene ring.

The term "bridged heterocyclyl" refers to a 5- to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. Specifically, the bridge including the two bridgeheads contains 1-6 atoms selected from carbon, oxygen, nitrogen and sulfur with no two heteroatoms (oxygen, nitrogen and sulfur) being connected to each other. One or more rings of a bridged heterocyclyl group may contain one or more double bonds, but none of the rings has a completely conjugated pi-electron system. Preferably, a bridged heterocyclyl is 6- to 14-membered, or 7- to 12-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2] octyl and 2-azabicyclo[3.3.2]decyl.

"Spiro heterocyclyl" refers to a 5- to 20-membered polycyclic heterocyclyl with rings connected through one common carbon atom (called a spiro atom), wherein said rings have one or more heteroatoms selected from the group consisting of N, O, S. SO or $SO_2$ heteroatoms as ring atoms, with the remaining ring atoms being C. Preferably a spiro heterocyclyl is 6- to 14-membered, and more preferably 7- to 10-membered. According to the number of common spiro atoms, a spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Representative examples of spiro heterocyclyls include, but are not limited to the following groups: 1,7-dioxaspiro[4.5]decyl, 2-oxa-7-aza-spiro [4.4]nonyl, 7-oxa spiro[3.5]nonyl, 5-oxa-spiro[2.4]heptyl, and 2-oxa-6-azaspiro[3.3]heptyl.

"N-linked heterocyclyl" disclosed herein refers to a heterocyclyl group which is connected to the other part of the molecule by a bond from a nitrogen atom of the heterocyclyl ring. "N-linked heterocyclyl comprising 0, 1 or 2 additional heteroatoms selected from nitrogen, oxygen or optionally oxidized sulfur as ring member(s)" refers to a heterocyclyl group which is connected to the other part of the molecule by a bond from a nitrogen atom of the heterocyclyl ring, and which comprises 0, 1 or 2 additional heteroatoms in addition to the nitrogen atom linked to the other part of the molecule.

"C-linked heterocyclyl" disclosed herein refers to a heterocyclyl group which is connected to the other part of the molecule by a bond from a carbon atom of the heterocyclyl ring. "Si-linked heterocyclyl" disclosed herein refers to a heterocyclyl group which is connected to the other part of the molecule by a bond from a silicon atom of the heterocyclyl ring.

The term "at least one substituent" disclosed herein includes, for example, from 1 to 4, such as from 1 to 3, further as 1 or 2, substituents, provided that the theory of valence is met. For example, "at least one substituent $R^d$"

disclosed herein includes from 1 to 4, such as from 1 to 3, further as 1 or 2, substituents selected from the list of $R^d$ as disclosed herein.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, the reference to one isomer applies to any of the possible isomers. Whenever the isomeric composition is unspecified, all possible isomers are included.

Compounds disclosed herein also comprise deuterated compounds. The term "deuterated compound" refers to a compound wherein one or more carbon-bound hydrogen(s) are replaced by one or more deuterium(s). Similarly, the term "deuterated" is be used herein to modify a chemical structure or an organic group or radical, wherein one or more carbon-bound hydrogen(s) are replaced by one or more deuterium(s), e.g., "deuterated-alkyl", "deuterated-cycloalkyl", "deuterated-heterocycloalkyl", "deuterated-aryl", "deuterated-morpholinyl", and the like. For example, the term "deuterated-alkyl" defined above refers to an alkyl group as defined herein, wherein at least one hydrogen atom bound to carbon is replaced by a deuterium. In a deuterated alkyl group, at least one carbon atom is bound to a deuterium; and it is possible for a carbon atom to be bound to more than one deuterium; it is also possible that more than one carbon atom in the alkyl group is bound to a deuterium.

The term "substantially pure" as used herein means that the target stereoisomer contains no more than 35%, such as no more than 30%, further such as no more than 25%, even further such 3' as no more than 20%, by weight of any other stereoisomer(s). In some embodiments, the term "substantially pure" means that the target stereoisomer contains no more than 10%, for example, no more than 5%, such as no more than 1%/c, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example; reverse-phase and normal phase; size exclusion; ion exchange, high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel. E. and Wilen, *S Stereochemistry of Organic Compounds*. New York: John Wiley & Sons. Inc., 1994: Lochmuller. C. H., et al. "Chromatographic resolution of enantiomers: Selective review." *J. Chromatogr.,* 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

The configuration of diastereomeric or enantiomeric isomers could be assigned by technologies including but not limited to: 1D- or 2D-NMR spectroscopy of compounds or their derivatives (e.g. Mosher ester); optical rotatory dispersion; circular dichroism spectroscopy; X-ray diffractometry; in silico calculation (e.g. QM or MMGBSA).

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined herein, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition". Throughout this specification and the claims which follow, unless the context requires otherwise, the term "comprise", and variations such as "comprises" and "comprising" are intended to specify, the presence of the features thereafter, but do not exclude the presence or addition of one or more other features. When used herein the term "comprising" can be substituted with the term "containing", "including" or sometimes "having".

Throughout this specification and the claims which follow, the term "Cn-m" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from the solvent's boiling temperature. A given reaction can be carried out in one solvent or mixture of solvents.

The selection of appropriate protecting group, can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Chiral analytic HPLC was used for the retention time analysis of different chiral examples, the conditions were divided into the methods as below according to the column, mobile phase, solvent ratio used.

Scheme I

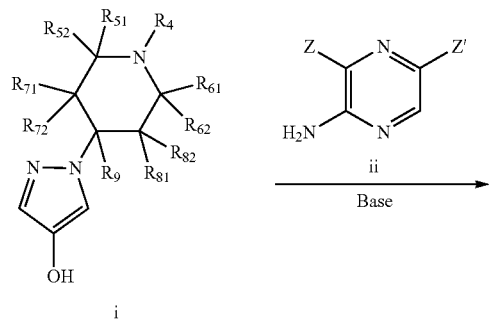

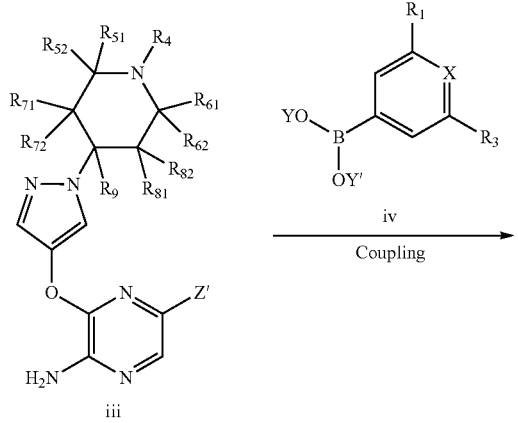

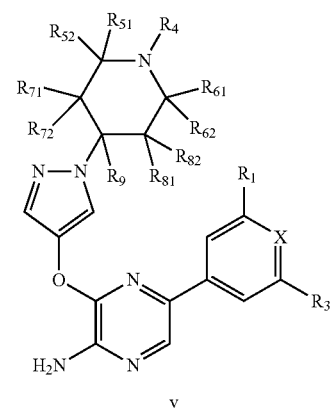

Y,Y' = H or alkyl (Y and Y' can be linked through a bond)
Z, Z' = Cl or Br or I

For example, compounds of Formula (I) can be formed as shown in Scheme I. Compound (i) can be deprotonated and react with 2-amino-3,5-dihalo pyrazine (ii) to give compound (iii); compound (iii) can be coupled with compound (iv) using transition metal catalyzed reaction to give compound (v) [i.e., Formula (I)].

Scheme II

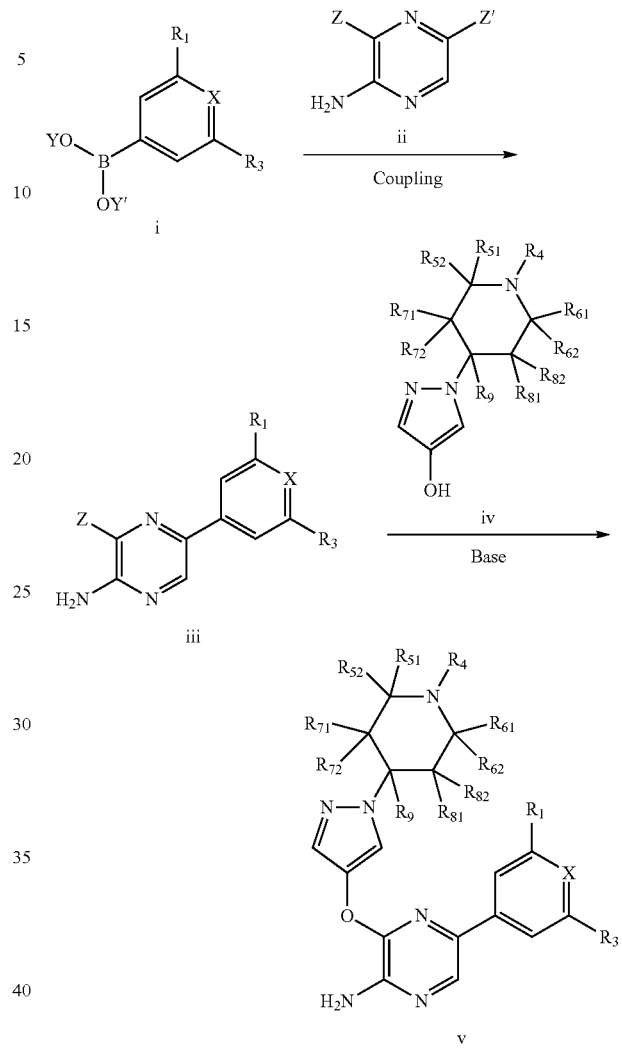

Y,Y' = H or alkyl (Y and Y' can be linked through a bond)
Z, Z' = Cl or Br or I

For example, compounds of Formula (I) can be formed as shown in Scheme II. Compound (i) can be coupled with 2-amino-3,5-dihalopyrazine (ii) to give compound (iii), which is then reacted with a deprotonated compound (iv) to give compound (v) [i.e., Formula (I)].

Scheme III

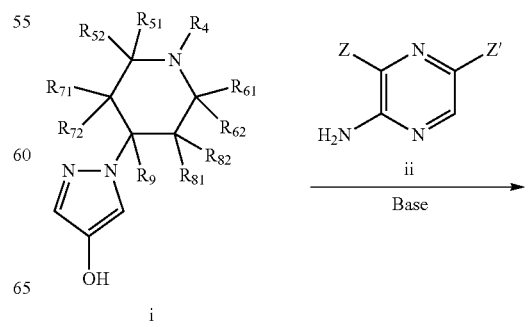

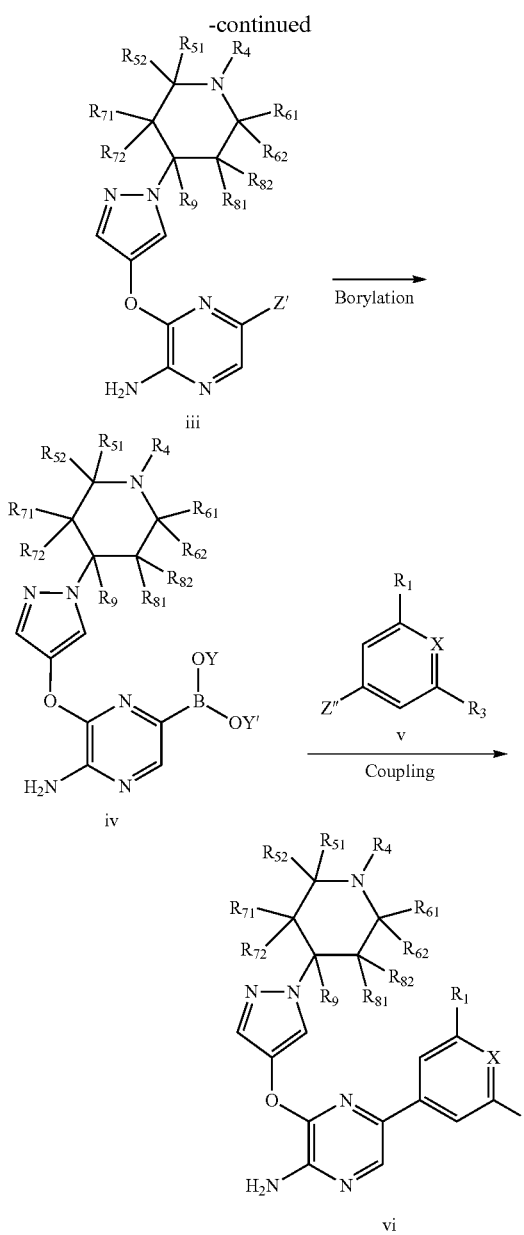

Y,Y' = H or alkyl (Y and Y' can be linked through a bond)
Z, Z' Z" = Cl or Br or I For example, compounds of Formula (I) can be formed as shown in Scheme III. Compound (i) can be deprotonated and react with 2-amino-3,5-dihalopyrazine (ii) to give compound (iii); compound (iii) can be borylated to give compound (iv); compound (iv) can be coupled with compound (v) using transition metal catalyzed reaction to give compound (vi) [i.e., Formula (I)].

Abbreviations
Et ethyl
Ac acetyl
THF tetrahydrofuran
Boc tert-butyloxycarbonyl
LC-MS liquid chromatograph mass spectrometer
DMF N,N-dimethylformamide
PE petroleum ether
DCM dichloromethane
BPD bis(pinacolato)diboron
dppf 1,1'-bis(diphenylphosphino)ferrocene
Me methyl
DMSO dimethyl sulfoxide
DIPEA N,N-diisopropylethylamine
HATU 2-(7-azabenzotriazol-1-yl)-N,N,N'N'-tetramethyluronium hexafluorophosphate
NMR nuclear magnetic resonance
HPLC high performance liquid chromatography
Pr propyl
Ms methanesulfonyl
DIAD diisopropyl azodicarboxylate
Ph phenyl
DMAC dimethylacetamide
TMS trimethylsilyl
Bu butyl
NCS N-chlorosuccinimide
XPhos dicyclohexyl(2',4',6'-triisopropyl-[1,1'-biphenyl]-2-yl)phosphane
dba dibenzylideneacetone
JohnPhos (2-biphenyl)di-tert-butylphosphine
TEMPO 2,2,6,6-tetramethylpiperidinooxy
TLC thin layer chromatography
TFA trifluoroacetic acid
XantPhos 4,5-Bis(diphenylphosphino)-9,9-dimethylxanthene
tR retention time
TBS tert-butyldimethylsilvl
TBAF tetra-n-butylammonium fluoride
DCE dichloroethane
NBS N-bromosuccinimide
Ts p-toluenesulfonyl
MTBE methyl tert-butyl ether Example A1

4-(5-amino-6-((1-(1-methylpiperidin-4-yl)-1H-pyrazol-4-yl)oxy)pyrazin-2-yl)-N-(2-(dimethylamino)ethyl)-2,6-dimethylbenzamide

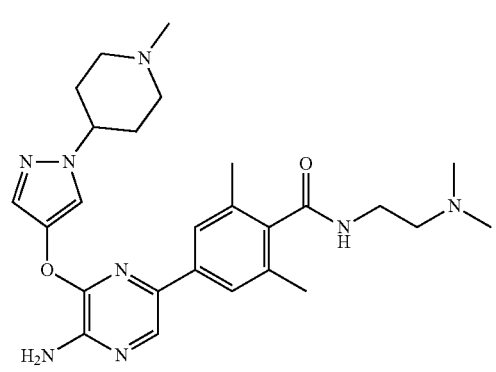 [SMILES: Cc1cc(-c2cnc(N)c(Oc3cnn(C4CCN(C)CC4)c3)n2)cc(C)c1C(=O)NCCN(C)C]

Step 1: tert-butyl 4-(4-hydroxy-1H-pyrazol-1-yl)piperidine-1-carboxylate

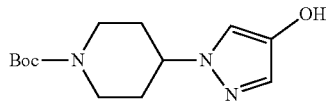 [SMILES: CC(C)(C)OC(=O)N1CCC(n2cc(O)cn2)CC1]

To a mixture of tert-butyl 4-(4-(4,4,5,5-tetramethyl-1,3,2-dioxaborolan-2-yl)-1H-pyrazol-1-yl)piperidine-1-carboxylate (23.5 g, 62.3 mmol) and NaOH (4.98 g, 124.5 mmol) in THF (400 mL) and water (80 mL) was added 30% $H_2O_2$(14.2 g, 124.5 mmol) dropwise at 0° C., then the mixture was warmed to room temperature and stirred for 1 h. Saturated $Na_2S_2O_3$ (50 mL) was added and the mixture was extracted with EtOAc (300 mL×2). The combined organic layer was washed with brine (100 mL), dried over $Na_2SO_4$, filtered, and the filtrate was concentrated under reduced pressure to give the title compound (14.5 g, 87%). LCMS (M+H)$^+$=268.

Step 2: tert-butyl 4-(4-((3-amino-6-bromopyrazin-2-yl)oxy)-1H-pyrazol-1-yl)piperidine-1-carboxylate

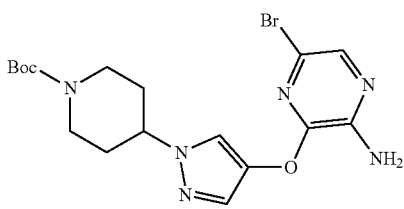 [SMILES: CC(C)(C)OC(=O)N1CCC(n2cc(Oc3nc(Br)cnc3N)cn2)CC1]

A mixture of tert-butyl 4-(4-hydroxy-1H-pyrazol-1-yl)piperidine-1-carboxylate (14.5 g, 54.2 mmol), $Cs_2CO_3$ (35.2 g, 108.4 mmol) and 3,5-dibromopyrazin-2-amine (13.7 g, 54.2 mmol) in DMF (250 mL) was stirred at 90° C. for 2 h then cooled to room temperature. Water (6(0) mL) was added and the mixture was extracted with EtOAc (500 mL×2). The combined organic layer was successively washed with water (300 mL×3), brine (300 mL), dried over $Na_2SO_4$, filtered, and the filtrate was concentrated under reduced pressure. The residue was purified by silica gel chromatography (PE/EtOAc=5/1 to 1/1) to give the title compound (18.5 g, 78%). LCMS (M+H)$^+$=439, 441.

Step 3: 5-bromo-3-((1-(piperidin-4-yl)-1H-pyrazol-4-yl)oxy)pyrazin-2-amine hydrochloride

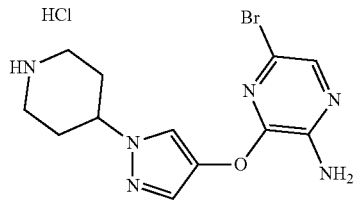 [SMILES: Cl ; Nc1ncc(Br)nc1Oc1cnn(C2CCNCC2)c1]

To a solution of tert-butyl 4-(4-((3-amino-6-bromopyrazin-2-yl)oxy)-H-pyrazol-1-yl)piperidine-1-carboxylate (18.5 g, 42.1 mmol) in dioxane (100 mL) was added HCl in dioxane (42.1 mL, 4 M, 168.4 mmol). The mixture was stirred for 2 h at room temperature. The precipitate was collected by filtration to give the title compound (15.8 g, 100%). LCMS (M+H)$^+$=339, 341.

Step 4: 5-bromo-3-((1-(1-methylpiperidin-4-yl)-1H-pyrazol-4-yl)oxy)pyrazin-2-amine

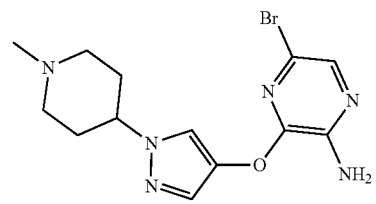 [SMILES: CN1CCC(n2cc(Oc3nc(Br)cnc3N)cn2)CC1]

To a solution of 5-bromo-3-((1-(piperidin-4-yl)-1H-pyrazol-4-yl)oxy)pyrazin-2-amine hydrochloride (13 g, 34.6 mmol) in MeOH (200 mL) was added 37% HCHO solution (11 mL, 138.5 mmol) and $NaBH(OAc)_3$(14.6 g, 69.2 mmol) at room temperature and the mixture was stirred for 16 h. The mixture was concentrated in vacuo, diluted with saturated $NaHCO_3$ solution (200 mL) and extracted with DCM (400 mL×2). The combined organic layer was washed with brine (100 mL), dried over anhydrous $Na_2SO_4$, filtered and the filtrated was concentrated under reduced pressure to give the title compound (12.0 g, 89%). LCMS (M+H)$^+$=353, 355.

Step 5: 4-bromo-N-(2-(dimethylamino)ethyl)-2,6-dimethylbenzamide

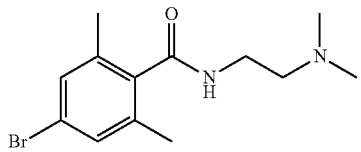 [SMILES: Cc1cc(Br)cc(C)c1C(=O)NCCN(C)C]

A solution of 4-bromo-2,6-dimethylbenzoic acid (4.2 g, 18.3 mmol) in $SOCl_2$ (30 mL) was stirred at reflux for 1 h then cooled to room temperature. The solvent was concentrated under reduced pressure. The residue was dissolved in dry DCM (50 mL) then N1,N1-dimethylethane-1,2-diamine (2.42 g, 27.5 mmol) and triethylamine (2.8 g, 27.5 mmol) was added dropwise at 0° C. The mixture was stirred for 3 h at room temperature, then quenched with saturated $NaHCO_3$ solution (50 mL) and extracted with DCM (50 mL×2). The combined organic layer was washed with brine (50 mL), dried over anhydrous $Na_2SO_4$, filtered and the filtrate was concentrated under reduced pressure to give the title compound (5.4 g, 98%). LCMS (M+H)$^+$=299, 301.

Step 6: N-(2-(dimethylamino)ethyl)-2,6-dimethyl-4-(4,4,5,5-tetramethyl-1,3,2-dioxaborolan-2-yl)benzamide

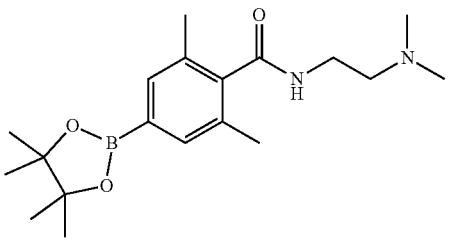

A mixture of 4-bromo-N-(2-(dimethylamino)ethyl)-2,6-dimethylbenzamide (5.4 g, 18 mmol), BPD (6.0 g, 23 mmol). Pd(dppf)Cl₂ (659 mg, 0.9 mmol) and AcOK (3.53 g, 36 mmol) in dioxane (70 mL) was heated to reflux under nitrogen overnight. The solution was cooled to room temperature, diluted with EtOAc (50 mL) and washed with brine (30 mL). The aqueous layer was extracted with EtOAc (100 mL). The combined organic layer was dried over Na₂SO₄, filtered and the filtrate was concentrated under reduced pressure. The crude was purified by silica gel chromatography (DCM/MeOH=30/1 to 20/1) to give the title compound (4.5 g, 72%). LC-MS (M+H)⁺=347.1.

Step 7: 4-(5-amino-6-((1-(1-methylpiperidin-4-yl)-1H-pyrazol-4-yl)oxy)pyrazin-2-yl)-N-(2-(dimethylamino)ethyl)-2,6-dimethylbenzamide To a solution of 5-bromo-3-((1-(1-methylpiperidin-4-yl)-1H-pyrazol-4-yl)oxy)pyrazin-2-amine (1.6 g, 4.5 mmol) and N-(2-(dimethylamino)ethyl)-2,6-dimethyl-4-(4,4,5,5-tetramethyl-1,3,2-dioxaborolan-2-yl)benzamide (1.87 g, 5.4 mmol) in dioxane (50 mL) and water (10 mL) was added K₂CO₃ (1.24 g, 9.0 mmol) and Pd(dppf)Cl₂ (0.2 g, 0.27 mmol) under nitrogen atmosphere. The mixture was stirred for 15 h at 90° C., then cooled to room temperature. The mixture was extracted with EtOAc (50 mL×3). The combined organic layer was concentrated under reduced pressure. The residue was purified by silica gel chromatography (DCM/MeOH=40/1 to 20/1) to give Example A1 (1.05 g, 47%). ¹H NMR (400 MHz, DMSO-d6) δ 8.23 (s, 1H), 8.2-8.14 (m, 1H), 8.11 (s, 1H), 7.58 (s, 1H), 7.49 (s, 2H), 6.72 (s, 2H), 4.18-4.06 (m, 1H), 3.25-3.32 (m, 2H), 2.90-2.80 (m, 2H), 2.42-2.34 (m, 2H), 2.23 (s, 6H), 2.20 (s, 3H), 2.18 (s, 6H), 2.12-1.93 (m, 6H). LCMS (M+H)⁺=493.5.

Example A2

3-(5-amino-6-((1-(1-methylpiperidin-4-yl)-1H-pyrazol-4-yl)oxy)pyrazin-2-yl)-N,5-dimethylbenzenesulfonamide

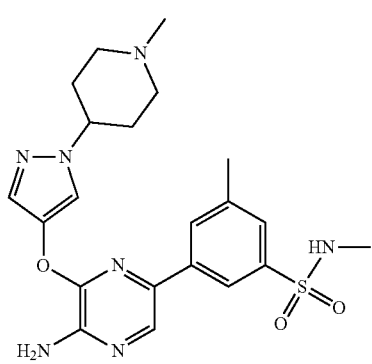 [SMILES: CNS(=O)(=O)c1cc(C)cc(-c2cnc(N)c(Oc3cnn(C4CCN(C)CC4)c3)n2)c1]

Step 1: 3-bromo-5-methylbenzenesulfonyl chloride

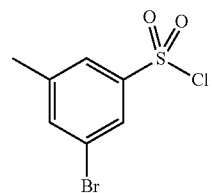

SOCl₂ (35.2 g, 295.6 mmol) was added to water (200 mL) dropwise at 0° C. and stirred at room temperature for overnight. The solution was cooled to 0° C. then CuCl (5.32 g, 53.8 mmol) was added, then the mixture was stirred at room temperature for 30 min to give mixture A. In a separated vessel, 3-bromo-5-methylaniline (10.0 g, 53.8 mmol) was dissolved in concentrated HCl (150 mL) then a solution of NaNO₂ (5.2 g, 75.3 mmol) in water (10 mL) was added dropwise at 0° C. and the mixture was stirred at room temperature for 30 min to give mixture B. Mixture B was added dropwise to mixture A at 0° C. and the final mixture was stirred at room temperature for 3 h. The reaction mixture was extracted with DCM (100 mL×3). The combined organic layer was washed with brine (100 mL), dried over Na₂SO₄ then filtered. The filtrate was concentrated under reduced pressure to give the title compound (11.9 g, 82%).

Step 2: 3-bromo-N,5-dimethylbenzenesulfonamide

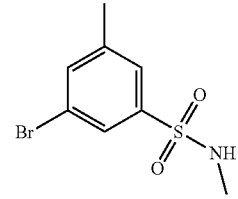

To a solution of 3-bromo-5-methylbenzenesulfonyl chloride (500 mg, 1.86 mmol) in pyridine (5 mL) was added MeNH₂ in THF (2.09 mL, 2 M, 4.18 mmol) at room temperature. The mixture was stirred for 2 h at room temperature then quenched with water (10 mL). The mixture was extracted with EtOAc (20 mL×3). The combined organic layer was washed with brine (10 mL), dried over Na₂SO₄ and filtered. The filtrate was concentrated under reduced pressure to give the title compound (238 mg, 49%). LC-MS (M+H)⁺=266.0.

Step 3: N,3-dimethyl-5-(4,4,5,5-tetramethyl-1,3,2-dioxaborolan-2-yl)benzenesulfonamide

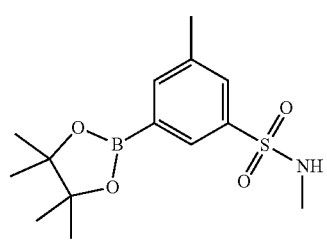

The title compound (101 mg, 42%) was prepared in a manner similar to that in Example A1 step 6 from 3-bromo-N,5-dimethylbenzenesulfonamide and BPD. LC-MS (M+H)⁺=312.1.

Step 4: 3-(5-amino-6-((1-(1-methylpiperidin-4-yl)-H-pyrazol-4-yl)oxy)pyrazin-2-yl)-N,5-dimethylbenzenesulfonamide Example A2 (16 mg, 4%) was prepared in a manner similar to that in Example A1 step 7 from N,3-dimethyl-5-(4,4,5,5-tetramethyl-1,3,2-dioxaborolan-2-yl)benzenesulfonamide and 5-bromo-3-(1-(1-methylpiperidin-4-yl)-1H-pyrazol-4-yloxy)pyrazin-2-amine. ¹H NMR (400 MHz DMSO-d6) δ 8.32 (s, 1H), 8.12 (s, 1H), 8.02 (s, 1H), 7.93 (s, 1H), 7.59 (s, 1H), 7.49 (s, 1H), 7.45-7.37 (m, 1H), 6.89 (s, 2H), 4.17-4.05 (m, 1H), 2.90-2.82 (m, 2H), 2.45-2.40 (m, 6H), 2.21 (s, 3H), 2.10-1.90 (m, 6H). LC-MS (M+H)⁺=458.2.

Example A3

4-(5-amino-6-(1-(1-methylpiperidin-4-yl)-1H-pyrazol-4-yloxy)pyrazin-2-yl)-N,2,6-trimethylbenzamide

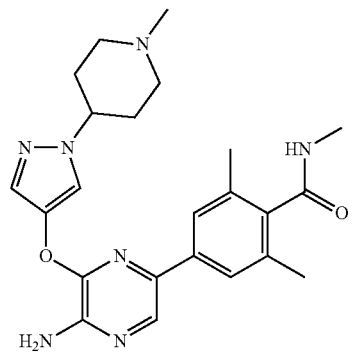 [SMILES: CNC(=O)c1c(C)cc(-c2cnc(N)c(Oc3cnn(C4CCN(C)CC4)c3)n2)cc1C]

Step 1: 4-bromo-N,2,6-trimethylbenzamide

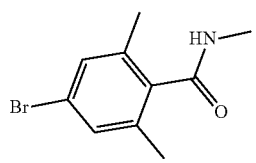

A solution of 4-bromo-2,6-dimethylbenzoic acid (5.0 g, 20.7 mmol), DIPEA (11.4 mL, 88.3 mmol), HATU (9.13 g, 22.8 mmol) and methylamine hydrochloride (2.95 g, 41.5 mmol) in DMF (20 mL) was stirred for 1 h at room temperature then concentrated under vacuum. The residue was purified by silica gel chromatography (PE/EtOAc=2/3) to give the title compound (4.5 g, 85%). LC-MS (M+1)⁺=242.1.

Step 2: N,2,6-trimethyl-4-(4,4,5,5-tetramethyl-1,3,2-dioxaborolan-2-yl)benzamide

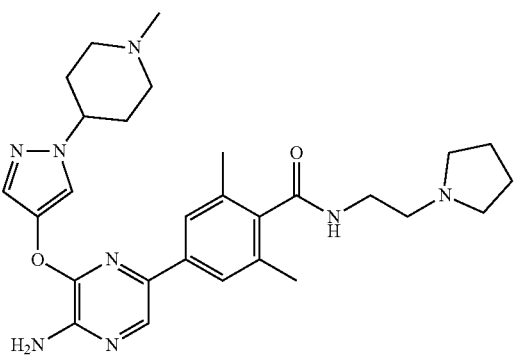

The title compound (206 mg, 45%) was prepared in a manner similar to that in Example A1 step 6 from 4-bromo-N,2,6-trimethylbenzamide and BPD. LC-MS (M+H)⁺=290.2.

Step 3: 4-(5-amino-6-(1-(1-methylpiperidin-4-yl)-1H-pyrazol-4-yloxy)pyrazin-2-yl)-N,2,6-trimethylbenzamide Example A3 (18 mg, 32%) was prepared in a manner similar to that in Example A1 step 7 from 5-bromo-3-(1-(1-methylpiperidin-4-yl)-1H-pyrazol-4-yloxy)pyrazin-2-amine and N,2,6-trimethyl-4-(4,4,5,5-tetramethyl-1,3,2-dioxaborolan-2-yl)benzamide. ¹H NMR (400 MHz, DMSO-d6) δ 8.22 (s, 1H), 8.15-8.07 (m, 2H), 7.57 (s, 1H), 7.48 (s, 2H), 6.70 (s, 1H), 4.19-4.03 (m, 1H), 2.88-2.79 (m, 2H), 2.74 (d, J=4.5 Hz, 3H), 2.23-2.16 (m, 9H), 2.12-1.86 (m, 6H). LC-MS (M+H)⁺=436.3.

Example A4

4-(5-amino-6-((1-(1-methylpiperidin-4-yl)-1H-pyrazol-4-yl)oxy)pyrazin-2-yl)-2,6-dimethyl-N-(2-(pyrrolidin-1-yl)ethyl)benzamide

Step 1: 4-(5-amino-6-((1-(1-methylpiperidin-4-yl)-1H-pyrazol-4-yl)oxy)pyrazin-2-yl)-2,6-dimethylbenzoic acid

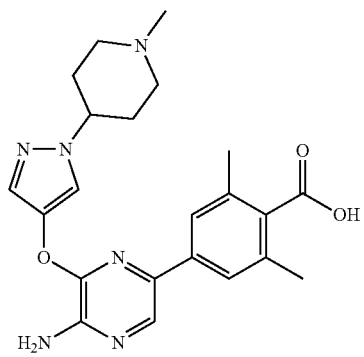 [SMILES: Cc1cc(-c2cnc(N)c(Oc3cnn(C4CCN(C)CC4)c3)n2)cc(C)c1C(=O)O]

To a solution of 5-bromo-3-((1-(1-methylpiperidin-4-yl)-1H-pyrazol-4-yl)oxy)pyrazin-2-amine (5.3 g, 15 mmol) and 2,6-dimethyl-4-(4,4,5,5-tetramethyl-1,3,2-dioxaborolan-2-yl)benzoic acid (5.0 g, 18 mmol) in dioxane (100 mL) and water (30 mL) was added $K_2CO_3$ (4.14 g, 30 mmol) and Pd(dppf)Cl$_2$ (0.73 g, 0.9 mmol) under nitrogen. After being stirred for 15 h at 90° C., the reaction mixture was cooled to room temperature and washed with EtOAc (50 mL). The aqueous phase was acidified to pH=2-3 with HCl (4 M). The precipitate was collected by filtration to give the title compound (3.2 g, 50.7%). LCMS (M+H)+=423.1.

Step 2: 4-(5-amino-6-((1-(1-methylpiperidin-4-yl)-1H-pyrazol-4-yl)oxy)pyrazin-2-yl)-2,6-dimethyl-N-(2-(pyrrolidin-1-yl)ethyl)benzamide To a solution of 4-(5-amino-6-((1-(1-methylpiperidin-4-yl)-1H-pyrazol-4-yl)oxy)pyrazin-2-yl)-2,6-dimethylbenzoic acid (60 mg, 0.14 mmol) in DMF (2.0 mL) was added DIPEA(57 mg, 0.42 mmol) and HATU (84 mg, 0.21 mmol) and 1-(2-aminoethyl)pyrrolidine (20 mg, 0.17 mmol) at room temperature. After 2 h, the mixture was extracted with DCM (4 mL×2). The combined organic layer was washed with brine (8 mL) and dried over anhydrous $Na_2SO_4$. After filtration, the filtrate was concentrated under reduced pressure. The crude product was purified by Prep-HPLC to give Example A4 (17 mg, 23%). $^1$H NMR (400 MHz, CD$_3$OD) δ 8.12 (s, 1H), 8.07 (s, 1H), 7.70 (s, 1H), 7.56-7.51 (m, 2H), 4.28-4.18 (m, 1H), 3.60-3.52 (m, 2H), 3.09-3.00 (m, 2H), 2.79-2.72 (m, 2H), 2.70-2.62 (m, 4H), 2.41-2.35 (m, 9H), 2.34-2.08 (m, 4H), 1.91-1.82 (m, 4H). LC-MS (M+H)+= 519.4.

Example A5

4-(5-amino-6-(1-(1-methylpiperidin-4-yl)-1H-pyrazol-4-yloxy)pyrazin-2-yl)-2,6-dimethyl-N-(2-(piperidin-1-yl)ethyl)benzamide

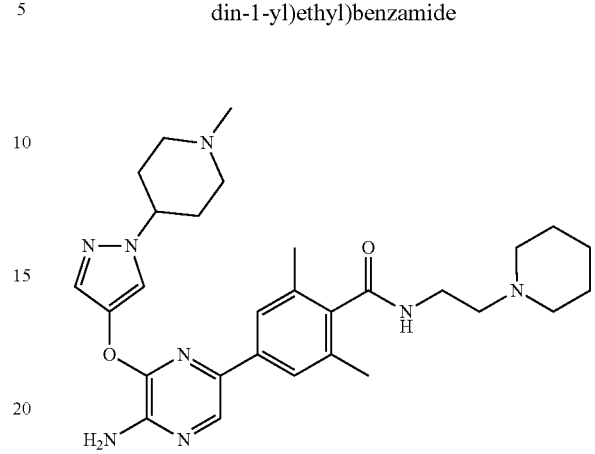

Example A5 (23 mg, 41%) was prepared in a manner similar to that in Example A4 step 2 from 4-(5-amino-6-(1-(1-methylpiperidin-4-yl)-1H-pyrazol-4-yloxy)pyrazin-2-yl)-2,6-dimethylbenzoic acid and 2-(piperidin-1-yl)ethanamine, 1H NMR (400 MHz, DMSO-d6) δ 8.23 (s, 1H), 8.15-8.06 (m, 2H), 7.58 (s, 1H), 7.50 (s, 2H), 6.72 (s, 2H), 4.19-4.07 (m, 1H), 3.37-3.33 (m, 2H), 2.89-2.80 (m, 2H), 2.44-2.33 (m, 6H), 2.25 (s, 6H), 2.20 (s, 3H), 2.12-1.92 (m, 6H), 1.54-1.44 (m, 4H), 1.43-1.34 (m, 2H). LC-MS (M+H)+= 533.4.

Example A6

3-(5-amino-6-((1-(1-methylpiperidin-4-yl)-1H-pyrazol-4-yl)oxy)pyrazin-2-yl)-5-methylbenzenesulfonamide

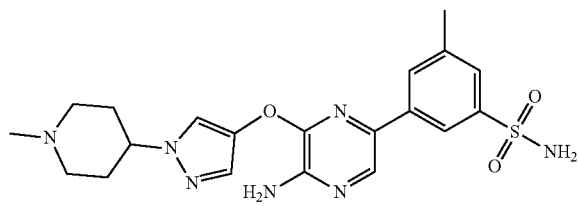 [SMILES: Cc1cc(-c2cnc(N)c(Oc3cnn(C4CCN(C)CC4)c3)n2)cc(S(N)(=O)=O)c1]

Step 1: 3-methyl-5-(4,4,5,5-tetramethyl-1,3,2-dioxaborolan-2-yl)benzenesulfonamide

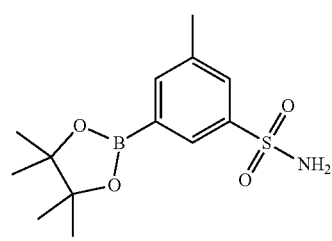 [SMILES: Cc1cc(B2OC(C)(C)C(C)(C)O2)cc(S(N)(=O)=O)c1]

The title compound (90 mg, 69%) was prepared in a manner similar to that in Example A1 step 6 from 3-bromo-5-methylbenzenesulfonamide and BPD.

Step 2: 3-(5-amino-6-((1-(1-methylpiperidin-4-yl)-1H-pyrazol-4-yl)oxy)pyrazin-2-yl)-5-methylbenzenesulfonamide Example A6 (29 mg, 24%) was prepared in a manner similar to that in Example A1 step 7 from 5-bromo-3-((1-(1-methylpiperidin-4-yl)-1H-pyrazol-4-yl)oxy)pyrazin-2-amine and 3-methyl-5-(4,4,5,5-tetramethyl-1,3,2-dioxaborolan-2-yl)benzenesulfonamide. $^1$H NMR (400 MHz, DMSO-d6) δ 8.30 (s, 1H), 8.13 (s, 1H), 8.10 (s, 1H), 7.88 (s, 1H), 7.59 (s, 1H), 7.55 (s, 1H), 7.32 (s, 2H), 6.89 (s, 2H), 4.19-4.07 (m, 1H), 2.89-2.82 (m, 2H), 2.41 (s, 3H), 2.20 (s, 3H), 2.10-1.90 (m, 6H). LC-MS (M+H)$^+$=444.2.

Example A7

3-(5-amino-6-((1-(1-methylpiperidin-4-yl)-1H-pyrazol-4-yl)oxy)pyrazin-2-yl)-5-methoxy-N-methylbenzenesulfonamide

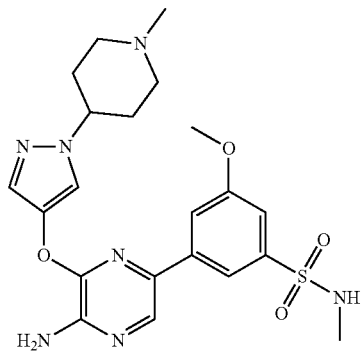 [SMILES: CNS(=O)(=O)c1cc(OC)cc(-c2cnc(N)c(Oc3cnn(C4CCN(C)CC4)c3)n2)c1]

Step 1: 3-bromo-5-methoxy-N-methylbenzenesulfonamide

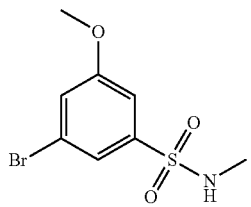

A solution of 3-bromo-5-methoxybenzenesulfonyl chloride (7.1 g, 25 mmol), methylamine hydrochloride (3.35 g, 50 mmol) and triethylamine (7.57 g, 75 mmol) in DCM (50 mL) was stirred at room temperature overnight. The mixture was concentrated under reduced pressure and the crude was purified by silica gel chromatography (PE/EtOAc=20/1 to 5/1) to give the title compound (3.0 g, 40%). LCMS (M+H)$^+$= 280.1.

Step 2: 3-methoxy-N-methyl-5-(4,4,5,5-tetramethyl-1,3,2-dioxaborolan-2-yl)benzenesulfonamide

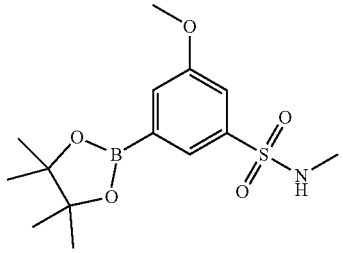

A mixture of 3-bromo-5-methoxy-N-methylbenzenesulfonamide (0.53 g, 1.9 mmol), BPD (0.53 g, 2.1 mmol), Pd(dppf)Cl$_2$-DCM (77.7 mg, 0.095 mmol) and AcOK (0.56 g, 5.7 mmol) in dioxane (15 mL) was warmed to reflux and stirred for overnight. After being cooled to room temperature, the mixture was filtered and the filtrate was concentrated under reduced pressure to give the title compound (0.60 g, 94%). LC-MS (M+H)$^+$=328.2.

Step 3: 3-(5-amino-6-((1-(1-methylpiperidin-4-yl)-1H-pyrazol-4-yl)oxy)pyrazin-2-yl)-5-methoxy-N-methylbenzenesulfonamide Example A7 (16 mg, 20%) was prepared in a manner similar to that in Example A1 step 7 from 5-bromo-3-((1-(1-methylpiperidin-4-yl)-1H-pyrazol-4-yl)oxy)pyrazin-2-amine and 3-methoxy-N-methyl-5-(4,4,5,5-tetramethyl-1,3,2-dioxaborolan-2-yl)benzenesulfonamide. $^1$H NMR (400 MHz, DMSO-d6) δ 8.35 (s, 1H), 8.09 (s, 1H), 7.81 (s, 1H), 7.69 (s, 1H), 7.67 (s, 1H), 7.47-7.39 (m, 1H), 7.18 (s, 1H), 6.91(s, 2H), 4.17-4.03 (m, 1H), 3.87 (s, 3H), 2.89-2.82 (m, 2H), 2.46-2.41 (d, J=4.2 Hz, 3H), 2.21 (s, 3H), 2.09-1.94 (m, 6H). LCMS (M+H)$^+$=474.4.

Example A8

5-(5-amino-6-((1-(1-methylpiperidin-4-yl)-1H-pyrazol-4-yl)oxy)pyrazin-2-yl)-N,2,3-trimethylbenzenesulfonamide

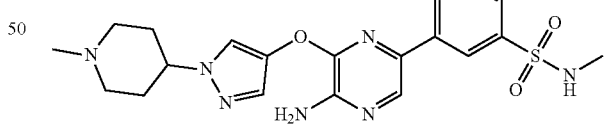

Step 1: 5-bromo-2,3-dimethylaniline

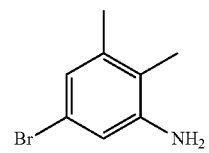

To a solution of 5-bromo-1,2-dimethyl-3-nitrobenzene (2.0 g, 8.26 mmol) and NH$_4$Cl (2.33 g, 41.3 mmol) in EtOH (12 mL) and H$_2$O (24 mL) was added iron powder (2.43 g, 41.3 mmol). The mixture was stirred for 2 h at 80° C. under nitrogen atmosphere. The mixture was cooled to room temperature and filtered. The filter cake was rinsed with DCM (10 mL×3) then the filtrate was concentrated under reduced pressure. The residue was diluted with water (10 mL) then was extracted with DCM (10 mL×2). The combined organic layer was washed with brine (10 mL), dried over anhydrous Na$_2$SO$_4$ then filtered. The filtrate was concentrated under reduced pressure and the residue was purified by silica gel chromatography (EtOAc/PE 0:1 to 1:9) to give the title compound (1.4 g, 85%). LC-MS (M+H)$^+$=199.8.

Step 2: 5-bromo-2,3-dimethylbenzenesulfonyl chloride

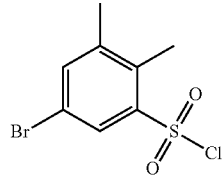

To a solution of 5-bromo-2,3-dimethylaniline (7M) mg, 3.16 mmol) in concentrated HCl (4.0 mL) and AcOH (8.0 mL) was added NaNO$_2$ (275 mg, 3.79 mmol) in water (2 mL) dropwise at −15° C. and the mixture was stirred for 30 min to prepare a diazonium salt. In the meanwhile, AcOH (8.0 mL) was bubbled with SO$_2$ (g) for 15 min, then CuCl (99 mg, 0.95 mmol) was added. SO$_2$ was kept bubbled until a fine suspension was obtained. The suspension was cooled to 5° C. then added to the aforementioned diazonium solution in portions. The mixture was warmed to room temperature, stirred for 2 h then cooled to 0° C. The reaction was quenched with iced water (8 mL) and extracted with EtOAc (8 mL×2). The combined organic layer was washed with saturated NaHCO$_3$ (10 mL×2) and water (20 mL), dried over anhydrous Na$_2$SO$_4$ then filtered. The filtrate was concentrated under reduced pressure and the crude (600 mg) was used in step 3 without further purification.

Step 3: 5-bromo-N,2,3-trimethylbenzenesulfonamide

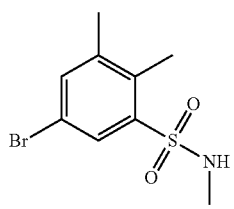

To a solution of 5-bromo-2,3-dimethylbenzenesulfonyl chloride (600 mg, 1.056 mmol) in pyridine (4.0 mL) was added methylamine in THF (2 M, 0.63 mL, 1.26 mmol) and the mixture was stirred for 2 h at room temperature. The mixture was concentrated and triturated with water (5 mL). The mixture was filtered and the filtrate was discarded. The filter cake was rinsed with DCM (5 mL×2) and the filtrate was concentrated under reduced pressure to give the title compound (300 mg, 34% over 2 steps). LC-MS (M+H)$^+$=278.0.

Step 4: N,2,3-trimethyl-5-(4,4,5,5-tetramethyl-1,3,2-dioxaborolan-2-yl)benzenesulfonamide

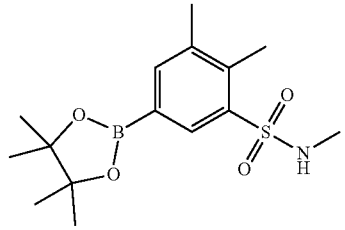

The title compound (227 mg, 68%) was prepared in a manner similar to that in Example A7 step 2 from 5-bromo-N,2,3-trimethylbenzenesulfonamide and BPD. LC-MS (M+H)$^+$=326.1.

Step 5: 5-(5-amino-6-((1-(1-methylpiperidin-4-yl)-1H-pyrazol-4-yl)oxy)pyrazin-2-yl)-N,2,3-trimethylbenzenesulfonamide Example A8 (7.3 mg, 9%) was prepared in a manner similar to that in Example A1 step 7 from N,2,3-trimethyl-5-(4,4,5,5-tetramethyl-1,3,2-dioxaborolan-2-yl)benzenesulfonamide and 5-bromo-3-(1-(1-methylpiperidin-4-yl)-1H-pyrazol-4-yloxy)pyrazin-2-amine. $^1$H NMR (300 MHz, DMSO-d6) δ 8.27 (s, 1H), 8.13 (s, 1H), 8.09 (s, 1H), 7.91 (s, 1H), 7.60 (s, 1H), 7.48 (s, 1H), 6.80 (s, 2H), 4.17-4.05 (m, 1H), 2.90-2.76 (m, 2H), 2.49-2.41 (m, 6H), 2.35 (s, 3H), 2.20 (s, 3H), 2.11-1.91 (m, 6H). LC-MS (M+H)$^+$=472.3.

Example A9

3-(5-amino-6-((1-(1-methylpiperidin-4-yl)-1H-pyrazol-4-yl)oxy)pyrazin-2-yl)-5-methyl-N-(2-(piperidin-1-yl)ethyl)benzenesulfonamide

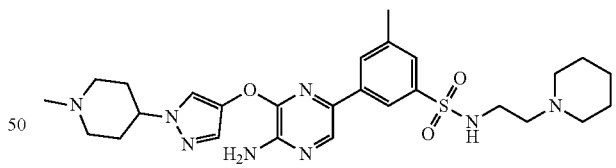

Step 1: 3-bromo-5-methyl-N-(2-(piperidin-1-yl)ethyl)benzenesulfonamide

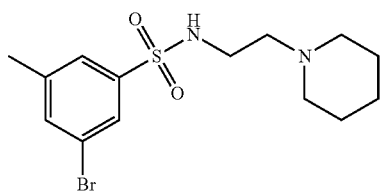 [SMILES: Cc1cc(Br)cc(S(=O)(=O)NCCN2CCCCC2)c1]

The titled compound (209 mg, 55%) was prepared in a manner similar to that in Example A2 step 2 from 3-bromo-5-methylbenzenesulfonyl chloride and 2-(piperidin-1-yl)ethan-1-amine. LC-MS (M+H)$^+$=361.1.

Step 2: 3-methyl-N-(2-(piperidin-1-yl)ethyl)-5-(4,4,5,5-tetramethyl-1,3,2-dioxaborolan-2-yl)benzenesulfonamide

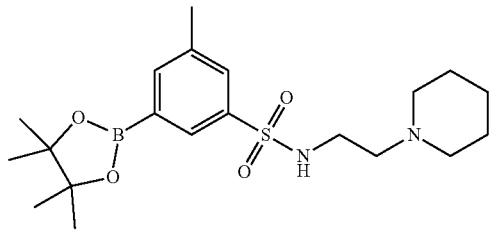 [SMILES: Cc1cc(B2OC(C)(C)C(C)(C)O2)cc(S(=O)(=O)NCCN2CCCCC2)c1]

The titled compound (117 mg, 49%) was prepared in a manner similar to that in Example A1 step 6 from 3-bromo-5-methyl-N-(2-(piperidin-1-yl)ethyl)benzenesulfonamide and BPD. LC-MS (M+H)$^+$=409.2.

Step 3: 3-(5-amino-6-((1-(1-methylpiperidin-4-yl)-1H-pyrazol-4-yl)oxy)pyrazin-2-yl)-5-methyl-N-(2-(piperidin-1-yl)ethyl)benzenesulfonamide Example A9 (22 mg, 17%) was prepared in a manner similar to that in Example A1 step 7 from 5-bromo-3-(1-(1-methylpiperidin-4-yl)-1H-pyrazol-4-yloxy)pyrazin-2-amine and 3-methyl-N-(2-(piperidin-1-yl)ethyl)-5-(4,4,5,5-tetramethyl-1,3,2-dioxaborolan-2-yl)benzenesulfonamide. $^1$H NMR (400 MHz, DMSO-d$_6$) δ 8.33 (s, 1H), 8.13 (s, 1H), 8.06 (s, 1H), 7.93 (s, 1H), 7.60 (s, 1H), 7.52 (s, 1H), 7.45 (s, 1H), 6.90 (s, 2H), 4.174.07 (m, 1H), 2.91-2.82 (m, 4H), 2.42 (s, 3H), 2.29-2.12 (m, 9H), 2.12-1.92 (m, 6H), 1.43-1.34 (m, 4H), 1.34-1.25 (m, 2H). LC-MS (M+H)$^+$=555.2.

Example A10

3-(5-amino-6-((1-(1-methylpiperidin-4-yl)-1H-pyrazol-4-yl)oxy)pyrazin-2-yl)-N-(2-cyanoethyl)-5-methylbenzenesulfonamide

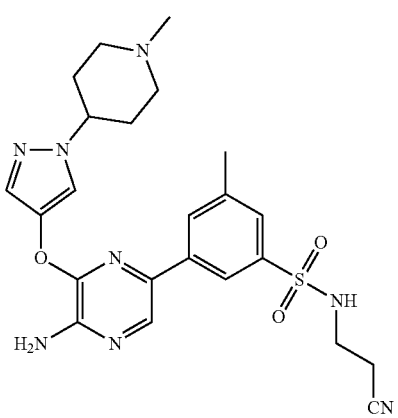 [SMILES: Cc1cc(-c2cnc(N)c(Oc3cnn(C4CCN(C)CC4)c3)n2)cc(S(=O)(=O)NCCC#N)c1]

Step 1: 3-bromo-N-(2-cyanoethyl)-5-methylbenzenesulfonamide

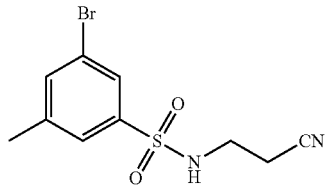 [SMILES: Cc1cc(Br)cc(S(=O)(=O)NCCC#N)c1]

A solution of 3-bromo-5-methylbenzenesulfonyl chloride (0.50 g, 1.85 mmol), 3-aminopropanenitrile (0.13 g, 1.85 mmol) and triethylamine (0.37 g, 3.7 mmol) in DCM (50 mL) was stirred at room temperature overnight. The mixture was removed under reduced pressure and the residue was purified by silica gel chromatograph (PE/EtOAc=5/1 to 1/1) to give the title compound (0.38 g, 59%). LCMS (M+H)$^+$= 303, 305.

Step 2: N-(2-cyanoethyl)-3-methyl-5-(4,4,5,5-tetramethyl-1,3,2-dioxaborolan-2-yl)benzenesulfonamide

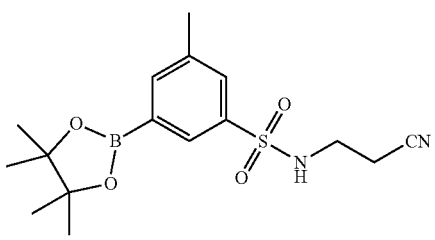 [SMILES: Cc1cc(B2OC(C)(C)C(C)(C)O2)cc(S(=O)(=O)NCCC#N)c1]

A mixture of 3-bromo-N-(2-cyanoethyl)-5-methylbenzenesulfonamide (0.37 g, 1.22 mmol), BPD (0.37 g, 1.46 mmol), Pd(dppf)Cl$_2$ (53.5 mg, 0.073 mmol) and AcOK (0.24 g, 2.43 mmol) in dioxane (15 mL) was heated to reflux overnight under nitrogen. The mixture was cooled to room temperature and diluted with EtOAc (20 mL). The mixture was washed with brine (30 mL), and the aqueous layer was extracted with EtOAc (20 mL). The combined organic layer was dried over Na$_2$SO$_4$, filtered and concentrated to give the title compound (0.40 g, 93.6%). LC-MS (M+H)$^+$=351.1.

Step 3: 3-(5-amino-6-((1-(1-methylpiperidin-4-yl)-1H-pyrazol-4-yl)oxy)pyrazin-2-yl)-N-(2-cyanoethyl)-5-methylbenzenesulfonamide Example A10 (70 mg, 25%) was prepared in a manner similar to that in Example A1 step 7 from 5-bromo-3-((1-(1-methylpiperidin-4-yl)-1H-pyrazol-4-yl)oxy)pyrazin-2-amine and N-(2-cyanoethyl)-3-methyl-5-(4,4,5,5-tetramethyl-1,3,2-dioxaborolan-2-yl)benzenesulfonamide. $^1$H NMR (400 MHz, DMSO-d6) δ 8.33 (s, 1H), 8.12 (s, 1H), 8.08-7.99 (m, 2H), 7.94 (s, 1H), 7.59 (s, 1H), 7.52 (s, 1H), 6.89 (s, 2H), 4.18-4.16 (m, 1H), 3.05-2.95 (m, 2H), 2.92-2.83 (m, 2H), 2.67-2.60 (m, 2H), 2.42 (s, 3H), 2.21 (s, 3H), 2.13-1.95 (m, 6H). LCMS (M+H)$^+$=497.4.

Example A11

N-(1-(3-(5-amino-6-((1-(1-methylpiperidin-4-yl)-1H-pyrazol-4-yl)oxy)pyrazin-2-yl)-5-methylphenyl)cyclopropyl)methanesulfonamide

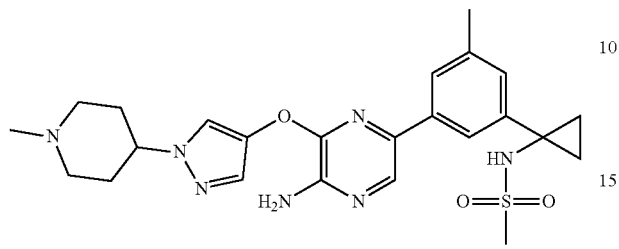

Step 1: 1-(3-bromo-5-methylphenyl)cyclopropan-1-amine

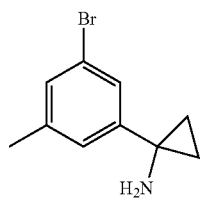

To a solution of 3-bromo-5-methylbenzonitrile (9.50 g, 48.5 mmol) and Ti(Oi-Pr)₄ (16.1 g, 56.6 mmol) in Et₂O (200 mL) was added ethylmagnesium bromide in Et₂O (3 M, 35.7 mL, 107 mmol) At −70° C. and the mixture was stirred for 10 min. The mixture was warmed to room temperature within 1 h, and then BFrEt₂O (12.3 mL, 86.5 mmol) was added. After 1 h, HCl (30 mL, 1 N) and Et₂O (100 mL) was added. Then aqueous NaOH (40 mL, 10%) was added and the mixture was extracted with ether (100 mL×3). The combined organic layer was dried over Na₂SO₄ and filtered. The filtrate was concentrated under reduced pressure and the residue was purified by silica gel chromatography (MeOH in DCM, 0% to 10%) to give the title compound (5.1 g, 44%). ¹H NMR (300 MHz, DMSO-d6) δ 7.41 (s, 1H), 7.32 (s, 1H), 7.17 (s, 1H), 2.28 (s, 2H), 1.31-1.08 (m, 4H).

Step 2: N-(1-(3-bromo-5-methylphenyl)cyclopropyl)methanesulfonamide

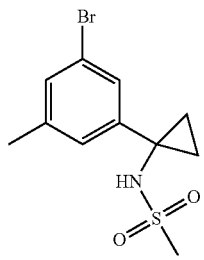 [SMILES: Cc1cc(Br)cc(C2(NS(C)(=O)=O)CC2)c1]

To a stirred solution of 1-(3-bromo-5-methylphenyl)cyclopropan-1-amine (1.0 g, 4.2 mmol) and triethylamine (1275 mg, 12.6 mmol) in acetonitrile (20 mL) was added MsCl (722 mg, 6.302 mmol) at 0° C. The mixture was stirred for overnight at room temperature then at 80° C. for 2 h. The mixture was cooled to room temperature and concentrated under reduced pressure. The residue was purified by silica gel chromatography (DCM/MeOH=15:1) to give the title compound (1.2 g, 89%). ¹H NMR (300 MHz, CDCl₃) δ 7.36 (s, 1H), 7.20 (s, 1H), 7.16 (s, 1H), 6.09 (s, 1H), 2.59 (s, 3H), 2.30 (s, 3H), 1.42-1.30 (m, 2H), 1.17-1.09 (m, 2H).

Step 3: N-(1-(3-methyl-5-(4,4,5,5-tetramethyl-1,3,2-dioxaborolan-2-yl)phenyl)cyclopropyl)methanesulfonamide

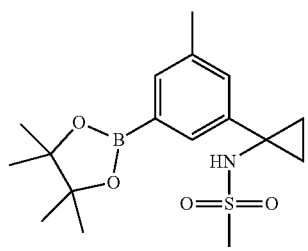 [SMILES: Cc1cc(B2OC(C)(C)C(C)(C)O2)cc(C2(NS(C)(=O)=O)CC2)c1]

The title compound (450 mg, 46%) was prepared in a manner similar to that in Example A1 step 6 from N-(1-(3-bromo-5-methylphenyl)cyclopropyl)methanesulfonamide and BPD. LC-MS (M+NH₄)=369.0.

Step 4: N-(1-(3-(5-amino-6-((1-(1-methylpiperidin-4-yl)-1H-pyrazol-4-yl)oxy)pyrazin-2-yl)-5-methylphenyl)cyclopropyl)methanesulfonamide Example A11 (23 mg, 17%) was prepared in a manner similar to that in Example A1 step 7 from 5-bromo-3-((1-(1-methylpiperidin-4-yl)-1H-pyrazol-4-yl)oxy)pyrazin-2-amine and N-(1-(3-methyl-5-(4,4,5,5-tetramethyl-1,3,2-dioxaborolan-2-yl)phenyl)cyclopropyl)methanesulfonamide. ¹H NMR (300 MHz, DMSO-d6) δ 8.22 (s, 2H), 8.14 (s, 1H), 7.66 (s, 1H), 7.57 (s, 1H), 7.50 (s, 1H), 7.15 (s, 1H), 6.72 (s, 2H), 4.19-4.07 (m, 1H), 2.91-2.81 (m, 2H), 2.51 (s, 3H), 2.31 (s, 3H), 2.18 (s, 3H), 2.10-1.91 (m, 6H), 1.29-1.20 (m, 2H), 1.21-1.06 (m, 2H). LC-MS (M+H)⁺=498.3.

Example A12

N-(3-(5-amino-6-((1-(1-methylpiperidin-4-yl)-1H-pyrazol-4-yl)oxy)pyrazin-2-yl)-5-methylphenethyl)methanesulfonamide

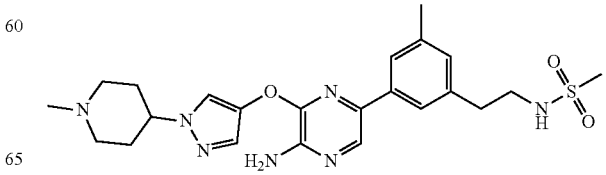

Step 1: 2-(3-bromo-5-methylphenyl)ethanamine hydrochloride

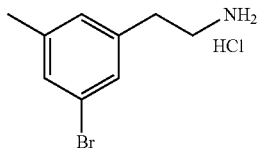

To a stirred solution of 2-(3-bromo-5-methylphenyl)acetonitrile (378 mg, 1.81 mmol) in MeOH (5 mL) was added Boc$_2$O (218 mg, 0.948 mmol), NiCl$_2$·6H$_2$O (118 mg, 0.470 mmol) and NaBH$_4$ (1109 mg, 27.8 mmol) under nitrogen at 0° C. The mixture was warmed to room temperature and stirred for 2 h. The mixture was concentrated under vacuum. The crude was dissolved in dioxane (10 mL) and HCl in dioxane (10 mL, 40 mmol, 4 M) was added. The resulting mixture was stirred for 3 h at room temperature. The mixture was concentrated under vacuum. The residue was triturated in ethyl acetate (3 mL). The precipitated was collected by filtration and rinsed with ethyl acetate (1 mL×3) to give the title compound (444 mg, 98%). LC-MS (M+H)$^+$=214.0.

Step 2: N-(3-bromo-5-methylphenethyl)methanesulfonamide

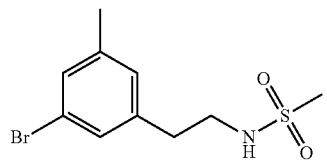

The title compound (334 mg, 64%) was prepared in a manner similar to that in Example A11 step 2 from 2-(3-bromo-5-methylphenyl)ethanamine hydrochloride and MsCl. LC-MS (M+H)$^+$=292.0.

Step 3: N-(3-methyl-5-(4,4,5,5-tetramethyl-1,3,2-dioxaborolan-2-yl)phenethyl)methanesulfonamide

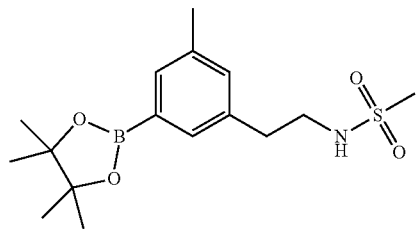

The compound 3 (214 mg, 55%) was prepared in a manner similar to that in Example A1 step 6 from N-(3-bromo-5-methylphenethyl)methanesulfonamide and BPD. LC-MS (M+H)+=340.2.

Step 4: N-(3-(5-amino-6-((1-(1-methylpiperidin-4-yl)-1H-pyrazol-4-yl)oxy)pyrazin-2-yl)-5-methylphenethyl)methanesulfonamide Example A12 (4.2 mg, 1%) was prepared in a manner similar to that in Example A1 step 7 from 5-bromo-3-((1-(1-methylpiperidin-4-yl)-1H-pyrazol-4-yl)oxy)pyrazin-2-amine and N-(3-methyl-5-(4,4,5,5-tetramethyl-1,3,2-dioxaborolan-2-yl)phenethyl)methanesulfonamide. $^1$H NMR (400 MHz, DMSO-d6) δ 8.24 (s, 1H), 8.12 (s, 1H), 7.59 (s, 1H), 7.51 (s, 2H), 7.14 (t, J=5.8 Hz, 1H), 6.98 (s, 1H), 6.70 (s, 2H), 4.19-4.07 (m, 1H), 3.23-3.14 (m, 2H), 2.90-2.86 (m, 2H), 2.85 (s, 3H), 2.75 (t, J=7.6 Hz, 2H), 2.31 (s, 3H), 2.21 (s, 3H), 2.10-1.90 (m, 6H). LC-MS (M+H)$^+$=486.3.

Example A13

3-(5-amino-6-((1-(piperidin-4-yl)-1H-pyrazol-4-yl)oxy)pyrazin-2-yl)-N,5-dimethylbenzenesulfonamide

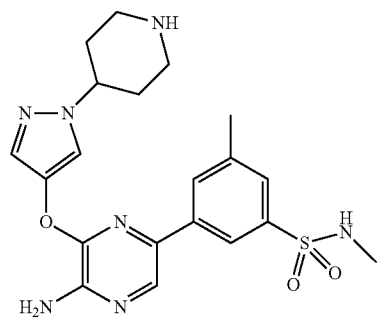 [SMILES: CNS(=O)(=O)c1cc(C)cc(-c2cnc(N)c(Oc3cnn(C4CCNCC4)c3)n2)c1]

Example A13 (27 mg, 19%) was prepared in a manner similar to that in Example A1 step 7 from 5-bromo-3-((1-(piperidin-4-yl)-1H-pyrazol-4-yl)oxy)pyrazin-2-amine hydrochloride and N,3-dimethyl-5-(4,4,5,5-tetramethyl-1,3,2-dioxaborolan-2-yl)benzenesulfonamide. $^1$H NMR (400 MHz, DMSO-d6) δ 8.32 (s, 1H), 8.11 (s, 1H), 8.02 (s, 1H), 7.94 (s, 1H), 7.58 (s, 1H), 7.49 (m, 2H), 6.90 (s, 2H), 4.27-4.12 (m, 1H), 3.11-3.00 (m, 2H), 2.70-2.54 (m, 3H), 2.43 (s, 6H), 2.07-1.95 (m, 2H), 1.90-1.73 (m, 2H). LC-MS (M+H)$^+$=444.3.

Example A14

3-(5-amino-6-((1-((1R,3s,5S)-8-methyl-8-azabicyclo[3.2.1]octan-3-yl)-1H-pyrazol-4-yl)oxy)pyrazin-2-yl)-N,5-dimethylbenzenesulfonamide

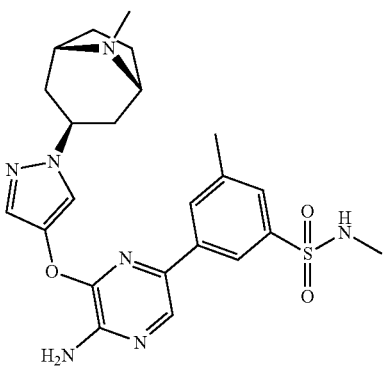 [SMILES: CNS(=O)(=O)c1cc(C)cc(-c2cnc(N)c(Oc3cnn([C@@H]4C[C@H]5CC[C@@H](C4)N5C)c3)n2)c1]

Step 1: tert-butyl (1R,3s,5S)-3-(4-(4,4,5,5-tetramethyl-1,3,2-dioxaborolan-2-yl)-1H-pyrazol-1-yl)-8-azabicyclo[3.2.1]octane-8-carboxylate

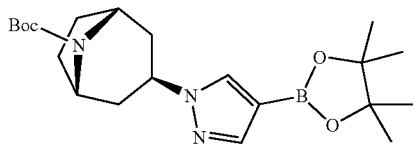 [SMILES: CC(C)(C)OC(=O)N1[C@@H]2CC[C@H]1C[C@H](n1cc(B3OC(C)(C)C(C)(C)O3)cn1)C2]

A solution of 4-(4,4,5,5-tetramethyl-1,3,2-dioxaborolan-2-yl)-1H-pyrazole (1.5 g, 7.73 mmol), tert-butyl (1R,3r,5S)-3-hydroxy-8-azabicyclo[3.2.1]octane-8-carboxylate (2.1 g, 9.27 mmol), DIAD (2.24 g, 11.6 mmol) and PPh$_3$ (3.0 g, 11.6 mmol) in THF (30 mL) was stirred at room temperature overnight under nitrogen. The solvent was removed and the residue was purified by silica gel chromatography (PE/EtOAc=10/1 to 5/1) to give the title compound (3.0 g, 95%). LCMS (M+H)$^+$=404.1.

Step 2: tert-butyl (1R,3s,5S)-3-(4-hydroxy-1H-pyrazol-1-yl)-8-azabicyclo[3.2.1]octane-8-carboxylate

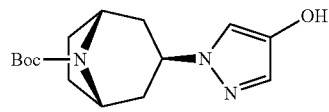 [SMILES: CC(C)(C)OC(=O)N1[C@@H]2CC[C@H]1C[C@H](n1cc(O)cn1)C2]

The title compound (1.5 g, 69%) was prepared in the same manner which described in compound A1 step 1 from tert-butyl (1R,3s,5S)-3-(4-(4,4,5,5-tetramethyl-1,3,2-dioxaborolan-1-yl)-1H-pyrazol-1-yl)-8-azabicyclo[3.2.1]octane-8-carboxylate. LCMS (M+H)$^+$=294.

Step 3: tert-butyl (1R,3s,5S)-3-(4-((3-amino-6-bromopyrazin-2-yl)oxy)-1H-pyrazol-1-yl)-8-azabicyclo[3.2.1]octane-8-carboxylate

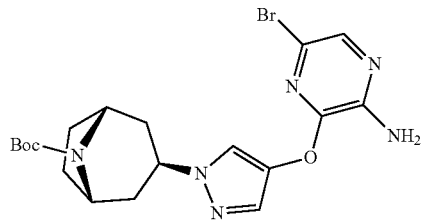 [SMILES: CC(C)(C)OC(=O)N1[C@@H]2CC[C@H]1C[C@H](n1cc(Oc3nc(Br)cnc3N)cn1)C2]

The title compound (0.35 g, 66%) was prepared in the same manner which described in compound A1 step 2 from tert-butyl (1R,3s,5S)-3-(4-hydroxy-1H-pyrazol-1-yl)-8-azabicyclo[3.2.1]octane-8-carboxylate and 3,5-dibromopyrazin-2-amine. LCMS (M+H)$^+$=465, 467.

Step 4: 3-((1-((1R,3s,5S)-8-azabicyclo[3.2.1]octan-3-yl)-1H-pyrazol-4-yl)oxy)-5-bromopyrazin-2-amine hydrochloride

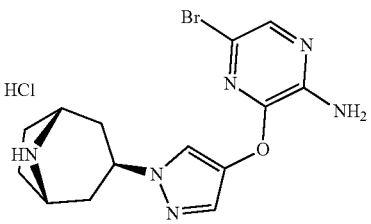 [SMILES: Cl ; Nc1ncc(Br)nc1Oc1cnn([C@@H]2C[C@H]3CC[C@@H](C2)N3)c1]

The title compound (0.30 g, 100%) was prepared in the same manner which described in compound A1 step 3 from tert-butyl (1R,3s,5S)-3-(4-((3-amino-6-bromopyrazin-2-yl)oxy)-1H-pyrazol-1-yl)-8-azabicyclo[3.2.1]octane-8-carboxylate. LCMS (M+H)$^+$=365, 367.

Step 5: 5-bromo-3-((1-((1R,3s,5S)-8-methyl-8-azabicyclo[3.2.1]octan-3-yl)-1H-pyrazol-4-yl)oxy)pyrazin-2-amine

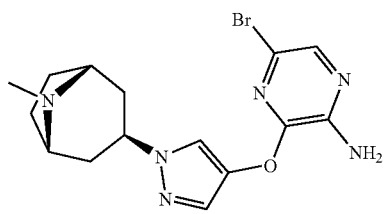 [SMILES: CN1[C@@H]2CC[C@H]1C[C@H](n1cc(Oc3nc(Br)cnc3N)cn1)C2]

The title compound (0.30 g, 99%) was prepared in the same manner which described in compound A1 step 4 from 3-((1-((1R,3s,5S)-8-azabicyclo[3.2,1]octan-3-yl)-1H-pyrazol-4-yl)oxy)-5-bromopyrazin-2-amine hydrochloride. LCMS (M+H)+=379, 381.

Step 6: 3-(5-amino-6-((1-((1R,3s,5S)-8-methyl-8-azabicyclo[3.2.1]octan-3-yl)-1H-pyrazol-4-yl)oxy)pyrazin-2-yl)-N,5-dimethylbenzenesulfonamide Example A14 (33 mg, 25%) was prepared in a manner similar to that in Example A1 step 7 from 5-bromo-3-((1-((1R,3s,5S)-8-methyl-8-azabicyclo[3.2.1]octan-3-yl)-1H-pyrazol-4-yl)oxy)pyrazin-2-amine and N,3-dimethyl-5-(4,4,5,5-tetramethyl-1,3,2-dioxaborolan-2-yl)benzenesulfonamide. $^1$H NMR (400 MHz, DMSO-d6) δ 8.33 (s, 1H), 8.13 (s, 1H), 8.04 (s, 1H), 7.95 (s, 1H), 7.61-7.53 (m, 2H), 7.50 (s, 1H), 6.90 (s, 2H), 4.55-4.40 (m, 1H), 3.21 (s, 2H), 2.43 (s, 6H), 2.25 (s, 3H), 2.16-2.05 (m, 2H), 2.05-1.95 (m, 2H), 1.89-1.81 (m, 2H), 1.74-1.65 (m, 2H). LCMS (M+H)$^+$=484.4.

Example A15

3-(5-amino-6-((1-(1-methylpiperidin-4-yl)-1H-pyrazol-4-yl)oxy)pyrazin-2-yl)-N-ethyl-5-methylbenzenesulfonamide

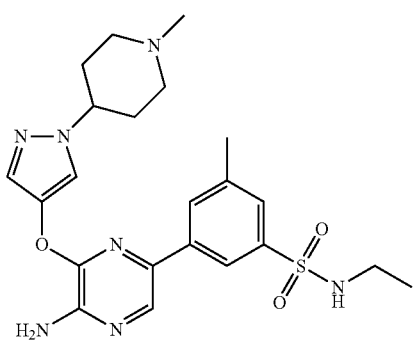 [SMILES: CCNS(=O)(=O)c1cc(C)cc(-c2cnc(N)c(Oc3cnn(C4CCN(C)CC4)c3)n2)c1]

Step 1: 3-bromo-N-ethyl-5-methylbenzenesulfonamide

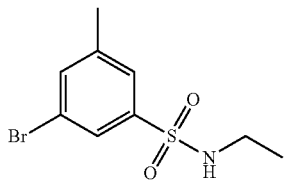

A solution of 3-bromo-5-methylbenzenesulfonyl chloride (2.67 g, 10 mmol), ethylamine hydrochloride (1.62 g, 20 mmol) and TEA (3.03 g, 30 mmol) in DCM (50 mL) was stirred at room temperature for overnight. The mixture was concentrated and the crude was purified by silica gel chromatograph (PE/EtOAc=20/1 to 5/1) to give the title compound (0.85 g, 31%). LCMS (M+H)$^+$=278, 280.

Step 2: N-ethyl-3-methyl-5-(4,4,5,5-tetramethyl-1,3,2-dioxaborolan-2-yl)benzenesulfonamide

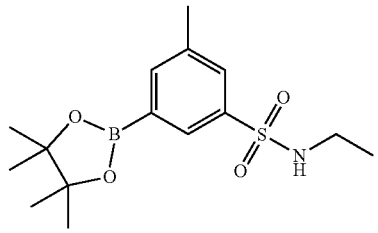 [SMILES: CCNS(=O)(=O)c1cc(C)cc(B2OC(C)(C)C(C)(C)O2)c1]

A mixture of 3-bromo-N-ethyl-5-methylbenzenesulfonamide (850 mg, 3.0 mmol), BPD (762 mg, 3.0 mmol), Pd(dppf)Cl$_2$·DCM (123 mg, 0.15 mmol) and AcOK (882 mg, 9.0 mmol) in dioxane (15 mL) was heated to reflux under nitrogen for overnight. The mixture was cooled to room temperature filtered. The filtrate was concentrated under reduced pressure to give the title compound (810 mg, 83%). LC-MS (M+H)$^+$=326.3.

Step 3: 3-(5-amino-6-((1-(1-methylpiperidin-4-yl)-H-pyrazol-4-yl)oxy)pyrazin-2-yl)-N-ethyl-5-methylbenzenesulfonamide Example A15 (48 mg, 34%) was prepared in a manner similar to that in Example A1 step 7 from N-ethyl-3-methyl-5-(4,4,5,5-tetramethyl-1,3,2-dioxaborolan-2-yl)benzenesulfonamide and 5-bromo-3-((1-(1-methylpiperidin-4-yl)-1H-pyrazol-4-yl)oxy)pyrazin-2-amine. $^1$H NMR (400 MHz, DMSO-d6) 8.31 (s, 1H), 8.11 (s, 1H), 8.02 (s, 1H), 7.92 (s, 1H), 7.60 (s, 1H), 7.50 (s, 2H), 6.90 (s, 2H), 4.20-4.05 (m, 1H), 2.92-2.85 (m, 2H), 2.83-2.75 (m, 2H), 2.42 (s, 3H), 2.22 (s, 3H), 2.12-1.94 (m, 6H), 0.98 (t, J=7.2 Hz, 3H). LCMS (M+H)$^+$=472.4.

Example A16

3-(5-amino-6-((1-(1-methylpiperidin-4-yl)-1H-pyrazol-4-yl)oxy)pyrazin-2-yl)-5-isopropoxy-N-methylbenzenesulfonamide; formic acid

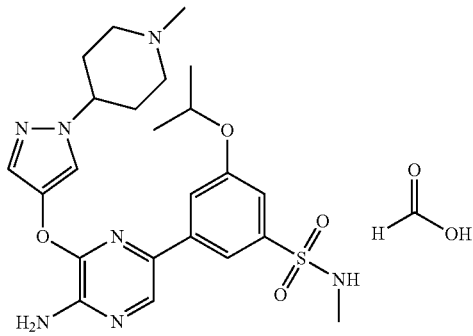

Step 1: 1-bromo-3-isopropoxy-5-nitrobenzene

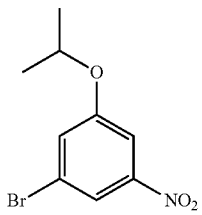

A mixture of 3-bromo-5-nitrophenol (5.45 g, 25 mmol) and 2-iodopropane (8.5 g, 50 mmol), K$_2$CO$_3$ (6.9 g, 50 mmol) in DMF (50 mL) was stirred at room temperature overnight. Water (150 mL) was added and the mixture was extracted with EtOAc (150 mL). The organic layer was dried over Na$_2$SO$_4$ and filtered. The filtrate was concentrated to get the title compound (6.3 g, 97%).

Step 2: 3-bromo-5-isopropoxyaniline

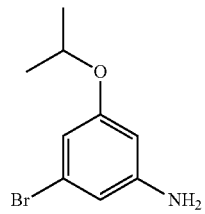

The title compound (4.8 g, 86%) was prepared in a manner similar to that in Example A8 step 1 from 1-bromo-3-isopropoxy-5-nitrobenzene. LC-MS (M+H)⁺=230.2.

Step 3: 3-bromo-5-isopropoxybenzenesulfonyl chloride

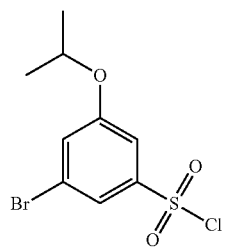

The title compound (4.6 g, 71%) was prepared in a manner similar to that in Example A8 step 2 from 3-bromo-5-isopropoxyaniline.

Step 4: 3-bromo-5-isopropoxy-N-methylbenzenesulfonamide

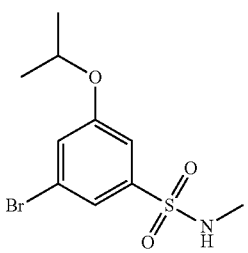 [SMILES: CNS(=O)(=O)c1cc(Br)cc(OC(C)C)c1]

The title compound (584 mg, 24%) was prepared in a manner similar to that in Example A8 step 3 from 3-bromo-5-isopropoxybenzenesulfonyl chloride. LCMS (M+H)⁺= 308, 310.

Step 5: 3-isopropoxy-N-methyl-5-(4,4,5,5-tetramethyl-1,3,2-dioxaborolan-2-yl)benzenesulfonamide

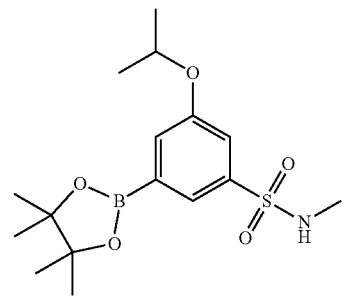

The title compound (600 mg, 96%) was prepared in a manner similar to that in Example A1 step 6 from 3-bromo-5-isopropoxy-N-methylbenzenesulfonamide and BPD. LC-MS (M+H)+=356.2.

Step 6: 3-(5-amino-6-((1-(1-methylpiperidin-4-yl)-1H-pyrazol-4-yl)oxy)pyrazin-2-yl)-5-isopropoxy-N-methylbenzenesulfonamide; formic acid Example A16 (20 mg, 37%) was prepared in a manner similar to that in Example A1 step 7 from 3-isopropoxy-N-methyl-5-(4,4,5,5-tetramethyl-1,3,2-dioxaborolan-2-yl)benzenesulfonamide and 5-bromo-3-((1-(1-methylpiperidin-4-yl)-1H-pyrazol-4-yl)oxy)pyrazin-2-amine. ¹H NMR (400 MHz, DMSO-d6) 8.33 (s, 1H), 8.17 (s, 1H), 8.09 (s, 1H), 7.77 (s, 1H), 7.58 (d, J=4.4 Hz, 2H), 7.45 (s, 1H), 7.14 (s, 1H), 6.92 (s, 2H), 4.78-4.64 (m, 1H), 4.15-4.05 (s, 1H), 2.95-2.85 (m, 2H), 2.43 (d, J=4.8 Hz, 3H), 2.23 (s, 3H), 2.13-1.96 (m, 6H), 1.31 (d, J=6.0 Hz, 6H). LCMS (M+H)⁺= 502.4.

Example A17

5-(5-amino-6-((1-(1-methylpiperidin-4-yl)-1H-pyrazol-4-yl)oxy)pyrazin-2-yl)-N-(2-(dimethylamino)ethyl)-2,3-dimethylbenzamide

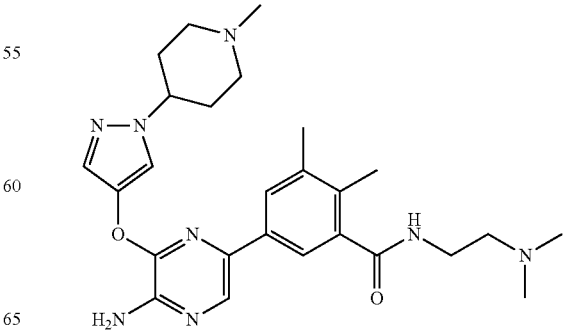

Step 1: 5-bromo-N-(2-(dimethylamino)ethyl)-2,3-dimethylbenzamide

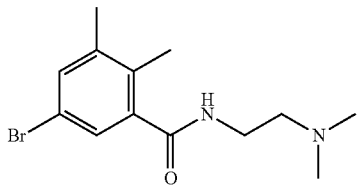 [SMILES: Cc1cc(Br)cc(C(=O)NCCN(C)C)c1C]

The title compound (400 mg, 89%) was prepared in a manner similar to that in Example A3 step 1 from 5-bromo-2,3-dimethylbenzoic acid and (2-aminoethyl)dimethylamine. LC-MS (M+H)$^+$=301.2.

Step 2: N-(2-(dimethylamino)ethyl)-2,3-dimethyl-5-(4,4,5,5-tetramethyl-1,3,2-dioxaborolan-2-yl)benzamide

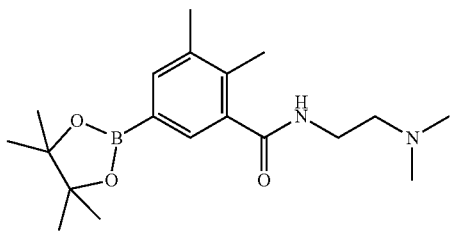

The title compound (185 mg, 47%) was prepared in a manner similar to that in Example A1 step 6 from 5-bromo-N-(2-(dimethylamino)ethyl)-2,3-dimethylbenzamide and BPD. LC-MS (M+H)$^+$=347.2.

Step 3: 5-(5-amino-6-((1-(1-methylpiperidin-4-yl)-1H-pyrazol-4-yl)oxy)pyrazin-2-yl)-N-(2-(dimethylamino)ethyl)-2,3-dimethylbenzamide Example A17 (26 mg, 21%) was prepared in a manner similar to that in Example A1 step 7 from 5-bromo-3-((1-(1-methylpiperidin-4-yl)-1H-pyrazol-4-yl)oxy)pyrazin-2-amine and N-(2-(dimethylamino)ethyl)-2,3-dimethyl-5-(4,4,5,5-tetramethyl-1,3,2-dioxaborolan-2-yl)benzamide. $^1$H NMR (400 MHz, DMSO-d6) δ 8.27-8.19 (m, 2H), 8.09 (s, 1H), 7.69 (s, 1H), 7.60 (s, 1H), 7.55 (s, 1H), 6.70 (s, 2H), 4.19-4.07 (m, 1H), 3.39-3.27 (m, 4H), 2.96-2.87 (m, 2H), 2.30-2.23 (m, 12H), 2.20 (s, 3H), 2.19-2.05 (m, 2H), 2.08-1.93 (m, 4H). LC-MS (M+H)$^+$=493.4.

Example A18

5-(5-amino-6-((1-(1-methylpiperidin-4-yl)-1H-pyrazol-4-yl)oxy)pyrazin-2-yl)-3-fluoro-N,2-dimethylbenzenesulfonamide

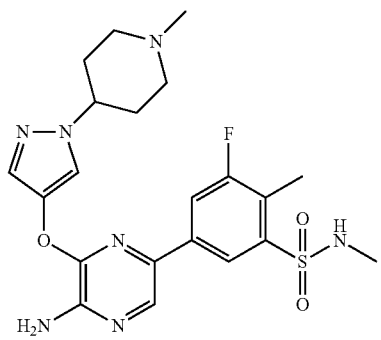 [SMILES: CNS(=O)(=O)c1cc(-c2cnc(N)c(Oc3cnn(C4CCN(C)CC4)c3)n2)cc(F)c1C]

Step 1: 5-bromo-3-fluoro-2-methylaniline

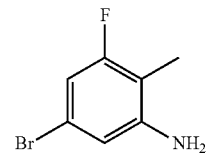

5-bromo-1-fluoro-2-methyl-3-nitrobenzene (9.96 g, 42.6 mmol) and iron powder (11.9 g, 213 mmol) was added to a mixture of concentrated HCl (10 mL), ethanol (100 mL) and water (2 mL). The mixture was heated to reflux for 1h, then cooled to room temperature. The mixture was filtered and the filtrate was concentrated under reduced pressure. The crude was partitioned between water (50 mL) and EtOAc (50 mL). The organic was separated, dried over Na$_2$SO$_4$ and filtered. The filtrate was concentrated under reduced pressure and the crude was purified by silica gel chromatography (PE/EtOAc=10:1) to give the title compound (3.5 g, 40%). LC-MS (M+H)$^+$=203.9, 205.9.

Step 2: 5-bromo-3-fluoro-N,2-dimethylbenzenesulfonamide

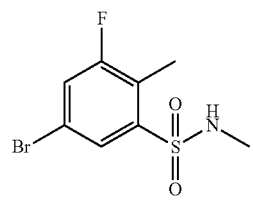

The title compound (1.0 g, 36%) was prepared in a manner similar to that in Example A2 step 1 and step 2 from 5-bromo-3-fluoro-2-methylaniline. LC-MS (M+H)$^+$=281.9 283.9.

Step 3: 3-fluoro-N,2-dimethyl-5-(4,4,5,5-tetramethyl-1,3,2-dioxaborolan-2-yl)benzenesulfonamide

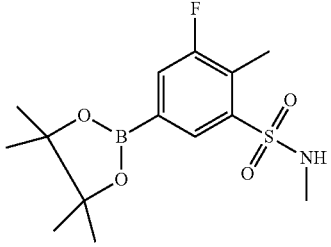

The title compound (400 mg, 100%) was prepared in a manner similar to that in Example A1 step 6 from 5-bromo-3-fluoro-N,2-dimethylbenzenesulfonamide and BPD. LC-MS (M+H)+=330.1.

Step 4: 5-(5-amino-6-((I-(1-methylpiperidin-4-yl)-H-pyrazol-4-yl)oxy)pyrazin-2-yl)-3-fluoro-N,2-dimethylbenzenesulfonamide Example A18 (70 mg, 26%) was prepared in a manner similar to that in Example A1 step 7 from 5-bromo-3-((I-(1-methylpiperidin-4-yl)-1H-pyrazol-4-yl)oxy)pyrazin-2-amine and 3-fluoro-N,2-dimethyl-5-(4,4,5,5-tetramethyl-1,3,2-dioxaborolan-2-yl)benzenesulfonamide. $^1$H NMR (400 MHz, DMSO-d6) δ 8.35 (s, 1H), 8.12 (s, 1H), 8.08 (s, 1H), 7.91 (d, J=10.9 Hz, 1H), 7.68 (s, 1H), 7.61 (s, 1H), 6.96 (s, 2H), 4.10 (dd, J=9.8, 4.8 Hz, 1H), 2.86 (d, J=10.4 Hz, 2H), 2.47 (s, 3H), 2.45 (s, 3H), 2.21 (s, 3H), 2.09-1.94 (m, 6H). LC-MS (M+H)=476.1.

Example A19

N-(4-(5-amino-6-((1-(1-methylpiperidin-4-yl)-1H-pyrazol-4-yl)oxy)pyrazin-2-yl)-2,6-dimethylbenzyl)methanesulfonamide

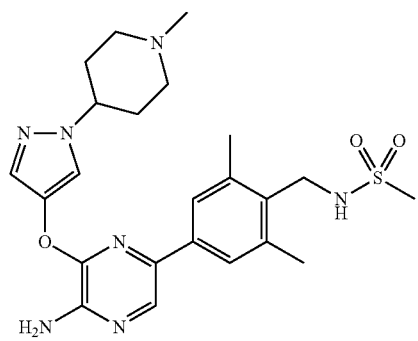 [SMILES: Cc1cc(-c2cnc(N)c(Oc3cnn(C4CCN(C)CC4)c3)n2)cc(C)c1CNS(C)(=O)=O]

Step 1:
1-(4-bromo-2,6-dimethylphenyl)methanamine

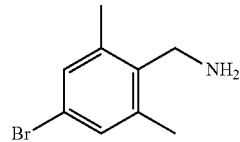

At 0° C., to a solution of 4-bromo-2,6-dimethylbenzonitrile (900 mg, 4.07 mmol) in THF (20 mL) was added BH$_3$-THF (1 M, 20 mL, 20 mmol) under nitrogen. The resulting mixture was stirred for 16 h at 80° C. under nitrogen atmosphere. The mixture was cooled to 0° C. and quenched by the addition of MeOH (5 mL) and ice water (5 mL). The mixture was then warmed to 70° C. and stirred for 2 h. The mixture was concentrated under reduced pressure and the residue was purified by silica gel chromatography (MeOH in DCM from 0% to 13% gradient) to give the title compound (868 mg, 99%). LC-MS (M+H)+=214.

Step 2:
N-(4-bromo-2,6-dimethylbenzyl)methanesulfonamide

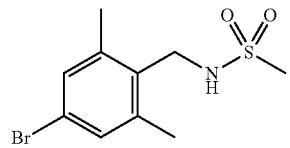

The title compound (504 mg, 85%) was prepared in a manner similar to that in Example A1 step 2 from 1-(4-bromo-2,6-dimethylphenyl)methanamine. LC-MS (M+H)+=292.0.

Step 3: N-(2,6-dimethyl-4-(4,4,5,5-tetramethyl-1,3,2-dioxaborolan-2-yl)benzyl)methanesulfonamide

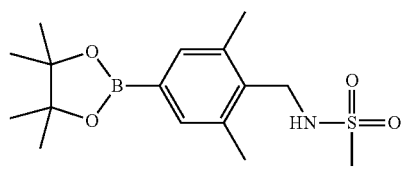 [SMILES: Cc1cc(B2OC(C)(C)C(C)(C)O2)cc(C)c1CNS(C)(=O)=O]

The title compound (418 mg, 80%) was prepared in a manner similar to that in Example A1 step 6 from N-(4-bromo-2,6-dimethylbenzyl)methanesulfonamide and BPD. LC-MS (M+NH$_4$)=357.2.

Step 4; N-(4-(5-amino-6-((1-(1-methylpiperidin-4-yl)-1H-pyrazol-4-yl)oxy)pyrazin-2-yl)-2,6-dimethylbenzyl)methanesulfonamide Example A19 (25 mg, 13%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)methanesulfonamide. $^1$H NMR (400 MHz, DMSO-d6) δ 8.22 (s, 1H), 8.10 (s, 1H), 7.57 (s, 1H), 7.49 (s, 2H), 7.08-6.99 (m, 1H), 6.70 (s, 2H), 4.18-4.04 (m, 3H), 2.93 (s, 3H), 2.89-2.79 (m, 2H), 2.36 (s, 6H), 2.19 (s, 3H), 2.11-1.89 (m, 6H). LC-MS (M+H)+=486.1.

Example A20

N-(1-(3-(5-amino-6-((1-(1-methylpiperidin-4-yl)-1H-pyrazol-4-yl)oxy)pyrazin-2-yl)-5-methylphenyl)cyclopropyl)benzenesulfonamide

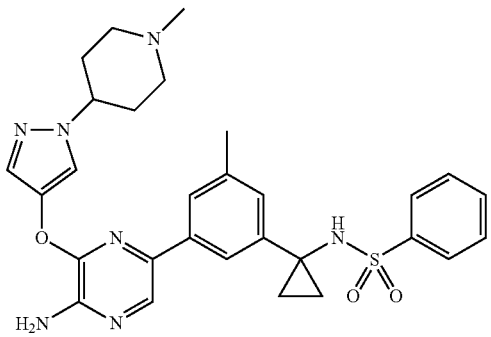 [SMILES: Cc1cc(-c2cnc(N)c(Oc3cnn(C4CCN(C)CC4)c3)n2)cc(C2(NS(=O)(=O)c3ccccc3)CC2)c1]

Step 1: tert-butyl (1-(3-bromo-5-methylphenyl)cyclopropyl)carbamate

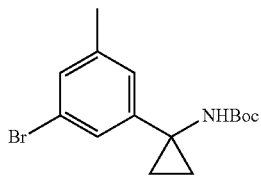 [SMILES: Cc1cc(Br)cc(C2(NC(=O)OC(C)(C)C)CC2)c1]

To a stirred solution of 1-(3-bromo-5-methylphenyl)cyclopropan-1-amine (1.50 g, 6.30 mmol) and triethylamine (2.77 mL, 27.3 mmol) in DCM (15 mL) was added Boc₂O (1.85 mL, 8.45 mmol) in portions at 0° C. The mixture was warmed to room temperature and stirred for 3 h, then diluted with water (60 mL). The mixture was extracted with DCM (60 mL×3). The combined organic layer was washed with brine, dried over Na₂SO₄ and filtered. The filtrate was concentrated under reduced pressure to give the title compound (1.53 g, 75%).

Step 2: tert-butyl (1-(3-methyl-5-(4,4,5,5-tetramethyl-1,3,2-dioxaborolan-2-vl)phenyl)cyclopropyl)carbamate

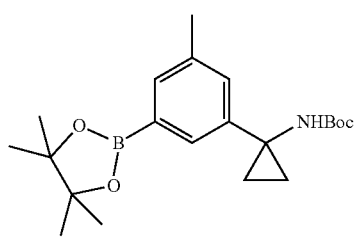 [SMILES: Cc1cc(B2OC(C)(C)C(C)(C)O2)cc(C2(NC(=O)OC(C)(C)C)CC2)c1]

The title compound (1.55 g, 94%) was prepared in a manner similar to that in Example A1 step 6 from tert-butyl (1-(3-bromo-5-methylphenyl)cyclopropyl)carbamate and BPD. LC-MS (M-t-Bu)+=318.2.

Step 3: tert-butyl (1-(3-(5-amino-6-((1-(1-methylpiperidin-4-yl)-1H-pyrazol-4-yl)oxy)pyrazin-2-yl)-5-methylphenyl)cyclopropyl)carbamate

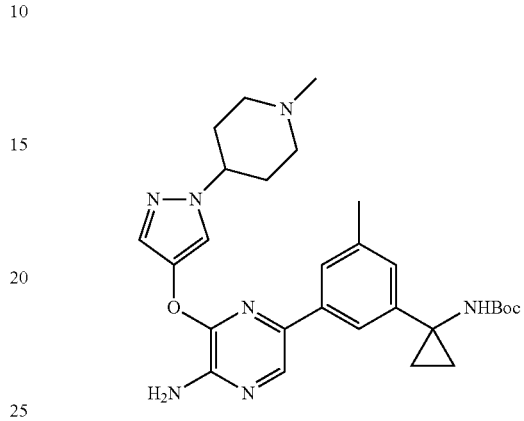

The title compound (688 mg, 81%) was prepared in a manner similar to that in Example A1 step 7 from 5-bromo-3-((1-(1-methylpiperidin-4-yl)-1H-pyrazol-4-yl)oxy)pyrazin-2-amine and tert-butyl (1-(3-methyl-5-(4,4,5,5-tetramethyl-1,3,2-dioxaborolan-2-yl)phenyl)cyclopropyl)carbamate. LC-MS (M+H)+=520.3.

Step 4: 5-(3-(1-aminocyclopropyl)-5-methylphenyl)-3-((1-(1-methylpiperidin-4-yl)-1H-pyrazol-4-yl)oxy)pyrazin-2-amine

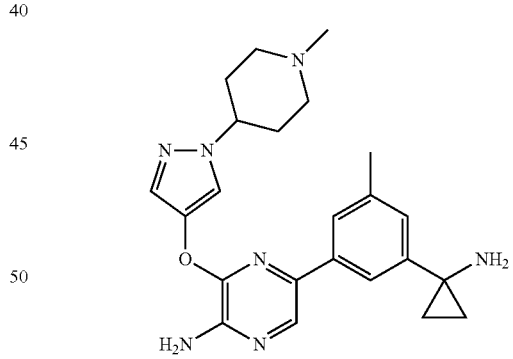

To a stirred solution of tert-butyl (1-(3-(5-amino-6-((1-(1-methylpiperidin-4-yl)-1H-pyrazol-4-yl)oxy)pyrazin-2-yl)-5-methylphenyl)cyclopropyl)carbamate (688 mg, 1.33 mmol) in MeOH (20 mL) was added HCl in MeOH (3 M, 4 mL, 12 mmol) dropwise at room temperature. After 2 h, the mixture was concentrated under vacuum. The residue was partitioned between saturated NaHCO₃ (30 mL) and DCM (30 mL). The organic layer was separated, dried over Na₂SO₄ and filtered. The filtrate was concentrated under reduced pressure and residue was purified by silica gel chromatography (DCM/MeOH=10:1) to give the title compound (450 mg, 81%). LC-MS (M+H)+=420.2.

Step 5: N-(1-(3-(5-amino-6-((1-(1-methylpiperidin-4-yl)-1H-pyrazol-4-yl)oxy)pyrazin-2-yl)-5-methylphenyl)cyclopropyl)benzenesulfonamide To a solution of 5-(3-(1-aminocyclopropyl)-5-methylphenyl)-3-((1-(1-methylpiperidin-4-yl)-1H-pyrazol-4-yl)oxy)pyrazin-2-amine (77 mg, 0.185 mmol) in pyridine (5 mL) was added benzenesulfonyl chloride (137 mg, 0.74 mmol) at room temperature under nitrogen. After 4 h, the mixture was concentrated under reduced pressure and the crude was purified by prep-HPLC (7.0 mg, 7%) to give Example A20. $^1$H NMR (400 MHz, DMSO-d6) δ 8.70 (br s, 1H), 8.15 (s, 1H), 8.08 (s, 1H), 7.59 (s, 1H), 7.57-7.51 (m, 2H), 7.43-7.27 (m, 5H), 6.84 (s, 1H), 6.70 (s, 2H), 4.22-4.09 (m, 1H), 2.90-2.83 (m, 2H), 2.19 (s, 3H), 2.14 (s, 3H), 2.10-1.94 (m, 6H), 1.17-1.11 (m, 2H), 1.06-1.00 (m, 2H). LC-MS (M+H)$^+$= 560.2.

Example A21

4-(5-amino-6-((1-(1-methylpiperidin-4-yl)-1H-pyrazol-4-yl)oxy)pyrazin-2-yl)-N-methoxy-2,6-dimethylbenzamide

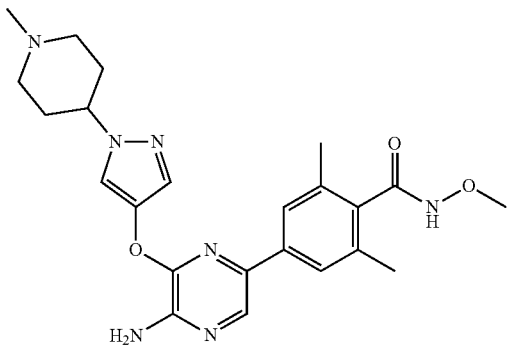

A solution of 4-(5-amino-6-((1-(1-methylpiperidin-4-yl)-1H-pyrazol-4-yl)oxy)pyrazin-2-yl)-2,6-dimethylbenzoic acid (240 mg, 0.568 mmol), O-methylhydroxylamine hydrochloride (71 mg, 0.852 mmol), HATU (324 mg, 0.852 mmol) and DIPEA (220 mg, 1.70 mmol) in DMF (10 mL) was stirred at room temperature overnight. The mixture was concentrated in vacuo and the crude was purified by silica gel chromatography to give Example A21 (20 mg, 8%). $^1$H NMR (400 MHz, DMSO-d6) δ 11.39 (s, 1H), 8.26 (s, 1H), 8.11 (s, 1H), 7.59 (s, 1H), 7.53 (s, 2H), 6.77 (s, 2H), 4.13 (s, 1H), 3.73 (s, 3H), 2.85 (d, J=10.6 Hz, 2H), 2.26 (s, 6H), 2.20 (s, 3H), 2.09-1.96 (m, 6H). LC-MS (M+H)$^+$=452.0.

Example A22

3-(5-amino-6-((1-(1-methylpiperidin-4-yl)-1H-pyrazol-4-yl)oxy)pyrazin-2-yl)-N-methyl-5-(methylamino)benzenesulfonamide

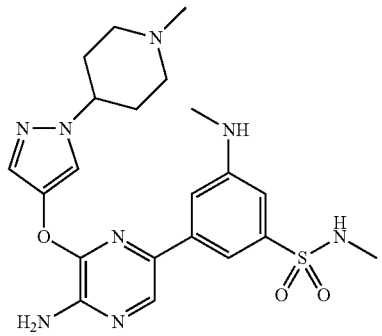 [SMILES: CNc1cc(-c2cnc(N)c(Oc3cnn(C4CCN(C)CC4)c3)n2)cc(S(=O)(=O)NC)c1]

Step 1: 3-bromo-N-methyl-5-nitroaniline

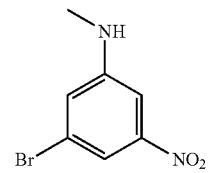

To mixture of 1-bromo-3-fluoro-5-nitrobenzene (4.0 g, 17.3 mmol) and methylamine hydrochloride (2.33 g, 34.5 mmol) in DMAC (30 mL) was added Cs$_2$CO$_3$ (6.0 g, 17.5 mmol) at room temperature. The mixture was warmed to 80° C., stirred for 2 h then cooled to room temperature. The mixture was extracted with EtOAc (100 mL×3). The combined organic layer was washed with brine (20 mL×3), dried over anhydrous Na$_2$SO$_4$ and filtered. The filtrate was concentrated under reduced pressure and the residue was purified by silica gel column chromatography (PE/EtOAc=5:1) to give the title compound (3.72 g, 93%). LC-MS (M+H)$^+$= 231.0.

Step 2: 5-bromo-N$^1$-methylbenzene-1,3-diamine

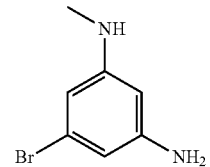

The title compound (3.0 g, 93%) was prepared in a manner similar to that in Example A8 step 1 from 3-bromo-N-methyl-5-nitroaniline. LC-MS (M+H)+=201.1.

Step 3: 3-bromo-5-(methylamino)benzenesulfonyl chloride

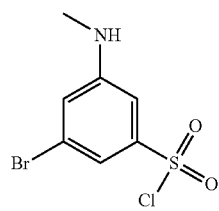

The title compound (562 mg, 40%) was prepared in a manner similar to that in Example A8 step 2 from 5-bromo-$N^1$-methylbenzene-1,3-diamine. LC-MS (M+H)$^+$=283.9.

Step 4: 3-bromo-N-methyl-5-(methylamino)benzenesulfonamide

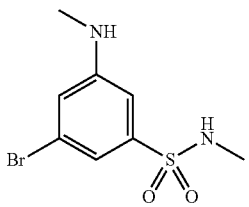

The title compound (200 mg, 36%) was prepared in a manner similar to that in Example A8 step 3 from 3-bromo-5-(methylamino)benzenesulfonyl chloride. LC-MS (M+H)$^+$=278.9.

Step 5: N-methyl-3-(methylamino)-5-(4,4,5,5-tetramethyl-1,3,2-dioxaborolan-2-yl)benzenesulfonamide

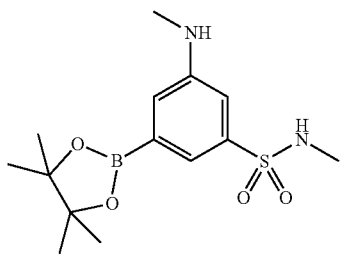

The title compound (110 mg, 94%) was prepared in a manner similar to that in Example A1 step 6 from 3-bromo-N-methyl-5-(methylamino)benzenesulfonamide and BPD. LC-MS (M+H)$^+$=327.2.

Step 6: 33-(5-amino-6-((1-(1-methylpiperidin-4-yl)-1H-pyrazol-4-yl)oxy)pyrazin-2-yl)-N-methyl-5-(methylamino)benzenesulfonamide Example A22 (8 mg, 8%) was prepared in a manner similar to that in Example A1 step 7 from 5-bromo-3-((1-(1-methylpiperidin-4-yl)-1H-pyrazol-4-yl)oxy)pyrazin-2-amine and N-methyl-3-(methylamino)-5-(4,4,5,5-tetramethyl-1,3,2-dioxaborolan-2-yl)benzenesulfonamide. $^1$H NMR (400 MHz, DMSO-d6) δ 8.20 (s, 1H), 8.08 (s, 1H), 7.62 (s, 1H), 7.40-7.34 (m, 1H), 7.33-7.27 (m, 1H), 7.19-7.15 (m, 1H), 6.88-6.84 (m, 1H), 6.82 (s, 2H), 6.26-6.19 (m, 1H), 4.15-4.03 (m, 1H), 2.90-2.80 (m, 2H), 2.75 (d, J=4.9 Hz, 3H), 2.42 (d, J=4.9 Hz, 3H), 2.20 (s, 3H), 2.10-1.88 (m, 6H). LC-MS (M+H)$^+$=473.0.

Example A23

3-(5-amino-6-((1-(1-methylpiperidin-4-yl)-1H-pyrazol-4-yl)oxy)pyrazin-2-yl)-N-methyl-5-(pyrrolidin-1-yl)benzenesulfonamide

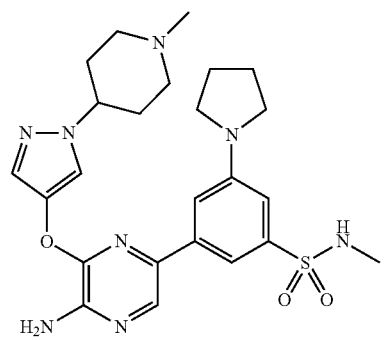 [SMILES: CNS(=O)(=O)c1cc(-c2cnc(N)c(Oc3cnn(C4CCN(C)CC4)c3)n2)cc(N2CCCC2)c1]

Step 1: 1-(3-bromo-5-nitrophenyl)pyrrolidine

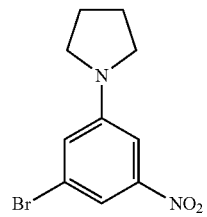 [SMILES: O=[N+]([O-])c1cc(Br)cc(N2CCCC2)c1]

The title compound (4.37 g, 93%) was prepared in a manner similar to that in Example A22 step 1 from 1-bromo-3-fluoro-5-nitrobenzene and pyrrolidine. LC-MS (M+H)$^+$=271.1.

Step 2: 3-bromo-5-(pyrrolidin-1-yl)aniline

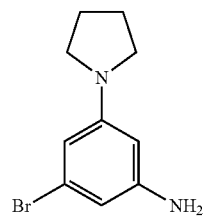

The title compound (3.18 g, 82%) was prepared in a manner similar to that in Example A8 step 1 from 1-(3-bromo-5-nitrophenyl)pyrrolidine. LC-MS (M+H)$^+$=241.1.

Step 3: 3-bromo-5-(pyrrolidin-1-yl)benzenesulfonyl chloride

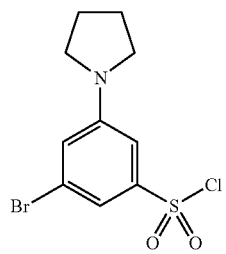 [SMILES: O=S(=O)(Cl)c1cc(Br)cc(N2CCCC2)c1]

The title compound (208 mg, 24%) was prepared in a manner similar to that in Example A8 step 2 from 3-bromo-5-(pyrrolidin-1-yl)aniline. LC-MS (M+H)$^+$=323.9.

Step 4: 3-bromo-N-methyl-5-(pyrrolidin-1-yl)benzenesulfonamide

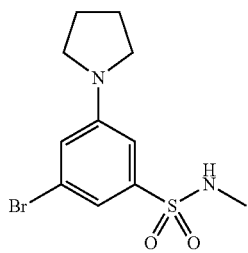 [SMILES: CNS(=O)(=O)c1cc(Br)cc(N2CCCC2)c1]

The title compound (145 mg, 88%) was prepared in a manner similar to that in Example A8 step 3 from 3-bromo-5-(pyrrolidin-1-yl)benzenesulfonyl chloride. LC-MS (M+H)$^+$=319.0.

Step 5: N-methyl-3-(pyrrolidin-1-yl)-5-(4,4,5,5-tetramethyl-1,3,2-dioxaborolan-2-yl)benzenesulfonamide

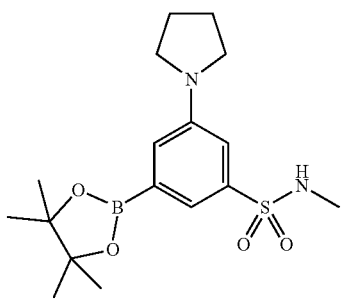

The title compound (149 mg, 89%) was prepared in a manner similar to that in Example A1 step 6 from 3-bromo-N-methyl-5-(pyrrolidin-1-yl)benzenesulfonamide and BPD. LC-MS (M+H)$^+$=367.3.

Step 6: 3-(5-amino-6-((1-(1-methylpiperidin-4-yl)-1H-pyrazol-4-yl)oxy)pyrazin-2-yl)-N-methyl-5-(pyrrolidin-1-yl)benzenesulfonamide Example A23 (6 mg, 6%) was prepared in a manner similar to that in Example A1 step 7 from 5-bromo-3-((1-(1-methylpiperidin-4-yl)-1H-pyrazol-4-yl)oxy)pyrazin-2-amine and N-methyl-3-(pyrrolidin-1-yl)-5-(4,4,5,5-tetramethyl-1,3,2-dioxaborolan-2-yl)benzenesulfonamide. $^1$H NMR (400 MHz, DMSO-d6) δ 8.27 (s, 1H), 8.12 (s, 1H), 7.59 (s, 1H), 7.43 (s, 1H), 7.35-7.30 (m, 1H), 7.21-7.16 (m, 1H), 6.84 (s, 2H), 6.80-6.77 (m, 1H), 4.15-4.03 (m, 1H), 3.33-3.27 (m, 4H), 2.91-2.83 (m, 2H), 2.42 (d, J=5.0 Hz, 3H), 2.21 (s, 3H), 2.10-1.90 (m, 10H). LC-MS (M+H)$^+$=513.3.

Example A24

3-(5-amino-6-((1-(1-cyclopropylpiperidin-4-yl)-1H-pyrazol-4-yl)oxy)pyrazin-2-yl)-N,5-dimethylbenzenesulfonamide

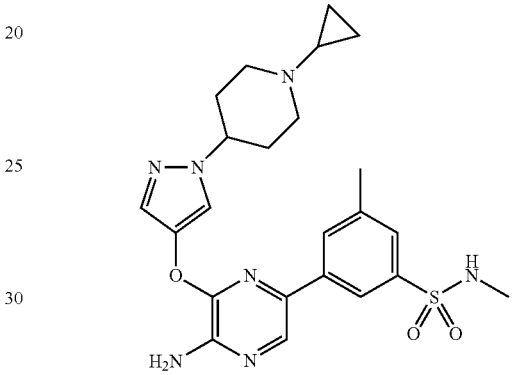

Step 1: 5-bromo-3-((1-(1-cyclopropylpiperidin-4-yl)-1H-pyrazol-4-yl)oxy)pyrazin-2-amine

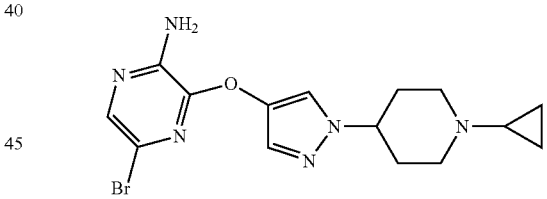

To a stirred solution of 5-bromo-3-((1-(piperidin-4-yl)-1H-pyrazol-4-yl)oxy)pyrazin-2-amine (100 mg, 0.286 mmol) and (1-ethoxycyclopropoxy)trimethylsilane (105 mg, 0.572 mmol) in MeOH (2 mL) and THF (2.00 mL) was added AcOH (0.30 mL) and NaBH$_3$CN (57 mg, 0.86 mmol) at room temperature and the mixture was heated to 60° C. under nitrogen for overnight. The mixture was cooled to room temperature and concentrated under reduced pressure. The residue was purified by silica gel chromatography (DCM/MeOH=6:1) to give the title compound (70 mg, 60%). LC-MS (M+H)$^+$=381.0.

Step 2: 3-(5-amino-6-((1-(1-cyclopropylpiperidin-4-yl)-1H-pyrazol-4-yl)oxy)pyrazin-2-yl)-N,5-dimethylbenzenesulfonamide Example A24 (27 mg, 26%) was prepared in a manner similar to that in Example A1 step 7 from 5-bromo-3-((1-(1-cyclopropylpiperidin-4-yl)-1H-pyrazol-4-yl)oxy)

pyrazin-2-amine and N,3-dimethyl-5-(4,4,5,5-tetramethyl-1,3,2-dioxaborolan-2-yl)benzenesulfonamide. $^1$H NMR (300 MHz, DMSO-4) δ8.31 (s, 1H), 8.11 (s, 1H), 8.00 (s, 1H), 7.93 (s, 1H), 7.57 (s, 1H), 7.49 (s, 1H), 7.41-7.30 (m, 1H), 6.87 (s, 2H), 4.24-4.08 (m, 1H), 3.10-2.95 (m, 2H), 2.46-2.26 (m, 8H), 2.10-1.99 (m, 2H), 1.98-1.80 (m, 2H), 1.66 (s, 1H), 0.48-0.26 (m, 4H). LC-MS (M+H)$^+$=484.2.

Example A25

N-(1-(3-(5-amino-6-((1-(1-methylpiperidin-4-yl)-H-pyrazol-4-yl)oxy)pyrazin-2-yl)-5-methylphenyl)cyclopropyl)-2,2,2-trifluoroethane-1-sulfonamide

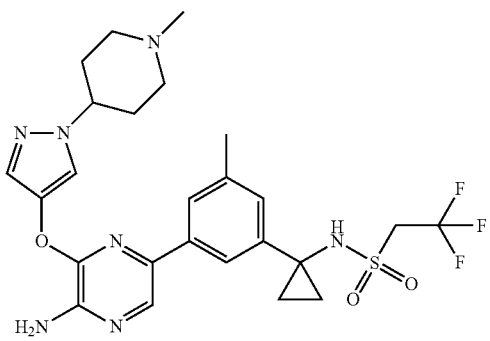 [SMILES: Cc1cc(-c2cnc(N)c(Oc3cnn(C4CCN(C)CC4)c3)n2)cc(C2(NS(=O)(=O)CC(F)(F)F)CC2)c1]

Example A25 (32 mg, 26%) was prepared in a manner similar to that in Example A20 step from 5-(3-(1-aminocyclopropyl)-5-methylphenyl)-3-((1-(1-methylpiperidin-4-yl)-1H-pyrazol-4-yl)oxy)pyrazin-2-amine and 2,2,2-trifluoroethanesulfonyl chloride. $^1$H NMR (300 MHz, DMSO-d$_6$) δ 8.92 (s, 1H), 8.23 (s, 1H), 8.16 (s, 1H), 7.62 (s, 1H), 7.59 (s, 1H), 7.53 (s, 1H), 7.15 (s, 1H), 6.75 (s, 2H), 4.23-4.07 (m, 1H), 4.07-3.89 (m, 2H), 2.95-2.81 (m, 2H), 2.33 (s, 3H), 2.22 (s, 3H), 2.15-1.94 (m, 6H), 1.39-1.29 (m, 2H), 1.28-1.13 (m, 2H). LC-MS (M+H)=566.3.

Example A26

1-(4-(5-amino-6-((1-(1-methylpiperidin-4-yl)-1H-pyrazol-4-yl)oxy)pyrazin-2-yl)-2,6-dimethylbenzyl)-3-methylurea

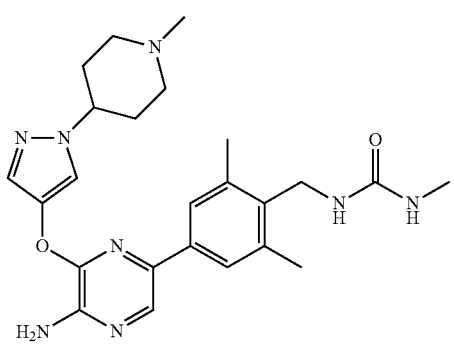 [SMILES: CNC(=O)NCc1c(C)cc(-c2cnc(N)c(Oc3cnn(C4CCN(C)CC4)c3)n2)cc1C]

Step 1:
1-(4-bromo-2,6-dimethylbenzyl)-3-methylurea

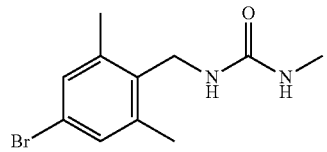

To a stirred solution of 1-(4-bromo-2,6-dimethylphenyl)methanamine (100 mg, 0.451 mmol) in DCM (20 mL) was added triethylamine (0.13 mL, 0.902 mmol) and triphosgene (45 mg, 0.144 mmol) at 0° C.. After 3 h, methylamine in THF (2 M, 0.45 mL, 0.90 mmol) was added. The mixture was warmed to room temperature and stirred for overnight. The resulting mixture was diluted with water (20 mL) and extracted with DCM (20 mL×3). Combined organic layer was dried over anhydrous Na$_2$SO$_4$ and filtered. The filtrate was concentrated under reduced pressure and the residue was purified by silica gel chromatography (DCM/MeOH=8:1) to give the title compound (55 mg, 45%). LC-MS (M+H)$^+$=271.1.

Step 2: 1-(2,6-dimethyl-4-(4,4,5,5-tetramethyl-1,3,2-dioxaborolan-2-yl)benzyl)-3-methylurea

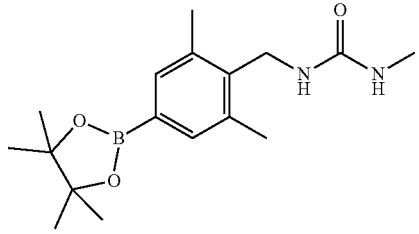

The title compound (44 mg, 68%) was prepared in a manner similar to that in Example A1 step 6 from 1-(4-bromo-2,6-dimethylbenzyl)-3-methylurea and BPD. LC-MS (M+H)=319.3.

Step 3: 1-(4-(5-amino-6-((1-(1-methylpiperidin-4-yl)-1H-pyrazol-4-yl)oxy)pyrazin-2-yl)-2,6-dimethylbenzyl)-3-methylurea Example A26 (11 mg, 20%) was prepared in a manner similar to that in Example A1 step 7 from 5-bromo-3-((1-(1-methylpiperidin-4-yl)-1H-pyrazol-4-yl)oxy)pyrazin-2-amine and 1-(2,6-dimethyl-4-(4,4,5,5-tetramethyl-1,3,2-dioxaborolan-2-yl)benzyl)-3-methylurea. $^1$H NMR (300 MHz, DMSO-d6) δ 8.19 (s, 1H), 8.10 (s, 1H), 7.57 (s, 1H), 7.46 (s, 2H), 6.66 (s, 2H), 5.96-5.83 (m, 1H), 5.60-5.49 (m, 1H), 4.21-4.03 (m, 3H), 2.92-2.79 (m, 2H), 2.53 (d, J=4.6 Hz, 3H), 2.32 (s, 6H), 2.19 (s, 3H), 2.12-1.97 (m, 6H). LC-MS (M+H)$^+$=465.2.

Example A27

3-(5-amino-6-((1-(1-ethylpiperidin-4-yl)-1H-pyrazol-4-yl)oxy)pyrazin-2-yl)-N,5-dimethylbenzenesulfonamide

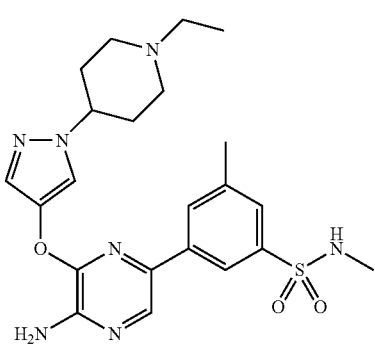 [SMILES: CCN1CCC(n2cc(Oc3nc(-c4cc(C)cc(S(=O)(=O)NC)c4)cnc3N)cn2)CC1]

Step 1: 3-(5-amino-6-((1-(piperidin-4-yl)-1H-pyrazol-4-yl)oxy)pyrazin-2-yl)-N,5-dimethylbenzenesulfonamide The title compound (2.0 g, 99%) was prepared in a manner similar to that in Example A1 step 7 from N,3-dimethyl-5-(4,4,5,5-tetramethyl-1,3,2-dioxaborolan-2-yl)benzenesulfonamide and 5-bromo-3-((1-(piperidin-4-yl)-1H-pyrazol-4-yl)oxy)pyrazin-2-amine. LC-MS (M+H)$^+$= 444.1.

Step 2: 3-(5-amino-6-((1-(1-ethylpiperidin-4-yl)-1H-pyrazol-4-yl)oxy)pyrazin-2-yl)-N,5-dimethylbenzenesulfonamide To a solution of 3-(5-amino-6-((1-(piperidin-4-yl)-1H-pyrazol-4-yl)oxy)pyrazin-2-yl)-N,5-dimethylbenzenesulfonamide (400 mg, 0.898 mmol) and acetaldehyde (200 mg, 4.49 mmol) in DCM (3 mL) was added AcOH (55 mg, 0.898 mmol) at 0° C. The mixture was stirred for 1.5 h at 0° C. under nitrogen, then NaBH$_3$CN (114 mg, 1.80 mmol) was added. After 1 h, the mixture was concentrated and the residue was purified by prep-HPLC to give Example A27 (53 mg, 12%). $^1$H NMR (400 MHz, DMSO-d6) δ 8.32 (s, 1H), 8.12 (s, 1H), 8.02 (s, 1H), 7.94 (s, 1H), 7.59 (s, 1H), 7.49 (s, 1H), 7.46-7.40 (m, 1H), 6.90 (s, 2H), 4.18-4.08 (m, 1H), 3.01-2.90 (m, 2H), 2.45-2.40 (m, 6H), 2.39-2.30 (m, 2H), 2.10-1.92 (m, 6H), 1.02 (t, J=7.2 Hz, 3H). LC-MS (M+H)+=472.1.

Example A28

3-(5-amino-6-((1-(1-(oxetan-3-ylmethyl)piperidin-4-yl)-1H-pyrazol-4-yl)oxy)pyrazin-2-yl)-N, 5-dimethylbenzenesulfonamide

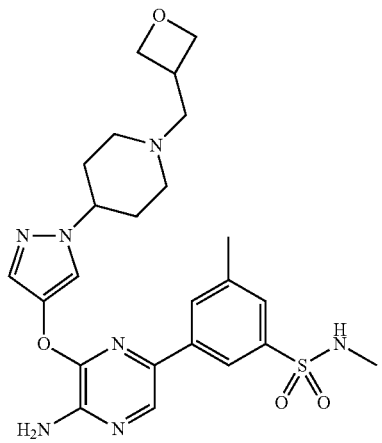 [SMILES: CNS(=O)(=O)c1cc(C)cc(-c2cnc(N)c(Oc3cnn(C4CCN(CC5COC5)CC4)c3)n2)c1]

Example A28 (14 mg, 20%) was prepared in a manner similar to that in Example A27 step 2 from 3-(5-amino-6-((1-(piperidin-4-yl)-1H-pyrazol-4-yl)oxy)pyrazin-2-yl)-N, 5-dimethylbenzenesulfonamide and oxetane-3-carbaldehyde. $^1$H NMR (300 MHz, DMSO-d6) δ 8.30 (s, 1H), 8.10 (s, 1H), 8.01-7.98 (m, 1H), 7.91 (s, 1H), 7.56 (s, 1H), 7.47 (s, 1H), 7.41-7.34 (m, 1H), 6.89 (s, 2H), 4.67-4.57 (m, 2H), 4.25 (t, J=6.1 Hz, 2H), 4.184.02 (m, 1H), 3.23-3.08 (m, 1H), 2.91-2.78 (m, 2H), 2.68-2.60 (m, 2H), 2.44-2.37 (m, 6H), 2.15-1.81 (m, 6H). LC-MS (M+H)$^+$=514.2.

Example A29

4-(4-(5-amino-6-((1-(1-methylpiperidin-4-yl)-1H-pyrazol-4-yl)oxy)pyrazin-2-yl)-2,6-dimethylphenyl)oxazolidin-2-one

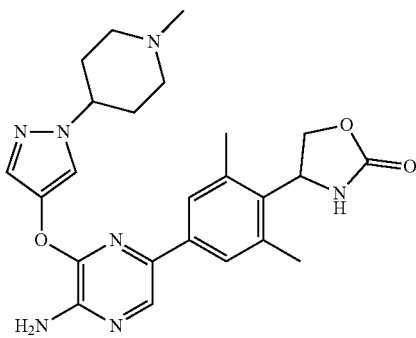 [SMILES: Cc1cc(-c2cnc(N)c(Oc3cnn(C4CCN(C)CC4)c3)n2)cc(C)c1C1COC(=O)N1]

Step 1:
2-amino-2-(4-bromo-2,6-dimethylphenyl)acetonitrile

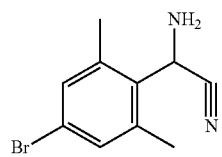

To a solution of 4-bromo-2,6-dimethylbenzaldehyde (5.0 g, 22.3 mmol) in MeOH (20 mL) was added $NH_3$ in MeOH (7 M, 26 mL, 178 mmol) and Ti(Oi-Pr)$_4$ (7.67 g, 25.6 mmol) at room temperature under nitrogen. After 2 h, TMSCN (2.33 g, 22.3 mmol) was added dropwise. After 24 h, iced water (100 mL) was added. The solid was filtered off and the filter cake was rinsed with EtOAc (20 mL×3). The filtrate was extracted with EtOAc (300 mL×3). The combined organic layer was washed with brine (150 mL), dried over $Na_2SO_4$ and filtered. The filtrate was concentrated under reduced pressure and the residue was purified by silica gel chromatography (EtOAc:hexane=3:2) to give the title compound (2.07 g, 39%).

Step 2: amino(4-bromo-2,6-dimethylphenyl)acetic acid hydrochloride

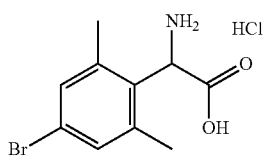

To the 2-amino-2-(4-bromo-2,6-dimethylphenyl)acetonitrile (1.71 g, 7.15 mmol) was added aqueous HCl (6 M, 90 mL) then the mixture was heated to 105° C. for overnight. The mixture was cooled to room temperature, and the solvent was evaporated under reduced pressure to about one third of the original volume. The precipitate was collected by filtration and dried under vacuum to give the title compound (865 mg, 41%). LC-MS (M+H)$^+$=258.1.

Step 3:
2-amino-2-(4-bromo-2,6-dimethylphenyl)ethan-1-ol hydrochloride

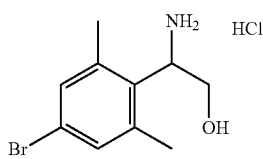

To a solution of LiBH$_4$ in THF (2.5 M, 7.6 mL, 7.540 mmol) was added TMSCl (1.72 g, 15.00 mmol) and amino (4-bromo-2,6-dimethylphenyl)acetic acid hydrochloride (779 mg, 2.65 mmol) at room temperature. After 12 h, the solution was cooled to 0° C. and MeOH (10 mL) and water (100 mL) was carefully added. After 15 min, saturated NaHCO$_3$(100 mL) was carefully added and the mixture was extracted with EtOAc (250 mL×3). The combined organic layer was washed with brine (100 mL), dried over Na$_2$SO$_4$ and filtered. The filtrate was concentrated under reduced pressure and the crude was purified by C18 chromatography (MeOH in 0.1% aqueous HCl) to give the title compound (370 mg, 50%). LC-MS (M+H)$^+$=244.0.

Step 4: 4-(4-bromo-2,6-dimethylphenyl)-1,3-oxazolidin-2-one

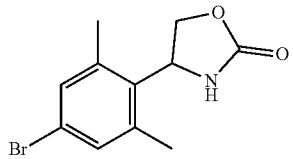

To a solution of 2-amino-2-(4-bromo-2,6-dimethylphenyl)ethan-1-ol hydrochloride (231 mg, 0.83 mmol) and triethylamine (303 mg, 2.85 mmol) in DCM (15 mL) was added triphosgene (148 mg, 0.47 mmol) in DCM (5 mL) dropwise at 0° C. under nitrogen. The mixture was warmed to room temperature and stirred for 3 h. Water (20 mL) was added and the mixture was extracted with DCM (80 mL×3). The combined organic layer was washed with brine (50 mL), dried over Na$_2$SO$_4$ and filtered. The filtrate was concentrated under reduced pressure and the residue was purified by silica gel chromatography (MeOH:DCM=1:9) to give the title compound (131 mg, 51%). LC-MS (M+H)$^+$=270.0.

Step 5: 4-(2,6-dimethyl-4-(4,4,5,5-tetramethyl-1,3,2-dioxaborolan-2-yl)phenyl)oxazolidin-2-one

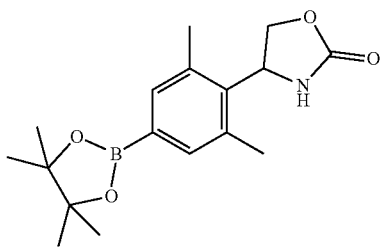 [SMILES: Cc1cc(B2OC(C)(C)C(C)(C)O2)cc(C)c1C1COC(=O)N1]

The compound 5 (125 mg, 94%) was prepared in a manner similar to that in Example A1 step 6 from 4-(4-bromo-2,6-dimethylphenyl)-1,3-oxazolidin-2-one and BPD. LC-MS (M+H)$^+$=318.3.

Step 6: 4-(4-(5-amino-6-((1-(1-methylpiperidin-4-yl)-1H-pyrazol-4-yl)oxy)pyrazin-2-yl)-2,6-dimethylphenyl)oxazolidin-2-one Example A29 (16 mg, 12%) was prepared in a manner similar to that in Example A1 step 7 from 5-bromo-3-((1-(1-methylpiperidin-4-yl)-1H-pyrazol-4-yl)oxy)pyrazin-2-amine and 4-(2,6-dimethyl-4-(4,4,5,5-tetramethyl-1,3,2-dioxaborolan-2-yl)phenyl)oxazolidin-2-one. $^1$H NMR (400 MHz, DMSO-d6) δ 8.25 (s, 1H), 8.12 (s, 1H), 7.96-7.91 (m, 1H), 7.59 (s, 1H), 7.51 (s, 2H), 6.73 (s, 2H), 5.47-5.37 (m, 1H), 4.77-4.68 (m, 1H), 4.20-4.07 (m, 2H), 2.91-2.82 (m, 2H), 2.37 (s, 6H), 2.22 (s, 3H), 2.05-1.91 (m, 6H). LC-MS (M+H)$^+$=464.1.

Example A30

3-(5-amino-6-((1-(1-methylpiperidin-4-yl)-1H-pyrazol-4-yl)oxy)pyrazin-2-yl)-5-(tert-butyl)-N-methylbenzenesulfonamide

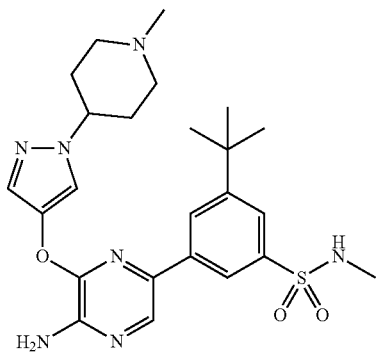 [SMILES: CNS(=O)(=O)c1cc(-c2cnc(N)c(Oc3cnn(C4CCN(C)CC4)c3)n2)cc(C(C)(C)C)c1]

Step 1: 3-bromo-5-tert-butylbenzene-1-sulfonyl chloride

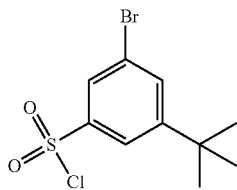

At −78° C., to a solution of 1,3-dibromo-5-tert-butylbenzene (1.00 g, 3.25 mmol) in THF (15 mL) was added n-BuLi in hexanes (2.5 M, 0.2 mL, 3.83 mmol) dropwise under nitrogen. After 30 min, $SO_2$ (g) was bubbled into the mixture for 1 h at the same temperature. The mixture was warmed to room temperature and stirred for overnight then concentrated under vacuum. To the crude was added DCM (15 mL) and NCS (457 mg, 3.25 mmol) at 0° C. The mixture was warmed to room temperature and stirred for 1 h. The mixture was filtered, and the filter cake was washed with DCM (50 mL×3). The filtrate was concentrated under reduced pressure to give the title compound (900 mg, crude).

Step 2: 3-bromo-5-tert-butyl-N-methylbenzenesulfonamide

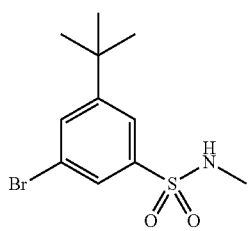 [SMILES: CNS(=O)(=O)c1cc(Br)cc(C(C)(C)C)c1]

The compound 1 (74 mg, 8% for 2 steps) was prepared in a manner similar to that in Example A8 step 3 from 3-bromo-5-tert-butylbenzene-1-sulfonyl chloride. LC-MS $(M+H)^+$=306.0.

Step 3: 3-tert-butyl-N-methyl-5-(4,4,5,5-tetramethyl-1,3,2-dioxaborolan-2-yl)benzenesulfonamide

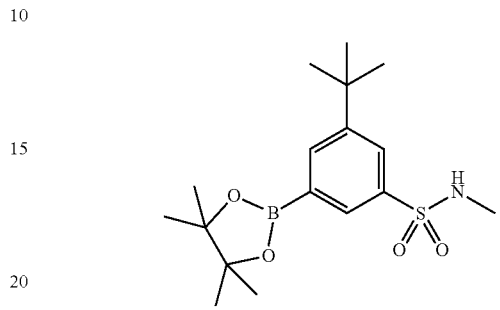

The title compound (67 mg, 79%) was prepared in a manner similar to that in Example A1 step 6 from 3-bromo-5-tert-butyl-N-methylbenzenesulfonamide and BPD. LC-MS (M+H)+=354.2.

Step 4: 3-(5-amino-6-((1-(1-methylpiperidin-4-yl)-1H-pyrazol-4-yl)oxy)pyrazin-2-yl)-5-(tert-butyl)-N-methylbenzenesulfonamide Example A30 (18 mg, 21%) was prepared in a manner similar to that in Example A1 step 7 from 5-bromo-3-((141-methylpiperidin-4-yl)-1H-pyrazol-4-yl)oxy)pyrazin-2-amine and 3-tert-butyl-N-methyl-5-(4,4,5,5-tetramethyl-1,3,2-dioxaborolan-2-yl)benzenesulfonamide. $^1$H NMR (300 MHz, DMSO-d6) δ 8.34 (s, 1H), 8.09 (s, 2H), 8.004-7.99 (m, 1H), 7.68-7.55 (m, 2H), 7.48-7.40 (m, 1H), 6.89 (s, 2H), 4.144.03 (m, 1H), 2.91-2.80 (m, 2H), 2.44-2.37 (m, 3H), 2.20 (s, 3H), 2.10-1.90 (m, 6H), 1.32 (s, 9H). LC-MS $(M+H)^+$=500.3.

Example A31

N-(4-(5-amino-6-((1-(1-methylpiperidin-4-yl)-1H-pyrazol-4-yl)oxy)pyrazin-2-yl)-2,6-dimethylbenzyl)tetrahydro-2H-pyran-4-sulfonamide

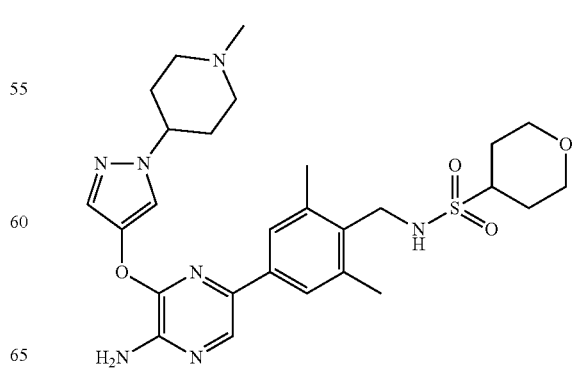

Step 1: N-(4-bromo-2,6-dimethylbenzyl)tetrahydro-2H-pyran-4-sulfonamide

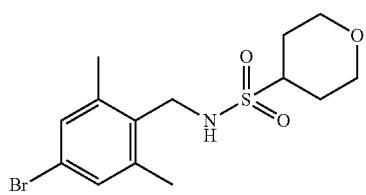 [SMILES: Cc1cc(Br)cc(C)c1CNS(=O)(=O)C1CCOCC1]

The title compound (123 mg, 48%) was prepared in a manner similar to that in Example A20 step 5 from 1-(4-bromo-2,6-dimethylphenyl)methanamine and oxane-4-sulfonyl chloride. LC-MS (M+H)$^+$=362.0.

Step 2: N-(2,6-dimethyl-4-(4,4,5,5-tetramethyl-1,3,2-dioxaborolan-2-yl)benzyl)tetrahydro-2H-pyran-4-sulfonamide

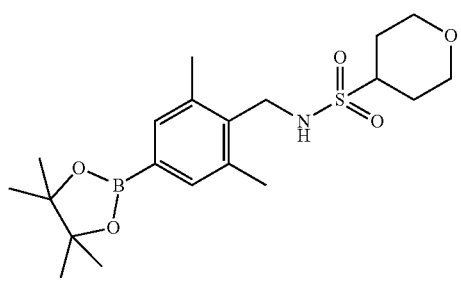 [SMILES: Cc1cc(B2OC(C)(C)C(C)(C)O2)cc(C)c1CNS(=O)(=O)C1CCOCC1]

The title compound (99 mg, 71%) was prepared in a manner similar to that in Example A1 step 6 from N-(4-bromo-2,6-dimethylbenzyl)tetrahydro-2H-pyran-4-sulfonamide and BPD. LC-MS (M+H)$^+$=410.2.

Step 3: N-(4-(5-amino-6-((1-(1-methylpiperidin-4-yl)-1H-pyrazol-4-yl)oxy)pyrazin-2-yl)-2,6-dimethylbenzyl)tetrahydro-2H-pyran-4-sulfonamide Example A31 (19 mg, 14%) was prepared in a manner similar to that in Example A1 step 7 from bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)tetrahydro-2H-pyran-4-sulfonamide. $^1$H NMR (400 MHz, DMSO-d6) δ 8.23 (s, 1H), 8.12 (s, 1H), 7.59 (s, 1H), 7.50 (s, 2H), 7.28-7.20 (m, 1H), 6.70 (s, 2H), 4.20-4.10 (m, 3H), 3.99-3.91 (m, 2H), 2.94-2.84 (m, 2H), 2.38 (s, 6H), 2.25 (s, 3H), 2.19-2.09 (m, 2H), 2.04-1.93 (m, 4H), 1.92-1.82 (m, 2H), 1.71-1.57 (m, 2H). LC-MS (M+H)$^+$=556.4.

Example A32

N-(4-(5-amino-6-((1-(1-methylpiperidin-4-yl)-1H-pyrazol-4-yl)oxy)pyrazin-2-yl)-2,6-dimethylbenzyl)cyclopropanesulfonamide

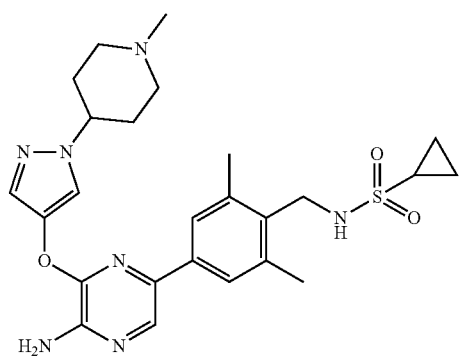 [SMILES: Cc1cc(-c2cnc(N)c(Oc3cnn(C4CCN(C)CC4)c3)n2)cc(C)c1CNS(=O)(=O)C1CC1]

Step 1: N-(4-bromo-2,6-dimethylbenzyl)cyclopropanesulfonamide

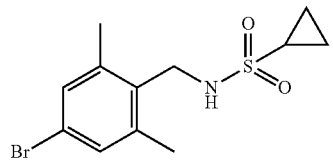 [SMILES: Cc1cc(Br)cc(C)c1CNS(=O)(=O)C1CC1]

The title compound (215 mg, 82%) was prepared in a manner similar to that in Example A20 step 5 from 1-(4-bromo-2,6-dimethylphenyl)methanamine and cyclopropanesulfonyl chloride. LC-MS (M+H)$^+$=318.0.

Step 2: N-(2,6-dimethyl-4-(4,4,5,5-tetramethyl-1,3,2-dioxaborolan-2-yl)benzyl)cyclopropanesulfonamide

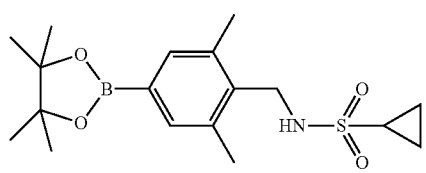 [SMILES: Cc1cc(B2OC(C)(C)C(C)(C)O2)cc(C)c1CNS(=O)(=O)C1CC1]

The title compound (119 mg, 71%) was prepared in a manner similar to that in Example A1 step 6 from N-(4-bromo-2,6-dimethylbenzyl)cyclopropanesulfonamide and BPD. LC-MS (M+NH$_4$)$^+$=383.2.

Step 3: N-(4-(5-amino-6-((1-(1-methylpiperidin-4-yl)-1H-pyrazol-4-yl)oxy)pyrazin-2-yl)-2,6-dimethylbenzyl)cyclopropanesulfonamide Example A32 (8 mg, 6%) was prepared in a manner similar to that in Example A1 final step from bromo-3-((1-(1-methylpiperidin-4-yl)-1H-pyrazol-4-yl)oxy)pyrazin-2- amine and N-(2,6-dimethyl-4-(4,4,5,5-tetramethyl-1,3,2-dioxaborolan-2-yl)benzyl)cyclopropanesulfonamide. ¹H NMR (300 MHz, DMSO-d₆) δ 8.22 (s, 1H), 8.11 (s, 1H), 7.58 (s, 1H), 7.49 (s, 2H), 7.13-7.05 (m, 11H), 6.69 (s, 2H), 4.23-4.08 (m, 3H), 2.99-2.83 (m, 2H), 2.65-2.55 (m, 1H), 2.37 (s, 6H), 2.30-2.21 (m, 3H), 2.16-2.04 (m, 6H), 0.99-0.91 (m, 4H). LC-MS (M+H)⁺=512.2.

Example A33

4-(5-amino-6-((1-(1-methylpiperidin-4-yl)-1H-pyrazol-4-yl)oxy)pyrazin-2-yl)-2-(difluoromethyl)-N-(2-(dimethylamino)ethyl)-6-methylbenzamide

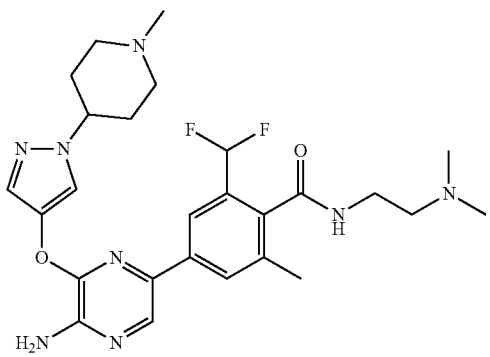 [SMILES: Cc1cc(-c2cnc(N)c(Oc3cnn(C4CCN(C)CC4)c3)n2)cc(C(F)F)c1C(=O)NCCN(C)C]

Step 1: ethyl 4-(dibenzylamino)-2-(difluoromethyl)-6-methylbenzoate

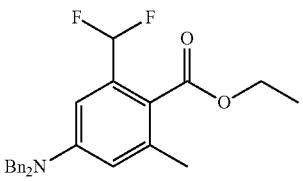

A mixture of pentane-2,4-dione (15 g, 150 mmol), dibenzylamine (44.3 g, 225 mmol) and zinc acetate (1.38 g, 7.5 mmol) was stirred at 50° C. for 2 days under nitrogen. Ethyl 4,4-difluoro-3-oxobutanoate (24.9 g, 150 mmol) and AcOH (300 mL) was added and the mixture was stirred at 120° C. for 3 h under nitrogen.

The mixture was concentrated under reduced pressure and the residue was taken up in water (300 mL). The pH of the mixture was adjusted to 8 with saturated NaHCO₃ and the mixture was extracted with EtOAc (300 mL×2). The combined organic layer was washed with brine (100 mL), dried over Na₂SO₄ and filtered. The filtrate was concentrated under reduced pressure and the crude was purified by silica gel chromatography (PE/EtOAc=10/1 to 5/1) to give the title compound (3.0 g, 5%). LCMS (M+H)+=410.1.

Step 2: ethyl 4-amino-2-(difluoromethyl)-6-methylbenzoate

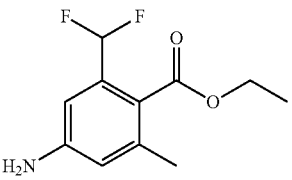 [SMILES: CCOC(=O)c1c(C)cc(N)cc1C(F)F]

Pd/C (10% loading) was added to a solution of ethyl 4-(dibenzylamino)-2-(difluoromethyl)-6-methylbenzoate (3.0 g, 7.31 mmol) in EtOH (30 mL) and AcOH (15 mL) under nitrogen, then the system was flushed with hydrogen. The mixture was stirred at room temperature overnight. The solid was filtered off and the filtrate was concentrated under reduced pressure. The residue was taken up in water (50 mL) and the pH of the mixture was adjusted to 8 with saturated NaHCO₃. The mixture was extracted with EtOAc (50 mL×2). The combined organic layer was washed with brine (30 mL), dried over Na₂SO₄ and filtered. The filtrate was concentrated under reduced pressure and the crude was purified by silica gel chromatography (PE/EtOAc=5/1 to 3/1) to give the title compound (1.4 g, 84%). LCMS (M+H)⁺=230.

Step 3: ethyl 4-bromo-2-(difluoromethyl)-6-methylbenzoate

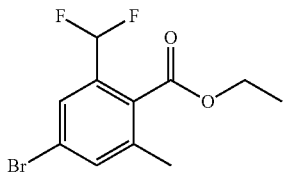 [SMILES: CCOC(=O)c1c(C)cc(Br)cc1C(F)F]

Copper bromide (1.37 g, 6.11 mmol) and t-butyl-nitrite (1.57 g, 15.3 mmol) was suspended in CH₃CN (40 mL). The mixture was cooled to 0° C. and ethyl 4-amino-2-(difluoromethyl)-6-methylbenzoate (1.4 g, 6.11 mmol) in CH₃CN (10 mL) was added dropwise. After 1 h, the mixture warmed to room temperature and stirred for 4 h. Water (30 mL) was added and the pH of the solution was adjusted to 2 with aqueous HCl (2 M). The mixture was extracted with EtOAc (20 mL×2). The combined organic layer was washed with brine (30 mL), dried over Na₂SO₄ and filtered. The filtrate was concentrated under reduced pressure and the crude was purified by silica gel chromatography (PE/EtOAc=5/1 to 3/1) to give the title compound (1.1 g, 61%). LCMS (M+H)⁺=293, 295.

Step 4:
4-bromo-2-(difluoromethyl)-6-methylbenzoic acid

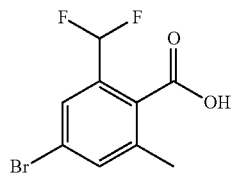

A mixture of ethyl 4-bromo-2-(difluoromethyl)-6-methylbenzoate (1.1 g, 3.75 mmol) and NaOH (0.6 g, 15 mmol) in dioxane (20 mL) and water (10 mL) was stirred at 80° C. for overnight. The mixture was cooled to room temperature and concentrated. Water (10 mL) was added and the pH of the mixture was adjusted to 2 with aqueous HCl (2 M). The precipitate was collected by filtration and dried under vacuum to give the title compound (0.60 g, 60%).

Step 5: 4-bromo-2-(difluoromethyl)-N-(2-(dimethylamino)ethyl)-6-methylbenzamide

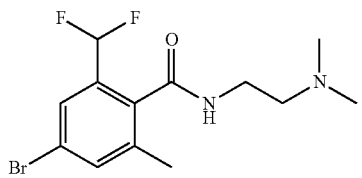 [SMILES: Cc1cc(Br)cc(C(F)F)c1C(=O)NCCN(C)C]

The title compound (0.64 g, 84%) was prepared in a manner similar to that in Example A1 step 5 from 4-bromo-2-(difluoromethyl)-6-methylbenzoic acid and N1,N1-dimethylethane-1,2-diamine. LCMS (M+H)$^+$=335, 337.

Step 6: 2-(difluoromethyl)-N-(2-(dimethylamino)ethyl)-6-methyl-4-(4,4,5,5-tetramethyl-1,3,2-dioxaborolan-2-yl)benzamide

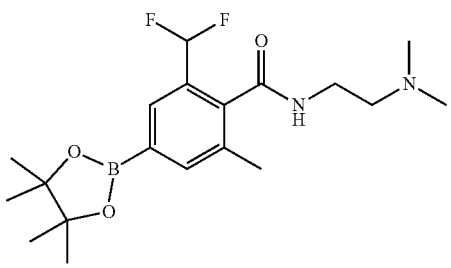

The title compound (0.40 g, 55%) was prepared in a manner similar to that in Example A1 step 6 from 4-bromo-2-(difluoromethyl)-N-(2-(dimethylamino)ethyl)-6-methylbenzamide and BPD. LC-MS (M+H)$^+$=383.1.

Step 7: 4-(5-amino-6-((1-(1-methylpiperidin-4-yl)-1H-pyrazol-4-yl)oxy)pyrazin-2-yl)-2-(difluoromethyl)-N-(2-(dimethylamino)ethyl)-6-methylbenzamide Example A33 (140 mg, 62%) was prepared in a manner similar to that in Example A1 step 6 from 5-bromo-3-((1-(1-methylpiperidin-4-yl)-1H-pyrazol-4-yl)oxy)pyrazin-2-amine and 2-(difluoromethyl)-N-(2-(dimethylamino)ethyl)-6-methyl-4-(4,4,5,5-tetramethyl-1,3,2-dioxaborolan-2-yl)benzamide. $^1$H NMR (400 MHz, DMSO-d6) δ 8.44 (t, J=5.7 Hz, 1H), 8.35 (s, 1H), 8.10 (s, 1H), 7.9 (s, 1H) 7.88 (s, 1H) 7.58 (s, 1H), 7.14-6.83 (m, 3H), 4.16-4.06 (m, 1H), 3.38-3.34 (m, 2H), 2.90-2.81 (m, 2H), 2.38 (t, J=6.5 Hz, 2H), 2.31 (s, 3H), 2.20 (s, 3H), 2.19 (s, 6H), 2.08-1.95 (m, 6H). LCMS (M+H)$^+$=529.5.

Example A34

(R)-4-(5-amino-6-((1-(1-methylpiperidin-4-yl)-1H-pyrazol-4-yl)oxy)pyrazin-2-yl)-N-(2-(3-fluoropyrrolidin-1-yl)ethyl)-2,6-dimethylbenzamide

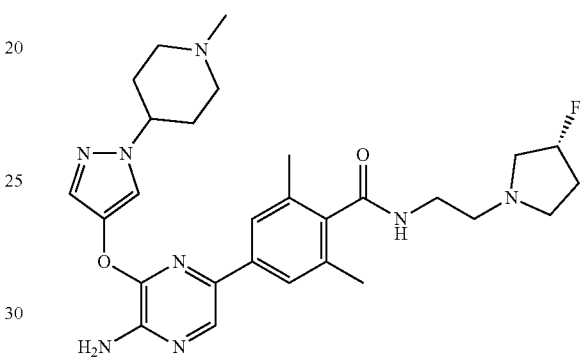

Step 1: (R)-2-(3-fluoropyrrolidin-1-yl)acetonitrile

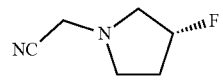

(R)-3-fluoropyrrolidine hydrochloride (1.0 g, 7.9 mmol), 2-bromoacetonitrile (0.55 mL, 7.9 mmol) and K$_2$CO$_3$ (3.3 g, 23.8 mmol) was suspended in CH$_3$CN (30 mL) and the mixture was heated to reflux for overnight. The mixture was cooled to room temperature, then partitioned between water (50 mL) and EtOAc (40 mL). The organic layer was dried over Na$_2$SO$_4$, filtered and the filtrate was concentrated in vacuo to give the title compound (1.0 g, 99%). LC-MS (M+H)$^+$=129.0.

Step 2: (R)-2-(3-fluoropyrrolidin-1-yl)ethan-1-amine

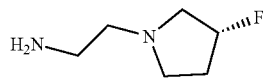

To a solution of (R)-2-(3-fluoropyrrolidin-1-yl)acetonitrile (1.0 g, 7.8 mmol) in THF (30 mL) was added LiAlH$_4$ (740 mg, 19.5 mmol) at 0° C., then the mixture was heated to reflux for overnight. The mixture was cool to room temperature and water (4.0 mL) was added. After 15 min, the mixture filtered and the filter cake was washed with THF (20 mL). The filtrate was dried over Na$_2$SO$_4$, filtered and the Step 3: (R)-4-bromo-N-(2-(3-fluoropyrrolidin-1-yl)ethyl)-2,6-dimethylbenzamide

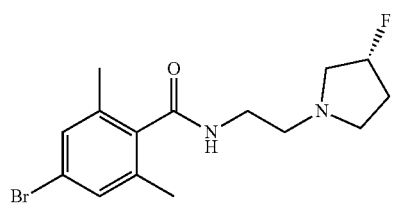 [SMILES: Cc1cc(Br)cc(C)c1C(=O)NCCN1CC[C@@H](F)C1]

The title compound (433 mg, 70%) was prepared in a manner similar to that in Example A3 step 1 from 4-bromo-2,6-dimethylbenzoic acid and (R)-2-(3-fluoropyrrolidin-1-yl)ethan-1-amine. LC-MS (M+H)=343.0.

Step 4: (R)-N-(2-(3-fluoropyrrolidin-1-yl)ethyl)-2,6-dimethyl-4-(4,4,5,5-tetramethyl-1,3,2-dioxaborolan-2-yl)benzamide

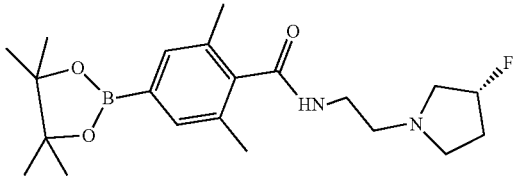 [SMILES: Cc1cc(B2OC(C)(C)C(C)(C)O2)cc(C)c1C(=O)NCCN1CC[C@@H](F)C1]

The title compound (90 mg, 30%) was prepared in a manner similar to that in Example A1 step 6 from (R)-4-bromo-N-(2-(3-fluoropyrrolidin-1-yl)ethyl)-2,6-dimethylbenzamide and BPD. LC-MS (M+H)⁺=391.2.

Step 5: (R)-4-(5-amino-6-((1-(1-methylpiperidin-4-yl)-1H-pyrazol-4-yl)oxy)pyrazin-2-yl)-N-(2-(3-fluoropyrrolidin-1-yl)ethyl)-2,6-dimethylbenzamide Example A34 (10 mg, 7%) was prepared in a manner similar to that in Example A1 step 7 from 5-bromo-3-((1-(1-methylpiperidin-4-yl)-1H-pyrazol-4-yl)oxy)pyrazin-2-amine and (R)-N-(2-(3-fluoropyrrolidin-1-yl)ethyl)-2,6-dimethyl-4-(4,4,5,5-tetramethyl-1,3,2-dioxaborolan-2-yl)benzamide. ¹H NMR (400 MHz, DMSO) δ 8.25-8.19 (m, 2H), 8.12 (s, 1H), 7.58 (s, 1H), 7.50 (s, 2H), 6.73 (s, 2H), 5.29-5.08 (m, 1H), 4.15-4.09 (m, 1H), 3.36 (d, J=6.5 Hz, 1H), 2.91-2.78 (m, 5H), 2.70-2.53 (m, 3H), 2.35-2.30 (m, 1H), 2.23 (s, 6H), 2.20 (s, 3H), 2.18-1.77 (m, 9H). LC-MS (M+H)⁺=537.3.

Example A35

5-(4-(5-amino-6-((1-(1-methylpiperidin-4-yl)-1H-pyrazol-4-yl)oxy)pyrazin-2-yl)-2,6-dimethylphenyl)morpholin-3-one

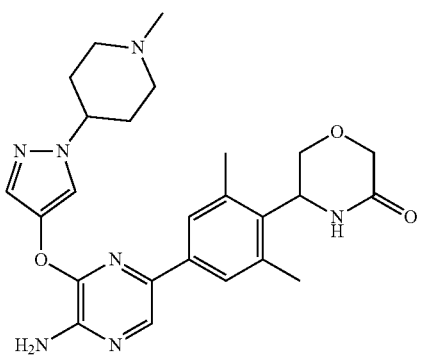 [SMILES: Cc1cc(-c2cnc(N)c(Oc3cnn(C4CCN(C)CC4)c3)n2)cc(C)c1C1COCC(=O)N1]

Step 1:
5-(4-bromo-2,6-dimethylphenyl)morpholin-3-one

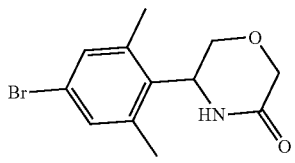 [SMILES: Cc1cc(Br)cc(C)c1C1COCC(=O)N1]

To a solution of 2-amino-2-(4-bromo-2,6-dimethylphenyl)ethan-1-ol hydrochloride (200 mg, 0.71 mmol) and triethylamine (203 mg, 1.91 mmol) in THF (15 mL) was added chloroacetyl chloride (91 mg, 0.76 mmol) dropwise at 0° C. under nitrogen. After 15 min, water (10 mL) was added. The mixture was extracted with EtOAc (10 mL×3). The combined organic layer was concentrated under reduced pressure. The residue was dissolved in THF (15 mL), and NaH (60%, 37 mg, 0.92 mmol) was added in portions at 0° C. The mixture was warmed to room temperature and stirred for 1.5 h. Saturated NH₄Cl (50 mL) was added and the mixture was extracted with EtOAc (50 mL×3). The combined organic layer was washed with brine (50 mL), dried over Na₂SO₄ and filtered. The filtrate was concentrated under reduced pressure and the residue was purified by silica gel chromatography (MeOH/DCM=1:12) to give the title compound (123 mg, 61%). LC-MS (M+H)⁺=284.0.

Step 2: 5-(2,6-dimethyl-4-(4,4,5,5-tetramethyl-1,3,2-dioxaborolan-2-yl)phenyl)morpholin-3-one

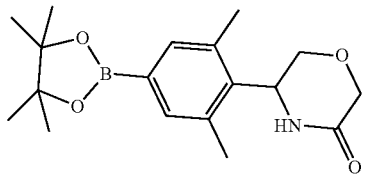 [SMILES: Cc1cc(B2OC(C)(C)C(C)(C)O2)cc(C)c1C1COCC(=O)N1]

The title compound (123 mg, 96%) was prepared in a manner similar to that in Example A1 step 6 from 5-(4-bromo-2,6-dimethylphenyl)morpholin-3-one and BPD. LC-MS (M+H)+=332.3.

Step 3: 5-(4-(5-amino-6-((1-(1-methylpiperidin-4-yl)-1H-pyrazol-4-yl)oxy)pyrazin-2-yl)-2,6-dimethylphenyl)morpholin-3-one Example A35 (16 mg, 16%) was prepared in a manner similar to that in Example A1 step 7 from 5-bromo-3-((1-(1-methylpiperidin-4-yl)-1H-pyrazol-4-yl)oxy)pyrazin-2-amine and 5-(2,6-dimethyl-4-(4,4,5,5-tetramethyl-1,3,2-dioxaborolan-2-yl)phenyl)morpholin-3-one. ¹H NMR (300 MHz, DMSO-d₆) δ 8.32 (s, 1H), 8.21 (s, 1H), 8.10 (s, 1H), 7.56 (s, 1H), 7.47 (s, 2H), 6.71 (s, 2H), 5.13-5.03 (m, 1H), 4.18-4.10 (m, 3H), 3.95-3.84 (m, 1H), 3.72-3.59 (m, 1H), 2.90-2.79 (m, 2H), 2.37 (s, 6H), 2.20 (s, 3H), 2.13-1.93 (m, 6H). LC-MS (M+H)+=478.2.

Example A36

1-(4-(5-amino-6-((1-(1-methylpiperidin-4-yl)-1H-pyrazol-4-yl)oxy)pyrazin-2-yl)-2,6-dimethylbenzyl)-3-ethylurea

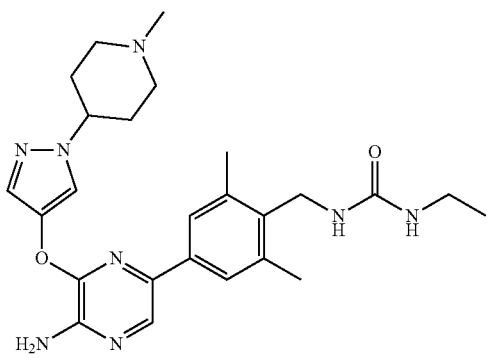 [SMILES: CCNC(=O)NCc1c(C)cc(-c2cnc(N)c(Oc3cnn(C4CCN(C)CC4)c3)n2)cc1C]

Step 1: 1-(4-bromo-2,6-dimethylbenzyl)-3-ethylurea

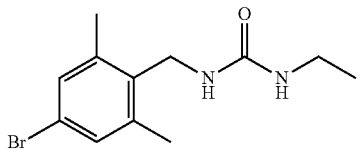 [SMILES: CCNC(=O)NCc1c(C)cc(Br)cc1C]

To a stirred solution of 1-(4-bromo-2,6-dimethylphenyl)methanamine (150 mg, 0.70 mmol) and triethylamine (142 mg, 1.40 mmol) in DCM (5 mL) was added ethyl isocyanate (50 mg, 0.70 mmol) in DCM (5 mL) dropwise at 0° C. The mixture was warmed to room temperature and stirred for 3 h. The mixture was partitioned between water (10 mL) and DCM (10 mL). The organic layer was separated, dried over anhydrous Na₂SO₄ and filtered. The filtrate was concentrated under reduced pressure to give the title compound (144 mg, 72%). LC-MS (M+H)+=287.1.

Step 2: 1-(2,6-dimethyl-4-(4,4,5,5-tetramethyl-1,3,2-dioxaborolan-2-yl)benzyl)-3-ethylurea

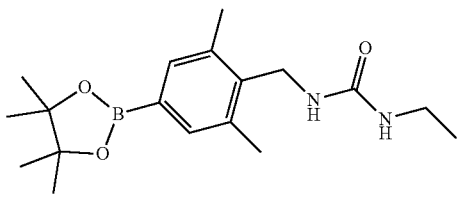 [SMILES: CCNC(=O)NCc1c(C)cc(B2OC(C)(C)C(C)(C)O2)cc1C]

The title compound (82 mg, 59%) was prepared in a manner similar to that in Example A1 step 6 from 1-(4-bromo-2,6-dimethylbenzyl)-3-ethylurea and BPD. LC-MS (M+H)+=333.1.

Step 3: 1-[[4-(5-amino-6-[1]-(1-methylpiperidin-4-yl)pyrazol-4-yl]oxy]pyrazin-2-yl)-2,6-dimethylphenyl]methyl]-3-ethylurea Example A36 (18 mg, 19%) was prepared in a manner similar to that in Example A1 step 7 from 5-bromo-3-((1-(1-methylpiperidin-4-yl)-1H-pyrazol-4-yl)oxy)pyrazin-2-amine and 1-(2,6-dimethyl-4-(4,4,5,5-tetramethyl-1,3,2-dioxaborolan-2-yl)benzyl)-3-ethylurea. ¹H NMR (300 MHz, DMSO-d6) δ 8.19 (s, 1H), 8.10 (s, 1H), 7.57 (s, 1H), 7.46 (s, 2H), 6.67 (s, 2H), 5.86-5.78 (m, 1H), 5.65-5.57 (m, 1H), 4.21-4.12 (m, 1H), 4.19-4.04 (m, 2H), 3.05-2.93 (m, 2H), 2.90-2.80 (m, 2H), 2.32 (s, 6H), 2.20 (s, 3H), 2.14-1.88 (m, 6H), 0.95 (t, J=7.1 Hz, 3H). LC-MS (M+H)+=479.4.

Example A37

1-(4-(5-amino-6-((1-(1-methylpiperidin-4-yl)-1H-pyrazol-4-yl)oxy)pyrazin-2-yl)-2,6-dimethylbenzyl)-3-cyclopentylurea

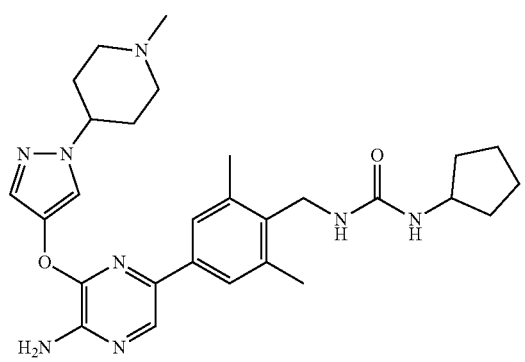 [SMILES: Cc1cc(-c2cnc(N)c(Oc3cnn(C4CCN(C)CC4)c3)n2)cc(C)c1CNC(=O)NC1CCCC1]

Step 1: 1-(4-bromo-2,6-dimethylbenzyl)-3-cyclopentylurea

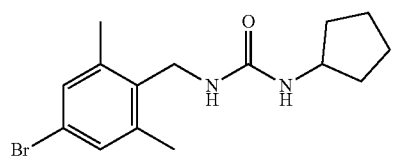 [SMILES: Cc1cc(Br)cc(C)c1CNC(=O)NC1CCCC1]

The title compound (68 mg, 45%) was prepared in a manner similar to that in Example A26 step 1 from 1-(4-bromo-2,6-dimethylphenyl)methanamine and cyclopentylamine. LC-MS (M−H)−=323.1.

Step 2: 1-cyclopentyl-36-dimethyl-4-(4,4,5,5-tetramethyl-1,3,2-dioxaborolan-2-yl)benzyl)urea

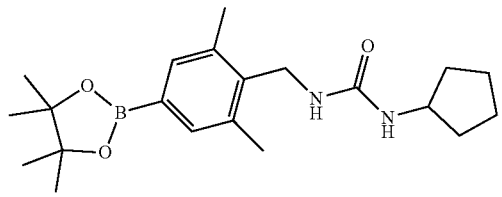 [SMILES: Cc1cc(B2OC(C)(C)C(C)(C)O2)cc(C)c1CNC(=O)NC1CCCC1]

The title compound (33 mg, 53%) was prepared in a manner similar to that in Example A1 step 6 from 1-(4-bromo-2,6-dimethylbenzyl)-3-cyclopentylurea and BPD. LC-MS (M+H)+=373.2.

Step 3: 1-(4-(5-amino-6-((1-(1-methylpiperidin-4-yl)-1H-pyrazol-4-yl)oxy)pyrazin-2-yl)-2,6-dimethylbenzyl)-3-cyclopentylurea Example A37 (9 mg, 8%) was prepared in a manner similar to that in Example A1 final step from 5-bromo-3-((1-(1-methylpiperidin-4-yl)-1H-pyrazol-4-yl)oxy)pyrazin-2-amine and 1-cyclopentyl-3-(2,6-dimethyl-4-(4,4,5,5-tetramethyl-1,3,2-dioxaborolan-2-yl)benzyl)urea. $^1$H NMR (300 MHz, DMSO-d6) δ 8.19 (s, 1H), 8.10 (s, 1H), 7.57 (s, 1H), 7.46 (s, 2H), 6.66 (s, 2H), 5.75-5.64 (m, 2H), 4.25-4.05 (m, 3H), 3.89-3.81 (m, 1H), 2.88-2.79 (m, 2H), 2.32 (s, 6H), 2.19 (s, 3H), 2.12-1.90 (m, 6H), 1.80-1.66 (m, 2H), 1.60-1.39 (m, 4H), 1.30-1.14 (m, 3H). LC-MS (M+H)+=519.4.

Example A38

N-(4-(5-amino-6-((1-(1-methylpiperidin-4-yl)-1H-pyrazol-4-yl)oxy)pyrazin-2-yl)-2,6-dimethylbenzyl)benzenesulfonamide

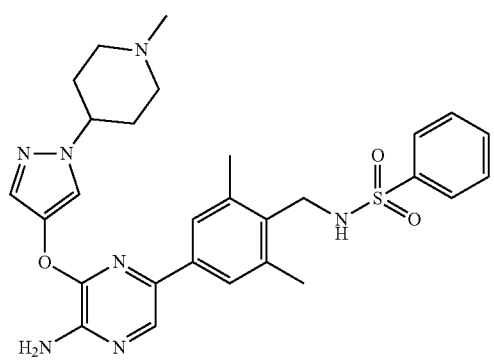 [SMILES: Cc1cc(-c2cnc(N)c(Oc3cnn(C4CCN(C)CC4)c3)n2)cc(C)c1CNS(=O)(=O)c1ccccc1]

Step 1: N-(4-bromo-2,6-dimethylbenzyl)benzenesulfonamide

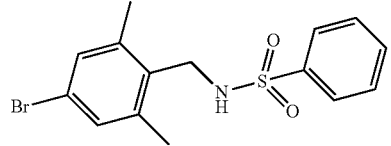 [SMILES: Cc1cc(Br)cc(C)c1CNS(=O)(=O)c1ccccc1]

The title compound (116 mg, 23%) was prepared in a manner similar to that in Example A20 step 5 from 1-(4-bromo-2,6-dimethylphenyl)methanamine and benzenesulfonyl chloride. LC-MS (M−H)−=352.0.

Step 2: N-(2,6-dimethyl-4-(4,4,5,5-tetramethyl-1,3,2-dioxaborolan-2-yl)benzyl)benzenesulfonamide

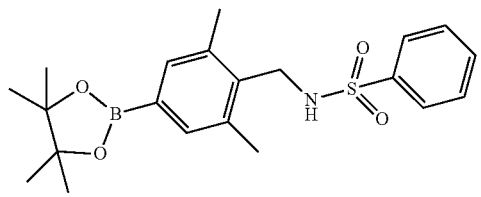 [SMILES: Cc1cc(B2OC(C)(C)C(C)(C)O2)cc(C)c1CNS(=O)(=O)c1ccccc1]

The title compound (190 mg, 64%) was prepared in a manner similar to that in Example A1 step 6 from N-(4-bromo-2,6-dimethylbenzyl)benzenesulfonamide and BPD. LC-MS (M−H)−=400.1.

Step 3: N-(4-(5-amino-6-((1-(1-methylpiperidin-4-yl)-1H-pyrazol-4-yl)oxy)pyrazin-2-yl)-2,6-dimethylbenzyl)benzenesulfonamide Example A38 (24 mg, 10%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)benzenesulfonamide. H NMR (400 MHz, DMSO-d6) δ 8.21 (s, 1H), 8.10 (s, 1H), 7.91-7.84 (m, 2H), 7.72-7.59 (m, 4H), 7.58 (s, 1H), 7.45 (s, 2H), 6.70 (s, 2H), 4.19-4.07 (m, 1H), 3.92-3.84 (m, 2H), 2.92-2.82 (m, 2H), 2.21 (d, J=13.2 Hz, 9H), 2.15-1.93 (m, 6H). LC-MS (M+H)+=548.4.

Example A39

N-(4-(5-amino-6-((1-(1-methylpiperidin-4-yl)-1H-pyrazol-4-yl)oxy)pyrazin-2-yl)-2,6-dimethylbenzyl)-4-methoxybenzenesulfonamide

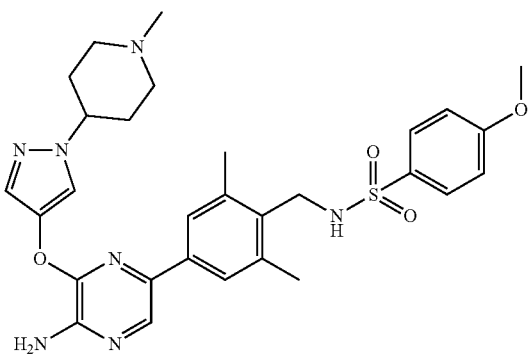 [SMILES: COc1ccc(S(=O)(=O)NCc2c(C)cc(-c3cnc(N)c(Oc4cnn(C5CCN(C)CC5)c4)n3)cc2C)cc1]

Step 1: N-(4-bromo-2,6-dimethylbenzyl)-4-methoxybenzenesulfonamide

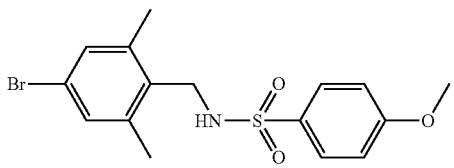 [SMILES: COc1ccc(S(=O)(=O)NCc2c(C)cc(Br)cc2C)cc1]

The title compound (107 mg, 20%) was prepared in a manner similar to that in Example A20 step 5 from 1-(4-bromo-2,6-dimethylphenyl)methanamine and 4-methoxybenzenesulfonyl chloride. LC-MS (M−H)⁻=382.0.

Step 2: N-(2,6-dimethyl-4-(4,4,5,5-tetramethyl-1,3,2-dioxaborolan-2-yl)benzyl)-4-methoxybenzenesulfonamide

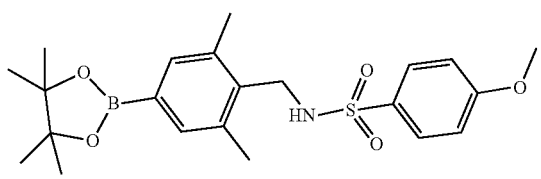

The title compound (118 mg, 98%) was prepared in a manner similar to that in Example A1 step 6 from N-(4-bromo-2,6-dimethylbenzyl)-4-methoxybenzenesulfonamide and BPD. LC-MS (M+H)⁺=432.3.

Step 3: N-(4-(5-amino-6-((1-(1-methylpiperidin-4-yl)-1H-pyrazol-4-yl)oxy)pyrazin-2-yl)-2,6-dimethyl-benzyl)-4-methoxybenzenesulfonamide Example A39 (26 mg, 18%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)-4-methoxybenzenesulfonamide.

¹H NMR (400 MHz, DMSO-d6) δ 8.21 (s, 1H), 8.10 (s, 1H), 7.84-7.76 (m, 2H), 7.58 (s, 1H), 7.51-7.47 (m, 1H), 7.45 (s, 2H), 7.18-7.10 (m, 2H), 6.70 (s, 2H), 4.22-4.07 (m, 1H), 3.87-3.81 (m, 5H), 2.95-2.85 (m, 2H), 2.26 (s, 3H), 2.21 (s, 6H), 2.14 (s, 3H), 2.17-1.97 (m, 6H). LC-MS (M+H)⁺=578.4.

Example A40

N-(4-(5-amino-6-((1-(1-methylpiperidin-4-yl)-1H-pyrazol-4-yl)oxy)pyrazin-2-yl)-2,6-dimethylbenzyl)cyclopentanesulfonamide

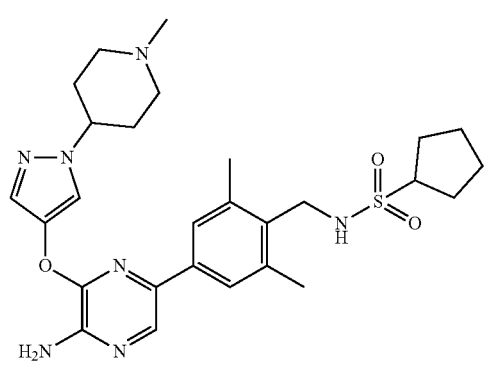 [SMILES: Cc1cc(-c2cnc(N)c(Oc3cnn(C4CCN(C)CC4)c3)n2)cc(C)c1CNS(=O)(=O)C1CCCC1]

Step 1: N-(4-bromo-2,6-dimethylbenzyl)cyclopentanesulfonamide

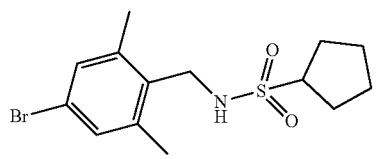 [SMILES: Cc1cc(Br)cc(C)c1CNS(=O)(=O)C1CCCC1]

The title compound (71 mg, 23%) was prepared in a manner similar to that in Example A20 step 5 from 1-(4-bromo-2,6-dimethylphenyl)methanamine and cyclopentanesulfonyl chloride. LC-MS (M−H)⁺=344.0.

Step 2: N-(2,6-dimethyl-4-(4,4,5,5-tetramethyl-1,3,2-dioxaborolan-2-yl)benzyl)cyclopentanesulfonamide

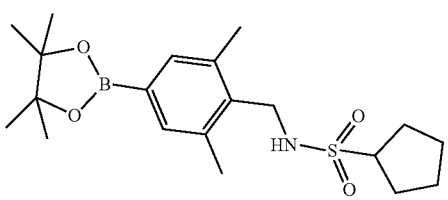 [SMILES: Cc1cc(B2OC(C)(C)C(C)(C)O2)cc(C)c1CNS(=O)(=O)C1CCCC1]

The title compound (78 mg, 96%) was prepared in a manner similar to that in Example A1 step 6 from N-(4- bromo-2,6-dimethylbenzyl)cyclopentanesulfonamide and BPD. LC-MS (M−H)⁻=392.2.

Step 3: N-(4-(5-amino-6-((1-(1-methylpiperidin-4-yl)-1H-pyrazol-4-yl)oxy)pyrazin-2-yl)-2,6-dimethylbenzyl)cyclopentanesulfonamide Example A40 (19 mg, 13%) was prepared in a manner similar to that in Example A1 final step from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)cyclopentanesulfonamide. ¹H NMR (300 MHz. DMSO-d6) δ 8.22 (s, 1H), 8.10 (s, 1H), 7.57 (s, 1H), 7.48 (s, 2H), 7.12-7.03 (m, 1H), 6.69 (s, 2H), 4.19-4.05 (m, 3H), 3.65-3.52 (m, 1H), 2.91-2.81 (m, 2H), 2.36 (s, 6H), 2.21 (s, 3H), 2.15-1.83 (m, 10H), 1.73-1.47 (m, 4H). LC-MS (M+H)⁺=540.4.

Example A41

3-(5-amino-6-((1-(1-methylpiperidin-4-yl)-1H-pyrazol-4-yl)oxy)pyrazin-2-yl)-N-methyl-5-(piperidin-1-yl)benzenesulfonamide

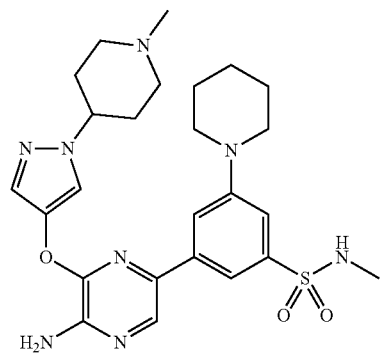 [SMILES: CNS(=O)(=O)c1cc(-c2cnc(N)c(Oc3cnn(C4CCN(C)CC4)c3)n2)cc(N2CCCCC2)c1]

Step 1: 3-bromo-5-fluoro-N-methylbenzenesulfonamide

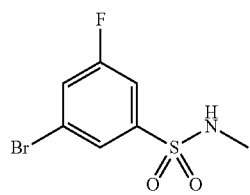

The title compound (1.62 g, 91%) was prepared in a manner similar to that in Example A8 step 3 from 3-bromo-5-fluorobenzenesulfonyl chloride. LC-MS (M+H)+=267.8.

Step 2: 3-bromo-N-methyl-5-(piperidin-1-yl)benzenesulfonamide

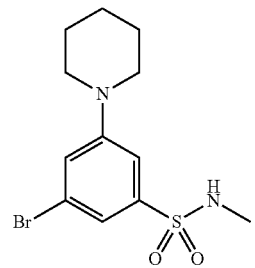 [SMILES: CNS(=O)(=O)c1cc(Br)cc(N2CCCCC2)c1]

A mixture of 3-bromo-5-fluoro-N-methylbenzenesulfonamide (255 mg, 0.951 mmol), piperidine (476 mg, 5.6 mmol) and K₂CO₃ (309 mg, 2.24 mmol) in DMF (3 mL) was stirred for 16 h at 120° C. under nitrogen. The mixture was cooled to room temperature and concentrated under reduced pressure. The residue was purified by C18 chromatography to give the title compound (274 mg, 86%). LC-MS (M+H)⁺=334.9.

Step 3: N-methyl-3-(piperidin-1-yl)-5-(4,4,5,5-tetramethyl-1,3,2-dioxaborolan-2-yl)benzenesulfonamide

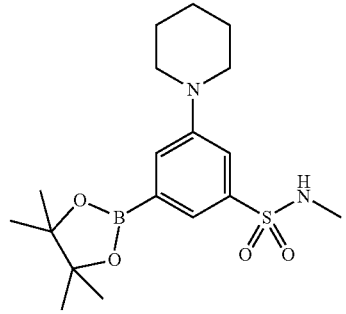

The title compound (257 mg, 82%) was prepared in a manner similar to that in Example A1 step 6 from 3-bromo-N-methyl-5-(piperidin-1-yl)benzenesulfonamide and BPD. LC-MS (M-pin)⁺=299.1.

Step 4: 3-(5-amino-6-((1-(1-methylpiperidin-4-yl)-1H-pyrazol-4-yl)oxy)pyrazin-2-yl)-N-methyl-5-(piperidin-1-yl)benzenesulfonamide Example A41 (25 mg, 18%) was prepared in a manner similar to that in Example A1 step 7 from 5-bromo-3-((1-(1-methylpiperidin-4-yl)-1H-pyrazol-4-yl)oxy)pyrazin-2-amine and N-methyl-3-(piperidin-1-yl)-5-(4,4,5,5-tetramethyl-1,3,2-dioxaborolan-2-yl)benzenesulfonamide. ¹H NMR (400 MHz, DMSO-d6) δ 8.31 (s, 1H), 8.10 (s, 1H), 7.62-7.54 (m, 3H), 7.38-7.31 (m, 1H), 7.17-7.14 (m, 1H), 6.86 (s, 2H), 4.15-4.02 (m, 1H), 3.28-3.20 (m, 4H), 2.91-2.82 (m, 2H), 2.41 (d, J=5.1 Hz, 3H), 2.21 (s, 3H), 2.10-1.89 (m, 6H), 1.67-1.55 (m, 6H). LC-MS (M+H)⁺=527.3.

Example A42

3-(5-amino-6-((1-(1-methylpiperidin-4-yl)-1H-pyrazol-4-yl)oxy)pyrazin-2-yl)-N-methyl-5-morpholinobenzenesulfonamide

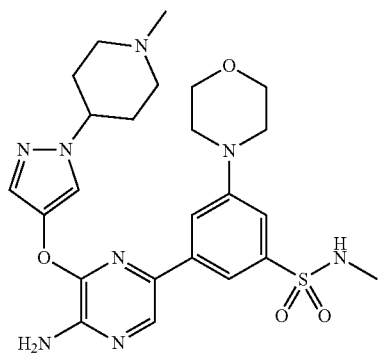 [SMILES: CNS(=O)(=O)c1cc(-c2cnc(N)c(Oc3cnn(C4CCN(C)CC4)c3)n2)cc(N2CCOCC2)c1]

Step 1: 3-bromo-N-methyl-5-morpholinobenzenesulfonamide

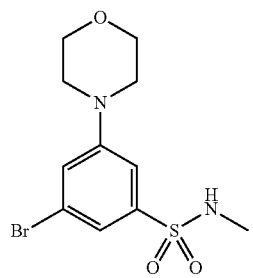 [SMILES: CNS(=O)(=O)c1cc(Br)cc(N2CCOCC2)c1]

The title compound (279 mg, 88%) was prepared in a manner similar to that in Example A41 step 2 from 3-bromo-5-fluoro-N-methylbenzenesulfonamide and morpholine. LC-MS (M+H)$^+$=334.8.

Step 2: N-methyl-3-morpholino-5-(4,4,5,5-tetramethyl-1,3,2-dioxaborolan-2-yl)benzenesulfonamide

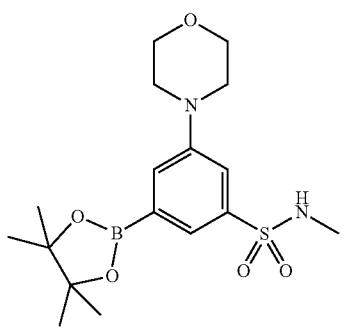

The title compound (144 mg, 66%) was prepared in a manner similar to that in Example A1 step 6 from 3-bromo-N-methyl-5-(morpholin-4-yl)benzenesulfonamide and BPD. LC-MS (M+H)$^+$=383.0.

Step 3: 3-(5-amino-6-((1-(1-methylpiperidin-4-yl)-1H-pyrazol-4-yl)oxy)pyrazin-2-yl)-N-methyl-5-morpholinobenzenesulfonamide Example A42 (28 mg, 21%) was prepared in a manner similar to that in Example A1 step 7 from 5-bromo-3-((1-(1-methylpiperidin-4-yl)-1H-pyrazol-4-yl)oxy)pyrazin-2-amine and N-methyl-3-morpholino-5-(4,4,5,5-tetramethyl-1,3,2-dioxaborolan-2-yl)benzenesulfonamide. $^1$H NMR (400 MHz, DMSO-d6) δ 8.34 (s, 1H), 8.11 (s, 1H), 7.65 (s, 1H), 7.63-7.56 (m, 2H), 7.40-7.34 (m, 1H), 7.18 (s, 1H), 6.88 (s, 2H), 4.15-4.04 (m, 1H), 3.81-3.72 (m, 4H), 3.27-3.18 (m, 4H), 2.91-2.83 (m, 2H), 2.42 (d, J=5.1 Hz, 3H), 2.21 (s, 3H), 2.11-1.88 (m, 6H). LC-MS (M+H)$^+$=529.3.

Example A43

(R)-3-(5-amino-6-((1-(1-methylpiperidin-4-yl)-1H-pyrazol-4-yl)oxy)pyrazin-2-yl)-N-methyl-5-(2-methylpyrrolidin-1-yl)benzenesulfonamide

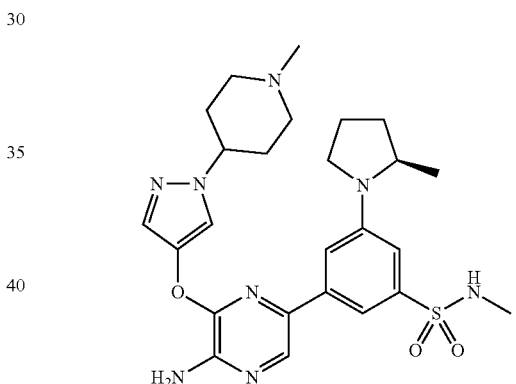

Step 1: (R)-3-bromo-N-methyl-5-(2-methylpyrrolidin-1-yl)benzenesulfonamide

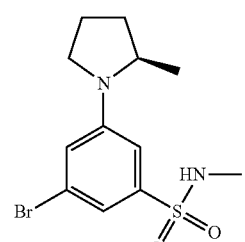

The title compound (286 mg, 90%) was prepared in a manner similar to that in Example A41 step 2 from 3-bromo-5-fluoro-N-methylbenzenesulfonamide and (2R)-2-methylpyrrolidine. LC-MS (M+H)$^+$=332.8.

Step 2: (R)-N-methyl-3-(2-methylpyrrolidin-1-yl)-5-(4,4,5,5-tetramethyl-1,3,2-dioxaborolan-2-yl)benzenesulfonamide

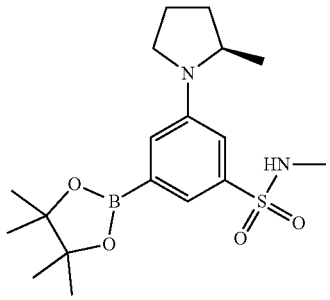

The title compound (202 mg, 74%) was prepared in a manner similar to that in Example A1 step 6 from (R)-3-bromo-N-methyl-5-(2-methylpyrrolidin-1-yl)benzenesulfonamide and BPD. LC-MS (M-pin)⁺=299.1.

Step 3: (R)-3-(5-amino-6-((1-(1-methylpiperidin-4-yl)-1H-pyrazol-4-yl)oxy)pyrazin-2-yl)-N-methyl-5-(2-methylpyrrolidin-1-yl)benzenesulfonamide Example A43 (39 mg, 30%) was prepared in a manner similar to that in Example A1 step 7 from 5-bromo-3-((1-(1-methylpiperidin-4-yl)-1H-pyrazol-4-yl)oxy)pyrazin-2-amine and (R)-N-methyl-3-(2-methylpyrrolidin-1-yl)-5-(4,4,5,5-tetramethyl-1,3,2-dioxaborolan-2-yl)benzenesulfonamide. ¹H NMR (400 MHz, DMSO-d6) δ 8.25 (s, 1H), 8.08 (s, 1H), 7.60 (s, 1H), 7.41 (s, 1H), 7.38-7.30 (m, 1H), 7.19 (s, 1H), 6.89-6.75 (m, 3H), 4.15-4.01 (m, 1H), 3.97-3.90 (m, 1H), 3.49-3.38 (m, 1H), 3.23-3.11 (m, 1H), 2.93-2.81 (m, 2H), 2.42 (d, J=5.1 Hz, 3H), 2.22 (s, 3H), 2.12-1.90 (m, 9H), 1.74-1.67 (m, 1H), 1.16-1.08 (m, 3H). LC-MS (M+H)⁺=527.3.

Example A44

N-(4-(5-amino-6-((1-(1-methylpiperidin-4-yl)-1H-pyrazol-4-yl)oxy)pyrazin-2-yl)-2,6-dimethylbenzyl)benzamide

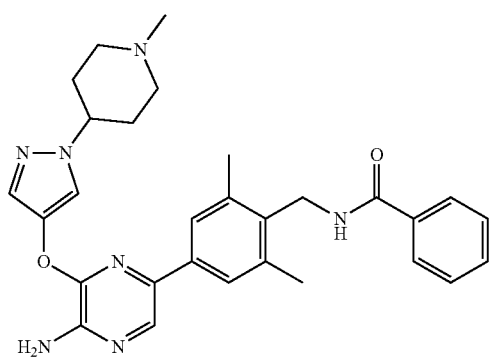 [SMILES: Cc1cc(-c2cnc(N)c(Oc3cnn(C4CCN(C)CC4)c3)n2)cc(C)c1CNC(=O)c1ccccc1]

Step 1: N-(4-bromo-2,6-dimethylbenzyl)benzamide

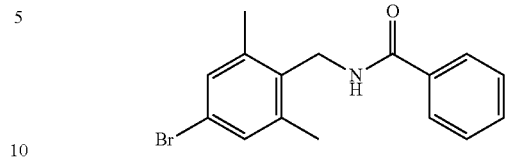

To a stirred mixture of 1-(4-bromo-2,6-dimethylphenyl)methanamine (150 mg, 0.70 mmol) and benzoyl chloride (394 mg, 2.80 mmol) in DCM (5 mL) was added triethylamine (213 mg, 2.10 mmol) dropwise at 0° C. under nitrogen. The mixture was warmed for room temperature and stirred for 2 h. The mixture was concentrated under reduced pressure. The residue was purified by silica gel chromatography (PE/EtOAc=8:1) to give the title compound (200 mg, 89%). LC-MS (M+H)⁺=318.1.

Step 2: N-(2,6-dimethyl-4-(4,4,5,5-tetramethyl-1,3,2-dioxaborolan-2-yl)benzyl)benzamide

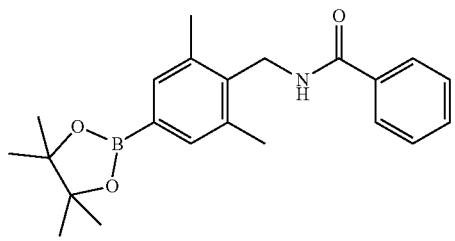 [SMILES: Cc1cc(B2OC(C)(C)C(C)(C)O2)cc(C)c1CNC(=O)c1ccccc1]

The title compound (146 mg, 66%) was prepared in a manner similar to that in Example A1 step 6 from N-(4-bromo-2,6-dimethylbenzyl)benzamide and BPD. LC-MS (M+H)⁺=366.1.

Step 3: N-(4-(5-amino-6-((1-(1-methylpiperidin-4-yl)-1H-pyrazol-4-yl)oxy)pyrazin-2-yl)-2,6-dimethylbenzyl)benzamide Example A44 (7 mg, 3%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)benzamide. ¹H NMR (400 MHz, DMSO-d6) δ 8.51-8.44 (m, 1H), 8.23 (s, 1H), 8.12 (s, 1H), 7.88-7.80 (m, 2H), 7.59 (s, 1H), 7.54-7.46 (m, 3H), 7.46-7.39 (m, 2H), 6.69 (s, 2H), 4.534.43 (m, 2H), 4.194.07 (m, 1H), 2.90-2.78 (m, 2H), 2.39 (app s, 6H), 2.20 (s, 3H), 2.12-1.90 (m, 6H). LC-MS (M+H)+=512.4.

Example A45

N-(4-(5-amino-6-((1-(1-methylpiperidin-4-yl)-1H-pyrazol-4-yl)oxy)pyrazin-2-yl)-2,6-dimethylbenzyl)acetamide

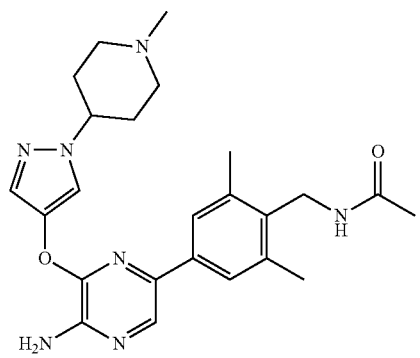 [SMILES: CC(=O)NCc1c(C)cc(-c2cnc(N)c(Oc3cnn(C4CCN(C)CC4)c3)n2)cc1C]

Step 1: N-(4-bromo-2,6-dimethylbenzyl)acetamide

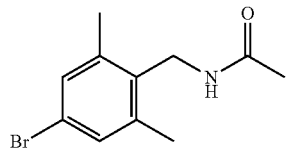

The title compound (131 mg, 84%) was prepared in a manner similar to that in Example A44 step 1 from 1-(4-bromo-2,6-dimethylphenyl)methanamine and AcCl. LC-MS (M+H)$^+$=256.0.

Step 2: N-(2,6-dimethyl-4-(4,4,5,5-tetramethyl-1,3,2-dioxaborolan-2-yl)benzyl)acetamide

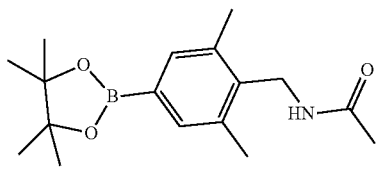 [SMILES: CC(=O)NCc1c(C)cc(B2OC(C)(C)C(C)(C)O2)cc1C]

The title compound (88 mg, 80%) was prepared in a manner similar to that in Example A1 step 6 from N-(4-bromo-2,6-dimethylbenzyl)benzamide and BPD. LC-MS (M+H)$^+$=304.3.

Step 3: N-(4-(5-amino-6-((1-(1-methylpiperidin-4-yl)-1H-pyrazol-4-yl)oxy)pyrazin-2-yl)-2,6-dimethylbenzyl)acetamide Example A45 (19 mg, 13%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)acetamide. $^1$H NMR (300 MHz, DMSO-d6) δ 8.20 (s, 1H), 8.10 (s, 1H), 7.87-7.80 (m, 2H), 7.57 (s, 1H), 7.50-7.45 (m, 2H), 6.68 (s, 2H), 4.28-4.20 (m, 2H), 4.19-4.07 (m, 1H), 2.91-2.80 (m, 2H), 2.35-2.29 (m, 6H), 2.20 (s, 3H), 2.13-1.90 (m, 6H), 1.79 (s, 3H). LC-MS (M+H)$^+$=450.4.

Example A46

N-(4-(5-amino-6-((1-(1-methylpiperidin-4-yl)-1H-pyrazol-4-yl)oxy)pyrazin-2-yl)-2-methylbenzyl)methanesulfonamide

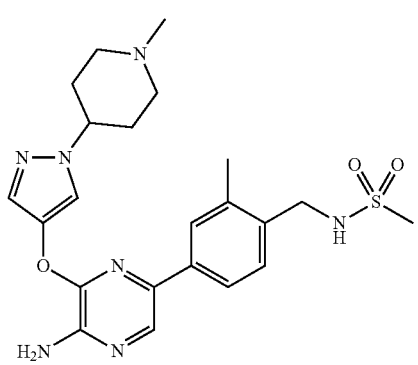 [SMILES: Cc1cc(-c2cnc(N)c(Oc3cnn(C4CCN(C)CC4)c3)n2)ccc1CNS(C)(=O)=O]

Step 1: (4-bromo-2-methylphenyl)methanamine

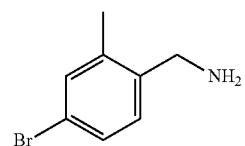

The title compound (2.29 g, 47%) was prepared in a manner similar to that in Example A19 step 1 from 4-bromo-2-methylbenzonitrile. LC-MS (M+H)$^+$=200.0.

Step 2: N-(4-bromo-2-methylbenzyl)methanesulfonamide

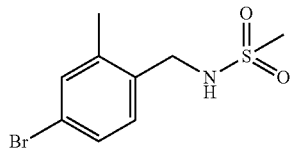

The title compound (377 mg, 59%) was prepared in a manner similar to that in Example A20 step 5 from (4-bromo-2-methylphenyl)methanamine and MsCl. LC-MS (M+H)$^+$=277.7.

Step 2: N-(2-methyl-4-(4,4,5,5-tetramethyl-1,3,2-dioxaborolan-2-yl)benzyl)methanesulfonamide

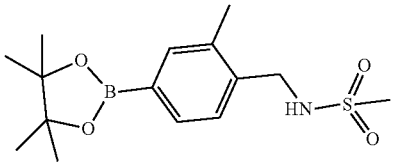

The title compound (142 mg, 71%) was prepared in a manner similar to that in Example A1 step 6 from N-(4-bromo-2-methylbenzyl)methanesulfonamide and BPD. LC-MS (M+H)+=326.2.

Step 3: N-(4-(5-amino-6-((1-(1-methylpiperidin-4-yl)-1H-pyrazol-4-yl)oxy)pyrazin-2-yl)-2-methylbenzyl)methanesulfonamide Example A46 (24 mg, 21%) was prepared in a manner similar to that in Example A1 step 7 from 5-bromo-3-((1-(1-methylpiperidin-4-yl)-1H-pyrazol-4-yl)oxy)pyrazin-2-amine and N-(2-methyl-4-(4,4,5,5-tetramethyl-1,3,2-dioxaborolan-2-yl)benzyl)methanesulfonamide. $^1$H NMR (400 MHz. DMSO-6) δ 8.24 (s, 1H), 8.09 (s, 1H), 7.70-7.58 (m, 3H), 7.39 (t, J=6.0 Hz, 1H), 7.33 (d, J=7.6 Hz, 1H), 6.70 (s, 2H), 4.22-4.06 (m, 3H), 2.95-2.81 (m, 5H), 2.33 (s, 3H), 2.21 (s, 3H), 2.11-1.92 (m, 6H). LC-MS (M+H)+=472.3.

Example A47

1-(4-(5-amino-6-((1-(1-methylpiperidin-4-yl)-1H-pyrazol-4-yl)oxy)pyrazin-2-yl)-2-methylbenzyl)-3-methylurea

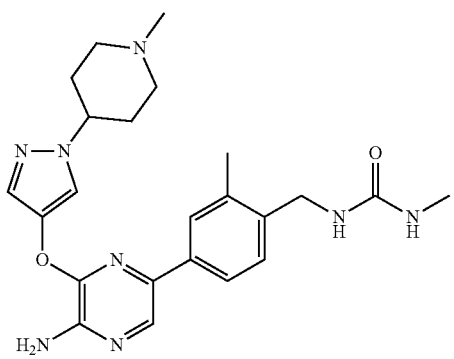 [SMILES: CNC(=O)NCc1ccc(-c2cnc(N)c(Oc3cnn(C4CCN(C)CC4)c3)n2)cc1C]

Step 1: 1-(4-bromo-2-methylbenzyl)-3-methylurea

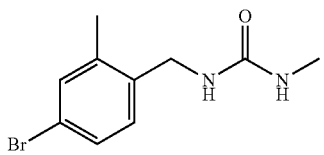

To a stirred mixture of 1-(4-bromo-2-methylphenyl)methanamine (460 mg, 2.292 mmol) and N-methylcarbamoyl chloride (338 mg, 3.43 mmol) in DCM (5 mL) was added triethylamine (473 mg, 4.58 mmol) at room temperature under nitrogen. After 3 h, the mixture was poured into water (50 mL) and extracted with DCM (50 mL×3). The combined organic layer was washed with brine (50 mL), dried over anhydrous Na$_2$SO$_4$ and filtered. The filtrate was concentrated under reduced pressure to give the title compound (550 mg, 93%). LC-MS (M+H)+=259.0.

Step 2: 1-methyl-3-(2-methyl-4-(4,4,5,5-tetramethyl-1,3,2-dioxaborolan-2-yl)benzyl)urea

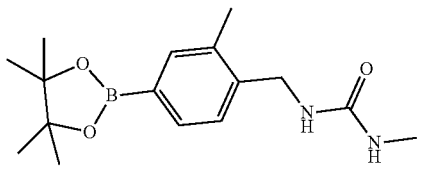

The title compound (140 mg, 68%) was prepared in a manner similar to that in Example A1 step 6 from 1-(4-bromo-2-methylbenzyl)-3-methylurea and BPD. LC-MS (M+H)+=305.0.

Step 3: 1-(4-(5-amino-6-((1-(1-methylpiperidin-4-yl)-1H-pyrazol-4-yl)oxy)pyrazin-2-yl)-2-methylbenzyl)-3-methylurea Example A47 (13 mg, 12%) was prepared in a manner similar to that in Example A1 step 7 from 5-bromo-3-((1-(1-methylpiperidin-4-yl)-1H-pyrazol-4-yl)oxy)pyrazin-2-amine and 1-methyl-3-(2-methyl-4-(4,4,5,5-tetramethyl-1,3,2-dioxaborolan-2-yl)benzyl)urea $^1$H NMR (400 MHz, DMSO-d6) δ 8.21 (s, 1H), 8.09 (s, 1H), 7.66-7.58 (m, 3H), 7.20 (d, J=8.0 Hz, 2H), 6.67 (s, 2H), 6.24 (t, J=5.6 Hz, 1H), 5.77 (q, J=4.8 Hz, 1H), 4.224.08 (m, 3H), 2.94-2.83 (m, 2H), 2.57 (d, J=4.4 Hz, 3H), 2.28 (s, 3H), 2.22 (s, 3H), 2.15-1.90 (m, 6H). LC-MS (M+H)+=451.4.

Example A48

5-(3,5-dimethyl-4-(((2,2,2-trifluoroethyl)amino)methyl)phenyl)-3-((1-(1-methylpiperidin-4-yl)-1H-pyrazol-4-yl)oxy)pyrazin-2-amine

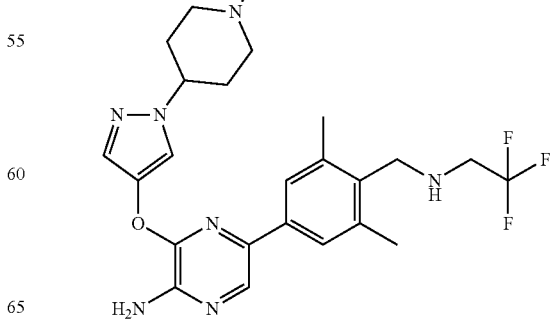

Step 1: 4-bromo-2,6-dimethyl-N-(2,2,2-trifluoroethyl)benzamide

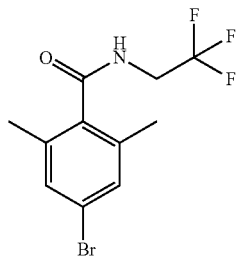 [SMILES: Cc1cc(Br)cc(C)c1C(=O)NCC(F)(F)F]

4-bromo-2,6-dimethylbenzoic acid (1.5 g, 6.55 mmol) and DMF (2 drops) was dissolved in DCM (20 mL). Oxalyl chloride (1.1 mL, 13.1 mmol) was added dropwise at 0° C. and the mixture was warmed to room temperature then stirred for 1 h. The mixture was concentrated under vacuum. The crude was dissolved in anhydrous THF (10 mL) then the solution was added dropwise to a mixture of 2,2,2-trifluoroethan-1-amine (714 mg, 7.20 mmol) and DIPEA (2.55 mL, 14.41 mmol) in anhydrous THF (20 mL) at 0° C. The mixture was warmed to room temperature then stirred for 2 h. Water (100 mL) was carefully added, and the mixture was extracted with EtOAc (50 mL×3). The combined organic layer was washed with brine (50 mL), dried over $Na_2SO_4$ then concentrated under vacuum. The residue was purified by silica gel chromatography to give the title compound (1.8 g, 89%). LC-MS (M+H)+=311.0.

Step 2: N-(4-bromo-2,6-dimethylbenzyl)-2,2,2-trifluoroethan-1-amine

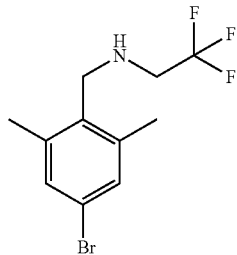 [SMILES: Cc1cc(Br)cc(C)c1CNCC(F)(F)F]

To 4-bromo-2,6-dimethyl-N-(2,2,2-trifluoroethyl)benzamide (1.7 g, 5.48 mmol) was added $BH_3$-THF complex (1.0 M, 22 mL, 22 mmol) and the mixture was heated to reflux for 24 h. The mixture was cooled to 0° C. and MeOH (10 mL) was added. The mixture was concentrated under reduced pressure. The residue was purified by silica gel chromatography to give the title compound (600 mg, 37%). LC-MS (M+H)+=297.0.

Step 3: 5-(3,5-dimethyl-4-(((2,2,2-trifluoroethyl)amino)methyl)phenyl)-34(1-(1-methylpiperidin-4-yl)-1H-pyrazol-4-yl)oxy)pyrazin-2-amine A solution of N-(4-bromo-2,6-dimethylbenzyl)-2,2,2-trifluoroethan-1-amine (200 mg, 0.675 mmol), BPD (257 mg, 1.01 mmol), KOAc (133 mg, 1.35 mmol) and Pd(dppl)C12 (25 mg, 0.034 mmol) in 1,4-dioxane (20 mL) was heated to reflux under $N_2$ for 2 h. The solution was cooled to room temperature, then 5-bromo-3-((1-(1-methylpiperidin-4-yl)-1H-pyrazol-4-yl)oxy)pyrazin-2-amine (239 mg, 0.675 mmol), $K_2CO_3$ (186 mg, 1.35 mmol), Pd(dppf)Cl$_2$ (25 mg, 0.034 mmol) and water (10 mL) was added. The mixture was heated to reflux under $N_2$ for 12 h then cooled to room temperature. The solvent was concentrated under reduced pressure to give Example A48 (80 mg, 24%). $^1$H NMR (400 MHz, DMSO-d6) δ 8.21 (s, 1H), 8.12 (s, 1H), 7.58 (s, 1H), 7.47 (s, 2H), 6.67 (s, 2H), 4.14-4.10 (m, 1H), 3.75 (d, J=6.5 Hz, 2H), 3.31-3.27 (m, 2H), 2.86 (d, J=11.2 Hz, 2H), 2.36 (s, 6H), 2.21 (s, 3H), 2.11-1.96 (m, 6H). LC-MS (M+H)+= 490.0.

Example A49

(R)-3-(5-amino-6-((1-(1-methylpiperidin-4-yl)-1H-pyrazol-4-yl)oxy)pyrazin-2-yl)-N-methyl-5-(3-methylmorpholino)benzenesulfonamide

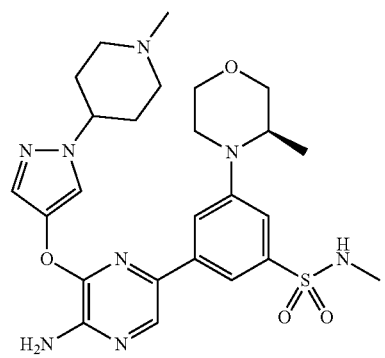 [SMILES: CNS(=O)(=O)c1cc(-c2cnc(N)c(Oc3cnn(C4CCN(C)CC4)c3)n2)cc(N2CCOC[C@H]2C)c1]

Step 1: 3-bromo-5-chloro-N-methylbenzenesulfonamide

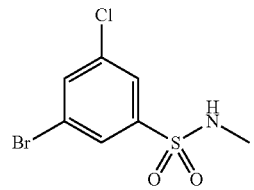

The title compound (596 mg, 61%) was prepared in a manner similar to that in Example A7 step 1 from 3-bromo-5-chlorobenzenesulfonyl chloride.

Step 2: (R)-3-chloro-N-methyl-5-(3-methylmorpholino)benzenesulfonamide

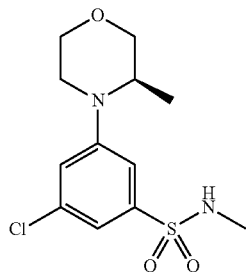 [SMILES: CNS(=O)(=O)c1cc(Cl)cc(N2CCOC[C@H]2C)c1]

To a stirred mixture of 3-bromo-5-chloro-N-methylbenzenesulfonamide (560 mg, 1.95 mmol) and (3R)-3-methylmorpholine (395 mg, 3.91 mmol) in dioxane (10 mL) was added Pd(dba)$_2$ (112 mg, 0.20 mmol), JohnPhos (58 mg, 0.20 mmol) and t-BuOK (43.9 mg, 0.39 mmol) at room temperature under nitrogen. The mixture was stirred for 2 h at 100° C. The mixture was cooled to room temperature and concentrated under vacuum. The residue was purified by C18 flash chromatography to give the title compound (268 mg, 45%). LC-MS (M+H)$^+$=305.0.

Step 3: (R)-N-methyl-3-(3-methylmorpholino)-5-(4,4,5,5-tetramethyl-1,3,2-dioxaborolan-2-yl)benzenesulfonamide

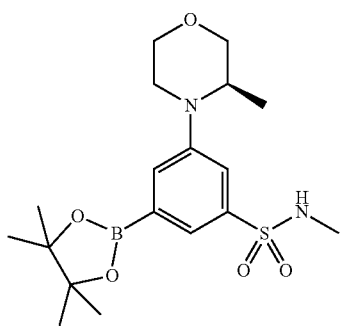

The title compound (248 mg, 83%) was prepared in a manner similar to that in Example A1 step 6 from (R)-3-chloro-N-methyl-5-(3-methylmorpholino)benzenesulfonamide and BPD. LC-MS (M-pin)$^+$=315.1.

Step 4: (R)-3-(5-amino-6-((1-(1-methylpiperidin-4-yl)-1H-pyrazol-4-yl)oxy)pyrazin-2-yl)-N-methyl-5-(3-methylmorpholino)benzenesulfonamide Example A49 (32 mg, 21%) was prepared in a manner similar to that in Example A1 step 7 from 5-bromo-3-((1-(1-methylpiperidin-4-yl)-1H-pyrazol-4-yl)oxy)pyrazin-2-amine and (R)-N-methyl-3-(3-methylmorpholino)-5-(4,4,5,5-tetramethyl-1,3,2-dioxaborolan-2-yl) benzenesulfonamide, 1H NMR (400 MHz, DMSO-d$_6$) δ 8.32 (s, 1H), 8.10 (s, 1H), 7.61-7.57 (m, 2H), 7.53 (m, 1H), 7.40-7.34 (m, 1H), 7.12 (s, 1H), 6.88 (s, 2H), 4.17-4.04 (m, 1H), 4.03-3.91 (m, 2H), 3.77-3.67 (m, 2H), 3.62-3.51 (m, 1H), 3.14-3.04 (m, 1H), 2.94-2.84 (m, 2H), 2.41 (d, J=5.2 Hz, 3H), 2.23 (s, 3H), 2.13-1.89 (m, 6H), 1.04 (d, J=6.5 Hz, 3H). LC-MS (M+H)$^+$=543.3.

Example A50

(3-(5-amino-6-((1-(1-methylpiperidin-4-yl)-1H-pyrazol-4-yl)oxy)pyrazin-2-yl)-5-methylphenyl)dimethylsilanol

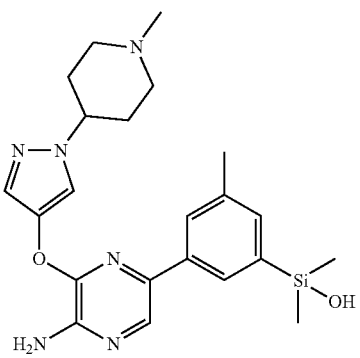 [SMILES: Cc1cc(-c2cnc(N)c(Oc3cnn(C4CCN(C)CC4)c3)n2)cc([Si](C)(C)O)c1]

Step 1: (3-bromo-5-methylphenyl)(chloromethyl)dimethylsilane

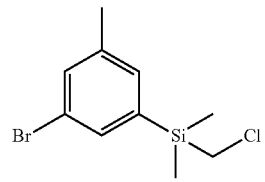

To a solution of 1,3-dibromo-5-methylbenzene (2.0 g, 8.0 mmol) in THF (20 mL) was added n-BuLi (2.5 M in hexane, 3.2 mL, 8.0 mmol) at −78° C. under nitrogen. After 1 h, chloro(chloromethyl)dimethylsilane (1.7 g, 12 mmol) was added. After 3 h, the mixture was warmed to room temperature, poured into water (60 mL). The mixture was extracted with EtOAc (60 mL×2). The combined organic layer was washed with brine (50 mL), dried over Na$_2$SO$_4$, filtered and concentrated under vacuum. The crude was purified by silica gel column chromatography (PE:EtOAc=5:1) to give the title compound (2.0 g, 90%). $^1$H NMR (400 MHz, CDCl$_3$) δ 7.20 (s, 1H), 7.14 (s, 1H), 7.01 (s, 1H), 2.71 (s, 2H), 2.11 (s, 3H), 0.18 (s, 6H).

Step 2: ((3-bromo-5-methylphenyl)dimethylsilyl)methyl acetate

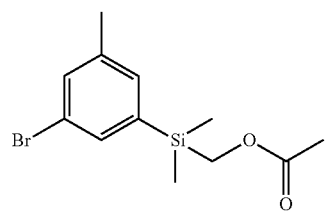 [SMILES: CC(=O)OC[Si](C)(C)c1cc(C)cc(Br)c1]

A mixture of (3-bromo-5-methylphenyl)(chloromethyl)dimethylsilane (2.0 g, 7.2 mmol) and KOAc (2.8 g, 28.8 mmol) in DMF (30 mL) was stirred for 3 h at 90° C. The mixture was cooled to room temperature then diluted with water (60 mL). The mixture was extracted with EtOAc (60 mL×2). The combined organic layer was washed with brine (50 mL), dried over Na₂SO₄, filtered and concentrated under vacuum. The crude was purified by silica gel column chromatography (PE:EtOAc=5:1) to give the title compound (1.6 g, 74%). $^1$H NMR (400 MHz, CDCl₃) δ 7.40 (s, 1H), 7.33 (s, 1H), 7.20 (s, 1H), 3.91 (s, 2H), 2.31 (s, 3H), 2.02 (s, 3H), 0.32 (s, 6H).

Step 3: ((3-bromo-5-methylphenyl)dimethylsilyl)methanol

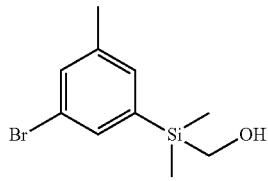

A solution of ((3-bromo-5-methylphenyl)dimethylsilyl) methyl acetate (1.6 g, 5.31 mmol) and K2CO₃ (1.46 g, 10.6 mmol) in MeOH (30 mL) was stirred for 4 h at room temperature then diluted with water (50 mL). The mixture was extracted with EtOAc (50 mL×2). The combined organic layer was washed with brine (50 mL), dried over Na₂SO₄, filtered and concentrated under vacuum. The crude was purified by silica gel column chromatography (PE:EtOAc=3:1) to give the title compound (1.2 g, 87%). $^1$H NMR (400 MHz, CDCl₃) δ 7.45 (s, 1H), 7.35 (s, 1H), 7.26 (s, 1H), 3.57 (s, 2H), 2.33 (s, 3H), 0.34 (s, 6H).

Step 4: (3-bromo-5-methylphenyl)dimethylsilanol

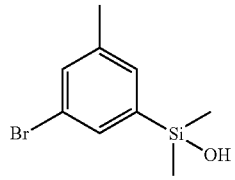

10% sodium hypochlorite (6.8 g, 9.1 mmol) was slowly added to an aqueous NaHCO₃ solution (0.50 M, 37 mL), then the solution was slowly added to a solution of ((3-bromo-5-methylphenyl)dimethylsilyl)methanol (1.2 g, 4.63 mmol), TEMPO (72 mg, 0.463 mmol), and KBr (55 mg, 0.463 mmol) in acetone (60 mL) at 0° C. The mixture was warmed to room temperature and stirred for 2 h. Then, saturated NH₄Cl (30 mL) was added, and the mixture was extracted with EtOAc (50 mL×3). The combined organic layer was washed with brine (50 mL), dried over Na₂SO₄, filtered and concentrated under vacuum. The crude was purified by silica gel column chromatography (PE:EtOAc=3:1) to give the title compound (0.80 g, 70%). $^1$H NMR (400 MHz, CDCl₃) δ 7.48 (s, 1H), 7.36 (s, 1H), 7.29 (s, 1H), 2.33 (s, 3H), 0.39 (s, 6H).

Step 5: dimethyl(3-methyl-5-(4,4,5,5-tetramethyl-1,3,2-dioxaborolan-2-yl)phenyl)silanol

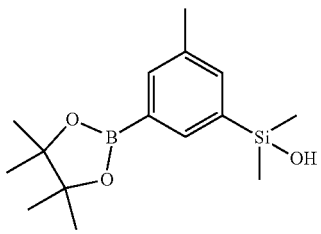

The title compound (500 mg, 70%) was prepared in a manner similar to that in Example A1 step 6 from (3-bromo-5-methylphenyl)dimethylsilanol and BPD. $^1$H NMR (400 MHz, CDCl₃) δ 7.84 (s, 1H), 7.67 (s, 1H), 7.52 (s, 1H), 2.37 (s, 3H), 1.35 (s, 12H), 0.41 (s, 6H). LCMS (M+H)⁺=293.1.

Step 6: (3-(5-amino-6-((1-(1-methylpiperidin-4-yl)-1H-pyrazol-4-yl)oxy)pyrazin-2-yl)-5-methylphenyl) dimethylsilanol Example A50 (30 mg, 16%) was prepared in a manner similar to that in Example A1 step 7 from 5-bromo-3-((1-(1-methylpiperidin-4-yl)-1H-pyrazol-4-yl)oxy)pyrazin-2-amine and dimethyl(3-methyl-5-(4,4,5,5-tetramethyl-1,3,2-dioxaborolan-2-yl)phenyl)silanol. $^1$H NMR (400 MHz, DMSO-d6) δ 8.23 (s, 1H), 8.14 (s, 1H), 7.82 (s, 1H), 7.65 (s, 1H), 7.59 (s, 1H), 7.27 (s, 1H), 6.71 (s, 2H), 6.03 (s, 1H), 4.25 4.08 (m, 1H), 2.96-2.86 (m, 2H), 2.33 (s, 3H), 2.26 (s, 3H), 2.16-1.97 (m, 6H), 0.25 (s, 6H). LCMS (M+H)⁺=439.3.

Example A51

1-(4-(5-amino-6-((1-(1-methylpiperidin-4-yl)-1H-pyrazol-4-yl)oxy)pyrazin-2-yl)-2,6-dimethylbenzyl)-3-(2,2,2-trifluoroethyl)urea

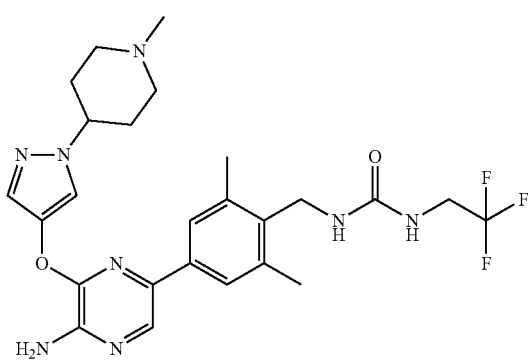 [SMILES: Cc1cc(-c2cnc(N)c(Oc3cnn(C4CCN(C)CC4)c3)n2)cc(C)c1CNC(=O)NCC(F)(F)F]

Step 1: tert-butyl (4-bromo-2,6-dimethylbenzyl)carbamate

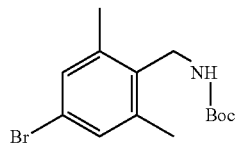

To a solution of (4-bromo-2,6-dimethylphenyl)methanamine (300 mg, 1.4 mmol) in THF (10 mL) was added triethylamine (283 mg, 2.8 mmol), (Boc)$_2$O (448 mg, 2.8 mmol) then the mixture was stirred for overnight at room temperature. EtOAc (10 mL) was added and the mixture was successively washed with H$_2$O (5 mL) and brine (5 mL), dried over Na$_2$SO$_4$ and concentrated under reduced pressure. The residue was purified by silica gel column (PE: EtOAc=20:1) to give the title compound (380 mg, 86%). LC-MS (M+H)$^+$=314.2, 316.2.

Step 2: tert-butyl (2,6-dimethyl-4-(4,4,5,5-tetramethyl-1,3,2-dioxaborolan-2-yl)benzyl)carbamate

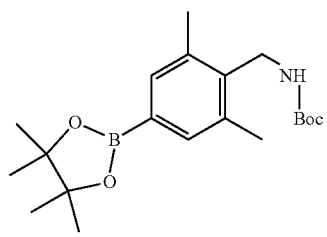 [SMILES: Cc1cc(B2OC(C)(C)C(C)(C)O2)cc(C)c1CNC(=O)OC(C)(C)C]

The title compound (250 mg, 69%) was prepared in a manner similar to that in Example A1 step 6 from tert-butyl (4-bromo-2,6-dimethylbenzyl)carbamate and BPD. LC-MS (M+H)$^+$=362.3.

Step 3: tert-butyl (4-(5-amino-6-((1-(1-methylpiperidin-4-yl)-1H-pyrazol-4-yl)oxy)pyrazin-2-yl)-2,6-dimethylbenzyl)carbamate

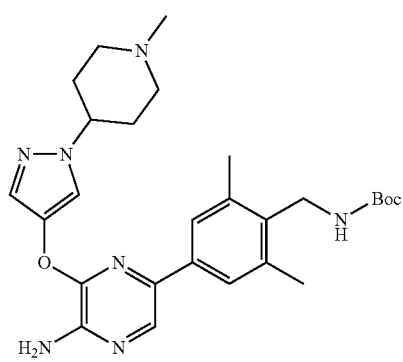 [SMILES: Cc1cc(-c2cnc(N)c(Oc3cnn(C4CCN(C)CC4)c3)n2)cc(C)c1CNC(=O)OC(C)(C)C]

5-bromo-3-((1-(1-methylpiperidin-4-yl)-1H-pyrazol-4-yl)oxy)pyrazin-2-amine (188 mg, 0.5 mmol), tert-butyl (2,6-dimethyl-4-(4,4,5,5-tetramethyl-1,3,2-dioxaborolan-2-yl)benzyl)carbamate (250 mg, 0.7 mmol), Pd(dppf)Cl$_2$·CH$_2$Cl$_2$ (43 mg, 0.05 mmol) and K$_2$CO$_3$ (219 mg, 1.6 mmol) was added in dioxane (10 mL) and H$_2$O (1 mL) under nitrogen and the mixture was heated to reflux for overnight. The mixture was cooled to room temperature and EtOAc (15 mL) was added. The mixture was washed with brine (10 mL×2), and the aqueous layer was back extracted with EtOAc (15 mL). The combined organic layer was dried over Na$_2$SO$_4$, filtered and concentrated under reduced pressure. The crude was purified by prep-TLC (DCM:MeOH=15:1) to give the title compound (180 mg, 67%). LC-MS (M+H)$^+$=508.6.

Step 4: 5-(4-(aminomethyl)-3,5-dimethylphenyl)-3-((1-(1-methylpiperidin-4-yl)-1H-pyrazol-4-yl)oxy) pyrazin-2-amine; bis-trifluoroacetic acid

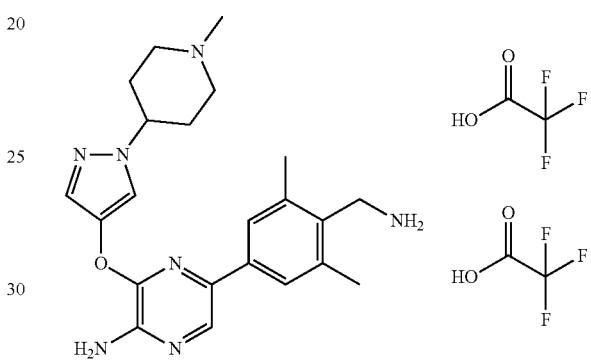

To a solution of tert-butyl (4-(5-amino-6-((1-(1-methylpiperidin-4-yl)-1H-pyrazol-4-yl)oxy)pyrazin-2-yl)-2,6-dimethylbenzyl)carbamate (180 mg, 0.36 mmol) in DCM (4 mL) was added TFA (2 mL) dropwise at 0° C. The mixture was stirred for 1 h at room temperature and then concentrated under vacuum to give the title compound (225 mg, 100%). LC-MS (M+H)$^+$=408.5.

Step 5: 1-(4-(5-amino-6-((1-(1-methylpiperidin-4-yl)-1H-pyrazol-4-yl)oxy)pyrazin-2-yl)-2,6-dimethylbenzyl)-3-(2,2,2-trifluoroethyl)urea A mixture of 2,2,2-trifluoroethan-1-amine (121 mg, 1.2 mmol) and pyridine (240 mg, 3.1 mmol) in DCM (5 mL) was cooled to 0° C. and a solution of triphosgene (134 mg, 0.45 mmol) in DCM (5 mL) was added dropwise. The reaction mixture was warmed to 35° C. and stirred for 1 h and then 25° C. for 2 h. An aliquot (1.0 mL) of the mixture was added to a solution of 5-(4-(aminomethyl)-3,5-dimethylphenyl)-3-((1-(1-methylpiperidin-4-yl)-1H-pyrazol-4-yl)oxy)pyrazin-2-amine; bis-trifluoroacetic acid (20 mg, 0.031 mmol) and triethylamine (15 mg, 0.15 mmol) in DCM (1.0 mL) at 0° C. After 3 h, DCM (10 mL) was added and the mixture was successively washed with H$_2$O (5 mL) and brine (5 mL), dried over Na$_2$SO$_4$, filtered and concentrated under vacuum. The residue was purified by prep-HPLC to give Example A51 (2.8 mg, 17%). $^1$H NMR (400 MHz, DMSO-d6) δ 8.22 (s, 1H), 8.12 (s, 1H), 7.58 (s, 1H), 7.49 (s, 2H), 6.70 (s, 2H), 6.26 (s, 2H), 4.24 (s, 2H), 4.16-4.10 (m, 1H), 3.86-3.79 (m, 2H), 2.86-2.81 (m, 2H), 2.34 (s, 6H), 2.21 (s, 3H), 2.03-1.92 (m, 6H). LC-MS (M+H)$^+$=533.4.

Example A52

2-(3-(5-amino-6-((1-(1-methylpiperidin-4-yl)-1H-pyrazol-4-yl)oxy)pyrazin-2-yl)-5-methylphenyl)propan-2-ol

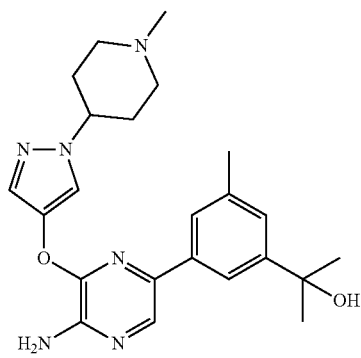 [SMILES: Cc1cc(-c2cnc(N)c(Oc3cnn(C4CCN(C)CC4)c3)n2)cc(C(C)(C)O)c1]

Step 1: methyl 3-methyl-5-(4,4,5,5-tetramethyl-1,3,2-dioxaborolan-2-yl)benzoate

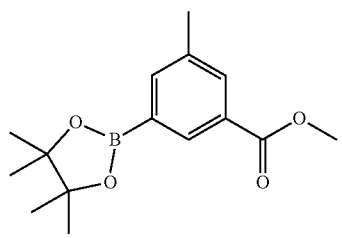

The title compound (800 mg, 96%) was prepared in a manner similar to that in Example A1 step 6 from 3-bromo-5-methylbenzoate and BPD. LC-MS (M+H)⁺=277.2.

Step 2: methyl 3-(5-amino-6-((1-(1-methylpiperidin-4-yl)-1H-pyrazol-4-yl)oxy)pyrazin-2-yl)-5-methylbenzoate

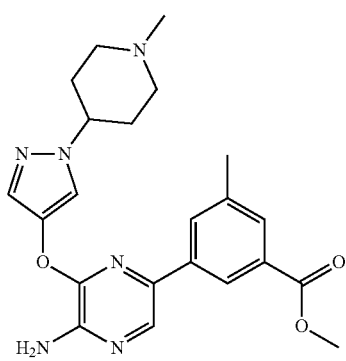 [SMILES: COC(=O)c1cc(C)cc(-c2cnc(N)c(Oc3cnn(C4CCN(C)CC4)c3)n2)c1]

The title compound (3M) mg, 71%) was prepared in a manner similar to that in Example A1 step 7 from 5-bromo-3-((1-(1-methylpiperidin-4-yl)-1H-pyrazol-4-yl)oxy)pyrazin-2-amine and methyl 3-methyl-5-(4,4,5,5-tetramethyl-1,3,2-dioxaborolan-2-yl)benzoate. LC-MS (M+H)⁺=423.3.

Step 3: 2-(3-(5-amino-6-((1-(1-methylpiperidin-4-yl)-1H-pyrazol-4-yl)oxy)pyrazin-2-yl)-5-methylphenyl)propan-2-ol To a solution of methyl 3-(5-amino-6-((1-(1-methylpiperidin-4-yl)-1H-pyrazol-4-yl)oxy)pyrazin-2-yl)-5-methylbenzoate (84 mg, 0.10 mmol) in anhydrous THF (3 mL) was added MeLi in Et$_2$O (1.6 M, 0.63 mL, 1.0 mmol) dropwise at −78° C. under nitrogen. The mixture was slowly warm to room temperature, then saturated NH$_4$Cl (50 mL) was added. The mixture was extracted by EtOAc (100 mL). The organic layer was concentrated under reduced pressure and purified by prep-HPLC to give Example A52 (20 mg, 24%). $^1$H NMR (400 MHz, DMSO-d$_6$) 8.21 (s, 1H), 8.14 (s, 1H), 7.73 (s, 1H), 7.59 (s, 1H), 7.48 (s, 1H), 7.22 (s, 1H), 6.68 (s, 2H), 5.02 (s, 1H), 4.20-4.11 (m, 1H), 2.89-2.75 (m, 2H), 2.22 (s, 3H), 2.07 (s, 3H), 2.05-1.94 (m, 6H), 1.43 (s, 6H). LCMS (M+H)⁺=423.3.

Example A53

1-(4-(5-amino-6-((1-(1-methylpiperidin-4-yl)-1H-pyrazol-4-yl)oxy)pyrazin-2-yl)-2,6-dimethylbenzyl)-3-(tert-butyl)urea

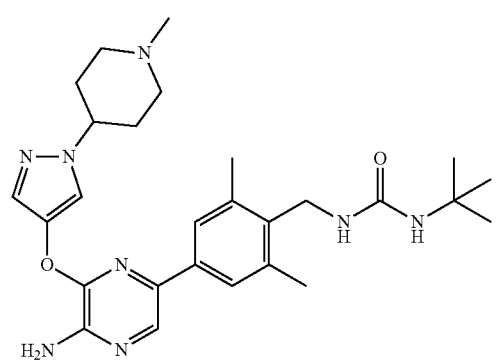 [SMILES: Cc1cc(-c2cnc(N)c(Oc3cnn(C4CCN(C)CC4)c3)n2)cc(C)c1CNC(=O)NC(C)(C)C]

To a stirred mixture of 5-(4-(aminomethyl)-3,5-dimethylphenyl)-3-((1-(1-methylpiperidin-4-yl)-1H-pyrazol-4-yl)oxy)pyrazin-2-amine; bis-trifluoroacetic acid (100 mg, 0.158 mmol) and Et$_3$N (90 mg, 0.89 mmol) in THF (20 mL) was added 2-isocyanato-2-methylpropane (25 mg, 0.252 mmol) at 0° C. The mixture was warmed to room temperature and stirred for 3 h, then concentrated under reduced pressure. The crude was purified by prep-HPLC to give Example A53 (19 mg, 24%). $^1$H NMR (400 MHz, DMSO-d$_6$) δ 8.33 (s, 1H), 8.16 (s, 1H), 8.02 (s, 1H), 7.94 (s, 1H), 7.64 (s, 1H), 7.49 (s, 1H), 7.43-7.35 (m, 1H), 6.91 (s, 2H), 4.65-4.52 (m, 1H), 3.59 (t, J=4.6 Hz, 4H), 2.64-2.54 (m, 3H), 2.43 (d. J=5.0 Hz, 6H), 2.37-2.25 (m, 6H). LC-MS (M+H)=507.4.

Example A54

3-(3-(5-amino-6-((1-(1-methylpiperidin-4-yl)-1H-pyrazol-4-yl)oxy)pyrazin-2-yl)-5-methylphenyl)oxetan-3-ol

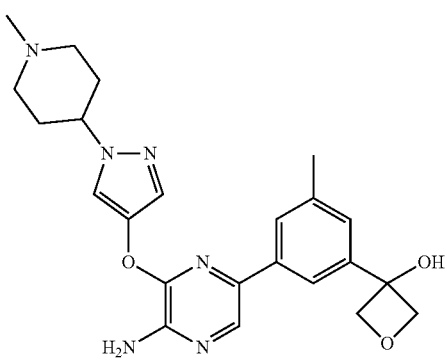 [SMILES: Cc1cc(-c2cnc(N)c(Oc3cnn(C4CCN(C)CC4)c3)n2)cc(C2(O)COC2)c1]

Step 1: 3-(3-chloro-5-methylphenyl)oxetan-3-ol

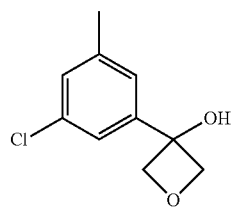

To a solution of 1-bromo-3-chloro-5-methylbenzene (2.0 g, 9.8 mmol) in THF (30 mL) was added n-BuLi in hexane (2.5 M, 3.9 mL, 9.8 mmol) at −78° C. under nitrogen. After 1 h, oxetan-3-one (1.06 g, 14.7 mmol) was added dropwise. The mixture was stirred for 3 h at −78° C. and warmed to room temperature. The mixture was poured into water (100 mL) and then extracted with EtOAc (100 mL×3). The combined organic layer was washed with brine (100 mL), dried over Na$_2$SO$_4$, filtered and concentrated under vacuum. The crude was purified by silica gel column chromatography (PE:EtOAc=3:1) to give the title compound (1.2 g, 62%). LC-MS (M+H)$^+$=199.0.

Step 2: 3-(3-methyl-5-(4,4,5,5-tetramethyl-1,3,2-dioxaborolan-2-yl)phenyl)oxetan-3-ol

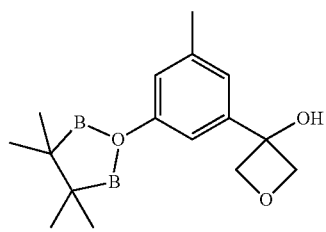

To a solution of 3-(3-chloro-5-methylphenyl)oxetan-3-ol (400 mg, 2.0 mmol) in dioxane (10 mL) was added BPD (667 mg, 2.6 mmol), dichlorobis(tricyclohexylphosphine)palladium(II) (179 mg, 0.24 mmol) and AcOK (297 mg, 3.03 mmol). The mixture was stirred for 16 h at 100° C., cooled to room temperature and poured into water (100 mL). The mixture was extracted with EtOAc (100 mL×3). The combined organic layer was washed with brine (100 mL), dried over Na$_2$SO$_4$, filtered and concentrated under vacuum. The crude was purified by silica gel column chromatography (PE:EtOAc=3:1) to give the title compound (184 mg, 31%). LC-MS (M+H)$^+$=291.1.

Step 3: 3-(3-(5-amino-6-((1-(1-methylpiperidin-4-yl)-1H-pyrazol-4-yl)oxy)pyrazin-2-yl)-5-methylphenyl)oxetan-3-ol To a mixture of 5-bromo-3-((1-(1-methylpiperidin-4-yl)-1H-pyrazol-4-yl)oxy)pyrazin-2-amine (150 mg, 0.43 mmol) in dioxane (9 mL) and water (3 mL) was added 3-(3-methyl-5-(4,4,5,5-tetramethyl-1,3,2-dioxaborolan-2-yl)phenyl)oxetan-3-ol (187 mg, 0.64 mmol), Pd(dppf)Cl$_2$ (35 mg, 0.04 mmol) and K$_2$CO$_3$ (178 mg, 1.29 mmol). The mixture was stirred for 16 h at 95° C., cooled to room temperature then poured into water (100 mL). The mixture was extracted with EtOAc (100 mL×3). The combined organic layer was washed with brine (100 mL), dried over Na$_2$SO$_4$, filtered and concentrated under vacuum. The crude was purified by prep-HPLC to give Example A54 (59 mg, 32%). $^1$H NMR (400 MHz, DMSO-d$_6$) δ 8.26 (s, 1H), 8.14 (s, 1H), 7.88 (s, 1H), 7.65-7.55 (m, 2H), 7.34 (s, 1H), 6.73 (s, 2H), 6.35 (s, 1H), 4.86-4.63 (m, 4H), 4.20-4.06 (m, 1H), 2.95-2.80 (m, 2H), 2.37 (s, 3H), 2.21 (s, 3H), 2.11-1.91 (m, 6H). LC-MS (M+H)$^+$=437.3.

Example A55

5-(3,5-dimethyl-4-((oxetan-3-ylamino)methyl)phenyl)-3-((1-(1-methylpiperidin-4-yl)-1H-pyrazol-4-yl)oxy)pyrazin-2-amine

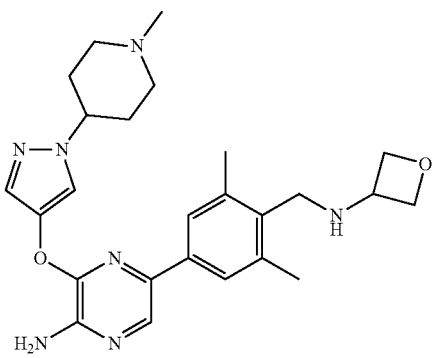 [SMILES: Cc1cc(-c2cnc(N)c(Oc3cnn(C4CCN(C)CC4)c3)n2)cc(C)c1CNC1COC1]

Step 1:
N-(4-bromo-2,6-dimethylbenzyl)oxetan-3-amine

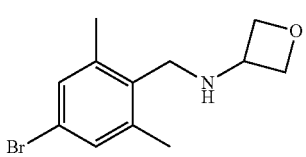

To a solution of 4-bromo-2,6-dimethylbenzaldehyde (3.0 g, 14 mmol) in DCM (60 mL) was added oxetan-3-amine (0.85 g, 11.7 mmol) and NaBH(OAc)₃ (5.0 g, 23.4 mmol) at room temperature. After 16 h, The mixture was quenched with saturated NaHCO₃ solution (50 mL) and extracted with DCM (50 mL×2). The combined organic layer was washed with brine (50 mL), dried over Na₂SO₄, filtered and concentrated under reduced pressure. The residue was purified by silica gel chromatography (PE/EtOAc=5/1 to 1/1) to give the title compound (2.0 g, 63%). LCMS (M+H)⁺=270, 272.

Step 2: N-(2,6-dimethyl-4-(4,4,5,5-tetramethyl-1,3,2-dioxaborolan-2-yl)benzyl)oxetan-3-amine

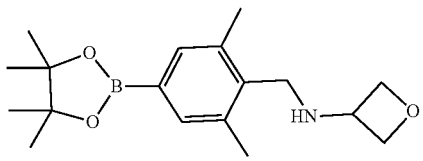 [SMILES: Cc1cc(B2OC(C)(C)C(C)(C)O2)cc(C)c1CNC1COC1]

The title compound (1.5 g, 63%) was prepared in a manner similar to that in Example A1 step 6 from N-(4-bromo-2,6-dimethylbenzyl)oxetan-3-amine and BPD. LCMS (M+H)⁺=318.2.

Step 3: 5-(3,5-dimethyl-4-((oxetan-3-ylamino)methyl)phenyl)-3-((1-(1-methylpiperidin-4-yl)-1H-pyrazol-4-yl)oxy)pyrazin-2-amine Example A55 (310 mg, 24%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)oxetan-3-amine. ¹H NMR (400 MHz, DMSO-d6) δ 8.21 (s, 1H), 8.12 (s, 1H), 7.58 (s, 1H), 7.49-7.44 (m, 2H), 6.67 (s, 2H), 4.67-4.58 (m, 2H), 4.40-4.30 (m, 2H), 4.19-4.09 (m, 1H), 3.96-3.86 (m, 1H), 3.60-3.52 (s, 2H), 2.90-2.80 (m, 2H), 2.36 (s, 6H), 2.21 (s, 3H), 2.11-1.96 (m, 6H). LCMS (M+H)⁺=464.3.

Example A56

5-(3,5-dimethyl-4-(((1-methyl-1H-pyrazol-3-yl)amino)methyl)phenyl)-3-((1-(1-methylpiperidin-4-yl)-1H-pyrazol-4-yl)oxy)pyrazin-2-amine

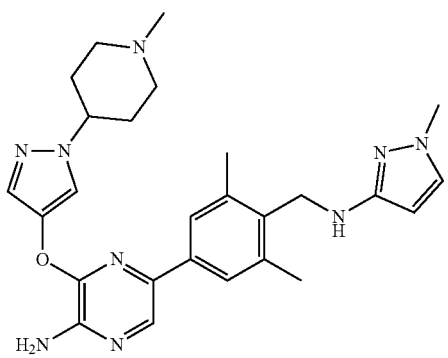 [SMILES: Cc1cc(-c2cnc(N)c(Oc3cnn(C4CCN(C)CC4)c3)n2)cc(C)c1CNc1ccn(C)n1]

Step 1: N-(4-bromo-2,6-dimethylbenzyl)-1-methyl-1H-pyrazol-3-amine

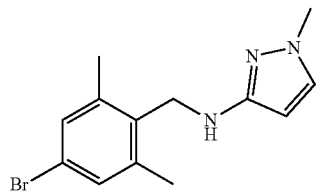 [SMILES: Cc1cc(Br)cc(C)c1CNc1ccn(C)n1]

To a stirred mixture of 4-bromo-2,6-dimethylbenzaldehyde (1.14 g, 5.1 mmol) and 1-methylpyrazol-3-amine (400 mg, 3.9 mmol) in MeOH (5 mL) was added AcOH (50 mg, 0.78 mmol) at room temperature. After 16 h, the mixture was cooled to 0° C. and NaBH₃CN (492 mg, 7.8 mmol) was added. The mixture was warmed to room temperature and stirred for 2 h. then cooled to 0° C. again. Water (5 mL) was added and the precipitate was collected by filtration. The solid was washed with EtOAc (10 mL×3) and dried under vacuum to give the title compound (600 mg, 35%). LC-MS (M+H)⁺=294.1.

Step 2: N-(2,6-dimethyl-4-(4,4,5,5-tetramethyl-1,3,2-dioxaborolan-2-yl)benzyl)-1-methyl-1H-pyrazol-3-amine

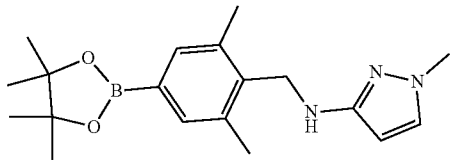

The title compound (116 mg, 50%) was prepared in a manner similar to that in Example A1 step 6 from N44-bromo-2,6-dimethylbenzyl)-1-methyl-1H-pyrazol-3-amine and BPD. LC-MS (M+H)⁺=342.1.

Step 3: 5-(3,5-dimethyl-4-(((1-methyl-1H-pyrazol-3-yl)amino)methyl)phenyl)-3-((1-(1-methylpiperidin-4-yl)-1H-pyrazol-4-yl)oxy)pyrazin-2-amine Example A56 (10 mg, 7%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)-1-methyl-1H-pyrazol-3-amine. ¹H NMR (400 MHz, DMSO-d₆) δ 8.22 (s, 1H), 8.12 (s, 1H), 7.59 (s, 1H), 7.49 (s, 2H), 7.33-7.28 (m, 1H), 6.67 (s, 2H), 5.44-5.40 (m, 1H), 4.98 (t, J=5.6 Hz, 1H), 4.19-4.07 (m, 3H), 3.63 (s, 3H), 2.90-2.81 (m, 2H), 2.36 (s, 6H), 2.20 (s, 3H), 2.12-1.90 (m, 6H). LC-MS (M+H)⁺=488.3.

Example A57

5-(3,5-dimethyl-4-(((1-methyl-1H-pyrazol-4-yl)amino)methyl)phenyl)-3-((1-(1-methylpiperidin-4-yl)-1H-pyrazol-4-yl)oxy)pyrazin-2-amine

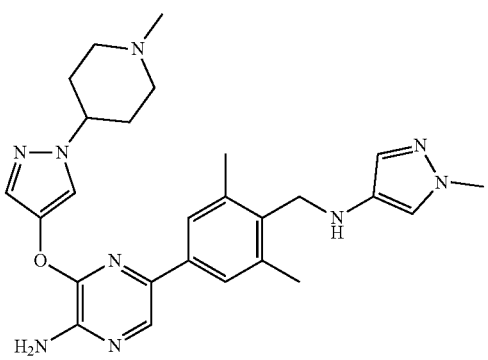 [SMILES: Cc1cc(-c2cnc(N)c(Oc3cnn(C4CCN(C)CC4)c3)n2)cc(C)c1CNc1cnn(C)c1]

Step 1: N-(4-bromo-2,6-dimethylbenzyl)-1-methyl-1H-pyrazol-4-amine

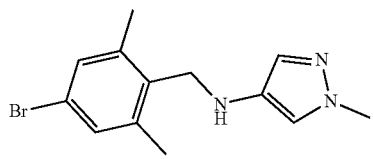 [SMILES: Cc1cc(Br)cc(C)c1CNc1cnn(C)c1]

The title compound (216 mg, 35%) was prepared in a manner similar to that in Example A56 step 1 from 4-bromo-2,6-dimethylbenzaldehyde and 1-methylpyrazol-4-amine. LC-MS (M+H)$^+$=294.0.

Step 2: N-(2,6-dimethyl-4-(4,4,5,5-tetramethyl-1,3,2-dioxaborolan-2-yl)benzyl)-1-methyl-1H-pyrazol-4-amine

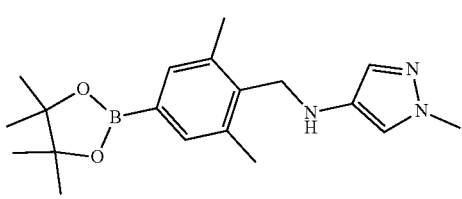

The title compound (162 mg, 57%) was prepared in a manner similar to that in Example A1 step 6 from N-(4-bromo-2,6-dimethylbenzyl)-1-methyl-1H-pyrazol-4-amine and BPD. LC-MS (M+H)$^+$=342.1.

Step 3: 5-(3,5-dimethyl-4-(((1-methyl-1H-pyrazol-4-yl)amino)methyl)phenyl)-3-((1-(1-methylpiperidin-4-yl)-1H-pyrazol-4-yl)oxy)pyrazin-2-amine Example A57 (20 mg, 15%) was prepared in a manner similar to that in Example A1 step 7 from 5-bromo-3-((1-(1-methylpiperidin-4-yl)-H-pyrazol-4-yl)oxy)pyrazin-2-amine and N-(2,6-dimethyl-4-(4,4,5,5-tetramethyl-1,3,2-dioxaborolan-2-yl)benzyl)-1-methyl-1H-pyrazol-4-amine. $^1$H NMR (400 MHz, DMSO-d$_6$) δ 8.22 (s, 1H), 8.12 (s, 1H), 7.59 (s, 1H), 7.50 (s, 2H), 7.14 (s, 1H), 6.99 (s, 1H), 6.68 (s, 2H), 4.30-4.22 (m, 1H), 4.194.07 (m, 1H), 3.96-3.87 (m, 2H), 3.71 (s, 3H), 2.90-2.81 (m, 2H), 2.35 (s, 6H), 2.20 (s, 3H), 2.11-1.91 (m, 6H). LC-MS (M+H)$^+$=488.3.

Example A58

4-(3-(5-amino-6-((1-(1-methylpiperidin-4-yl)-1H-pyrazol-4-yl)oxy)pyrazin-2-yl)-5-methylphenyl)tetrahydro-2H-pyran-4-ol

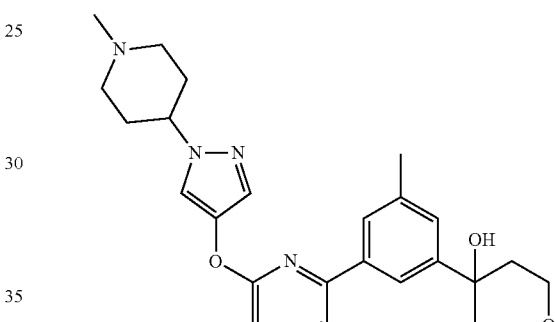

Step 1: 4-(3-bromo-5-methylphenyl)tetrahydro-2H-pyran-4-ol

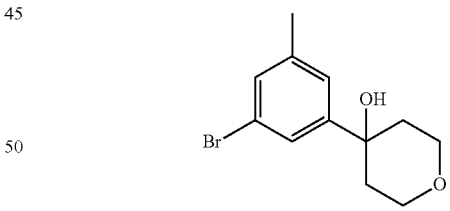

To a solution of 1,3-dibromo-5-methylbenzene (2.0 g, 8.0 mmol) in THF (5 mL) was added n-BuLi in hexane (1.6 M, 5 mL, 8.0 mmol) at −78° C. dropwise under N2. After 0.5 h, tetrahydro-4H-pyran-4-one (960 mg, 9.6 mmol) was added dropwise. After another 1 h, to the mixture was added saturated NH$_4$Cl (10 mL). After being warmed to room temperature, the mixture was diluted with water (10 mL) and the mixture was extracted with EtOAc (40 mL×2). The combined organic layer was washed with brine (50 mL), dried over Na$_2$SO$_4$, filtered and concentrated under vacuum. The crude was purified by prep-TLC (PE:EtOAc=2:1) to give the title compound (1.2 g, 55%). LC-MS (M+H)$^+$= 271.1, 273.1.

Step 2: 4-(3-methyl-5-(4,4,5,5-tetramethyl-1,3,2-dioxaborolan-2-yl)phenyl)tetrahydro-2H-pyran-4-ol

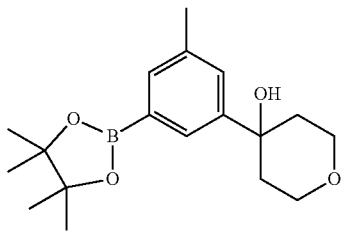 [SMILES: Cc1cc(B2OC(C)(C)C(C)(C)O2)cc(C2(O)CCOCC2)c1]

A mixture of 4-(3-bromo-5-methylphenyl)tetrahydro-2H-pyran-4-ol (1.0 g, 3.7 mmol), BPD (1.88 g, 7.4 mmol), Pd(dppf)Cl$_2$ (302 mg, 0.37 mmol) and AcOK (1.0 g, 11.1 mmol) was in dioxane (30 mL) was heated to reflux under nitrogen for overnight. The mixture was cooled to room temperature then diluted with EtOAc (60 mL). The mixture was washed with brine (30 mL×2), and the combined aqueous layer was extracted with EtOAc (30 mL). The combined organic layer was dried over Na$_2$SO$_4$, filtered and concentrated under reduced pressure. The crude was purified by prep-TLC (PE/EtOAc=2:1) to give the title compound (1.0 g, 85%). LC-MS (M+H)$^+$=319.3.

Step 3: 4-(3-(5-amino-6-((1-(1-methylpiperidin-4-yl)-1H-pyrazol-4-yl)oxy)pyrazin-2-yl)-5-methylphenyl)tetrahydro-2H-pyran-4-ol Example A58 (10 mg, 7%) was prepared in a manner similar to that in Example A1 step 7 from 5-bromo-3-((1-(1-methylpiperidin-4-yl)-1H-pyrazol-4-yl)oxy)pyrazin-2-amine and 4-(3-methyl-5-(4,4,5,5-tetramethyl-1,3,2-dioxaborolan-2-yl)phenyl)tetrahydro-2H-pyran-4-ol. $^1$H NMR (40( ) MHz, DMSO-d6) δ 8.19 (s, 1H), 8.09 (s, 1H), 7.7 (s, 1H), 7.47 (s, 1H), 7.2 (s, 1H), 6.65 (s, 2H), 4.95 (s, 1H), 4.06-4.07 (m, 1H), 3.77-3.64 (m, 4H), 2.82 (d, J=9.2, 2H), 2.29 (s, 3H), 2.15 (s, 3H), 2.0-1.9 (m, 7H), 1.5 (d, J=13.6). LC-MS (M+H)$^+$=465.2.

Compound A59

(R)-3-(3-(5-amino-6-((1-(1-methylpiperidin-4-yl)-1H-pyrazol-4-yl)oxy)pyrazin-2-yl)-5-(3-methylmorpholino)phenyl)oxetan-3-ol

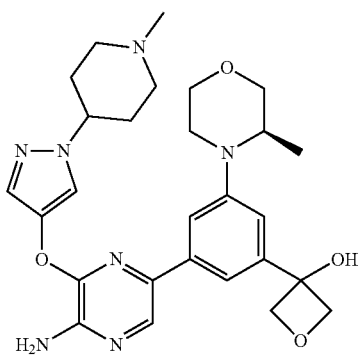

Step 1: (R)-4-(3,5-dibromophenyl)-3-methylmorpholine

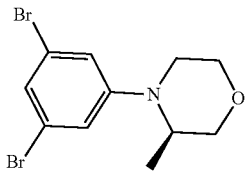

To a solution of 1,3-dibromo-5-iodobenzene (2.0 g, 5.5 mmol) in dioxane (20 mL) was added (R)-3-methylmorpholine (558 mg, 5.5 mmol), Pd$_2$(dba)$_3$ (250 mg, 0.28 mmol), XantPhos (310 mg, 0.55 mmol) and Cs$_2$CO$_3$ (2.0 g, 6.1 mmol) under nitrogen and the mixture was heated to reflux for overnight. The mixture was cooled to room temperature and concentrated in vacuo. The crude was purified by silica gel chromatography (PE:EtOAc=20:1) to give the title compound (1.0 g, 54%). LC-MS (M+H)$^+$=335.9, 337.9.

Step 2: (R)-3-(3-bromo-5-(3-methylmorpholino)phenyl)oxetan-3-ol

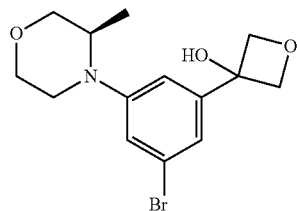 [SMILES: C[C@@H]1COCCN1c1cc(Br)cc(C2(O)COC2)c1]

The title compound (150 mg, 31%) was prepared in a manner similar to that in Example A54 step 1 from (R)-4-(3,5-dibromophenyl)-3-methylmorpholine and oxetan-3-one. LC-MS (M+H)$^+$=328.0.

Step 3: (R)-3-(3-(3-methylmorpholino)-5-(4,4,5,5-tetramethyl-1,3,2-dioxaborolan-2-yl)phenyl)oxetan-3-ol

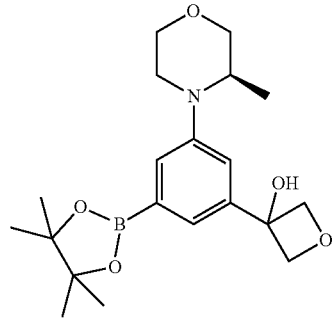 [SMILES: C[C@@H]1COCCN1c1cc(B2OC(C)(C)C(C)(C)O2)cc(C2(O)COC2)c1]

The title compound (147 mg, 85%) was prepared in a manner similar to that in Example A1 step 6 from (R)-3-(3-bromo-5-(3-methylmorpholino)phenyl)oxetan-3-ol and BPD. LC-MS (M+H)$^+$=376.2.

Step 4: (R)-3-(345-amino-6-((1-(1-methylpiperidin-4-yl)-1H-pyrazol-4-yl)oxy)pyrazin-2-yl)-5-(3-methylmorpholino)phenyl)oxetan-3-ol Example A59 (10 mg, 5%) was prepared in a manner similar to that in Example A1 step 7 from 5-bromo-3-((1-(1-methylpiperidin-4-yl)-1H-pyrazol-4-yl)oxy)pyrazin-2-amine and (R)-3-(3-(3-methylmorpholino)-5-(4,4,5,5-tetramethyl-1,3,2-dioxaborolan-2-yl)phenyl)oxetan-3-ol. $^1$H NMR (400 MHz, DMSO-d6) δ 8.22 (s, 1H), 8.08 (s, 1H), 7.53 (s, 1H), 7.48 (s, 1H), 7.23 (s, 1H), 6.97 (s, 1H), 6.67 (s, 2H), 6.25 (s, 1H), 4.76-4.60 (m, 4H), 4.10-3.98 (m, 1H), 3.91-3.78 (m, 2H), 3.75-3.59 (m, 2H), 3.58-3.48 (m, 1H), 3.22-3.12 (m, 1H), 3.07-2.95 (m, 1H), 2.87-2.76 (m, 2H), 2.17 (s, 3H), 2.05-1.79 (m, 6H), 1.00-0.90 (m, 3H). LC-MS (M+H)$^+$=522.2.

Example A60

5-(3,5-dimethyl-4-(((3-methyloxetan-3-yl)amino)methyl)phenyl)-3-((1-(1-methylpiperidin-4-yl)-1H-pyrazol-4-yl)oxy)pyrazin-2-amine

Step 1: N-(4-bromo-2,6-dimethylbenzyl)-3-methyloxetan-3-amine

The title compound (1.6 g, 81%) was prepared in a manner similar to that in compound A55 step 1 from 4-bromo-2,6-dimethylbenzaldehyde and 3-methyloxetan-3-amine. LCMS (M+H)$^+$=284, 286.

Step 2: N-(2,6-dimethyl-4-(4,4,5,5-tetramethyl-1,3,2-dioxaborolan-2-yl)benzyl)-3-methyloxetan-3-amine The title compound (0.70 g, 38%) was prepared in a manner similar to that in compound A1 step 6 from N-(4-bromo-2,6-dimethylbenzyl)-3-methyloxetan-3-amine and BPD. LCMS (M+H)$^+$=332.2.

Step 3: 5-(3,5-dimethyl-4-(((3-methyloxetan-3-yl)amino)methyl)phenyl)-3-((1-(1-methylpiperidin-4-yl)-1H-pyrazol-4-yl)oxy)pyrazin-2-amine Example A60 (105 mg, 52%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)-3-methyloxetan-3-amine. $^1$H NMR (400 MHz, DMSO-d6) δ 8.21 (s, 1H), 8.12 (s, 1H), 7.59 (s, 1H), 7.50-7.42 (m, 2H), 6.67 (s, 2H), 4.60-4.50 (m, 2H), 4.30-4.21 (m, 2H), 4.19-4.07 (m, 1H), 3.59 (s, 2H), 2.91-2.82 (m, 2H), 2.38 (s, 6H), 2.21 (s, 3H), 2.11-1.96 (m, 6H), 1.48 (s, 3H). LCMS (M+H)$^+$=478.3.

Example A61A/A61B (S)-5-(3-(5-amino-6-((1-(1-methylpiperidin-4-yl)-1H-pyrazol-4-yl)oxy)pyrazin-2-yl)-5-methylphenyl)pyrrolidin-2-one & (R)-5-(3-(5-amino-6-((1-(1-methylpiperidin-4-yl)-1H-pyrazol-4-yl)oxy)pyrazin-2-yl)-5-methylphenyl)pyrrolidin-2-one

171

-continued

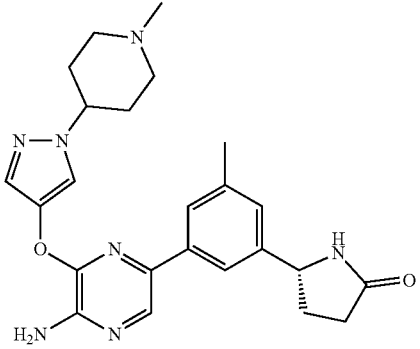

Step 1:
4-(3-bromo-5-methylphenyl)-2-hydroxy-4-oxobutanoic acid

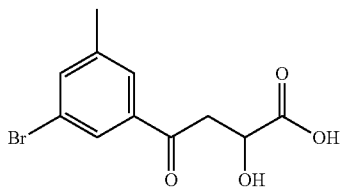 [SMILES: Cc1cc(Br)cc(C(=O)CC(O)C(=O)O)c1]

To a solution of 1-(3-bromo-5-methylphenyl)ethanone (4.26 g, 19.6 mmol) in AcOH (70 mL) was added 2-oxoacetic acid (2.90 g, 19.6 mmol) at room temperature. The mixture was stirred for 8 h at 120° C. under nitrogen. The mixture was cooled to room temperature and concentrated under reduced pressure. The residue was purified by silica gel chromatography (PE:EtOAc=2:1) to give the title compound (2.24 g, 40%). LCMS (M+H)$^+$=286.9.

Step 2:
4-(3-bromo-5-methylphenyl)-4-oxobut-2-enoic acid

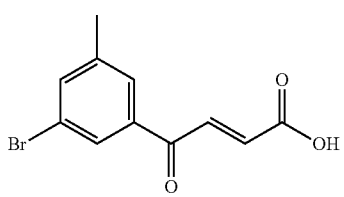

To a solution of 4-(3-bromo-5-methylphenyl)-2-hydroxy-4-oxobutanoic acid (2.8 g, 7.87 mmol) in AcOH (60 mL) was added concentrated HCl (20 mL) dropwise at room temperature. The mixture was stirred for overnight at 120° C. under nitrogen atmosphere. The mixture was cooled to room temperature and diluted with water (50 mL). The mixture was extracted with ethyl acetate (200 mL×3). The combined organic layer was washed with brine (100 mL), dried over Na$_2$SO$_4$ and filtered. The solvent was evaporated under reduced pressure to give the title compound (1.8 g, 84%). LCMS (M+H)$^+$=266.6.

172

Step 3: 4-(3-bromo-5-methylphenyl)-4-oxobutanoic acid

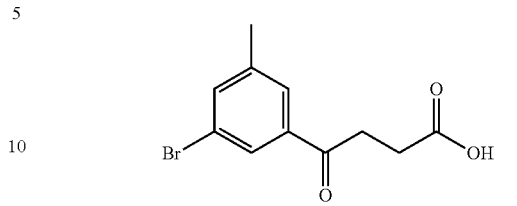

To a stirred a solution of 4-(3-bromo-5-methylphenyl)-4-oxobut-2-enoic acid (2.0 g, 6.63 mmol) in AcOH (18 mL) and H$_2$O (6 mL) was added Zn powder (500 mg, 7.26 mmol) at room temperature. After 3 h, the mixture diluted with of water (50 mL), and filtered. The solid with rinsed with EtOAc (10 mL). The filtrate was extracted with ethyl acetate (60 mL×3). The combined organic layer was washed with brine, dried over Na$_2$SO$_4$ and filtered. The solvent was evaporated under reduced pressure and the residue was purified by silica gel chromatography (PE:EtOAc=3:1) to give the title compound (1.6 g, 89%). LCMS (M+H)$^+$=270.9.

Step 4:
5-(3-bromo-5-methylphenyl)pyrrolidin-2-one

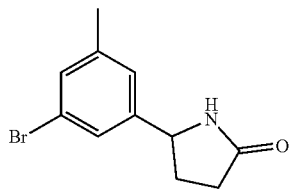

To a solution of 4-(3-bromo-5-methylphenyl)-4-oxobutanoic acid (400 mg, 1.47 mmol) in EtOH (10 mL) was added NH$_4$OAc (7.2 g, 88.4 mmol) and NaBH$_2$CN (488.0 mg, 7.38 mmol) in portions at room temperature. The mixture was stirred for 5 h at 80° C. under nitrogen. The mixture was cooled to room temperature and diluted with water (50 mL). The mixture was extracted with ethyl acetate (50 mL×3). The combined organic layer was washed with brine (50 mL), dried over Na$_2$SO$_4$ and filtered. The solvent was evaporated under reduced pressure, the residue was purified by prep-HPLC to give the title compound (246 mg, 66%). LCMS (M+H)$^+$=254.0.

Step 5: 5-(3-methyl-5-(4,4,5,5-tetramethyl-1,3,2-dioxaborolan-2-yl)phenyl)pyrrolidin-2-one

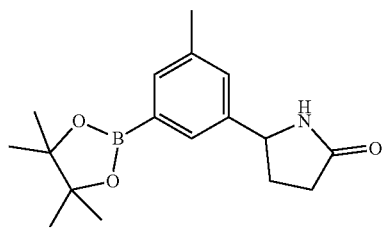 [SMILES: Cc1cc(B2OC(C)(C)C(C)(C)O2)cc(C2CCC(=O)N2)c1]

The title compound (149 mg, 89%) was prepared in a manner similar to that in Example A1 step 6 from 5-(3-bromo-5-methylphenyl)pyrrolidin-2-one and BPD. LC-MS (M+H)⁺=302.2.

Step 6

(S)-5-(3-(5-amino-6-((1-(1-methylpiperidin-4-yl)-1H-pyrazol-4-yl)oxy)pyrazin-2-yl)-5-methylphenyl)pyrrolidin-2-one & (R)-5-(3-(5-amino-6-((1-(1-methylpiperidin-4-yl)-1H-pyrazol-4-yl)oxy)pyrazin-2-yl)-5-methylphenyl)pyrrolidin-2-one Examples A61A/A61B were prepared in a manner similar to that in Example A1 step 7 from 5-(3-methyl-5-(4,4,5,5-tetramethyl-1,3,2-dioxaborolan-2-yl)phenyl)pyrrolidin-2-one and 5-bromo-3-((1-(1-methylpiperidin-4-yl)-1H-pyrazol-4-yl)oxy)pyrazin-2-amine, then the isomers were separated by chiral-HPLC. Analytical chiral-HPLC condition: CHIRALPAK IC3, 4.6×50 mm; (Hexane:DCM=3:1, contains 0.1% Et₂NH):IPA=1:1:1 mL/min; 25° C.

Example A61A ((R)-5-(3-(5-amino-6-((1-(1-methylpiperidin-4-yl)-1H-pyrazol-4-yl)oxy)pyrazin-2-yl)-5-methylphenyl)pyrrolidin-2-one): (34 mg, 20%) ¹H NMR (400 MHz, DMSO-d6) δ 8.24 (s, 1H), 8.12 (s, 1H), 8.07 (s, 1H), 7.60-7.53 (m, 3H), 7.04 (s, 1H), 6.74 (s, 2H), 4.694.59 (m, 1H), 4.20-4.10 (m, 1H), 2.89-2.79 (m, 2H), 2.48-2.40 (m, 1H), 2.33 (s, 3H), 2.29-2.20 (m, 2H), 2.20 (s, 3H), 2.12-1.91 (m, 6H), 1.85-1.73 (m, 1H). LC-MS (M+H)⁺=448.3. Chiral HPLC: tR=3.50 min.

Example A61B ((S)-5-(3-(5-amino-6-((1-(1-methylpiperidin-4-yl)-1H-pyrazol-4-yl)oxy)pyrazin-2-yl)-5-methylphenyl)pyrrolidin-2-one): (30 mg, 18%) ¹H NMR (400 MHz, DMSO-d₆) δ 8.24 (s, 1H), 8.12 (s, 1H), 8.07 (s, 1H), 7.60-7.53 (m, 3H), 7.04 (s, 1H), 6.74 (s, 2H), 4.69-4.59 (m, 1H), 4.20-4.10 (m, 1H), 2.89-2.79 (m, 2H), 2.48-2.40 (m, 1H), 2.33 (s, 3H), 2.29-2.20 (m, 2H), 2.20 (s, 3H), 2.12-1.91 (m, 6H), 1.85-1.73 (m, 1H). LC-MS (M+H)⁺=448.3. Chiral HPLC: tR=5.00 min.

Example A62

5-(4-[[(dimethylsulfamoyl)amino]methyl]-3,5-dimethylphenyl)-3-[11-(1-methylpiperidin-4-yl)pyrazol-4-yl]oxy]pyrazin-2-amine

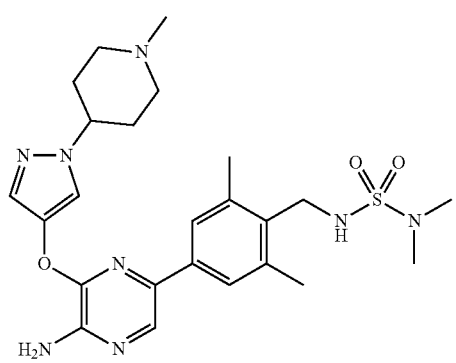 [SMILES: Cc1cc(-c2cnc(N)c(Oc3cnn(C4CCN(C)CC4)c3)n2)cc(C)c1CNS(=O)(=O)N(C)C]

Step 1: [[(4-bromo-2,6-dimethylphenyl)methyl]sulfamoyl]dimethylamine

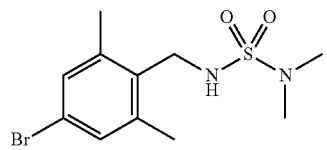 [SMILES: Cc1cc(Br)cc(C)c1CNS(=O)(=O)N(C)C]

The title compound (375 mg, 71%) was prepared in a manner similar to that in Example A1 1 step 2 from 1-(4-bromo-2,6-dimethylphenyl)methanamine and dimethylsulphamoyl chloride. LC-MS (M+H)⁺=320.9.

Step 2: ([[2,6-dimethyl-4-(4,4,5,5-tetramethyl-1,3,2-dioxaborolan-2-yl)phenyl]methyl]sulfamoyl)dimethylamine

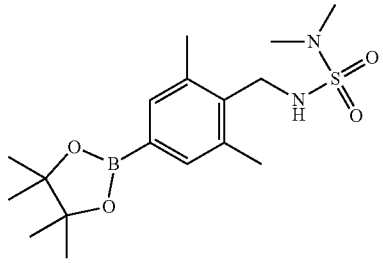 [SMILES: Cc1cc(B2OC(C)(C)C(C)(C)O2)cc(C)c1CNS(=O)(=O)N(C)C]

The title compound (168 mg, 59%) was prepared in a manner similar to that in Example A1 step 6 from [[(4-bromo-2,6-dimethylphenyl)methyl]sulfamoyl]dimethylamine and BPD. LC-MS (M+H)⁺=369.0.

Step 3: 5-(4-[[(dimethylsulfamoyl)amino]methyl]-3,5-dimethylphenyl)-3-[[1-(1-methylpiperidin-4-yl)pyrazol-4-yl]oxy]pyrazin-2-amine Example A62 (35 mg, 17%) was prepared in a manner similar to that in Example A1 step 7 from 5-bromo-3-((1-(1-methylpiperidin-4-yl)-1H-pyrazol-4-yl)oxy)pyrazin-2-amine and ([12,6-dimethyl-4-(4,4,5,5-tetramethyl-1,3,2-dioxaborolan-2-yl)phenyl]methyl]sulfamoyl)dimethylamine. ¹H NMR (300 MHz, DMSO-d₆) δ 8.22 (s, 1H), 8.10 (s, 1H), 7.57 (s, 1H), 7.48 (s, 2H), 7.27 (t, J=5.4 Hz, 1H), 6.69 (s, 2H), 4.184.08 (m, 1H), 4.08-4.02 (m, 2H), 2.90-2.78 (m, 2H), 2.69 (s, 6H), 2.36 (s, 6H), 2.19 (s, 3H), 2.13-1.90 (m, 6H). LC-MS (M+H)⁺=515.2.

Example A63

3-(4-(5-amino-6-((1-(1-methylpiperidin-4-yl)-1H-pyrazol-4-yl)oxy)pyrazin-2-yl)-2,6-dimethylphenyl)oxetan-3-ol

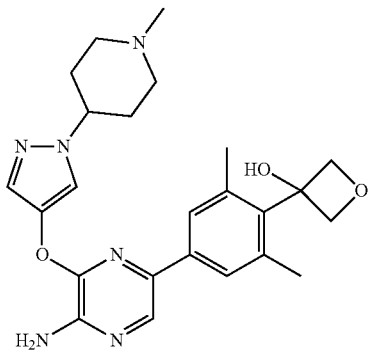 [SMILES: Cc1cc(-c2cnc(N)c(Oc3cnn(C4CCN(C)CC4)c3)n2)cc(C)c1C1(O)COC1]

Step 1: 3-(4-chloro-2,6-dimethylphenyl)oxetan-3-ol

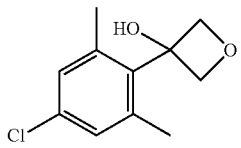

To a stirred solution of 5-chloro-2-iodo-1,3-dimethylbenzene (798 mg, 3.0 mmol) in anhydrous THF (10 mL) was added n-BuLi in hexanes (2.5 M, 1.2 mL, 3.0 mmol) dropwise at −78° C. under nitrogen. After 3 h, oxetan-3-one (216 mg, 3.0 mmol) was added. The mixture was warm to room temperature within 30 min, then saturated NH$_4$Cl solution (50 mL) was added. The mixture was extracted with EtOAc (50 mL). The organic layer was separated, dried over Na$_2$SO$_4$, filtered and concentrated under reduced pressure. The crude was purified by prep-TLC give the title compound (250 mg, 39%). LC-MS (M−OH)$^+$=195.2.

Step 2: 3-(2,6-dimethyl-4-(4,4,5,5-tetramethyl-1,3,2-dioxaborolan-2-yl)phenyl)oxetan-3-ol

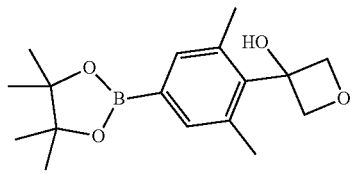 [SMILES: Cc1cc(B2OC(C)(C)C(C)(C)O2)cc(C)c1C1(O)COC1]

A mixture of 3-(4-chloro-2,6-dimethylphenyl)oxetan-3-ol (250 mg, 1.17 mmol), BPD (444 mg, 1.75 mmol), dichlorobis(tricyclohexylphosphine)palladium(II) (258 mg, 0.35 mmol) and AcOK (344 mg, 3.51 mmol) in dioxane (30 mL) was heated to reflux under nitrogen for overnight. The mixture was cooled to room temperature and concentrated under vacuum. The crude was purified by silica gel chromatography (PE:EtOAc=10:1) to give the title compound (350 mg, 98%). LC-MS (M−OH)+=287.2.

Step 3: 3-(4-(5-amino-6-((1-(1-methylpiperidin-4-yl)-1H-pyrazol-4-yl)oxy)pyrazin-2-yl)-2,6-dimethylphenyl)oxetan-3-ol Example A63 (55 mg, 41%) was prepared in a manner similar to that in Example A1 step 7 from 3-(2,6-dimethyl-4-(4,4,5,5-tetramethyl-1,3,2-dioxaborolan-2-yl)phenyl)oxetan-3-ol and 5-bromo-3-((1-(1-methylpiperidin-4-yl)-1H-pyrazol-4-yl)oxy)pyrazin-2-amine. $^1$H NMR (400 MHz, DMSO-d$_6$) δ 8.22 (s, 1H), 8.11 (s, 1H), 7.58 (s, 1H), 7.44 (s, 2H), 6.71 (s, 2H), 6.13 (s, 1H), 5.05 (s, 2H), 4.58 (s, 2H), 4.18-4.04 (m, 1H), 2.90-2.80 (m, 2H), 2.21 (s, 3H), 2.13 (s, 6H), 2.08-1.94 (m, 6H). LCMS (M+H)+=451.2.

Example A64

1-(4-(5-amino-6-((1-(1-methylpiperidin-4-yl)-1H-pyrazol-4-yl)oxy)pyrazin-2-yl)-2,6-dimethylbenzyl)-3-(1-(trifluoromethyl)cyclopropyl)urea

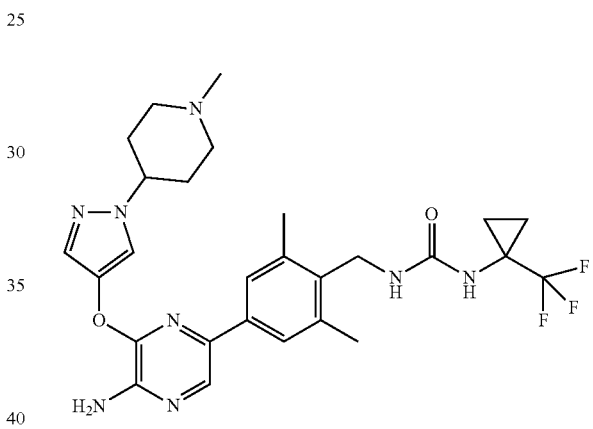

A mixture of 1-(trifluoromethyl)cyclopropane-1-carboxylic acid (18 mg, 0.12 mmol), diphenylphosphonic azide (33 mg, 0.12 mmol) and Et$_3$N (12 mg, 0.12 mmol) in toluene (1 mL) was heated to refluxed for 2 h. The mixture was concentrated under reduced pressure and re-dissolved in THF (1 mL). The solution was added dropwise to a solution of 5-(4-(aminomethyl)-3,5-dimethylphenyl)-3-((1-(1-methylpiperidin-4-yl)-1H-pyrazol-4-yl)oxy)pyrazin-2-amine; bis-trifluoroacetic acid (50 mg, 0.079 mmol) and Et$_3$N (24 mg, 0.24 mmol) in THF (1 mL) at 0° C. After 3 h, EtOAc (10 mL) was added and the organic layer was successively washed with H$_2$O (5 mL), brine (5 mL), dried over Na$_2$SO$_4$, filtered and concentrated under vacuum. The residue was purified by prep-HPLC to give Example A64 (24 mg, 55%), 1H NMR (400 MHz, DMSO-d6) δ 8.21 (s, 1H), 8.12 (s, 1H), 7.58 (s, 1H), 7.49 (s, 2H), 6.70 (s, 2H), 6.58 (s, 1H), 5.97 (s, 1H), 4.21 (s, 2H), 4.20-4.11 (m, 1H), 2.88-2.83 (m, 2H), 2.33 (s, 6H), 2.21 (s, 3H), 2.11-1.94 (m, 6H), 1.16 (s, 2H), 1.02 (s, 2H). LC-MS (M+H)+=559.3.

Example A65

1-(3-(5-amino-6-((1-(1-methylpiperidin-4-yl)-1H-pyrazol-4-yl)oxy)pyrazin-2-yl)-5-methylphenyl)cyclopentan-1-ol

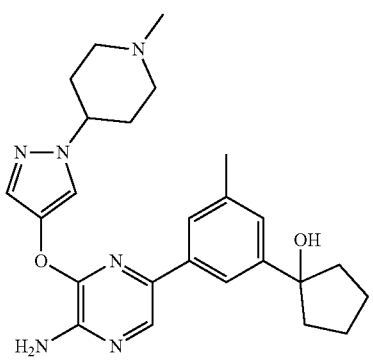 [SMILES: Cc1cc(-c2cnc(N)c(Oc3cnn(C4CCN(C)CC4)c3)n2)cc(C2(O)CCCC2)c1]

Step 1: 1-(3-bromo-5-methylphenyl)cyclopentan-1-ol

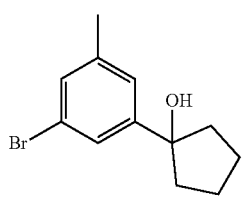

The title compound (1.5 g, 74%) was prepared in a manner similar to that in Example A54 step 1 from 1,3-dibromo-5-methylbenzene and cyclo pentanone. LCMS (M–OH)$^+$=237,239.

Step 2: 1-(3-methyl-5-(4,4,5,5-tetramethyl-1,3,2-dioxaborolan-2-yl)phenyl)cyclopentan-1-ol

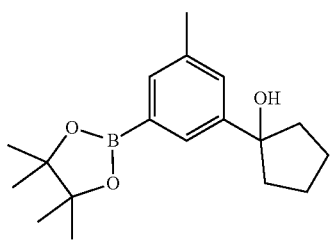 [SMILES: Cc1cc(B2OC(C)(C)C(C)(C)O2)cc(C2(O)CCCC2)c1]

The title compound (1.2 g, 71%) was prepared in a manner similar to that in Example A1 step 6 from 1-(3-bromo-5-methylphenyl)cyclopentan-1-ol and BPD. LCMS (M–OH)$^+$=285.

Step 3: 1-(3-(5-amino-6-((1-(1-methylpiperidin-4-yl)-1H-pyrazol-4-yl)oxy)pyrazin-2-yl)-5-methylphenyl)cyclopentan-1-ol Example A65 (50 mg, 27%) was prepared in a manner similar to that in Example A1 step 7 from 5-bromo-3-((1-(1-methylpiperidin-4-yl)-1H-pyrazol-4-yl)oxy)pyrazin-2-amine and 1-(3-methyl-5-(4,4,5,5-tetramethyl-1,3,2-dioxaborolan-2-yl)phenyl)cyclopentan-1-ol. $^1$H NMR (400 MHz, DMSO-d6) δ 8.17 (s, 1H), 8.08 (s, 1H), 7.68 (s, 1H), 7.54 (s, 1H), 7.44 (s, 1H), 7.18 (s, 1H), 6.64 (s, 2H), 4.71 (s, 1H), 4.14-4.02 (m, 1H), 2.90-2.80 (m, 2H), 2.28 (s, 3H), 2.19 (s, 3H), 2.12-1.91 (m, 6H), 1.86-1.66 (m, 8H). LCMS (M+H)$^+$= 449.4.

Example A66

5-(3,5-dimethyl-4-morpholinophenyl)-3-((1-(1-methylpiperidin-4-yl)-1H-pyrazol-4-yl)oxy)pyrazin-2-amine

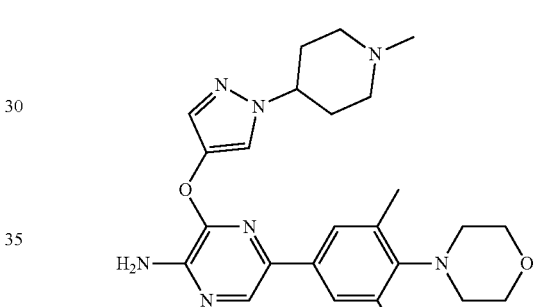

Step 1: 4-(4-chloro-2,6-dimethylphenyl)morpholine

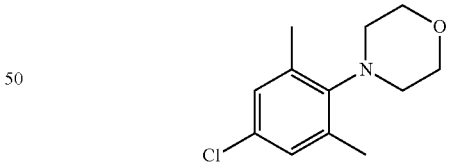

A mixture of 2-bromo-5-chloro-1,3-dimethylbenzene (1.1 g, 5.0 mmol), morpholine (522 mg, 6.0 mmol), XantPhos (286 mg, 0.50 mmol), Pd(dba)$_2$(287 mg, 0.50 mmol) and t-BuOK (1.12 g, 10 mmol) in toluene (30 mL) was heated to reflux overnight under nitrogen. The mixture was cooled to room temperature, concentrated under vacuum then diluted with water (100 mL). The mixture was extracted with DCM (100 mL). The organic layer was separated and concentrated under reduced pressure. The crude was purified by prep-TLC (PE:EA=10:1) to give the title compound (200 mg, 18%). LC-MS (M+H)$^+$=226.1.

Step 2: 4-(2,6-dimethyl-4-(4,4,5,5-tetramethyl-1,3,2-dioxaborolan-2-yl)phenyl)morpholine

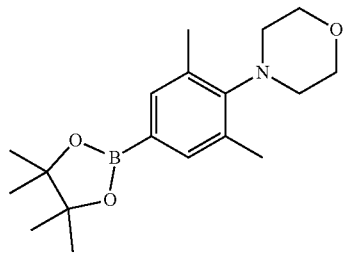 [SMILES: Cc1cc(B2OC(C)(C)C(C)(C)O2)cc(C)c1N1CCOCC1]

A mixture of 4-(4-chloro-2,6-dimethylphenyl)morpholine (100 mg, 0.44 mmol), BPD (168 mg, 0.66 mmol), dichlorobis(tricyclohexylphosphine)palladium(II) (96 mg, 0.13 mmol) and AcOK (130 mg, 1.32 mmol) in dioxane (10 mL) was heated to reflux for overnight under nitrogen. The mixture was cooled to room temperature and concentrated under reduced pressure. The crude was purified by silica gel chromatography (PE:EA=10:1) to give the title compound (130 mg, 93%). LC-MS (M+H)$^+$=228.1.

Step 3: 5-(3,5-dimethyl-4-morpholinophenyl)-3-((1-(1-methylpiperidin-4-yl)-1H-pyrazol-4-yl)oxy)pyrazin-2-amine Example A66 (28 mg, 30%) was prepared in a manner similar to that in Example A1 step 7 from 4-(2,6-dimethyl-4-(4,4,5,5-tetramethyl-1,3,2-dioxaborolan-2-yl)phenyl)morpholine and 5-bromo-3-((1-(1-methylpiperidin-4-yl)-1H-pyrazol-4-yl)oxy)pyrazin-2-amine. $^1$H NMR (400 MHz, DMSO-d$_6$) δ 8.17 (s, 1H), 8.11 (s, 1H), 7.58 (s, 1H), 7.45 (s, 2H), 6.64 (s, 2H), 4.15-4.10 (m, 1H), 3.69-3.67 (m, 4H), 3.01-2.97 (m, 4H), 2.87-2.85 (m, 2H), 2.32 (s, 6H), 2.21 (s, 3H), 2.09-1.96 (m, 6H). LCMS (M+H)$^+$=464.2.

Example A67

N-(4-(5-amino-6-((1-(1-methylpiperidin-4-yl)-1H-pyrazol-4-yl)oxy)pyrazin-2-yl)-2,6-dimethylbenzyl)oxazol-2-amine

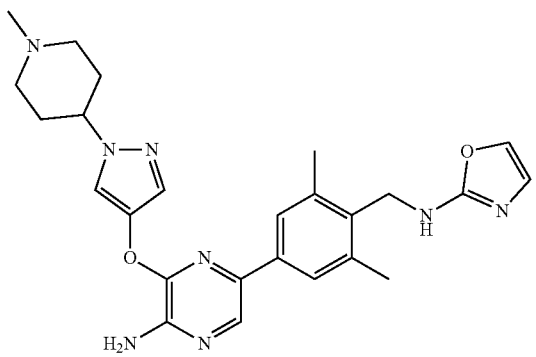 [SMILES: Cc1cc(-c2cnc(N)c(Oc3cnn(C4CCN(C)CC4)c3)n2)cc(C)c1CNc1ncco1]

Step 1: N-(4-bromo-2,6-dimethylbenzyl)oxazol-2-amine

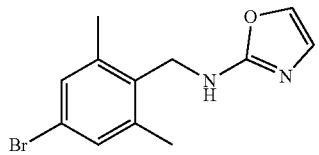 [SMILES: Cc1cc(Br)cc(C)c1CNc1ncco1]

To a solution of 4-bromo-2,6-dimethylbenzaldehyde (1.0 g, 4.72 mmol) in dioxane (30 mL) was added 4-methylbenzenesulfonohydrazide (877 mg, 4.72 mmol). The solution was stirred for 3 h at 60° C. and cooled to room temperature, then t-BuOLi (755 mg, 9.44 mmol), CuI (116 mg, 0.61 mmol) and oxazol-2-amine (265 mg, 3.16 mmol) was added. The mixture was stirred for 3 h at 100° C. under nitrogen and cooled to room temperature. The mixture was poured into water (100 mL) and then extracted with EtOAc (100 mL×3). The combined organic layer was washed with brine (100 mL), dried over Na$_2$SO$_4$, filtered and concentrated under vacuum. The crude was purified by silica gel chromatography (PE:EtOAc=1:1) to give the title compound (580 mg, 44%). LC-MS (M+H)$^+$=281.0, 283.0.

Step 2: N-(2,6-dimethyl-4-(4,4,5,5-tetramethyl-1,3,2-dioxaborolan-2-yl)benzyl)oxazol-2-amine

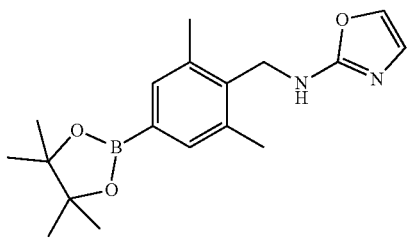 [SMILES: Cc1cc(B2OC(C)(C)C(C)(C)O2)cc(C)c1CNc1ncco1]

The title compound (500 mg, 74%) was prepared in a manner similar to that in Example A1 step 6 from N-(4-bromo-2,6-dimethylbenzyl)oxazol-2-amine and BPD. LC-MS (M+H)$^+$=329.3.

Step 3: N-(4-(5-amino-6-((1-(1-methylpiperidin-4-yl)-1H-pyrazol-4-yl)oxy)pyrazin-2-yl)-2,6-dimethylbenzyl)oxazol-2-amine Example A67 (62 mg, 30%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)oxazol-2-amine. $^1$H NMR (400 MHz, DMSO-d$_6$) δ 8.18 (s, 1H), 8.07 (s, 1H), 7.55 (s, 1H), 7.45 (s, 2H), 7.37 (s, 1H), 7.17 (s, 1H), 6.73 (s, 1H), 6.66 (s, 2H), 4.30 (s, 2H), 4.20-4.03 (m, 1H), 2.92-2.82 (m, 2H), 2.32 (s, 6H), 2.23 (s, 3H), 2.17-1.90 (m, 6H). LC-MS (M+H)$^+$=475.3.

Example A68

5-(3,5-dimethyl-4-((1-methyl-1H-1,2,4-triazol-3-yl)amino)methyl)phenyl)-3-((1-(1-methylpiperidin-4-yl)-1H-pyrazol-4-yl)oxy)pyrazin-2-amine

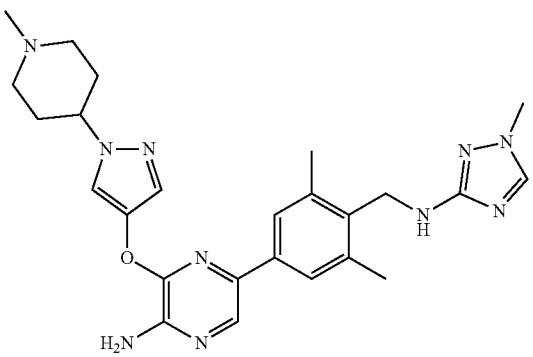 [SMILES: Cc1cc(-c2cnc(N)c(Oc3cnn(C4CCN(C)CC4)c3)n2)cc(C)c1CNc1ncn(C)n1]

Step 1: N-(4-bromo-2,6-dimethylbenzyl)-1-methyl-1H-1,2,4-triazol-3-amine

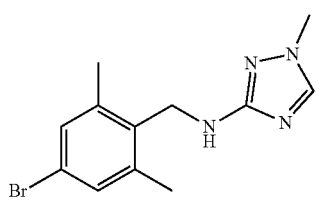 [SMILES: Cc1cc(Br)cc(C)c1CNc1ncn(C)n1]

The title compound (400 mg, 29%) was prepared in a manner similar to that in Example A67 step 1 from 4-bromo-2,6-dimethylbenzaldehyde and 1-methyl-1H-1,2,4-triazol-3-amine. LC-MS (M+H)$^+$=295.1, 297.2.

Step 2: N-(2,6-dimethyl-4-(4,4,5,5-tetramethyl-1,3,2-dioxaborolan-2-yl)benzyl)-1-methyl-1H-1,2,4-triazol-3-amine

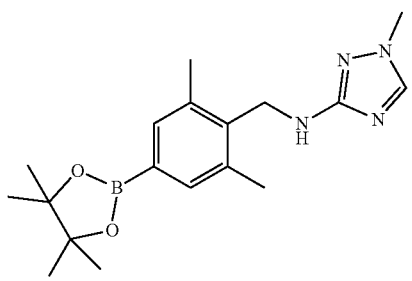 [SMILES: Cc1cc(B2OC(C)(C)C(C)(C)O2)cc(C)c1CNc1ncn(C)n1]

The title compound (290 mg, 62%) was prepared in a manner similar to that in Example A1 step 7 from N-(4-bromo-2,6-dimethylbenzyl)-1-methyl-1H-1,2,4-triazol-3-amine and BPD. LC-MS (M+H)$^+$=343.3.

Step 3: 5-(3,5-dimethyl-4-(((1-methyl-1H-1,2,4-triazol-3-yl)amino)methyl)phenyl)-3-((1-(1-methylpiperidin-4-yl)-1H-pyrazol-4-yl)oxy)pyrazin-2-amine Example A68 (66 mg, 32%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)-1-methyl-1H-1,2,4-triazol-3-amine. $^1$H NMR (400 MHz. DMSO-d$_6$) δ 8.22 (s, 1H), 8.12 (s, 1H), 7.97 (s, 1H), 7.60 (s, 1H), 7.47 (s, 2H), 6.68 (s, 2H), 5.80 (s, 1H), 4.24 (s, 2H), 4.21-4.10 (m, 1H), 3.66 (s, 3H), 3.00-2.83 (m, 2H), 2.37 (s, 6H), 2.27 (s, 3H), 2.22-1.92 (m, 6H). LC-MS (M+H)$^+$=489.3.

Example A69

3-(3-(5-amino-6-((1-(1-methylpiperidin-4-yl)-1H-pyrazol-4-yl)oxy)pyrazin-2-yl)-5-methylphenyl)tetrahydrofuran-3-ol

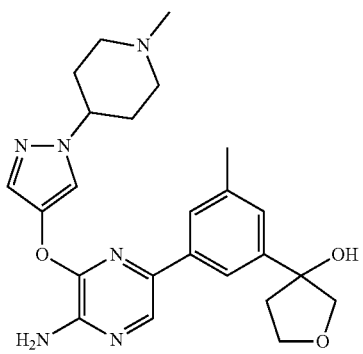 [SMILES: Cc1cc(-c2cnc(N)c(Oc3cnn(C4CCN(C)CC4)c3)n2)cc(C2(O)CCOC2)c1]

Step 1: 3-(3-bromo-5-methylphenyl)oxolan-3-ol

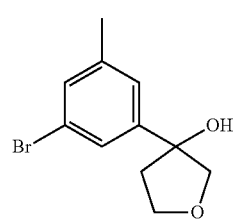

The title compound (434 mg, 44%) was prepared in a manner similar to that in Example A54 step 1 from 1,3-dibromo-5-methylbenzene and dihydrofuran-3-one. LC-MS (M−OH)$^+$=239.0.

Step 2: 3-(3-methyl-5-(4,4,5,5-tetramethyl-1,3,2-dioxaborolan-2-yl)phenyl)tetrahydrofuran-3-ol

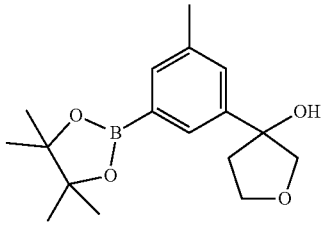 [SMILES: Cc1cc(B2OC(C)(C)C(C)(C)O2)cc(C2(O)CCOC2)c1]

The title compound (89 mg, 78%) was prepared in a manner similar to that in Example A1 step 6 from 3-(3-bromo-5-methylphenyl)oxolan-3-ol and BPD. LC-MS (M-OH)=287.3.

Step 3: 3-(3-(5-amino-6-((1-(1-methylpiperidin-4-yl)-1H-pyrazol-4-yl)oxy)pyrazin-2-yl)-5-methylphenyl)tetrahydrofuran-3-ol Example A69 (25 mg, 17%) was prepared in a manner similar to that in Example A1 step 7 from 5-bromo-3-((1-(1-methylpiperidin-4-yl)-1H-pyrazol-4-yl)oxy)pyrazin-2-amine and 3-(3-methyl-5-(4,4,5,5-tetramethyl-1,3,2-dioxaborolan-2-yl)phenyl)tetrahydrofuran-3-ol. $^1$H NMR (400 MHz, DMSO-d$_6$) δ 8.24 (s, 1H), 8.13 (s, 1H), 7.76 (s, 1H), 7.59 (s, 1H), 7.54 (s, 1H), 7.24 (s, 1H), 6.71 (s, 2H), 5.39 (s, 1H), 4.17-4.05 (m, 1H), 4.06-3.94 (m, 2H), 3.83-3.72 (m, 2H), 2.92-2.82 (m, 2H), 2.34 (s, 3H), 2.32-2.23 (m, 1H), 2.21 (s, 3H), 2.15-1.91 (m, 7H). LC-MS (M+H)$^+$=451.3.

Example A70

2-(3-(5-amino-6-((1-(1-methylpiperidin-4-yl)-1H-pyrazol-4-yl)oxy)pyrazin-2-yl)-5-methylphenyl)butan-2-ol

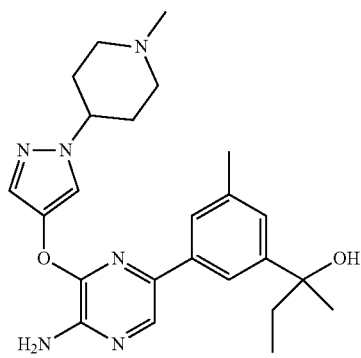 [SMILES: CCC(C)(O)c1cc(C)cc(-c2cnc(N)c(Oc3cnn(C4CCN(C)CC4)c3)n2)c1]

Step 1: 2-(3-bromo-5-methylphenyl)butan-2-ol

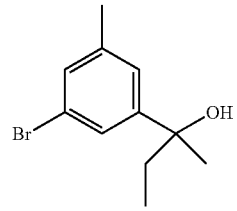

The title compound (447 mg, 41%) was prepared in a manner similar to that in Example A54 step 1 from 1,3-dibromo-5-methylbenzene and butan-2-one. LC-MS (M-OH)=224.9.

Step 2: 2-(3-methyl-5-(4,4,5,5-tetramethyl-1,3,2-dioxaborolan-2-yl)phenyl)butan-2-ol

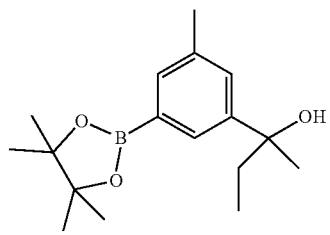 [SMILES: CCC(C)(O)c1cc(C)cc(B2OC(C)(C)C(C)(C)O2)c1]

The title compound (207 mg, 90%) was prepared in a manner similar to that in Example A1 step 6 from 2-(3-bromo-5-methylphenyl)butan-2-ol and BPD. LC-MS (M-OH)$^+$=273.1.

Step 3: 2-(3-(5-amino-6-((1-(1-methylpiperidin-4-yl)-1H-pyrazol-4-yl)oxy)pyrazin-2-yl)-5-methylphenyl)butan-2-ol Example A70 (20 mg, 19%) was prepared in a manner similar to that in Example A1 step 7 from 5-bromo-3-((1-(1-methylpiperidin-4-yl)-1H-pyrazol-4-yl)oxy)pyrazin-2-amine and 2-(3-methyl-5-(4,4,5,5-tetramethyl-1,3,2-dioxaborolan-2-yl)phenyl)butan-2-ol. $^1$H NMR (400 MHz, DMSO-d$_6$) δ 8.21 (s, 1H), 8.14 (s, 1H), 7.69 (s, 1H), 7.59 (s, 1H), 7.47 (s, 1H), 7.17 (s, 1H), 6.65 (s, 2H), 4.80 (s, 1H), 4.17-4.05 (m, 1H), 2.90-2.82 (m, 2H), 2.33 (s, 3H), 2.21 (s, 3H), 2.11-1.92 (m, 6H), 1.77-1.62 (m, 2H), 1.40 (s, 3H), 0.70 (t, J=7.3 Hz, 3H). LC-MS (M+H)$^+$=437.3.

Example A71

N-(4-(5-amino-6-((l-(1-methylpiperidin-4-yl)-1H-pyrazol-4-yl)oxy)pyrazin-2-yl)-2,6-dimethylbenzyl)morpholine-4-sulfonamide

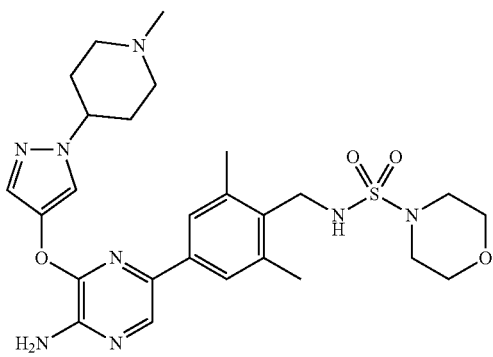 [SMILES: Cc1cc(-c2cnc(N)c(Oc3cnn(C4CCN(C)CC4)c3)n2)cc(C)c1CNS(=O)(=O)N1CCOCC1]

Step 1: N-(4-bromo-2,6-dimethylbenzyl)morpholine-4-sulfonamide

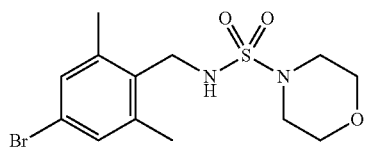 [SMILES: Cc1cc(Br)cc(C)c1CNS(=O)(=O)N1CCOCC1]

The title compound (295 mg, 62%) was prepared in a manner similar to that in Example A11 step 2 from 1-(4-bromo-2,6-dimethylphenyl)methanamine hydrochloride and morpholine-4-sulfonyl chloride. LC-MS (M+H)$^+$=362.9.

Step 2: N-(2,6-dimethyl-4-(4,4,5,5-tetramethyl-1,3,2-dioxaborolan-2-yl)benzyl)morpholine-4-sulfonamide

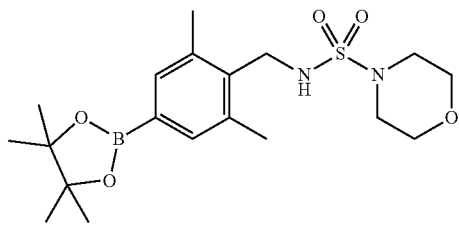 [SMILES: Cc1cc(B2OC(C)(C)C(C)(C)O2)cc(C)c1CNS(=O)(=O)N1CCOCC1]

The title compound (130 mg, 47%) was prepared in a manner similar to that in Example A1 step 6 from N-(4-bromo-2,6-dimethylbenzyl)morpholine-4-sulfonamide and BPD. LC-MS (M+H)$^+$=411.1.

Step 3: N-(4-(5-amino-6-((1-(1-methylpiperidin-4-yl)-1H-pyrazol-4-yl)oxy)pyrazin-2-yl)-2,6-dimethylbenzyl)morpholine-4-sulfonamide Example A71 (19 mg, 13%) was prepared in a manner similar to that in Example A1 step 7 from 5-bromo-3-((1-(1-methylpiperidin-4-yl)-1H-pyrazol-4-yl)oxy)pyrazin-2-amine and N-(2,6-dimethyl-4-(4,4,5,5-tetramethyl-1,3,2-dioxaborolan-2-yl)benzyl)morpholine-4-sulfonamide. $^1$H NMR (400 MHz, DMSO-d6) δ 8.23 (s, 1H), 8.12 (s, 1H), 7.60 (s, 1H), 7.50 (s, 3H), 6.71 (s, 2H), 4.22-4.12 (m, 1H), 4.12-4.07 (m, 2H), 3.59-3.52 (m, 4H), 3.05-2.98 (m, 4H), 2.94-2.87 (m, 2H), 2.38 (s, 6H), 2.25 (s, 3H), 2.17-2.10 (m, 2H), 2.10-1.92 (m, 4H). LC-MS (M+H)$^+$=557.4.

Example A72

3-(3-(5-amino-6-((1-(1-methylpiperidin-4-yl)-1H-pyrazol-4-yl)oxy)pyrazin-2-yl)-5-morpholinophenyl)oxetan-3-ol

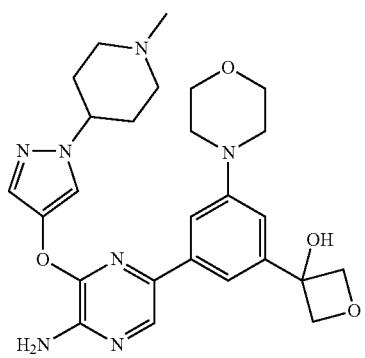 [SMILES: CN1CCC(n2cc(Oc3nc(-c4cc(N5CCOCC5)cc(C5(O)COC5)c4)cnc3N)cn2)CC1]

Step 1: 4-(3,5-dibromophenyl)morpholine

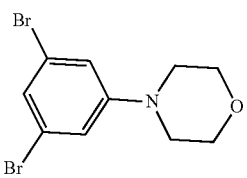 [SMILES: Brc1cc(Br)cc(N2CCOCC2)c1]

The title compound (1.2 g, 37%) was prepared in a manner similar to that in Example A59 step 1 from 1,3-dibromo-5-iodobenzene and morpholine. LCMS (M+H)$^+$=322.

Step 2: 3-(3-bromo-5-morpholinophenyl)oxetan-3-ol

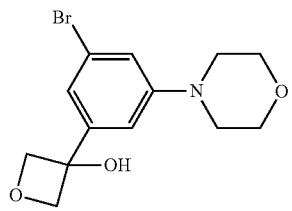 [SMILES: OC1(c2cc(Br)cc(N3CCOCC3)c2)COC1]

The title compound (0.75 g, 64%) was prepared in a manner similar to that in Example A54 step 1 from 4-(3,5-dibromophenyl)morpholine and oxetan-3-one. LCMS (M+H)$^+$=314, 1s 316.

Step 3: 3-(3-morpholino-5-(4,4,5,5-tetramethyl-1,3,2-dioxaborolan-2-yl)phenyl)oxetan-3-ol

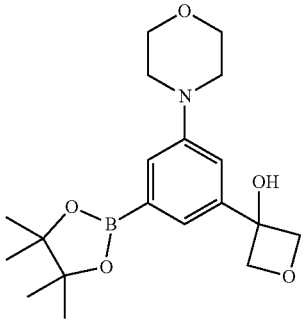 [SMILES: CC1(C)OB(c2cc(N3CCOCC3)cc(C3(O)COC3)c2)OC1(C)C]

The title compound (0.73 g, 85%) was prepared in a manner similar to that in Example A1 step 6 from 3-(3-bromo-5-morpholinophenyl)oxetan-3-ol and BPD. LCMS (M+H)⁺=362.

Step 4: 3-(3-(5-amino-6-((1-(1-methylpiperidin-4-yl)-1H-pyrazol-4-yl)oxy)pyrazin-2-yl)-5-morpholinophenyl)oxetan-3-ol Example A72 (100 mg, 51%) was prepared in a manner similar to that in Example A1 step 7 from 5-bromo-3-((1-(1-methylpiperidin-4-yl)-1H-pyrazol-4-yl)oxy)pyrazin-2-amine and 3-(3-morpholino-5-(4,4,5,5-tetramethyl-1,3,2-dioxaborolan-2-yl)phenyl)oxetan-3-ol. ¹H NMR (400 MHz, DMSO-d6) δ 8.28 (s, 1H), 8.14 (s, 1H), 7.58 (s, 1H), 7.56 (s, 1H), 7.33 (s, 1H), 7.06 (s, 1H), 6.73 (s, 2H), 6.31 (s, 1H), 4.79-4.69 (m, 4H), 4.164.04 (m, 1H), 3.81-3.72 (m, 4H), 3.22-3.12 (m, 4H), 2.91-2.83 (m, 2H), 2.22 (s, 3H), 2.11-1.94 (m, 6H). LCMS (M+H)⁺=508.5.

Example A73

3-(5-(5-amino-6-(141-methylpiperidin-4-yl)-1H-pyrazol-4-yloxy)pyrazin-2-yl)-2,3-dimethylphenyl)oxetan-3-ol

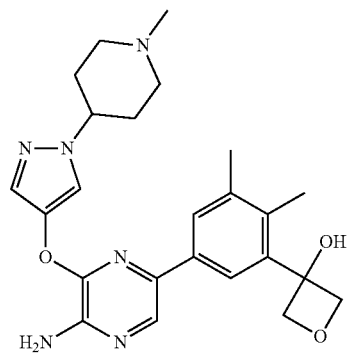 [SMILES: Cc1cc(-c2cnc(N)c(Oc3cnn(C4CCN(C)CC4)c3)n2)cc(C2(O)COC2)c1C]

Step 1: 1-bromo-5-chloro-2,3-dimethylbenzene

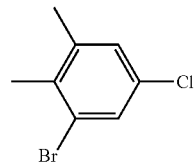

The title compound (385 mg, 46%) was prepared in a manner similar to that in Example A84 step 1 from 3-bromo-4,5-dimethylaniline.

Step 2: 3-(5-chloro-2,3-dimethylphenyl)oxetan-3-ol

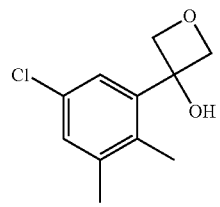

The title compound (304 mg, 82%) was prepared in a manner similar to that in Example A54 step 1 from 1-bromo-5-chloro-2,3-dimethylbenzene and oxetan-3-one. LC-MS (M-OH)⁺=195.0.

Step 3: 3-(2,3-dimethyl-5-(4,4,5,5-tetramethyl-1,3,2-dioxaborolan-2-yl)phenyl)oxetan-3-ol

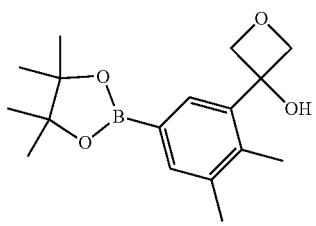 [SMILES: Cc1cc(B2OC(C)(C)C(C)(C)O2)cc(C2(O)COC2)c1C]

The titled compound (264 mg, 65%) was prepared in a manner similar to that in Example A54 step 2 from 3-(5-chloro-2,3-dimethylphenyl)oxetan-3-ol. LC-MS (M−OH)⁺=287.1. Step 4: 3-(5-(5-amino-6-(1-(1-methylpiperidin-4-yi)-1H-pyrazol-4-yloxy)pyrazin-2-yl)-2,3-dimethylphenyl)oxetan-3-ol Example A73 (23 mg, 19%) was prepared in a manner similar to that in Example A1 step 7 from 5-bromo-3-((1-(1-methylpiperidin-4-yl)-1H-pyrazol-4-yl)oxy)pyrazin-2-amine and 3-(2,3-dimethyl-5-(4,4,5,5-tetramethyl-1,3,2-dioxaborolan-2-yl)phenyl)oxetan-3-ol, 1H NMR (300 MHz, DMSO-d₆) δ 8.24 (s, 1H), 8.07 (s, 1H), 7.63-7.54 (m, 2H), 7.50 (s, 1H), 6.64 (s, 2H), 6.10 (s, 1H), 5.01 (d, J=6.7 Hz, 2H), 4.71 (d, J=6.7 Hz, 2H), 4.15-4.01 (m, 1H), 2.92-2.80 (m, 2H), 2.24 (s, 3H), 2.19 (s, 3H), 2.10-1.90 (m, 9H). LC-MS (M+H)=451.3.

Example A74A/A74B (S)-3-(3-(5-amino-6-((1-(1-methylpiperidin-4-yl)-1H-pyrazol-4-yl)oxy)pyrazin-2-yl)-5-methylphenyl)tetrahydrofuran-3-ol & (R)-3-(3-(5-amino-6-((1-(1-methylpiperidin-4-yl)-1H-pyrazol-4-yl)oxy)pyrazin-2-yl)-5-methylphenyl)tetrahydrofuran-3-ol

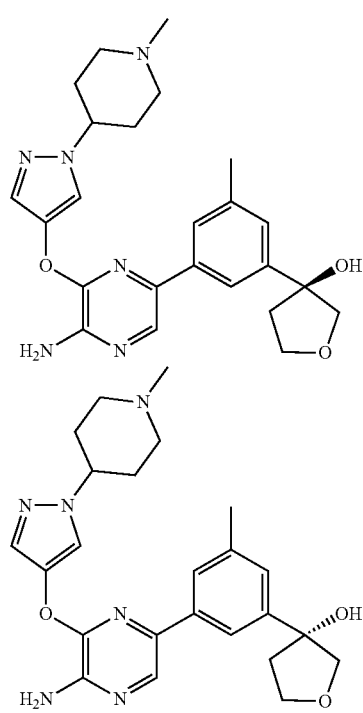

Example A69 (700 mg) was separated by chiral-HPLC to give Example A74A/A74B, j5 Analytical chiral-HPLC condition: CHIRALPAK IA3, 4.6×50 mm, 3 μm; (Hexane:DCM=3:1, contains 0.1% Et₂NH):EtOH=9:1; 1 mL/min; 25° C.

Example A74A ((S)-3-(3-(5-amino-64(1-(1-methylpiperidin-4-yl)-1H-pyrazol-4-yl)oxy)pyrazin-2-yl)-5-methylphenyl)tetrahydrofuran-3-ol): (228 mg, 33%) ¹H NMR (400 MHz, DMSO-dQ) 5-8.22 (s, 1H), 8.12 (s, 1H), 7.74 (s, 1H), 7.57 (s, 1H), 7.52 (s, 1H), 7.24 (s, 1H), 6.68 (s, 2H), 5.37 (s, 1H), 4.154.03 (m, 1H), 4.04-3.92 (m, 2H), 3.81-3.70 (m, 2H), 2.91-2.82 (m, 2H), 2.34 (s, 3H), 2.32-2.23 (m, 1H), 2.21 (s, 3H), 2.15-1.91 (m, 7H). LC-MS (M+H)⁺=451.3. Chiral HPLC: tR=1.59 min.

Example A74B ((R)-3-(3-(5-amino-6-((1-(1-methylpiperidin-4-yl)-1H-pyrazol-4-yl)oxy)pyrazin-2-yl)-5-methylphenyl)tetrahydrofuran-3-ol): (252 mg, 36%) ¹H NMR (400 MHz, DMSO-d₆) ¹H NMR (300 MHz, DMSO-d₆) δ 8.24 (s, 1H), 8.13 (s, 1H), 7.76 (s, 1H), 7.59 (s, 1H), 7.54 (s, 1H), 7.24 (s, 1H), 6.69 (s, 2H), 5.38 (s, 1H), 4.17-4.05 (m, 1H), 4.06-3.94 (m, 2H), 3.83-3.72 (m, 2H), 2.92-2.82 (m, 2H), 2.34 (s, 3H), 2.32-2.23 (m, 1H), 2.21 (s, 3H), 2.15-1.91 (m, 7H). LC-MS (M+H)⁺=451.3. Chiral HPLC: tR=2.08 mim.

Example A75

5-(4-(3,6-dihydro-2H-pyran-4-yl)-3,5-dimethylphenyl)-3-((141-methylpiperidin-4-yl)-1H-pyrazol-4-yl)oxy)pyrazin-2-amine

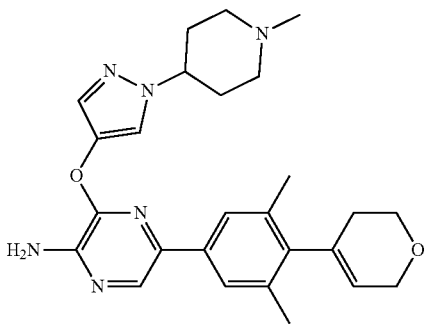 [SMILES: Cc1cc(-c2cnc(N)c(Oc3cnn(C4CCN(C)CC4)c3)n2)cc(C)c1C1=CCOCC1]

Step 1: 4-(4-bromo-2,6-dimethylphenyl)-3,6-dihydro-2H-pyran

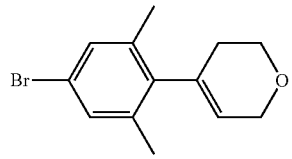

A mixture of 5-bromo-2-iodo-1,3-dimethylbenzene (1.55 g, 5.0 mmol), 2-(3,6-dihydro-2H-pyran-4-yl)-4,4,5,5-tetramethyl-1,3,2-dioxaborolane (1.15 g, 5.5 mmol), Pd(dppf)C;₂·DCM (204 mg, 0.25 mmol) and K₂CO₃(2.07 g, 15 mmol) in dioxane (20 mL) and water (2 mL) was stirred at 100° C. overnight under nitrogen. The mixture was cooled to room temperature, diluted with water (100 mL) and extracted by DCM (100 mL). The organic layer was dried over Na₂SO₄, filtered and concentrated under reduced pressure. The residue was purified by silica gel prep-TLC (PE:EtOAc=10:1) to give the title compound (772 mg, 58%). LC-MS (M+H)⁺=267.0, 1s 269.1.

Step 2: 2-(4-(3,6-dihydro-2H-pyran-4-yl)-3,5-dimethylphenyl)-4,4,5,5-tetramethyl-1,3,2-dioxaborolane

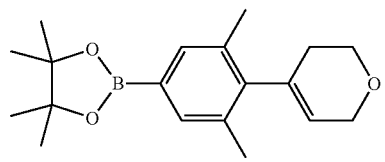 [SMILES: Cc1cc(B2OC(C)(C)C(C)(C)O2)cc(C)c1C1=CCOCC1]

4-(4-bromo-2,6-dimethylphenyl)-3,6-dihydro-2H-pyran (772 mg, 2.9 mmol), BPD (810 mg, 3.19 mmol), Pd(dppf)Cl₂ DCM (118 mg, 0.145 mmol) and AcOK (853 mg, 8.7 mmol) was added in dioxane (10 mL) under nitrogen. The reaction mixture was heated to reflux overnight. The mixture was cooled to room temperature and concentrated, then the residue was purified by silica gel column chromatography (PE:EtOAc=10:1) to give the title compound (900 mg, 98%). LC-MS (M+H)+=315.3.

Step 3: 5-(4-(3,6-dihydro-2H-pyran-4-yl)-3,5-dimethylphenyl)-3-((1-(1-methylpiperidin-4-yl)-1H-pyrazol-4-yl)oxy)pyrazin-2-amine Example A75 (57 mg, 62%) was prepared in a manner similar to that in Example A1 step 7 from 2-(4-(3,6-dihydro-2H-pyran-4-yl)-3,5-dimethylphenyl)-4,4,5,5-tetramethyl-1,3,2-dioxaborolane and 5-bromo-3-((1-(1-methylpiperidin-4-yl)-1H-pyrazol-4-yl)oxy)pyrazin-2-amine. $^1$H NMR (400 MHz, DMSO-d$_5$) δ 8.14 (s, 1H), 8.05 (s, 1H), 7.53 (s, 1H), 7.43 (s, 2H), 6.61 (s, 2H), 5.47-5.40 (m, 1H), 4.13 (s, 3H), 3.81-3.72 (m, 2H), 2.94-2.79 (m, 2H), 2.25-1.88 (m, 17H). LCMS (M+H)+=461.3.

Example A76

(R)-3-(3-(5-amino-6-((1-(1-methylpiperidin-4-yl)-1H-pyrazol-4-yl)oxy)pyrazin-2-yl)-5-(3-(methoxymethyl)morpholino)phenyl)oxetan-3-ol

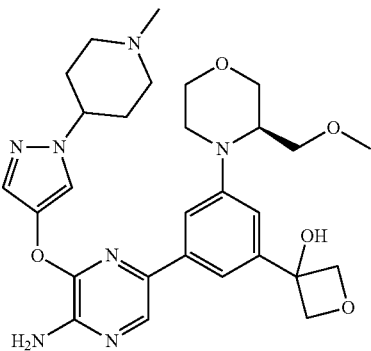 [SMILES: COC[C@@H]1COCCN1c1cc(-c2cnc(N)c(Oc3cnn(C4CCN(C)CC4)c3)n2)cc(C2(O)COC2)c1]

Step 1: (R)-4-(3,5-dibromophenyl)-3-(methoxymethyl)morpholine

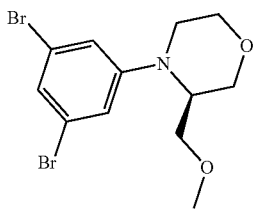 [SMILES: COC[C@@H]1COCCN1c1cc(Br)cc(Br)c1]

The title compound (0.41 g, 37%) was prepared in a manner similar to that in Example A59 step 1 from 1,3-dibromo-5-iodobenzene and (R)-3-(methoxymethyl)morpholine. LCMS (M+H)+=366.

Step 2: (R)-3-(3-bromo-5-(3-(methoxymethyl)morpholino)phenyl)oxetan-3-ol

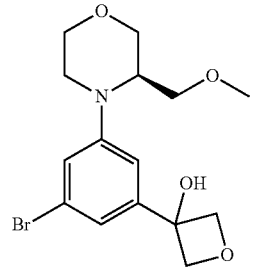 [SMILES: COC[C@@H]1COCCN1c1cc(Br)cc(C2(O)COC2)c1]

The title compound (0.14 g, 35%) was prepared in a manner similar to that in Example A54 step 1 from (R)-4-(3,5-dibromophenyl)-3-(methoxymethyl)morpholine and oxetan-3-one. LCMS (M+H)+=358,360.

Step 3: (R)-3-(3-(3-(methoxymethyl)morpholino)-5-(4,4,5,5-tetramethyl-1,3,2-dioxaborolan-2-yl)phenyl)oxetan-3-ol

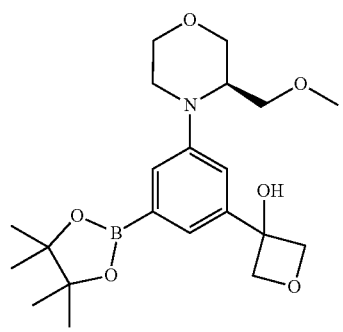

The title compound (0.14 g, 88%) was prepared in a manner similar to that in Example A1 step 6 from (R)-3-(3-bromo-5-(3-(methoxymethyl)morpholino)phenyl)oxetan-3-ol and BPD. LCMS (M+H)+=406.

Step 4: (R)-3-(3-(5-amino-6-((1-(1-methylpiperidin-4-yl)-1H-pyrazol-4-yl)oxy)pyrazin-2-yl)-5-(3-(methoxymethyl)morpholino)phenyl)oxetan-3-ol Example A76 (45 mg, 21%) was prepared in a manner similar to that in Example A1 step 7 from 5-bromo-3-((1-(1-methylpiperidin-4-yl)-1H-pyrazol-4-yl)oxy)pyrazin-2-amine and (R)-3-(3-(3-(methoxymethyl)morpholino)-5-(4,4,5,5-tetramethyl-1,3,2-dioxaborolan-2-yl)phenyl)oxetan-3-ol. $^1$H NMR (400 MHz, DMSO-d6) δ 8.27 (s, 1H), 8.13 (s, 1H), 7.57 (s, 1H), 7.52 (s, 1H), 7.30 (s, 1H), 7.04 (s, 1H), 6.73 (s, 2H), 6.31 (s, 1H), 4.78-4.69 (m, 4H), 4.15-4.05 (m, 1H), 3.98-3.86 (m, 3H), 3.70-3.53 (m, 3H), 3.32-3.26 (m, 1H), 3.19 (s, 3H), 3.17-3.13 (m, 1H), 3.12-3.03 (m, 1H), 2.91-2.82 (m, 2H), 2.21 (s, 3H), 2.07-1.93 (m, 6H). LCMS (M+H)+=552.2.

Example A77

5-(3,5-dimethyl-4-(2-oxa-6-azaspiro[3.3]heptan-6-yl)phenyl)-3-((1-(1-methylpiperidin-4-yl)-1H-pyrazol-4-yl)oxy)pyrazin-2-amine

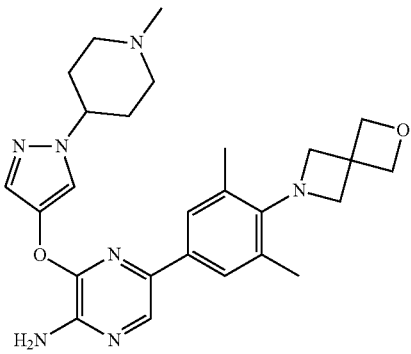 [SMILES: Cc1cc(-c2cnc(N)c(Oc3cnn(C4CCN(C)CC4)c3)n2)cc(C)c1N1CC2(COC2)C1]

Step 1: 6-(4-chloro-2,6-dimethylphenyl)-2-oxa-6-azaspiro[3.3]heptane

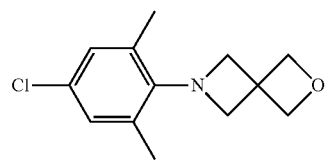 [SMILES: Cc1cc(Cl)cc(C)c1N1CC2(COC2)C1]

To a solution of 2-bromo-5-chloro-1,3-dimethylbenzene (200 mg, 0.87 mmol) in dioxane (6 mL) was added 2-oxa-6-azaspiro[3.3]heptane (181 mg, 1.73 mmol), Cs$_2$CO$_3$ (891 mg, 2.60 mmol), P(t-Bu)$_3$ Palladacycle Gen, 3 (53 mg, 0.09 mmol) and P(t-Bu)$_3$-HBF$_4$ (27 mg, 0.09 mmol) at room temperature then the mixture was warmed to 90° C. and stirred for 5 h under nitrogen. The mixture was cooled to room temperature and concentrated under vacuum. The residue was purified by silica gel chromatography, eluting with MeOH in DCM (0% to 13% gradient) to give the title compound (163 mg, 79%). LC-MS (M+H)$^+$=238.2.

Step 2: 6-(2,6-dimethyl-4-(4,4,5,5-tetramethyl-1,3,2-dioxaborolan-2-yl)phenyl)-2-oxa-6-azaspiro[3.3]heptane

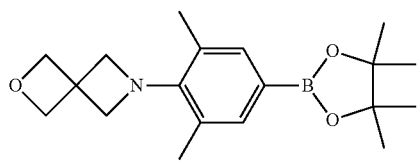 [SMILES: Cc1cc(B2OC(C)(C)C(C)(C)O2)cc(C)c1N1CC2(COC2)C1]

The title compound (175 mg, 78%) was prepared in a manner similar to that in Example A54 step 1 from 6-(4-chloro-2,6-dimethylphenyl)-2-oxa-6-azaspiro[3.3]heptane. LC-MS (M+H)$^+$=330.0.

Step 3: 5-(3,5-dimethyl-4-(2-oxa-6-azaspiro[3.3]heptan-6-yl)phenyl)-3-((1-(1-methylpiperidin-4-yl)-1H-pyrazol-4-yl)oxy)pyrazin-2-amine Example A77 (7 mg, 9%) was prepared in a manner similar to that in Example A1 step 7 from 5-bromo-3-((1-(1-methylpiperidin-4-yl)-1H-pyrazol-4-yl)oxy)pyrazin-2-amine and 6-(2,6-dimethyl-4-(4,4,5,5-tetramethyl-1,3,2-dioxaborolan-2-yl)phenyl)-2-oxa-6-azaspiro[3.3]heptane. $^1$H NMR (400 MHz, DMSO-d$_6$) δ 8.08 (s, 2H), 7.78 (s, 1H), 7.28 (s, 2H), 6.45 (s, 2H), 4.68 (s, 4H), 4.27 (s, 4H), 4.174.07 (m, 1H), 2.91-2.82 (m, 2H), 2.23 (d, J=14.3 Hz, 9H), 2.13-1.91 (m, 6H). LC-MS (M+H)$^+$=476.4.

Example A78

3-(3-(5-amino-6-((1-(1-methylpiperidin-4-yl)-1H-pyrazol-4-yl)oxy)pyrazin-2-yl)-5-(2-oxa-6-azaspiro[3.3]heptan-6-yl)phenyl)oxetan-3-ol

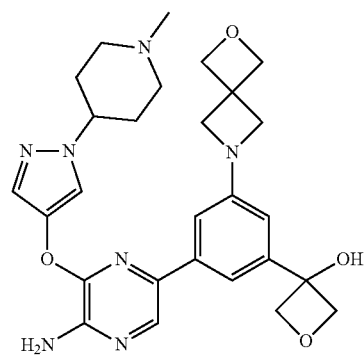 [SMILES: CN1CCC(n2cc(Oc3nc(-c4cc(N5CC6(COC6)C5)cc(C5(O)COC5)c4)cnc3N)cn2)CC1]

Step 1: 6-(3-bromo-5-chlorophenyl)-2-oxa-6-azaspiro[3.3]heptane

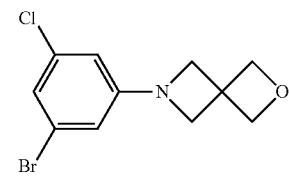 [SMILES: Clc1cc(Br)cc(N2CC3(COC3)C2)c1]

The title compound (650 mg, 49%) was prepared in a manner similar to that in Example A22 step 1 from 1-bromo-3-chloro-5-fluorobenzene and 2-oxa-6-azaspiro[3.3]heptane. LC-MS (M+H)$^+$=287.9.

Step 2: 3-(3-chloro-5-(2-oxa-6-azaspiro[3.3]heptan-6-yl)phenyl)oxetan-3-ol

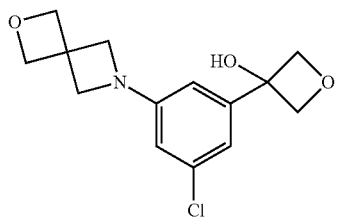 [SMILES: OC1(c2cc(Cl)cc(N3CC4(COC4)C3)c2)COC1]

The title compound (320 mg, 66%) was prepared in a manner similar to that in Example A54 step 1 from 6-(3-bromo-5-chlorophenyl)-2-oxa-6-azaspiro[3.3]heptane and 3-oxetanone. LC-MS (M+H)⁺=282.0.

Step 3: 3-(3-(2-oxa-6-azaspiro[3.3]heptan-6-yl)-5-(4,4,5,5-tetramethyl-1,3,2-dioxaborolan-2-yl)phenyl)oxetan-3-ol

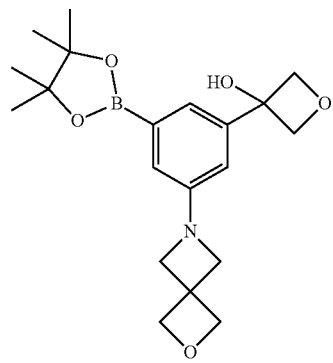 [SMILES: CC1(C)OB(c2cc(N3CC4(COC4)C3)cc(C3(O)COC3)c2)OC1(C)C]

The title compound (134 mg, 51%) was prepared in a manner similar to that in Example A1 step 6 from 3-(3-chloro-5-(2-oxa-6-azaspiro[3.3]heptan-6-yl)phenyl)oxetan-3-ol and BPD. LC-MS (M+H)⁺=374.1.

Step 4: 3-(3-(5-amino-6-((1-(1-methylpiperidin-4-yl)-1H-pyrazol-4-yl)oxy)pyrazin-2-yl)-5-(2-oxa-6-azaspiro[3.3]heptan-6-yl)phenyl)oxetan-3-ol Example A78 (17 mg, 12%) was prepared in a manner similar to that in Example A1 step 6 from 3-(3-(2-oxa-6-azaspiro[3.3]heptan-6-yl)-5-(4,4,5,5-tetramethyl-1,3,2-dioxaborolan-2-yl)phenyl)oxetan-3-ol and 5-bromo-3-((1-(1-methylpiperidin-4-yl)-1H-pyrazol-4-yl)oxy)pyrazin-2-amine. ¹H NMR (300 MHz, DMSO-d₆) δ 8.21 (s, 1H), 8.14 (s, 1H), 7.56 (s, 1H), 7.43 (s, 1H), 6.82 (s, 1H), 6.69 (s, 2H), 6.55 (s, 1H), 6.27 (s, 1H), 4.77-4.64 (m, 8H), 4.19-4.07 (m, 1H), 4.01 (s, 4H), 2.91-2.82 (m, 2H), 2.20 (s, 3H), 2.11-1.90 (m, 6H). LC-MS (M+H)⁺=520.4.

Example A79

3-(3-(5-amino-6-((1-(1-methylpiperidin-4-yl)-1H-pyrazol-4-yl)oxy)pyrazin-2-yl)-5-(tetrahydro-2H-pyran-4-yl)phenyl)oxetan-3-ol

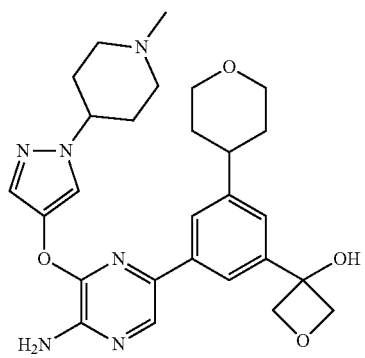 [SMILES: CN1CCC(n2cc(Oc3nc(-c4cc(C5CCOCC5)cc(C5(O)COC5)c4)cnc3N)cn2)CC1]

Step 1: 4-(3,5-dibromophenyl)oxan-4-ol

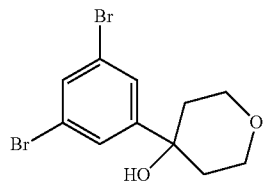 [SMILES: OC1(c2cc(Br)cc(Br)c2)CCOCC1]

The title compound (3.2 g, 30;%) was prepared in a manner similar to that in Example A58 step 1 from 1,3,5-tribromobenzene and tetrahydropyran-4-one. ¹H NMR (300 MHz, DMSO-d₆) δ 7.70-7.61 (m, 3H), 5.31 (s, 1H), 3.77-3.60 (m, 4H), 2.02-1.82 (m, 2H), 1.52-1.41 (m, 2H).

Step 2: 4-(3,5-dibromophenyl)-tetrahydro-2H-pyran

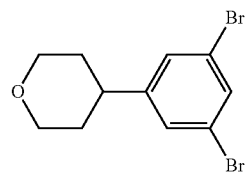 [SMILES: Brc1cc(Br)cc(C2CCOCC2)c1]

A mixture of 4-(3,5-dibromophenyl)oxan-4-ol (300 mg, 0.89 mmol), Et·SiH (1.56 g, 13.4 mmol) and TFA (1.63 g, 14.3 mmol) in DCM (5 mL) was stirred for overnight at 40° C. under nitrogen. The mixture was cooled to room temperature and concentrated under vacuum. The residue was purified by reverse phase chromatography to give the title compound (100 mg, 28%).

Step 3: 3-(3-bromo-5-(tetrahydro-2H-pyran-4-yl)phenyl)oxetan-3-ol

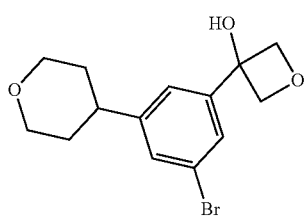 [SMILES: OC1(c2cc(Br)cc(C3CCOCC3)c2)COC1]

The title compound (150 mg, 17%) was prepared in a manner similar to that in Example A54 step 1 from 4-(3,5-dibromophenyl)oxane and 3-oxetanone.

Step 4: 3-(3-(tetrahydro-2H-pyran-4-yl)-5-(4,4,5,5-tetramethyl-1,3,2-dioxaborolan-2-yl)phenyl)oxetan-3-ol

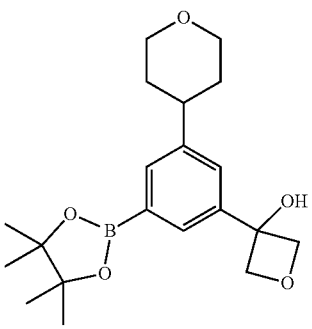 [SMILES: CC1(C)OB(c2cc(C3CCOCC3)cc(C3(O)COC3)c2)OC1(C)C]

The title compound (44 mg, 13%) was prepared in a manner similar to that in Example A1 step 6 from 343-bromo-5-(tetrahydro-2H-pyran-4-yl)phenyl)oxetan-3-ol.

Step 5: 3-(3-(5-amino-6-((1-(1-methylpiperidin-4-yl)-1H-pyrazol-4-yl)oxy)pyrazin-2-yl)-5-(tetrahydro-2H-pyran-4-yl)phenyl)oxetan-3-ol Example A79 (22 mg, 10%) was prepared in a manner similar to that in Example A1 step 7 from 5-bromo-3-((1-(1-methylpiperidin-4-yl)-1H-pyrazol-4-yl)oxy)pyrazin-2-amine and 3-(3-(tetrahydro-2H-pyran-4-yl)-5-(4,4,5,5-tetramethyl-1,3,2-dioxaborolan-2-yl)phenyl)oxetan-3-ol. $^1$H NMR (300 MHz, DMSO-d) δ 8.29 (s, 1H), 8.16 (s, 1H), 7.92 (s, 1H), 7.65 (s, 1H), 7.58 (s, 1H), 7.40 (s, 1H), 6.73 (s, 2H), 6.35 (s, 1H), 4.82-4.71 (m, 4H), 4.18-4.04 (m, 1H), 4.02-3.93 (m, 2H), 3.53-3.39 (m, 2H), 2.92-2.76 (m, 3H), 2.22 (s, 3H), 2.11-1.92 (m, 6H), 1.79-1.67 (m, 4H). LC-MS (M+H)$^+$=507.0.

Example A80A/A80B (R)-3-(3-(5-amino-6-((1-(1-methylpiperidin-4-yl)-1H-pyrazol-4-yl)oxy)pyrazin-2-yl)-5-((R)-3-methylmorpholino)phenyl)tetrahydrofuran-3-ol & (S)-3-(3-(5-amino-6-((1-(1-methylpiperidin-4-yl)-1H-pyrazol-4-yl)oxy)pyrazin-2-yl)-5-((R)-3-methylmorpholino)phenyl)tetrahydrofuran-3-ol

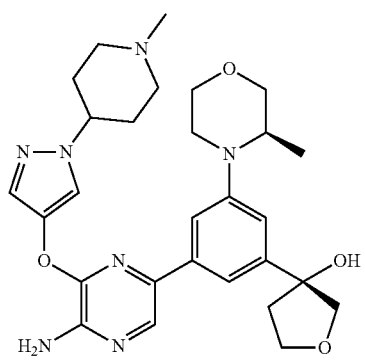

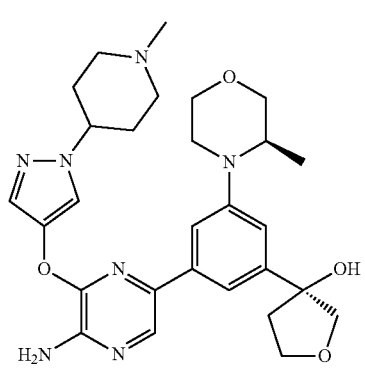

Step 1: 3-(3-bromo-5-((R)-3-methylmorpholino)phenyl)tetrahydrofuran-3-ol

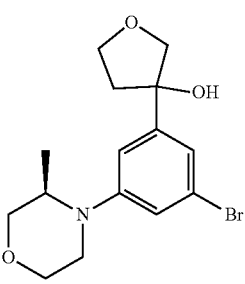 [SMILES: C[C@@H]1COCCN1c1cc(Br)cc(C2(O)CCOC2)c1]

The title compound (500 mg, 48%) was prepared in a manner similar to that in Example A54 step 1 from (3R)-4-(3,5-dibromophenyl)-3-methylmorpholine and dihydrofuran-3-one. LC-MS (M+H)$^+$=341.9.

Step 2: 3-(3-((R)-3-methylmorpholino)-5-(4,4,5,5-tetramethyl-1,3,2-dioxaborolan-2-yl)phenyl)tetrahydrofuran-3-ol

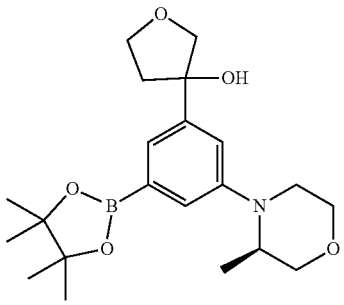 [SMILES: C[C@@H]1COCCN1c1cc(B2OC(C)(C)C(C)(C)O2)cc(C2(O)CCOC2)c1]

The title compound (300 mg, 65%) was prepared in a manner similar to that in Example A1 step 6 from 3-(3-bromo-5-((R)-3-methylmorpholino)phenyl)tetrahydrofuran-3-ol and BPD. LC-MS (M+H)⁺=390.1.

Step 3: (R)-3-(3-(5-amino-6-((-(1-methylpiperidin-4-yl)-1H-pyrazol-4-yl)oxy)pyrazin-2-yl)-5-((R)-3-methylmorpholino)phenyl)tetrahydrofuran-3-ol & (S)-3-(3-(5-amino-6-((1-(1-methylpiperidin-4-yl)-1H-pyrazol-4-yl)oxy)pyrazin-2-yl)-5-((R)-3-methylmorpholino)phenyl)tetrahydrofuran-3-ol Examples A80A/A80B were prepared in a manner similar to that in Example A1 step 7 from 5-bromo-3-((1-(1-methylpiperidin-4-yl)-1H-pyrazol-4-yl)oxy)pyrazin-2-amine and 3-(3-((R)-3-methylmorpholino)-5-(4,4,5,5-tetramethyl-1,3,2-dioxaborolan-2-yl)phenyl)tetrahydrofuran-3-ol, then the isomers were separated by chiral-HPLC. Analytical chiral-HPLC condition: CHIRALPAK IA3, 4.6×50 mm, 3 μm; (Hexane:DCM=3:1, contains 0.1% Et₂NH):IPA=4:1; 1 mL/min; 25° C.

Example A80A ((S)-3-(3-(5-amino-6-((1-(1-methylpiperidin-4-yl)-1H-pyrazol-4-yl)oxy)pyrazin-2-yl)-5-((R)-3-methylmorpholino)phenyl)tetrahydrofuran-3-ol): (22 mg, 35%) ¹H NMR (300 MHz, DMSO-d6) δ 8.25 (s, 1H), 8.12 (s, 1H), 7.58 (s, 1H), 7.39 (s, 1H), 7.22 (s, 1H), 6.99 (s, 1H), 6.69 (s, 2H), 5.35 (s, 1H), 4.18-3.51 (m, 10H), 3.26-3.16 (m, 1H), 3.13-2.98 (m, 1H), 2.92-2.82 (m, 2H), 2.39-2.24 (m, 1H), 2.22 (s, 3H), 2.17-1.88 (m, 7H), 1.00 (d, J=6.4 Hz, 3H). LC-MS (M+H)⁺=536.4. Chiral HPLC: tR=1.55 min.

Example A80B ((R)-3-(3-(5-amino-6-((1-(1-methylpiperidin-4-yl)-1H-pyrazol-4-yl)oxy)pyrazin-2-yl)-5-((R)-3-methylmorpholino)phenyl)tetrahydrofuran-3-ol): (23 mg, 39%) ¹H NMR (300 MHz, DMSO-d₆) δ 8.25 (s, 1H), 8.12 (s, 1H), 7.58 (s, 1H), 7.39 (s, 1H), 7.22 (s, 1H), 6.99 (s, 1H), 6.69 (s, 2H), 5.35 (s, 1H), 4.18-3.51 (m, 10H), 3.26-3.16 (m, 1H), 3.13-2.98 (m, 1H), 2.92-2.82 (m, 2H), 2.39-2.24 (m, 1H), 2.22 (s, 3H), 2.17-1.88 (m, 7H), 1.00 (d, J=6.4 Hz, 3H). LC-MS (M+H)⁺=536.4. Chiral HPLC: tR=2.57 min.

Example A81

3-(5-(5-amino-64(l1-(1-methylpiperidin-4-yl)-1H-pyrazol-4-yl)oxy)pyrazin-2-yl)-3-methyl-2-(prop-1-yn-1-yl)phenyl)oxetan-3-ol

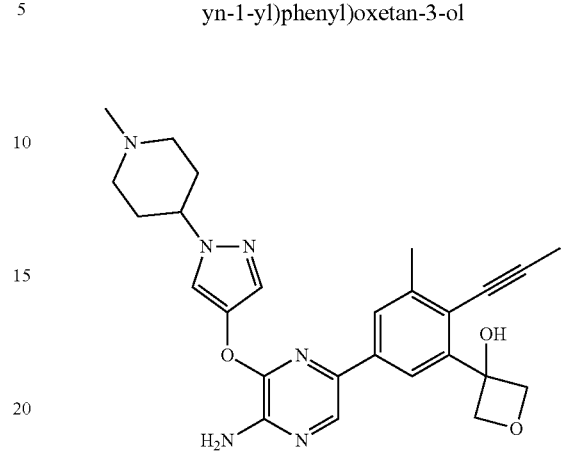

Step 1: 1-bromo-5-chloro-2-iodo-3-methylbenzene

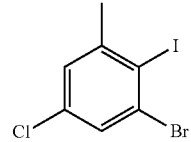

A suspension of 2-bromo-4-chloro-6-methylaniline (5.0 g, 22.8 mmol) in water (40 mL) and conc. HCl (30 mL) was cooled to −5° C. To the above suspension was added an aqueous solution of NaNO₂ (1.73 g, 25.1 mmol) dropwise while keeping the temperature below 0° C. After 30 min, the mixture was added slowly into KI (4.54 g, 27.4 mmol) in 300 mL ice water with vigorous stirring. The mixture was stirred overnight at room temperature. The mixture was extracted with of EtOAc (400 mL×2). The combined organic layer was washed with NaHSO₃, dried over Na₂SO₄, filtered and concentrated. The residue was purified by silica gel chromatograph with PE to give the title compound (4.5 g, 60%).

Step 2: 1-bromo-5-chloro-3-methyl-2-(prop-1-yn-1-yl)benzene

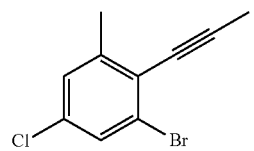

To a solution of 1-bromo-5-chloro-2-iodo-3-methylbenzene (2.0 g, 6.1 mmol) in toluene (30 mL) was added trimethyl(prop-1-yn-1-yl)silane (680 mg, 6.1 mmol), triethylamine (1.85 g, 18.3 mmol), CuI (348 mg, 1.8 mmol), Pd(PPh₃)₄ (352 mg, 0.3 mmol) and TBAF (1.6 g, 6.1 mmol). The mixture was stirred for overnight at room temperature under nitrogen. EtOAc (100 mL) was added and the organic phase was successively washed with H₂O (50 mL), brine (50 mL), dried over Na₂SO₄, filtered and concentrated under vacuum. The residue was purified by silica gel chromatograph with PE to give the title compound (1.2 g, 82%). $^1$H NMR (400 MHz, DMSO-d6) δ 7.64 (s, 1H), 7.43 (s, 1H), 2.40 (s, 3H), 2.15 (s, 3H).

Step 3: 3-(5-chloro-3-methyl-2-(prop-1-yn-1-yl)phenyl)oxetan-3-ol

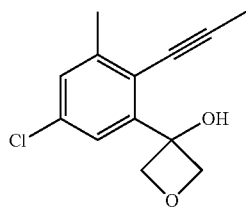 [SMILES: CC#Cc1c(C)cc(Cl)cc1C1(O)COC1]

To a solution of 1-bromo-5-chloro-3-methyl-2-(prop-1-yn-1-yl)benzene (1.2 g, 5.0 mmol) in THF (10 mL) was added n-BuLi (2.5 M in hexane, 2 mL) at −78° C. dropwise under nitrogen. After 40 min, oxetan-3-one (357 mg, 5.0 mmol) was added dropwise at −78° C. and the mixture was stirred for another 2 h. The mixture was quenched by saturated NH₄Cl (30 mL), warmed to room temperature, diluted with EtOAc (40 mL) and washed with brine (15 mL×2). The organic layer was dried over Na₂SO₄, filtered and concentrated. The residue was purified by silica gel chromatograph, with PE:EtOAc=14:5 to give the title compound (770 mg, 66%). LC-MS (M+H)$^+$=237.2.

Step 4: 3-(3-methyl-2-(prop-1-yn-1-yl)-5-(4,4,5,5-tetramethyl-1,3,2-dioxaborolan-2-yl)phenyl)oxetan-3-ol

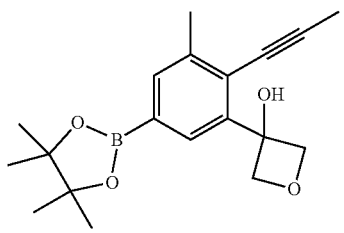 [SMILES: CC#Cc1c(C)cc(B2OC(C)(C)C(C)(C)O2)cc1C1(O)COC1]

To a solution of 3-(5-chloro-3-methyl-2-(prop-1-yn-1-yl)phenyl)oxetan-3-ol (300 mg, 1.3 mmol) in dioxane (10 mL) was added BPD (645 mg, 2.6 mmol), KOAc (250 mg, 2.5 mmol), Pd₂(dba)₃ (116 mg, 0.13 mmol) and XPhos (121 mg, 0.25 mmol). The mixture was stirred for overnight at 110° C. under nitrogen. The mixture was cooled to room temperature, diluted with EtOAc (40 mL), then successively washed with H₂O (15 mL) and brine (15 mL). The organic layer was dried over Na₂SO₄, filtered and concentrated. The residue was purified by silica gel chromatograph with PE:EtOAc=1:1 to give the title compound (360 mg, 86%). LC-MS (M+H)$^+$=329.3.

Step 5: 3-(5-(5-amino-6-((1-(1-methylpiperidin-4-yl)-1H-pyrazol-4-yl)oxy)pyrazin-2-yl)-3-methyl-2-(prop-1-yn-1-yl)phenyl)oxetan-3-ol To a solution of 3-(3-methyl-2-(prop-1-yn-1-yl)-5-(4,4,5,5-tetramethyl-1,3,2-dioxaborolan-2-yl)phenyl)oxetan-3-ol (300 mg, 0.91 mmol) in dioxane (10 mL) and water (1 mL) was added 5-bromo-3-((1-(1-methylpiperidin-4-yl)-1H-pyrazol-4-yl)oxy)pyrazin-2-amine (322 mg, 0.91 mmol), K2CO₃ (628 mg, 4.6 mmol) and Pd(dppf)Cl₂ DCM (74 mg, 0.09 mmol), then the mixture was warmed to at 100° C. under nitrogen. After 1 h, the mixture cooled to room temperature, diluted with EtOAc (30 mL), then successively washed with H₂O (15 mL) and brine (15 mL). The organic layer was dried over Na₂SO₄, filtered and concentrated. The residue was purified by silica gel prep-TLC, developing with MeOH:DCM=1:4, then further purified by prep-HPLC to give Example A81 (6 mg, 14%), 1H NMR (400 MHz, DMSO-d6) δ 8.31 (s, 1H), 8.10 (s, 1H), 7.70 (s, 1H), 7.58 (s, 1H), 7.55 (s, 1H), 6.81 (s, 2H), 6.04 (s, 1H), 5.11 (d, J=6.9 Hz, 2H), 4.68 (d. J=6.9 Hz, 2H), 4.17-4.06 (m, 1H), 2.90-2.83 (m, 2H), 2.38 (s, 3H), 2.21 (s, 3H), 2.09 (s, 3H), 2.06-1.94 (m, 6H). LC-MS (M+H)$^+$=475.4.

Example A82

3-(3-(5-amino-6-((1-(1-methylpiperidin-4-yl)-1H-pyrazol-4-yl)oxy)pyrazin-2-yl)-5-(methoxymethyl)phenyl)oxetan-3-ol

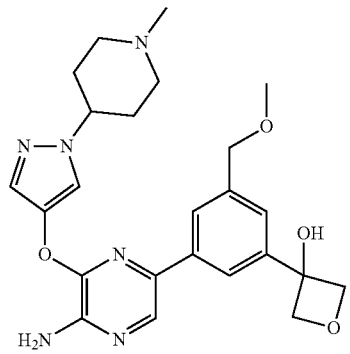 [SMILES: COCc1cc(-c2cnc(N)c(Oc3cnn(C4CCN(C)CC4)c3)n2)cc(C2(O)COC2)c1]

Step 1: (3,5-dibromophenyl)methanol

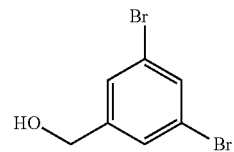

To a solution of 3,5-dibromobenzoic acid (2.0 g, 7.1 mmol) in THF (20 mL) was added BH₃ in THF (1.0 M, 14 mL, 14 mmol). The mixture was stirred at room temperature for overnight, then methanol (10 mL) was carefully added. The mixture was concentrated under reduced pressure, and the residue was purified by silica gel chromatograph (PE:EtOAc=5:1) to give the title compound (1.8 g, 95%). LC-MS (M+H)$^+$=265.8, 267.8.

Step 2: 1,3-dibromo-5-(methoxymethyl)benzene

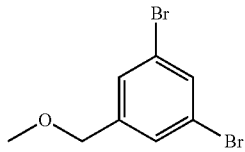

To a solution of (3,5-dibromophenyl)methanol (1.8 g, 6.7 mmol) in THF (20 mL) was added NaH (60%, 330 mg, 8.25 mmol) at room temperature. After 1 h, MeI (0.70 mL, 11.2 mmol) was added. The mixture was stirred at room temperature for overnight. Saturated NH$_4$Cl (10 mL) and water (10 mL) was added. The mixture was extracted with EtOAc (40 mL×2). The combined organic layer was washed with brine (50 mL×3), dried over Na$_2$SO$_4$, filtered and concentrated under vacuum. The residue was purified by silica gel chromatograph (PE:EtOAc=5:1) to give the title compound (1.5 g, 78%). LC-MS (M+H)$^+$=278.9, 280.9.

Step 3: 3-(3-bromo-5-(methoxymethyl)phenyl)oxetan-3-ol

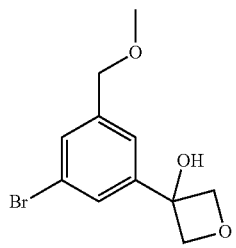

The title compound (550 mg, 34%) was prepared in a manner similar to that in Example A54 step 1 from 1,3-dibromo-5-(methoxymethyl)benzene and oxetan-3-one. LC-MS (M+H)$^+$=273.0, 275.0.

Step 4: 3-(3-(methoxymethyl)-5-(4,4,5,5-tetramethyl-1,3,2-dioxaborolan-2-yl)phenyl)oxetan-3-ol

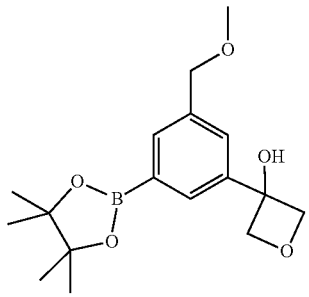 [SMILES: COCc1cc(B2OC(C)(C)C(C)(C)O2)cc(C2(O)COC2)c1]

The title compound (500 mg, 77%) was prepared in a manner similar to that in Example A1 step 6 from 3-(3-bromo-5-(methoxymethyl)phenyl)oxetan-3-ol and BPD. LC-MS (M+H)$^+$=321.2.

Step 5: 3-(3-(5-amino-6-((1-(1-methylpiperidin-4-yl)-1H-pyrazol-4-yl)oxy)pyrazin-2-yl)-5-(methoxymethyl)phenyl)oxetan-3-ol Example A82 (20 mg, 15%) was prepared in a manner similar to that in Example A1 step 7 from 5-bromo-3-((1-(1-methylpiperidin-4-yl)-1H-pyrazol-4-yl)oxy)pyrazin-2-amine and 3-(3-(methoxymethyl)-5-(4,4,5,5-tetramethyl-1,3,2-dioxaborolan-2-yl)phenyl)oxetan-3-ol. $^1$H NMR (400 MHz, DMSO-d6) δ 8.28 (s, 1H), 8.15 (s, 1H), 8.01 (s, 1H), 7.72 (s, 1H), 7.59 (s, 1H), 7.47 (s, 1H), 6.78 (s, 2H), 6.42 (s, 1H), 4.79-4.71 (m, 4H), 4.47 (s, 2H), 4.11-4.08 (m, 1H), 3.32 (s, 3H), 2.88-2.85 (m, 2H), 2.21 (s, 3H), 2.0-1.9(m, 6H). LC-MS (M+H)$^+$=467.2.

Example A83

3-(5-(5-amino-6-((1-(1-methylpiperidin-4-yl)-1H-pyrazol-4-yl)oxy)pyrazin-2-yl)-3-methyl-2-(2-oxa-6-azaspiro[3.3]heptan-6-yl)phenyl)tetrahydrofuran-3-ol

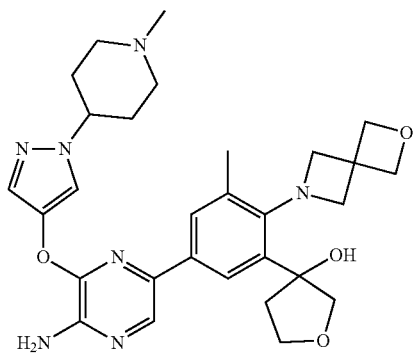 [SMILES: Cc1cc(-c2cnc(N)c(Oc3cnn(C4CCN(C)CC4)c3)n2)cc(C2(O)CCOC2)c1N1CC2(COC2)C1]

Step 1: 3-((1-(1-methylpiperidin-4-yl)-1H-pyrazol-4-yl)oxy)-5-(4,4,5,5-tetramethyl-1,3,2-dioxaborolan-2-yl)pyrazin-2-amine

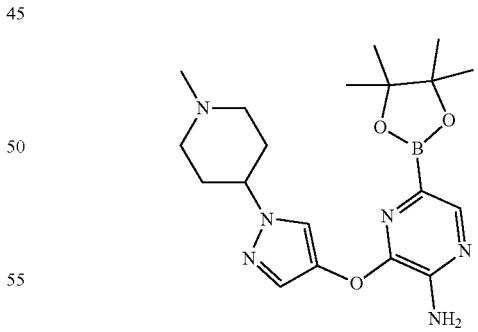

A mixture of 5-bromo-3-((1-(1-methylpiperidm-4-yl)-1H-pyrazol-4-yl)oxy)pyrazn-2-amine (2.0 g, 5.66 mmol) and BPD (2.88 g, 11.3 mmol) and Pd$_2$(dba)$_3$ (0.26 g, 0.283 mmol) and tricyclohexylphosphine (0.12 g, 0.425 mmol) and KOAc (1.11 g, 11.3 mmol) in dioxane (20 mL) was stirred for overnight at 110° C. under nitrogen. The mixture was cooled to room temperature and concentrated under reduced pressure. The residue was purified by reverse phase chromatography with acetonitrile/water to give the title compound (1.5 g, 66%). ¹H NMR (400 MHz, DMSO-d₆) δ 8.01 (s, 1H), 7.90 (s, 1H), 7.56 (s, 1H), 6.97 (s, 2H), 4.15-4.03 (m, 1H), 2.87-2.78 (m, 4H), 2.20 (s, 3H), 2.08-1.79 (m, 4H), 1.16 (s, 12H). LC-MS (M-pin+H)⁺=319.0.

Step 2: 6-(2-bromo-4-chloro-6-methylphenyl)-2-oxa-6-azaspiro[3.3]heptane

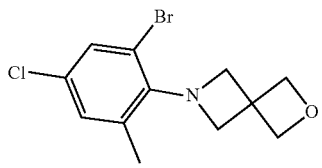 [SMILES: Cc1cc(Cl)cc(Br)c1N1CC2(COC2)C1]

To a solution of 1-bromo-5-chloro-2-iodo-3-methylbenzene (2.0 g, 5.5 mmol) in dioxane (20 mL) and 2-oxa-6-azaspiro[3.3]heptane (630 mg, 6.04 mmol) was added Cs₂CO₃ (2.83 g, 8.24 mmol), Pd₂(dba)₃ (159 mg, 0.17 mmol), and XantPhos (201 mg, 0.33 mmol) under nitrogen then the mixture was warmed to 90° C. After 16 h, the mixture was cooled to room temperature and concentrated under reduced pressure. The residue was purified by silica gel chromatography, eluting with EtOAc in PE (0% to 30% gradient) to give the title compound (1.52 g, 91%). LC-MS (M+1)⁺=301.9.

Step 3: 3-(5-chloro-3-methyl-2-(2-oxa-6-azaspiro[3.3]heptan-6-yl)phenyl)tetrahydrofuran-3-ol

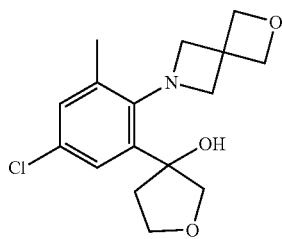 [SMILES: Cc1cc(Cl)cc(C2(O)CCOC2)c1N1CC2(COC2)C1]

The title compound (150 mg, 37%) was prepared in a manner similar to that in Example A54 step 1 from 6-(2-bromo-4-chloro-6-methylphenyl)-2-oxa-6-azaspiro[3.3]heptane and dihydrofuran-3-one. LC-MS (M+1)⁺=310.0.

Step 4: 3-(5-(5-amino-6-((1-(1-methylpiperidin-4-yl)-1H-pyrazol-4-yl)oxy)pyrazin-2-yl)-3-methyl-2-(2-oxa-6-azaspiro[3.3]heptan-6-yl)phenyl)tetrahydrofuran-3-ol To a solution of 3-(5-chloro-3-methyl-2-(2-oxa-6-azaspiro[3.3]heptan-6-yl)phenyl)tetrahydrofuran-3-ol (100 mg, 0.31 mmol) in dioxane (2 mL) and H₂O (0.20 mL) was added 3-((1-(1-methylpiperidin-4-yl)-1H-pyrazol-4-yl)oxy)-5-(4,4,5,5-tetramethyl-1,3,2-dioxaborolan-2-yl)pyrazin-2-amine (230 mg, 0.57 mmol), K₂CO₃ (89 mg, 0.62 mmol) and dichlorobis(tricyclohexylphosphine)palladium (II) (24 mg, 0.03 mmol) under nitrogen. The mixture was warmed to 100° C. and stirred for 2 h. The mixture was cooled to room temperature and diluted with water (30 mL). The mixture was extracted with DCM (30 mL×3). The combined organic layers were washed with brine (30 mL), dried over Na₂SO₄, filtered and concentrated under reduced pressure. The residue was purified by prep-HPLC to give Example A83 (25 mg, 15%) obtained. ¹H NMR (300 MHz, DMSO-d6) δ 8.22 (s, 1H), 8.12 (s, 1H), 7.76 (s, 1H), 7.59 (s, 2H), 6.72 (s, 2H), 5.93 (s, 1H), 4.824.76 (m, 4H), 4.21-3.96 (m, 7H), 3.94-3.85 (m, 1H), 3.76 (d, J=8.9 Hz, 1H), 2.92-2.83 (m, 2H), 2.41 (s, 3H), 2.37-2.25 (m, 1H), 2.22 (s, 3H), 2.20-2.14 (m, 1H), 2.08-1.97 (m, 6H). LC-MS (M+H)⁺=548.4.

Example A84

3-(5-(5-amino-6-((1-(1-methylpiperidin-4-yl)-1H-pyrazol-4-yl)oxy)pyrazin-2-yl)-2-chloro-3-methylphenyl)oxetan-3-ol

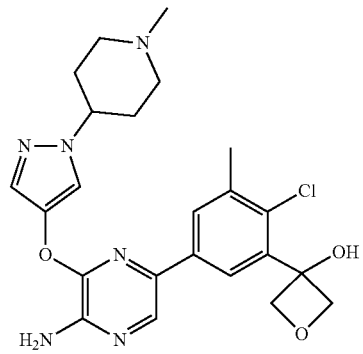 [SMILES: Cc1cc(-c2cnc(N)c(Oc3cnn(C4CCN(C)CC4)c3)n2)cc(C2(O)COC2)c1Cl]

Step 1: 1-bromo-2,5-dichloro-3-methylbenzene

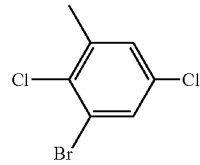

To a solution of 2-bromo-4-chloro-6-methylaniline (1.5 g, 6.46 mmol) in acetonitrile (10 mL) was added t-BuNO2 (1.05 g, 9.7 mmol) and CuCl2 (1.10 g, 7.8 mmol) under nitrogen. The mixture was warmed to 60° C. and stirred for 15 h. The mixture was cooled to room temperature and concentrated under vacuum. The residue was purified by silica gel chromatography, eluting with DCM in PE (0% to 10% gradient) to give the title compound (1.36 g, 88%). ¹H NMR (400 MHz, DMSO-d6) δ 7.78 (s, 1H), 7.55 (s, 1H), 2.44 (s, 3H).

Step 2: 3-(2,5-dichloro-3-methylphenyl)oxetan-3-ol

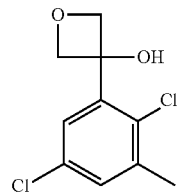

The title compound (159 mg, 48%) was prepared in a manner similar to that in Example A54 step 1 from 1-bromo-2,5-dichloro-3-methylbenzene and 3-oxetanone. LC-MS (M+H)⁺=233.0.

Step 3: 3-(2-chloro-3-methyl-5-(4,4,5,5-tetramethyl-1,3,2-dioxaborolan-2-yl)phenyl)oxetan-3-ol

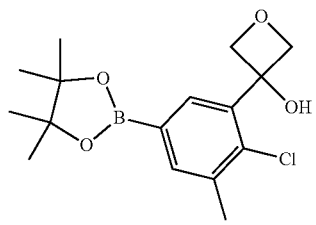 [SMILES: Cc1cc(B2OC(C)(C)C(C)(C)O2)cc(C2(O)COC2)c1Cl]

The title compound (125 mg, 63%) was prepared in a manner similar to that in Example A54 step 2 from 3-(2,5-dichloro-3-methylphenyl)oxetan-3-ol and BPD. LC-MS (M+H)⁺=325.0.

Step 4: 3-(5-(5-amino-6-((1-(1-methylpiperidin-4-yl)-1H-pyrazol-4-yl)oxy)pyrazin-2-yl)-2-chloro-3-methylphenyl)oxetan-3-ol

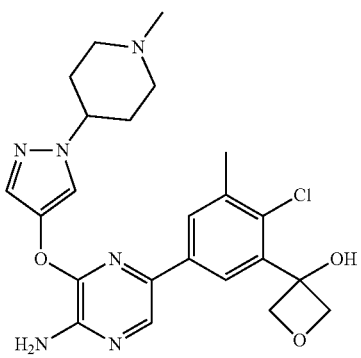 [SMILES: Cc1cc(-c2cnc(N)c(Oc3cnn(C4CCN(C)CC4)c3)n2)cc(C2(O)COC2)c1Cl]

Example A84 (19 mg, 18%) was prepared in a manner similar to that in Example A1 step 7 from 5-bromo-3-((1-(1-methylpiperidin-4-yl)-1H-pyrazol-4-yl)oxy)pyrazin-2-amine and 3-(2-chloro-3-methyl-5-(4,4,5,5-tetramethyl-1,3,2-dioxaborolan-2-yl)phenyl)oxetan-3-ol, 1H NMR (400 MHz, DMSO-$d_6$) δ 8.34 (s, 1H), 8.10 (s, 1H), 7.81 (s, 1H), 7.65-7.57 (m, 2H), 6.81 (s, 2H), 6.23 (s, 1H), 5.08 (d, J=7.1 Hz, 2H), 4.71 (d, J=7.0 Hz, 2H), 4.184.05 (m, 1H), 2.91-2.83 (m, 2H), 2.37 (s, 3H), 2.21 (s, 3H), 2.10-1.95 (m, 6H). LC-MS (M+H)⁺=471.3.

Example A85

(S)-3-(3-(5-amino-6-((1-(1-methylpiperidin-4-yl)-1H-pyrazol-4-yl)oxy)pyrazin-2-yl)-5-(2-(hydroxymethyl)pyrrolidin-1-yl)phenyl)oxetan-3-ol

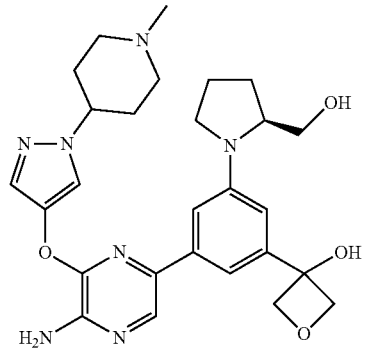 [SMILES: CN1CCC(n2cc(Oc3nc(-c4cc(N5CCC[C@H]5CO)cc(C5(O)COC5)c4)cnc3N)cn2)CC1]

Step 1: (S)-(1-(3,5-dibromophenyl)pyrrolidin-2-yl)methanol

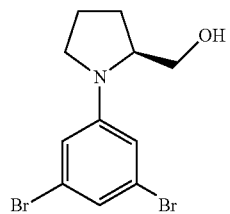 [SMILES: OC[C@@H]1CCCN1c1cc(Br)cc(Br)c1]

The title compound (1.87 g, 20%) was prepared in a manner similar to that in A59 step 1 from 1,3-dibromo-5-iodobenzene and (S)-prolinol. LC-MS (M+H)⁺=335.8.

Step 2: (S)-2-(((tert-butyldimethylsilyl)oxy)methyl)-1-(3,5-dibromophenyl)pyrrolidine

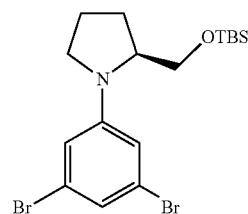 [SMILES: CC(C)(C)[Si](C)(C)OC[C@@H]1CCCN1c1cc(Br)cc(Br)c1]

To a stirred solution of (S)-(1-(3,5-dibromophenyl)pyrrolidin-2-yl)methanol (1.0 g, 3.0 mmol) in DMF (10 mL) was added TBSCl (0.90 g, 6.0 mmol) and imidazole (0.41 g, 6.0 mmol) at room temperature. The mixture was stirred for 16 h at 50° C. under nitrogen. The mixture was cooled to room temperature and poured into water (30 mL), then successively extracted with DCM (30 mL×2). The combined organic layer was washed with brine, dried over Na₂SO₄, filtered and concentrated under reduced pressure. The residue was purified by flash chromatography, eluting with EtOAc in PE (0% to 20% gradient) to give the title compound (787 mg, 59%). LC-MS (M+H)⁺=449.1.

Step 3: (S)-3-(3-bromo-5-(2-(((tert-butyldimethylsilyl)oxy)methyl)pyrrolidin-1-yl)phenyl)oxetan-3-ol

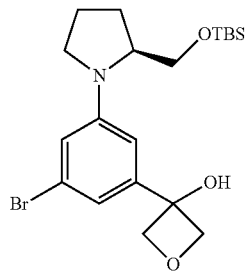 [SMILES: CC(C)(C)[Si](C)(C)OC[C@@H]1CCCN1c1cc(Br)cc(C2(O)COC2)c1]

The title compound (292 mg, 42%) was prepared in a manner similar to that in Example A54 step 1 from (S)-2-(((tert-butyldimethylsilyl)oxy)methyl)-1-(3,5-dibromophenyl)pyrrolidine and 3-oxetanone. LC-MS (M+H)$^+$=443.9.

Step 4: (S)-3-(3-(2-(((tert-butyldimethylsilyl)oxy)methyl)pyrrolidin-1-yl)-5-(4,4,5,5-tetramethyl-1,3,2-dioxaborolan-2-yl)phenyl)oxetan-3-ol

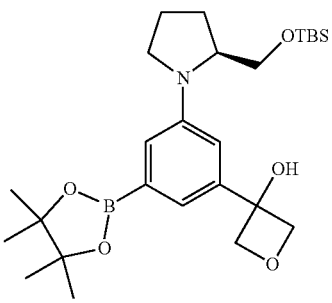 [SMILES: CC1(C)OB(c2cc(N3CCC[C@H]3CO[Si](C)(C)C(C)(C)C)cc(C3(O)COC3)c2)OC1(C)C]

The title compound (127 mg, 58%) was prepared in a manner similar to that in Example A1 step 6 from 3(S)-3-(3-bromo-5-(2-(((tert-butyldimethylsilyl)oxy)methyl)pyrrolidin-1-yl)phenyl)oxetan-3-ol and BPD. LC-MS (M+H)$^+$=490.2.

Step 5: (S)-3-(3-(5-amino-6-((1-(1-methylpiperidin-4-yl)-1H-pyrazol-4-yl)oxy)pyrazin-2-yl)-5-(2-(((tert-butyldimethylsilyl)oxy)methyl)pvrrolidin-1-yl)phenyl)oxetan-3-ol

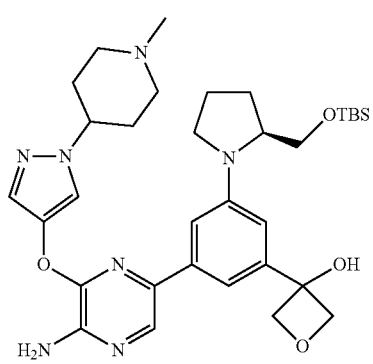 [SMILES: CN1CCC(n2cc(Oc3nc(-c4cc(N5CCC[C@H]5CO[Si](C)(C)C(C)(C)C)cc(C5(O)COC5)c4)cnc3N)cn2)CC1]

The title compound (117 mg, 900%) was prepared in a manner similar to that in Example A1 step 7 from 5-bromo-3-((1-(1-methylpiperidin-4-yl)-1H-pyrazol-4-yl)oxy)pyrazin-2-amine and (S)-3-(3-(2-(((tert-butyldimethylsilyl)oxy)methyl)pyrrolidin-1-yl)-5-(4,4,5,5-tetramethyl-1,3,2-dioxaborolan-2-yl)phenyl)oxetan-3-ol. LC-MS (M+H)$^+$=636.4.

Step 6: 3(S)-3-(3-(5-amino-6-((1-(1-methylpiperidin-4-yl)-1H-pyrazol-4-yl)oxy)pyrazin-2-yl)-5-(2-(hvdroxymethyl)pyrrolidin-1-yl)phenyl)oxetan-3-ol To a stirred solution of (S)-3-(3-(5-amino-6-((1-(1-methylpiperidin-4-yl)-1H-pyrazol-4-yl)oxy)pyrazin-2-yl)-5-(2-(((tert-butyldimethylsilyl)oxy)methyl)pvrrolidin-1-yl)phenyl)oxetan-3-ol (100 mg, 0.157 mmol) in THF (5 mL) was added TBAF (82.3 mg, 0.314 mmol) at room temperature and kept for 1 h under nitrogen. The mixture was concentrated under reduced pressure. The residue was purified by prep-HPLC to give Example A85 (31 mg, 37%). $^1$H NMR (400 MHz, DMSO-d$_6$) δ 8.22 (s, 1H), 8.13 (s, 1H), 7.60 (s, 1H), 7.33 (s, 1H), 6.99 (s, 1H), 6.76 (s, 1H), 6.66 (s, 2H), 6.23 (s, 1H), 4.81 (s, 1H), 4.76-4.72 (m, 4H), 4.17-4.04 (m, 1H), 3.81-3.72 (m, 1H), 3.58-3.50 (m, 1H), 3.48-3.39 (m, 1H), 3.26-3.16 (m, 1H), 3.16-3.06 (m, 1H), 2.90-2.81 (m, 2H), 2.21 (s, 3H), 2.10-1.83 (m, 10H). LC-MS (M+H)$^+$=522.4.

Example A86

3-(5-(5-amino-6-((1-(1-methylpiperidin-4-yl)-1H-pyrazol-4-yl)oxy)pyrazin-2-yl)-2-(3,6-dihydro-2H-pyran-4-yl)-3-methylphenyl)oxetan-3-ol

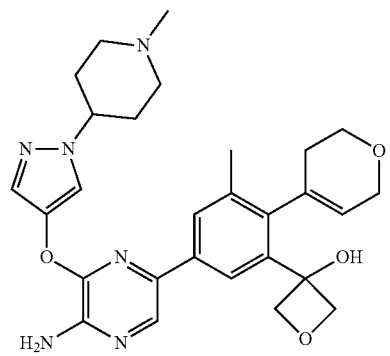 [SMILES: Cc1cc(-c2cnc(N)c(Oc3cnn(C4CCN(C)CC4)c3)n2)cc(C2(O)COC2)c1C1=CCOCC1]

Step 1: 4-(2-bromo-4-chloro-6-methylphenyl)-3,6-dihydro-2H-pyran

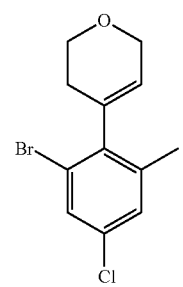

The title compound (446 mg, 56%) was prepared in a manner similar to that in Example A75 step 1 from 1-bromo-5-chloro-2-iodo-3-methylbenzene and 2-(3,6-dihydro-2H-pyran-4-yl)-4,4,5,5-tetramethyl-1,3,2-dioxaborolane. $^1$H NMR (400 MHz, DMSO-d$_6$) δ 7.59 (s, 1H), 7.38 (s, 1H), 5.60 (s, 1H), 4.27-4.11 (m, 2H), 3.91-3.75 (m, 2H), 2.62-2.58 (m, 2H), 2.27 (s, 3H).

Step 2: 3-(5-chloro-2-(3,6-dihydro-2H-pyran-4-yl)-3-methylphenyl)oxetan-3-ol

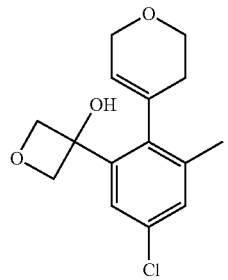

The title compound (286 mg, 66%) was prepared in a manner similar to that in Example A54 step 1 from 4-(2-bromo-4-chloro-6-methylphenyl)-3,6-dihydro-2H-pyran and 3-oxetanone. $^1$H NMR (300 MHz, DMSO-d$_6$) δ 7.27 (s, 1H), 7.02 (s, 1H), 6.20 (s, 1H), 5.59 (s, 1H), 5.05 (d, J=7.1 Hz, 1H), 4.91 (d, J=6.9 Hz, 1H), 4.55-4.45 (m, 2H), 4.23-4.03 (m, 2H), 3.87-3.66 (m, 2H), 2.55-2.46 (m, 2H), 2.21 (s, 3H).

Step 3: 3-(2-(3,6-dihydro-2H-pyran-4-yl)-3-methyl-5-(4,4,5,5-tetramethyl-1,3,2-dioxaborolan-2-yl)phenyl)oxetan-3-ol

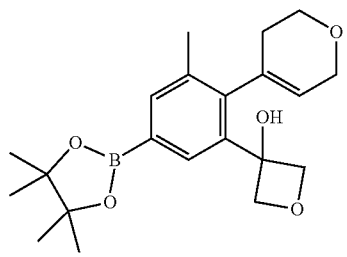 [SMILES: Cc1cc(B2OC(C)(C)C(C)(C)O2)cc(C2(O)COC2)c1C1=CCOCC1]

The title compound (369 mg, 97%) was prepared in a manner similar to that in Example A54 step 2 from 3-(5-chloro-2-(3,6-dihydro-2H-pyran-4-yl)-3-methylphenyl)oxetan-3-ol and BPD. LC-MS (M−H$_2$O+H)=355.2.

Step 4: 3-(5-(5-amino-6-((1-(1-methylpiperidin-4-yl)-1H-pyrazol-4-yl)oxy)pyrazin-2-yl)-2-(3,6-dihydro-2H-pyran-4-yl)-3-methylphenyl)oxetan-3-ol Example A86 (20 mg, 49%) was prepared in a manner similar to that in Example A1 step 7 from 5-bromo-3-((1-(1-methylpiperidin-4-yl)-1H-pyrazol-4-yl)oxy)pyrazin-2-amine and 3-(2-(3,6-dihydro-2H-pyran-4-yl)-3-methyl-5-(4,4,5,5-tetramethyl-1,3,2-dioxaborolan-2-yl)phenyl)oxetan-3-ol, 1H NMR (30) MHz, DMSO-4) δ 8.26 (s, 1H), 8.10 (s, 1H), 7.64 (s, 1H), 7.60 (s, 1H), 7.43 (s, 1H), 6.72 (s, 2H), 6.10 (s, 1H), 5.59 (s, 1H), 5.11 (d, J=6.9 Hz, 1H), 4.% (d, J=6.7 Hz, 1H), 4.54 (t, J=6.3 Hz, 2H), 4.214.05 (s, 3H), 3.87-3.70 (m, 2H), 2.92-2.82 (m, 2H), 2.43-2.29 (m, 2H), 2.27-2.17 (m, 6H), 2.11-1.92((m, 6H). LC-MS (M+H)$^+$=519.4.

Example A87

3-(5-(5-amino-6-((1-(1-methylpiperidin-4-yl)-1H-pyrazol-4-yl)oxy)pyrazin-2-yl)-2-(1,3-dioxolan-2-yl)-3-methylphenyl)oxetan-3-ol

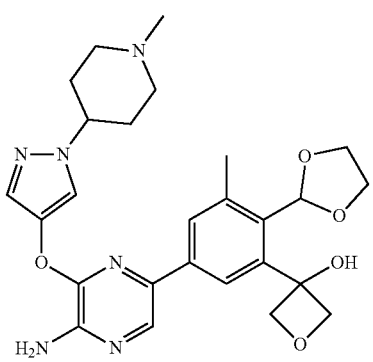 [SMILES: Cc1cc(-c2cnc(N)c(Oc3cnn(C4CCN(C)CC4)c3)n2)cc(C2(O)COC2)c1C1OCCO1]

Step 1: 2-bromo-4-chloro-6-methylbenzaldehyde

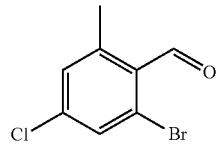

To a solution of 4-chloro-2-methylbenzaldehyde (14 g, 86 mmol) in DCE (280 mL) was added NBS(N-bromosuccinimide) (19.3 g, 103 mmol), TFA (56.0 mL, 757 mmol), 4-chloro-2-(trifluoromethyl)aniline (3.54 g, 17.2 mmol), and Pd(OAc)$_2$ (2.03 g, 8.60 mmol) at room temperature. The mixture was stirred for overnight at 60° C. under nitrogen. The mixture was cooled to room temperature and concentrated under reduced pressure. The residue was purified by flash chromatography, eluting with DCM in PE (0% to 25% gradient) to give the title compound (17 g, 85%), 1H NMR (300 MHz, DMSO-d6) δ 10.30 (s, 1H), 7.79 (s, 1H), 7.51 (s, 1H), 2.50 (s, 3H).

Step 2: 2-(2-bromo-4-chloro-6-methylphenyl)-1,3-dioxolane

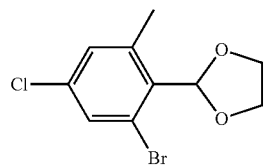

To a stirred solution of 2-bromo-4-chloro-6-methylbenzaldehyde (14.0 g, 59.9 mmol) in toluene (500 mL) was added TsOH (2.17 g, 12.0 mmol) and ethylene glycol (5.87 g, 89.9 mmol) at room temperature. The mixture was stirred for overnight at 120° C. under a Dean-Stark receiver. The mixture was cooled to room temperature and concentrated under reduced pressure. The residue was purified by flash chromatography eluting with DCM in PE (0% to 40% gradient) to give the title compound (13.0 g, 79%). $^1$H NMR (400 MHz, DMSO-d6) δ 7.62 (s, 1H), 7.37 (s, 1H), 6.13 (s, 1H), 4.22-3.93 (m, 4H).

Step 3: 3-(5-chloro-2-(1,3-dioxolan-2-yl)-3-methylphenyl)oxetan-3-ol

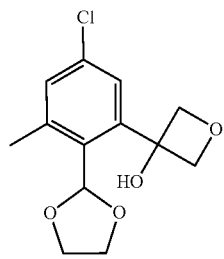 [SMILES: Cc1cc(Cl)cc(C2(O)COC2)c1C1OCCO1]

The title compound (9.45 g, 77%) was prepared in a manner similar to that in Example A54 step 1 from 2-(2-bromo-4-chloro-6-methylphenyl)-1,3-dioxolane and 3-oxetanone. $^1$H NMR (300 MHz, DMSO-d6) δ 7.28 (s, 1H), 7.18 (s, 1H), 6.49 (s, 1H), 5.52 (s, 1H), 4.99 (d, J=6.9 Hz, 2H), 4.68 (d, J=6.7 Hz, 2H), 4.15-4.08 (m, 2H), 3.95-3.88 (m, 2H), 2.38 (s, 3H). LC-MS (M+H)$^+$=271.0.

Step 4: 3-(2-(1,3-dioxolan-2-yl)-3-methyl-5-(4,4,5,5-tetramethyl-1,3,2-dioxaborolan-2-yl)phenyl)oxetan-3-ol

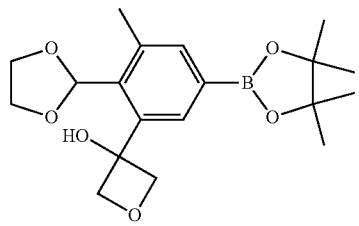 [SMILES: Cc1cc(B2OC(C)(C)C(C)(C)O2)cc(C2(O)COC2)c1C1OCCO1]

The title compound (240 mg, 95%) was prepared in a manner similar to that in Example A54 step 2 from 3-(5-chloro-2-(1,3-dioxolan-2-yl)-3-methylphenyl)oxetan-3-ol and BPD. LC-MS (M+H)$^+$=363.2.

Step 5: 3-(5-(5-amino-6-((1-(1-methylpiperidin-4-yl)-1H-pyrazol-4-yl)oxy)pyrazin-2-yl)-2-(1,3-dioxolan-2-yl)-3-methylphenyl)oxetan-3-ol Example A87 (33 mg, 30%) was prepared in a manner similar to that in Example A1 step 7 from 5-bromo-3-((1-(1-methylpiperidin-4-yl)-1H-pyrazol-4-yl)oxy)pyrazin-2-amine and 3-(2-(1,3-dioxolan-2-yl)-3-methyl-5-(4,4,5,5-tetramethyl-1,3,2-dioxaborolan-2-yl)phenyl)oxetan-3-ol. $^1$H NMR (300 MHz, DMSO-d$_6$) δ 8.34 (s, 1H), 8.11 (s, 1H), 7.65 (s, 1H), 7.60 (s, 1H), 7.54 (s, 1H), 6.80 (s, 2H), 6.38 (s, 1H), 5.56 (s, 1H), 5.07-4.98 (m, 2H), 4.75-4.67 (m, 2H), 4.20-4.07 (m, 3H), 3.94-3.88 (m, 2H), 2.92-2.82 (m, 2H), 2.41 (s, 3H), 2.21 (s, 3H), 2.13-1.92 (m, 6H). LC-MS (M+H)=509.3.

Example A88

3-(3-(5-amino-6-((1-(1-methylpiperidin-4-yl)-1H-pyrazol-4-yl)oxy)pyrazin-2-yl)-5-methylphenyl)tetrahydro-2H-pyran-3-ol

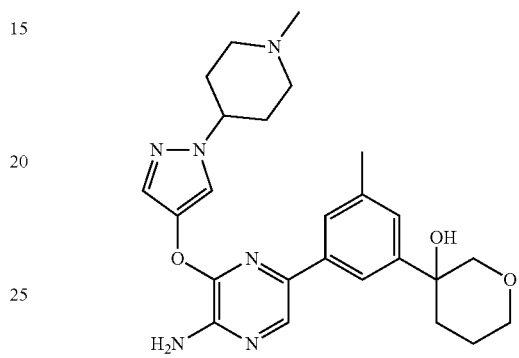

Step 1:
3-(3-bromo-5-methylphenyl)tetrahydro-2H-pyran-3-ol

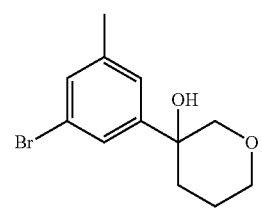

The title compound (1.8 g, 83%) was prepared in a manner similar to that in Example A54 step 1 from 1,3-dibromo-5-methylbenzene and dihydro-2H-pyran-3(4H)-one. LCMS (M−OH)$^+$=253, 255.

Step 2: 3-(3-methyl-5-(4,4,5,5-tetramethyl-1,3,2-dioxaborolan-2-yl)phenyl)tetrahydro-2H-pyran-3-ol

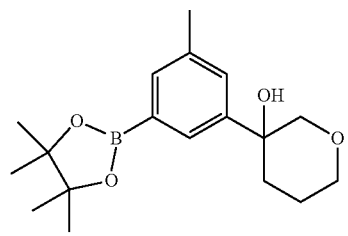 [SMILES: Cc1cc(B2OC(C)(C)C(C)(C)O2)cc(C2(O)CCCOC2)c1]

The title compound (2.0 g, 94%) was prepared in a manner similar to that in Example A1 step 6 from 3-(3-bromo-5-methylphenyl)tetrahydro-2H-pyran-3-ol and BPD. LCMS (M−OH)$^+$=301.

Step 3: 3-(3-(5-amino-6-((1-(1-methylpiperidin-4-yl)-1H-pyrazol-4-yl)oxy)pyrazin-2-yl)-5-methylphenyl)tetrahydro-2H-pyran-3-ol Example A88 (165 mg, 84%) was prepared in a manner similar to that in Example A1 step 7 from 5-bromo-3-((1-(1-methylpiperidin-4-yl)-1H-pyrazol-4-yl)oxy)pyrazin-2-amine and 3-(3-methyl-5-(4,4,5,5-tetramethyl-1,3,2-dioxaborolan-2-yl)phenyl)tetrahydro-2H-pyran-3-ol. $^1$H NMR (400 MHz, DMSO-d6) δ 8.24 (s, 1H), 8.21 (s, 1H), 7.86 (s, 1H), 7.58 (s, 1H), 7.54 (s, 1H), 7.27 (s, 1H), 6.71 (s, 2H), 5.26 (s, 1H), 4.20-4.05 (m, 1H), 3.88-3.74 (m, 1H), 3.64-3.58 (m, 1H), 3.56-3.38 (m, 2H), 2.94-2.81 (m, 2H), 2.34 (s, 3H), 2.22 (s, 3H), 2.11-1.96 (m, 8H), 1.77-1.67 (m, 1H), 1.48-1.37 (m, 1H). LCMS (M+H)$^+$=465.5.

Example A89

3-(3-(5-amino-6-((1-(1-methylpiperidin-4-yl)-1H-pyrazol-4-yl)oxy)pyrazin-2-yl)-5-((R)-3-methylmorpholino)phenyl)tetrahydro-2H-pyran-3-ol

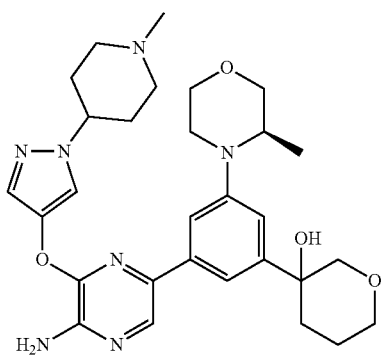 [SMILES: C[C@@H]1COCCN1c1cc(-c2cnc(N)c(Oc3cnn(C4CCN(C)CC4)c3)n2)cc(C2(O)CCCOC2)c1]

Step 1: 3-(3-bromo-5-((R)-3-methylmorpholino)phenyl)tetrahydro-2H-pyran-3-ol

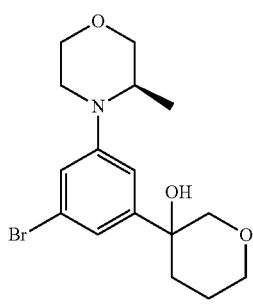

To a solution of (R)-4-(3,5-dibromophenyl)-3-methylmorpholine (900 mg, 2.70 mmol) in THF (20 mL) was added n-BuLi (2.5 M in hexane, 1.08 mL) dropwise at −78° C. under nitrogen, then stirred for 30 min at −78° C. dihydro-2H-pyran-3(4H)-one (405 mg, 4.05 mmol) was added dropwise at this temperature and stirred for another 2 h. The mixture was quenched by saturated NH$_4$Cl (30 mL), warmed to room temperature, and extracted with EtOAc (100 mL). The organic layer was successively washed with water (100 mL) and brine (100 mL), dried over Na$_2$SO$_4$, filtered and concentrated under vacuum. The residue was purified by prep-TLC with PE:EtOAc=1:3 to give the title compound (800 mg, 83%). LC-MS (M+H)$^+$=356.2, 358.3.

Step 2: 3-(3-((R)-3-methylmorpholino)-5-(4,4,5,5-tetramethyl-1,3,2-dioxaborolan-2-yl)phenyl)tetrahydro-2H-pyran-3-ol

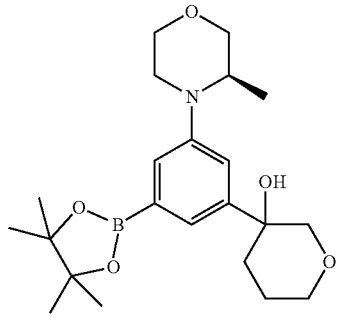 [SMILES: C[C@@H]1COCCN1c1cc(B2OC(C)(C)C(C)(C)O2)cc(C2(O)CCCOC2)c1]

To a solution of 3-(3-bromo-5-((R)-3-methylmorpholino)phenyl)tetrahydro-2H-pyran-3-ol (800 mg, 2.25 mmol) in dioxane (15 mL) was added BPD (744 mg, 2.93 mmol), KOAc (331 mg, 3.37 mmol) and Pd(dppf)C12-CH$_2$Cl$_2$ (184 mg, 0.22 mmol). The mixture was stirred for overnight at 100° C. under nitrogen. The mixture was cooled to room temperature, diluted with EtOAc (50 mL), successively washed with water (50 mL), brine (50 mL), dried over Na$_2$SO$_4$, filtered and concentrated under vacuum. The residue was purified by prep-TLC with EtOAc to give the title compound (684 mg, 75%). LC-MS (M+H)$^+$=404.2.

Step 3: 3-(3-(5-amino-6-((1-(1-methylpiperidin-4-yl)-1H-pyrazol-4-yl)oxy)pyrazin-2-yl)-5-((R)-3-methylmorpholino)phenyl)tetrahydro-2H-pyran-3-ol To a solution of 5-bromo-3-((1-(1-methylpiperidin-4-yl)-1H-pyrazol-4-yl)oxy)pyrazin-2-amine (300 mg, 0.85 mmol) in dioxane (10 mL) and water (1 mL) were added 3-(3-((R)-3-methylmorpholino)-5-(4,4,5,5-tetramethyl-1,3,2-dioxaborolan-2-yl)phenyl)tetrahydro-2H-pyran-3-ol (684 mg, 1.69 mmol), K$_2$CO$_3$ (351 mg, 2.55 mmol) and Pd(dppf)Cl$_2$·CH$_2$Cl$_2$ (69 mg, 0.08 mmol), then stirred for 5 h at 100° C. under nitrogen. The mixture was cooled to room temperature, diluted with EtOAc (50 mL), successively washed with water (50 mL), brine (50 mL), dried over Na$_2$SO$_4$, filtered and concentrated under vacuum. The residue was purified by prep-TLC with MeOH:DCM=1:7, followed by prep-HPLC to give the title compound (190 mg, 41%). $^1$H NMR (400 MHz, DMSO-d6) δ 8.24 (s, 1H), 8.17 (s, 1H), 7.57 (s, 1H), 7.47 (s, 1H), 7.21 (s, 1H), 7.02 (s, 1H), 6.69 (s, 2H), 5.17 (s, 1H), 4.15-4.05 (m, 1H), 3.94-3.85 (m, 2H), 3.83-3.70 (m, 2H), 3.68-3.40 (m, 5H), 3.26-3.13 (m, 1H), 3.13-2.91 (m, 1H), 2.93-2.79 (m, 2H), 2.22 (s, 3H), 2.14-1.90 (m, 8H), 1.79-1.65 (m, 1H), 1.51-1.38 (m, 11H), 1.03-0.94 (m, 3H). LC-MS (M+H)$^+$=550.2.

Example 90A/90B (S)-3-(3-(5-amino-6-((1-(1-methylpiperidin-4-yl)-1H-pyrazol-4-yl)oxy)pyrazin-2-yl)-5-((R)-3-methylmorpholino)phenyl)tetrahydro-2H-pyran-3-ol & (R)-3-(3-(5-amino-6-((1-(1-methylpiperidin-4-yl)-1H-pyrazol-4-yl)oxy)pyrazin-2-yl)-5-((R)-3-methylmorpholino)phenyl)tetrahydro-2H-pyran-3-ol

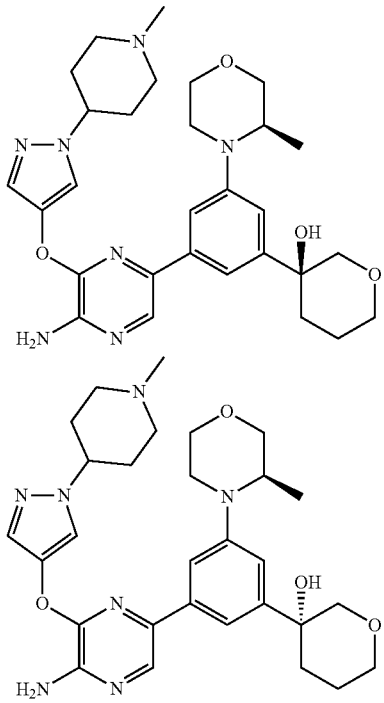

Examples A90A/A90B were prepared by chiral-HPLC separation of 3-(3-(5-amino-6-((1-(1-methylpiperidin-4-yl)-1H-pyrazol-4-yl)oxy)pyrazin-2-yl)-5-((R)-3-methylmorpholino)phenyl)tetrahydro-2H-pyran-3-ol (97 mg). Analytical chiral-HPLC condition: CHIRALPAK IH3, 4.6×50 mm, 3 μm; (MTBE, contains 0.1% Et₂NH):EtOH=9:1:1 mL.% min; 25° C.

Example A90A: (38 mg, 39%) ¹H NMR (400 MHz, DMSO46) δ 8.24 (s, 1H), 8.17 (s, 1H), 7.57 (s, 1H), 7.47 (s, 1H), 7.21 (s, 1H), 7.02 (s, 1H), 6.68 (s, 2H), 5.16 (s, 1H), 4.20-4.04 (m, 1H), 3.94-3.85 (m, 2H), 3.83-3.70 (m, 2H), 3.68-3.40 (m, 5H), 3.25-3.16 (m, 1H), 3.10-2.99 (m, 1H), 2.93-2.79 (m, 2H), 2.23 (s, 3H), 2.13-1.93 (m, 8H), 1.75-1.65 (m, 1H), 1.51-1.38 (m, 1H), 1.03-0.94 (m, 3H). LC-MS (M+H)⁺=550.2. Chiral HPLC: tR=1.28 min.

Example A90B: (45.2 mg, 46%)¹H NMR (400 MHz, DMSO-d6) δ 8.24 (s, 1H), 8.17 (s, 1H), 7.57 (s, 1H), 7.47 (s, 1H), 7.21 (s, 1H), 7.02 (s, 1H), 6.69 (s, 2H), 5.17 (s, 1H), 4.15-4.05 (m, 1H), 3.94-3.85 (m, 2H), 3.83-3.70 (m, 2H), 3.68-3.40 (m, 5H), 3.26-3.13 (m, 1H), 3.09-2.98 (m, 1H), 2.93-2.79 (m, 2H), 2.22 (s, 3H), 2.14-1.90 (m, 8H), 1.79-1.69 (m, 1H), 1.48-1.38 (m, 11H), 1.03-0.94 (m, 3H). LC-MS (M+H)⁺=550.4. Chiral HPLC: tR=1.73 nin.

Example A91

1-(3-(5-amino-6-((1-(1-methylpiperidin-4-yl)-1H-pyraol-4-yl)oxy)pyrazin-2-yl)-5-(3-hydroxyoxetan-3-yl)phenyl)pyrrolidin-2-one

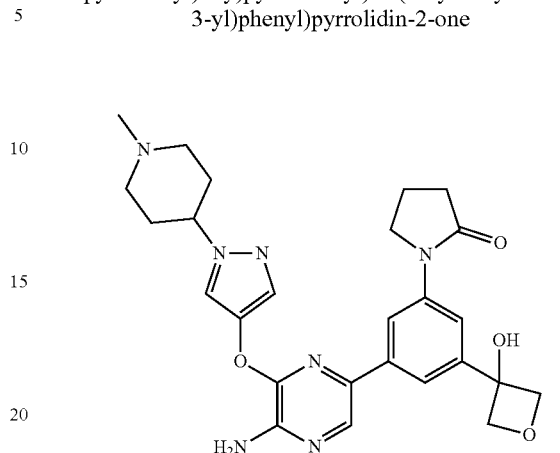

Step 1: 1-(3,5-dibromophenyl)-2,5-dimethyl-1H-pyrrole

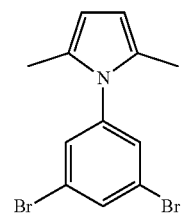

To a solution of 3,5-dibromoaniline (5.0 g, 20 mmol), hexane-2,5-dione (2.5 g, 22 mmol) and TsOH (68.8 mg, 0.4 mmol) in toluene (30 mL) was heated to reflux under Dean-Stark receiver for 3 h. The mixture was cooled to room temperature, diluted with EtOAc (50 mL), successively washed with 1 N HCl (30 mL) and brine (30 mL), dried over Na₂SO₄, filtered and concentrated under vacuum. The residue was purified by silica gel column chromatography to give the title compound (6.0 g, 90%). LC-MS (M+H)⁺= 327.9, 329.9, 331.9.

Step 2: 3-(3-bromo-5-(2,5-dimethyl-1H-pyrrol-1-yl)phenyl)oxetan-3-ol

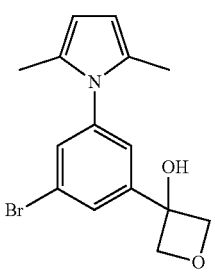 [SMILES: Cc1ccc(C)n1-c1cc(Br)cc(C2(O)COC2)c1]

To a solution of 1-(3,5-dibromophenyl)-2,5-dimethyl-1H-pyrrole (6.0 g, 18.2 mmol) in THF (20 ml), was added n-BuLi (2.5 M in hexane, 8 mL, 20.2 mmol) at −78° C. under nitrogen. After 0.5 h, oxetan-3-one (1.9 g, 27.3 mmol) was added dropwise. The mixture was stirred at −78° C. for 1 h. Saturated NH₄Cl (10 mL) was added and the mixture was warmed to room temperature then extracted with EtOAc (40 mL×2). The combined organic layer was washed with brine (50 mL×3), dried over Na₂SO₄, filtered and concentrated under vacuum. The residue was purified by silica gel column chromatography to give the title compound (4.0 g, 68%). LC-MS (M+H)⁺=322.0.

Step 3: 3-(3-amino-5-bromophenyl)oxetan-3-ol

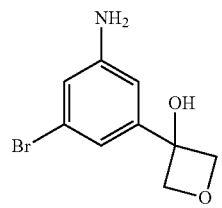

To a solution of 3-(3-bromo-5-(2,5-dimethyl-1H-pyrrol-1-yl)phenyl)oxetan-3-ol (1.0 g, 3.1 mmol) in EtOH (14 mL) and water (7 mL) was added hydroxylamine hydrochloride (6.5 g, 93 mmol) and KOH (3.4 g, 62 mmol). The mixture was heated to 1(0° C. for overnight then cooled to room temperature. Water (20 mL) was added and the mixture was extracted with EtOAc (40 mL×2). The combined organic layer was washed with brine (50 mL×3), dried over Na₂SO₄, filtered and concentrated under vacuum. The residue was purified by prep-TLC to give the title compound (700 mg, 92%). LC-MS (M+H)⁺=244.0.

Step 4: ethyl 4-((3-bromo-5-(3-hydroxyoxetan-3-yl)phenyl)amino)butanoate

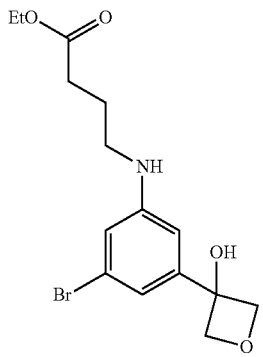 [SMILES: CCOC(=O)CCCNc1cc(Br)cc(C2(O)COC2)c1]

To a solution of 3-(3-anuno-5-bromophenyl)oxetan-3-ol (400 mg, 1.64 mmol) in DMF (5 mL) was added K2CO₃ (452 mg, 3.28 mmol) and ethyl 4-bromobutanoate (703 mg, 3.6 mmol). The mixture was stirred at 100° C. for overnight. The mixture was cooled to room temperature then water (20 mL) was added. The mixture was extracted with EtOAc (40 mL×2). The combined organic layer was washed with brine (20 mL×3), dried over Na₂SO₄, filter and concentrated under vacuum. The residue was purified by prep-TLC to give the title compound (120 mg, 20%). LC-MS (M+H)⁺=358.1.

Step 5: 1-(3-bromo-5-(3-hydroxyoxetan-3-yl)phenyl)pyrrolidin-2-one

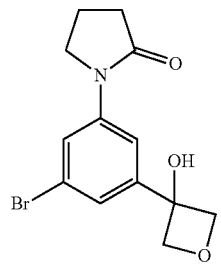

To a solution of ethyl 4-((3-bromo-5-(3-hydroxyoxetan-3-yl)phenyl)amino)butanoate (120 mg, 0.33 mmol) in 1,4-dioxane (5 mL) was added TFA (190 mg, 1.67 mmol) and the mixture was stirred at 100° C. for overnight. The mixture was cooled to room temperature and concentrated. The crude was purified by prep-TLC to give the title compound (80 mg, 76%). LC-MS (M+H)⁺=312.1

Step 6: 1-(3-(3-hydroxyoxetan-3-yl)-5-(4,4,5,5-tetramethyl-1,3,2-dioxaborolan-2-yl)phenyl)pyrrolidin-2-one

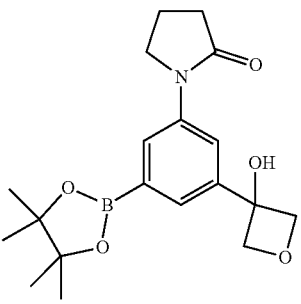 [SMILES: CC1(C)OB(c2cc(N3CCCC3=O)cc(C3(O)COC3)c2)OC1(C)C]

A mixture 1-(3-bromo-5-(3-hydroxyoxetan-3-yl)phenyl)pyrrolidin-2-one (80 mg, 0.25 mmol), BPD (127 mg, 0.5 mmol), Pd(dppf)Cl₂ (20 mg, 0.025 mmol) and AcOK (73.5 mg, 0.75 mmol) in dioxane (10 mL) was heated to reflux under nitrogen for overnight. The mixture was cooled to room temperature, EtOAc (60 mL) was added and the organic layer was washed with brine (20 mL×2), and the combined aqueous layer was back extracted with EtOAc (30 mL). The combined organic layer was dried over Na₂SO₄, filtered and concentrated under reduced pressure. The residue was purified by prep-TLC to give the title compound (50 mg, 54%). LC-MS (M+H)⁺=360.2.

Step 7: 1-(3-(5-amino-6-((1-(1-methylpiperidin-4-yl)-1H-pyrazol-4-yl)oxy)pyrazin-2-yl)-5-(3-hydroxyoxetan-3-yl)phenyl)pyrrolidin-2-one A mixture of 5-bromo-3-((1-(1-methylpiperidin-4-yl)-1H-pyrazol-4-yl)oxy)pyrazin-2-amine (50 mg, 0.14 mmol), 1-(3-(3-hvdroxyoxetan-3-yl)-5-(4,4,5,5-tetramethyl-1,3,2-dioxaborolan-2-yl)phenyl)pyrrolidin-2-one (50 mg, 0.14 mmol), Pd(dppf)C12 (12 mg, 0.014 mmol) and K₂CO₃ (38 mg, 0.28 mmol) in dioxane (10 mL) and H₂O (3 mL) was heated to reflux under nitrogen for overnight. The mixture was cooled to room temperature, then added EtOAc (30 mL). The mixture was washed with brine (10 mL×2), and the aqueous layer was back extracted with EtOAc (20 mL). The combined organic layer was dried over $Na_2SO_4$, filtered and concentrated under reduced pressure. The residue was purified by prep-HPLC to give Example A91 (13 mg, 18%). $^1$H NMR (400 MHz, DMSO-d6) δ 8.28 (s, 1H), 8.23 (s, 1H), 8.10 (s, 1H), 7.8 (s, 1H), 7.59 (s, 1H), 6.81 (s, 2H), 6.45 (s, 1H), 4.79-4.73 (m, 4H), 4.15-4.18 (m, 1H), 3.91-3.90 (m, 2H), 2.88-2.86 (m, 2H), 2.48-2.50 (m, 2H), 2.21 (s, 3H), 2.11-1.98 (m, 8H). LC-MS (M+H)=506.2.

Example A92

3-(5-(5-amino-6-((1-(1-methylpiperidin-4-yl)-1H-pyrazol-4-yl)oxy)pyrazin-2-yl)-3-methyl-2-(7-oxa-2-azaspiro[3.5]nonan-2-yl)phenyl)tetrahydrofuran-3-ol

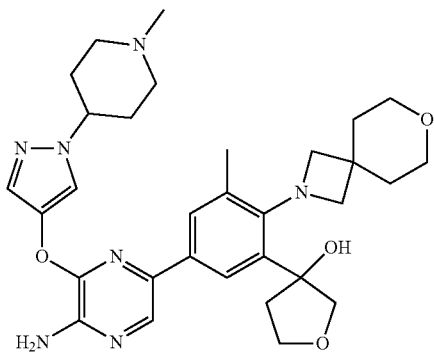 [SMILES: Cc1cc(-c2cnc(N)c(Oc3cnn(C4CCN(C)CC4)c3)n2)cc(C2(O)CCOC2)c1N1CC2(CCOCC2)C1]

Step 1: 2-(2-bromo-4-chloro-6-methylphenyl)-7-oxa-2-azaspiro[3.5]nonane

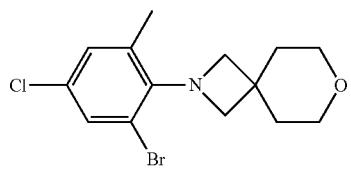 [SMILES: Cc1cc(Cl)cc(Br)c1N1CC2(CCOCC2)C1]

The title compound (1.13 g, 63%) was prepared in a manner similar to that in Example A83 step 2 from 1-bromo-5-chloro-2-iodo-3-methylbenzene and 7-oxa-2-azaspiro[3.5]nonane. LC-MS (M+H)$^+$=330.0.

Step 2: 3-(5-chloro-3-methyl-2-(7-oxa-2-azaspiro[3.5]nonan-2-yl)phenyl)tetrahydrofuran-3-ol

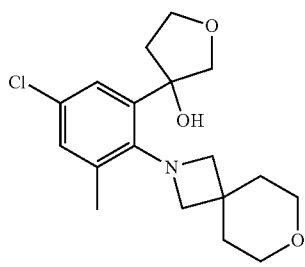 [SMILES: Cc1cc(Cl)cc(C2(O)CCOC2)c1N1CC2(CCOCC2)C1]

The title compound (100 mg, 31%) was prepared in a manner similar to that in Example A54 step 1 from 2-(2-bromo-4-chloro-6-methylphenyl)-7-oxa-2-azaspiro[3.5]nonane and dihydrofuran-3-one. LC-MS (M+H)$^+$=338.1.

Step 3: 3-(5-(5-amino-6-((1-(1-methylpiperidin-4-yl)-1H-pyrazol-4-yl)oxy)pyrazin-2-yl)-3-methyl-2-(7-oxa-2-azaspiro[3.5]nonan-2-yl)phenyl)tetrahydrofuran-3-ol Example A92 (32 mg, 25%) was prepared in a manner similar to that in Example A83 step 4 from 3-(5-chloro-3-methyl-2-(7-oxa-2-azaspiro[3.5]nonan-2-yl)phenyl)tetrahydrofuran-3-ol and 3-((1-(1-methylpiperidin-4-yl)-1H-pyrazol-4-yl)oxy)-5-(4,4,5,5-tetramethyl-1,3,2-dioxaborolan-2-yl)pyrazin-2-amine. $^1$H NMR (400 MHz, DMSO-d$_6$) δ 8.22 (s, 1H), 8.12 (s, 1H), 7.77 (d, J=2.2 Hz, 1H), 7.59 (d, J=2.9 Hz, 2H), 6.72 (s, 2H), 6.29 (s, 1H), 4.15-4.07 (m, 1H), 4.05-3.98 (m, 1H), 4.02-3.93 (m, 1H), 3.97-3.88 (m, 1H), 3.86-3.77 (m, 3H), 3.69 (d, J=6.5 Hz, 2H), 3.59-3.52 (m, 4H), 2.90-2.83 (m, 2H), 2.56 (s, 3H), 2.43-2.31 (m, 1H), 2.21 (s, 3H), 2.19-2.10 (m, 1H), 2.10-1.94 (m, 6H), 1.85-1.78 (m, 4H). LC-MS (M+H)$^+$=576.5.

Example A93

3-(5-(5-amino-6-((1-(1-methylpiperidin-4-yl)-1H-pyrazol-4-yl)oxy)pyrazin-2-yl)-2-fluoro-3-methylphenyl)tetrahydrofuran-3-ol

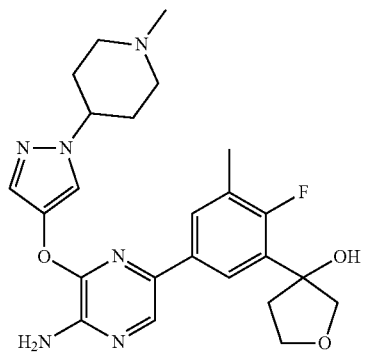 [SMILES: Cc1cc(-c2cnc(N)c(Oc3cnn(C4CCN(C)CC4)c3)n2)cc(C2(O)CCOC2)c1F]

Step 1: 3-(5-chloro-2-fluoro-3-methylphenyl)-tetrahydrofuran-3-ol

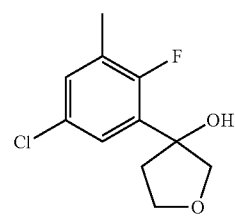

The title compound (400 mg, 95%) was prepared in a manner similar to that in Example A54 step 1 from 1-bromo-5-chloro-2-fluoro-3-methylbenzene and dihydrofuran-3-one. LC-MS (M-OH)=213.0.

Step 2: 3-(5-(5-amino-6-((1-(1-methylpiperidin-4-yl)-1H-pyrazol-4-yl)oxy)pyrazin-2-yl)-2-fluoro-3-methylphenyl)tetrahydrofuran-3-ol Example A93 (36 mg, 14%) was prepared in a manner similar to that in Example A83 step 4 from 3-(5-chloro-2- fluoro-3-methylphenyl)-tetrahydrofuran-3-ol and 3-((1-(1-methylpiperidin-4-yl)-1H-pyrazol-4-yl)oxy)-5-(4,4,5,5-tetramethyl-1,3,2-dioxaborolan-2-yl)pyrazin-2-amine. ¹H NMR (400 MHz, DMSO-d₆) δ 8.23 (s, 1H), 8.14 (s, 1H), 7.94-7.87 (m, 1H), 7.73-7.67 (m, 1H), 7.61 (s, 1H), 6.73 (s, 2H), 5.56 (s, 1H), 4.18-4.06 (m, 1H), 4.06-3.82 (m, 4H), 2.90-2.83 (m, 2H), 2.42-2.30 (m, 1H), 2.29-2.24 (m, 3H), 2.23-2.16 (m, 4H), 2.11-1.93 (m, 6H). LC-MS (M+H)⁺= 469.1.

Example A94

3-(3-(5-amino-6-((1-(1-methylpiperidin-4-yl)-1H-pyrazol-4-yl)oxy)pyrazin-2-yl)-5-((R)-3-methylmorpholino)phenyl)-2-methyltetrahydrofuran-3-ol

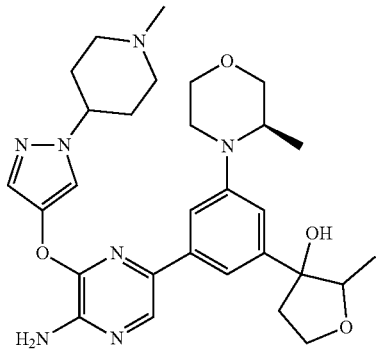 [SMILES: CC1OCCC1(O)c1cc(-c2cnc(N)c(Oc3cnn(C4CCN(C)CC4)c3)n2)cc(N2CCOC[C@H]2C)c1]

Step 1: 3-(3-bromo-5-((R)-3-methylmorpholino)phenyl)-2-methyltetrahydrofuran-3-ol

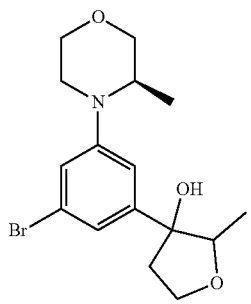 [SMILES: CC1OCCC1(O)c1cc(Br)cc(N2CCOC[C@H]2C)c1]

To a solution of (R)-4-(3,5-dibromophenyl)-3-methylmorpholine (570 mg, 1.7 mmol) in THF (5 mL) was added n-BuLi (2.5 M in hexane, 0.68 mL, 1.7 mmol) dropwise at −78° C. under nitrogen, then stirred for 30 min at −78° C. 2-methyldihydrofuran-3(2H)-one (257 mg, 2.6 mmol) was added dropwise at this temperature and stirred for another 2 h. The mixture was quenched by saturated NH₄Cl (15 mL) and warmed to room temperature. The mixture was extracted with EtOAc (25 mL), successively washed with H₂O (15 mL) and brine (15 mL), dried over Na₂SO₄, filtered and concentrated under vacuum. The residue was purified by prep-TLC with PE:EtOAc=1:3 to give the title compound (500 mg, 82%). LC-MS (M+H)⁺=356.1, 358.1.

Step 2: 2-methyl-3-(3-((R)-3-methylmorpholino)-5-(4,4,5,5-tetramethyl-1,3,2-dioxaborolan-2-yl)phenyl)tetrahydrofuran-3-ol

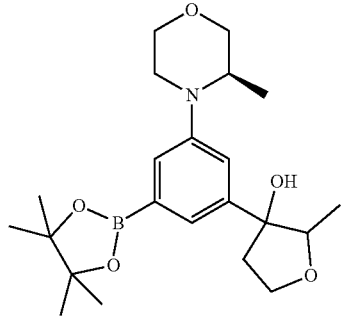

To a solution of 3-(3-bromo-5-((R)-3-methylmorpholino)phenyl)-2-methyltetrahydrofuran-3-ol (500 mg, 1.4 mmol) in dioxane (10 mL) was added BPD (715 mg, 2.8 mmol), KOAc (275 mg, 2.8 mmol) and Pd(dppf)Cl₂·CH₂Cl₂ (115 mg, 0.1 mmol), then the mixture stirred for overnight at 100° C. under nitrogen. The mixture was cooled to room temperature, diluted with EtOAc (30 mL), washed with H₂O (15 mL), brine (15 mL), dried over Na₂SO₄, filtered and concentrated under vacuum. The residue was purified by prep-TLC with EtOAc to give the title compound (550 mg, 97%). LC-MS (M+H)=404.4.

Step 3: 3-(3-(5-amino-6-((1-(1-methylpiperidin-4-yl)-1H-pyrazol-4-yl)oxy)pyrazin-2-yl)-5-((R)-3-methylmorpholino)phenyl)-2-methyltetrahydrofuran-3-ol To a solution of 5-bromo-3-((1-(1-methylpiperidin-4-yl)-1H-pyrazol-4-yl)oxy)pyrazin-2-amine (480 mg, 1.4 mmol) in dioxane (10 mL) and water (1 mL) were added 2-methyl-3-((R)-3-methylmorpholino)-5-(4,4,5,5-tetramethyl-1,3,2-dioxaborolan-2-yl)phenyl)tetrahydrofuran-3-ol (550 mg, 1.4 mmol), K₂CO₃ (565 mg, 4.1 mmol) and Pd(dppf)Cl₂·CH₂Cl₂ (112 mg, 0.14 mmol), then the mixture stirred for 5 h at 100° C. under nitrogen. The mixture was cooled to room temperature and diluted with EtOAc (40 mL). The organic layer was washed with H₂O (20 mL), brine (20 mL), dried over Na₂SO₄, filtered and concentrated under vacuum. The residue was purified by prep-TLC with MeOH:DCM=1:7, then by prep-HPLC to give Example A94 (66 mg, 9%). ¹HNMR (400 MHz. DMSO-d₆) δ 8.25 (s, 1H), 8.13 (s, 1H), 7.57 (s, 1H), 7.41-7.36 (m, 1H), 7.19 (s, 1H), 7.04-6.98 (m, 1H), 6.69 (s, 2H), 5.10 (s, 1H), 4.14-4.04 (m, 1H), 4.04-3.96 (m, 1H), 3.95-3.85 (m, 3H), 3.84-3.78 (m, 1H), 3.77-3.68 (m, 2H), 3.62-3.53 (m, 1H), 3.23-3.17 (m, 1H), 3.09-3.00 (m, 1H), 2.90-2.82 (m, 2H), 2.21 (s, 3H), 2.16-1.94 (m, 7H), 0.98 (d, J=6.5 Hz, 3H), 0.94 (d, J=6.1 Hz, 3H). LC-MS (M+H)⁺=550.3.

Example A95A/A95B (2R,3S)-3-(3-(5-amino-6-((1-(1-methylpiperidin-4-yl)-1H-pyrazol-4-yl)oxy)pyrazin-2-yl)-5-((R)-3-methylmorpholino)phenyl)-2-methyltetrahydrofuran-3-ol & (2S,3R)-3-(3-(5-amino-6-((1-(1-methylpiperidin-4-yl)-1H-pyrazol-4-yl)oxy)pyrazin-2-yl)-5-((R)-3-methylmorpholino)phenyl)-2-methyltetrahydrofuran-3-ol

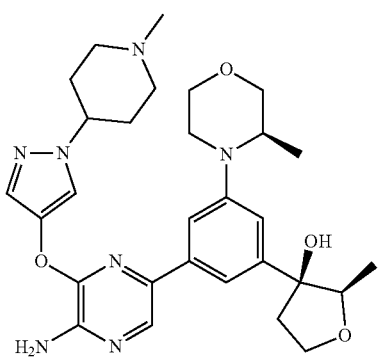

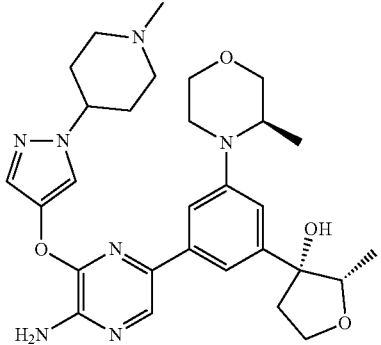

Examples A95A/A95B were prepared by chiral-HPLC separation of 3-(3-(5-amino-6-((1-(1-methylpiperidin-4-yl)-1H-pyrazol-4-yl)oxy)pyrazin-2-yl)-5-((R)-3-methylmorpholino)phenyl)-2-methyltetrahydrofuran-3-ol (66 mg). Analytical chiral-HPLC condition: CHIRALPAK IA3, 4.6× 50 mm, 3 μm; (hexane, contains 0.5% 2 M $NH_3$ in MeOH):EtOH=7:3; 1 mL/min; 25° C.

ExampleA95A: (23 mg, 35%) 1HNMR (400 MHz, DMSO-d6) δ 8.25 (s, 1H), 8.13 (s, 1H), 7.57 (s, 1H), 7.41-7.36 (m, 1H), 7.19 (s, 1H), 7.04-6.98 (m, 1H), 6.69 (s, 2H), 5.10 (s, 1H), 4.14-4.04 (m, 1H), 4.04-3.96 (m, 1H), 3.95-3.85 (m, 3H), 3.84-3.78 (m, 1H), 3.77-3.68 (m, 2H), 3.62-3.53 (m, 1H), 3.23-3.17 (m, 1H), 3.09-3.00 (m, 1H), 2.90-2.82 (m, 2H), 2.23 (s, 3H), 2.16-1.94 (m, 7H), 0.98 (d, J=6.5 Hz, 3H), 0.94 (d, J=6.1 Hz, 3H). LC-MS (M+H)$^+$=550.3. Chiral HPLC: tR=2.19 min.

Example A95B: (23 mg, 35%)$^1$HNMR (400 MHz, DMSO-d6) δ 8.25 (s, 1H), 8.12 (s, 1H), 7.57 (s, 1H), 7.41-7.36 (m, 1H), 7.19 (s, 1H), 7.04-6.98 (m, 1H), 6.69 (s, 2H), 5.10 (s, 1H), 4.14-4.04 (m, 1H), 4.04-3.96 (m, 1H), 3.95-3.85 (m, 3H), 3.84-3.78 (m, 1H), 3.77-3.68 (m, 2H), 3.62-3.53 (m, 1H), 3.25-3.17 (m, 1H), 3.09-3.00 (m, 1H), 2.93-2.82 (m, 2H), 2.22 (s, 3H), 2.16-1.94 (m, 7H), 0.98 (d, J=6.5 Hz, 3H), 0.94 (d, J=6.1 Hz, 3H). LC-MS (M+H)$^-$=550.3. Chiral HPLC: tR=2.99 min.

Example A96

3-(5-(5-amino-64(l1-(1-methylpiperidin-4-yl)-1H-pyrazol-4-yl)oxy)pyrazin-2-yl)-3-methyl-2-morpholinophenyl)tetrahydrofuran-3-ol

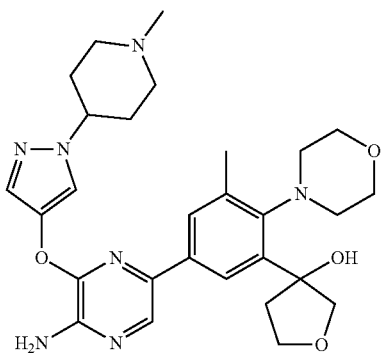 [SMILES: Cc1cc(-c2cnc(N)c(Oc3cnn(C4CCN(C)CC4)c3)n2)cc(C2(O)CCOC2)c1N1CCOCC1]

Step 1:
4-(2-bromo-4-chloro-6-methylphenyl)morpholine

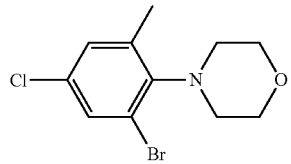

A mixture of 1-bromo-5-chloro-2-iodo-3-methylbenzene (3.0 mg, 8.3 mmol), $Pd_2(dba)_3$ (241 mg, 0.25 mmol), XantPhos (304 mg, 0.50 mmol), t-BuONa (927 mg, 9.2 mmol) and morpholine (764 mg, 8.3 mmol) in toluene (30 mL) was stirred for 16 h at 110° C. under nitrogen. The mixture was filtered, and the filter cake was washed with DCM (15 mL×3). The filtrate was concentrated under reduced pressure. The residue was purified by reverse phase flash chromatography to give the title compound (820 mg, 31%). LC-MS (M+H)$^+$=291.9.

Step 2: 4-(4-chloro-2-(2,5-dihydrofuran-3-yl)-6-methylphenyl)morpholine

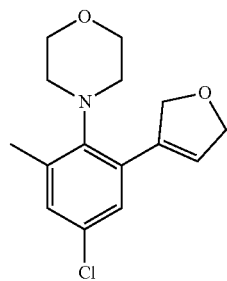 [SMILES: Cc1cc(Cl)cc(C2=CCOC2)c1N1CCOCC1]

The title compound (473 mg, 47%) was prepared in a manner similar to that in Example A75 step 1 from 4-(2-bromo-4-chloro-6-methylphenyl)morpholine and 2-(2,5-dihydrofuran-3-yl)-4,4,5,5-tetramethyl-1,3,2-dioxaborolane. LC-MS (M+H)⁺=280.1.

Step 3: 3-(5-chloro-3-methyl-2-morpholinophenyl)tetrahydrofuran-3-ol

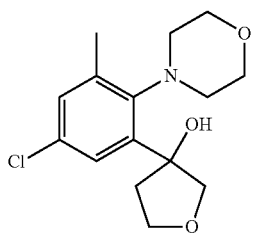 [SMILES: Cc1cc(Cl)cc(C2(O)CCOC2)c1N1CCOCC1]

At 0° C., to a solution of tris(2,2,6,6-tetramethyl-3,5-heptanedionato) manganese(III) (108 mg, 0.17 mmol) and 4-(4-chloro-2-(2,5-dihydrofuran-3-yl)-6-methylphenyl)morpholine (500 mg, 1.70 mmol) in DCM (5 mL) was added i-PrOH (3.5 mL), phenylsilane (387 mg, 3.40 mmol). The mixture was stirred for 3 h at 0° C. under oxygen. The mixture was concentrated under vacuum. The residue was purified by reverse phase chromatography to give the title compound (170 mg, 34%). LC-MS (M+H)⁺=298.2.

Step 4: 3-(5-(5-amino-6-((1-(1-methylpiperidin-4-yl)-1H-pyrazol-4-yl)oxy)pyrazin-2-yl)-3-methyl-2-morpholinophenyl)tetrahydrofuran-3-ol Example A96 (90 mg, 35%) was prepared in a manner similar to that in Example A83 step 4 from 3-(5-chloro-3-methyl-2-morpholinophenyl)tetrahydrofuran-3-ol and 3-((1-(1-methylpiperidin-4-yl)-1H-pyrazol-4-yl)oxy)-5-(4,4,5,5-tetramethyl-1,3,2-dioxaborolan-2-yl)pyrazin-2-amine. ¹H NMR (400 MHz, DMSO-d₆) δ 8.23 (s, 1H), 8.11 (s, 1H), 7.76 (s, 1H), 7.61-7.55 (m, 2H), 6.72 (s, 2H), 5.95 (s, 1H), 4.36-4.29 (m, 1H), 4.174.07 (m, 1H), 3.99-3.89 (m, 2H), 3.87-3.81 (m, 1H), 3.81-3.74 (m, 2H), 3.70-3.59 (m, 2H), 3.56-3.46 (m, 1H), 3.39-3.34 (m, 1H), 2.91-2.82 (m, 3H), 2.74-2.67 (m, 1H), 2.43 (s, 3H), 2.42-2.31 (m, 1H), 2.30-2.23 (m, 1H), 2.21 (s, 3H), 2.07-1.96 (m, 6H). LC-MS (M+H)⁺=536.4.

Example A97A/A97B (S)-3-(5-(5-amino-6-((1-(1-methylpiperidin-4-yl)-1H-pyrazol-4-yl)oxy)pyrazin-2-yl)-3-methyl-2-morpholinophenyl)tetrahydrofuran-3-ol & (R)-3-(5-(5-amino-6-((1-(1-methylpiperidin-4-yl)-1H-pyrazol-4-yl)oxy)pyrazin-2-yl)-3-methyl-2-morpholinophenyl)tetrahydrofuran-3-ol

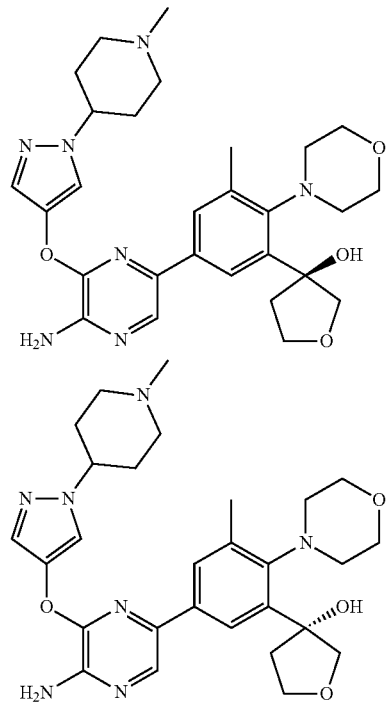

Examples A97A/A97B were prepared by chiral-HPLC separation of 3-(5-(5-amino-6-((1-(1-methylpiperidin-4-yl)-1H-pyrazol-4-yl)oxy)pyrazin-2-yl)-3-methyl-2-morpholinophenyl)tetrahydrofuran-3-ol (58 mg). Analytical chiral-HPLC condition: CHIRALPAK1A3, 4.6×50 mm, 3 μm; (hexane:DCM=3:1, contains 0.1% Et₂NH):EtOH=7:3; 1 mL/min; 25° C.

Example A97A: (26 mg, 45%)¹H NMR (400 MHz, DMSO-d₆) δ 8.23 (s, 1H), 8.10 (s, 1H), 7.76 (s, 1H), 7.61-7.55 (m, 2H), 6.72 (s, 2H), 5.95 (s, 1H), 4.35-4.29 (m, 1H), 4.15-4.07 (m, 1H), 3.99-3.87 (m, 2H), 3.87-3.81 (m, 1H), 3.81-3.73 (m, 2H), 3.70-3.59 (m, 2H), 3.56-3.45 (m, 1H), 3.42-3.30 (m, 1H), 2.91-2.82 (m, 3H), 2.74-2.66 (m, 1H), 2.43 (s, 3H), 2.42-2.31 (m, 1H), 2.31-2.22 (m, 1H), 2.20 (s, 3H), 2.09-1.93 (m, 6H). LC-MS (M+H)⁺=536.4. Chiral HPLC: tR=1.54 min.

Example A97B1: (26 mg, 45%) ¹H NMR (400 MHz, DMSO-d₆) δ 8.23 (s, 1H), 8.10 (s, 1H), 7.76 (s, 1H), 7.61-7.55 (m, 2H), 6.72 (s, 2H), 5.95 (s, 1H), 4.36-4.29 (m, 1H), 4.17-4.07 (m, 1H), 3.99-3.87 (m, 2H), 3.87-3.81 (m, 1H), 3.81-3.73 (m, 2H), 3.70-3.59 (m, 2H), 3.56-3.45 (m, 1H), 3.42-3.32 (M, 1H), 2.91-2.83 (m, 3H), 2.74-2.67 (m, 1H), 2.43 (s, 3H), 2.39-2.31 (M, 1H), 2.31-2.23 (m, 1H), 2.21 (s, 3H), 2.09-1.94 (m, 6H). LC-MS (M+H)⁺=536.4. Chiral HPLC: tR=2.14 min.

Example A98

3-(3-(5-amino-6-((1-(1-methylpiperidin-4-yl)-1H-pyrazol-4-yl)oxy)pyrazin-2-yl)-5-(1,4-oxazepan-4-yl)phenyl)tetrahydrofuran-3-ol

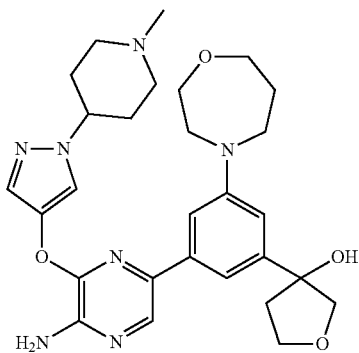 [SMILES: CN1CCC(n2cc(Oc3nc(-c4cc(N5CCCOCC5)cc(C5(O)CCOC5)c4)cnc3N)cn2)CC1]

Step 1: 4-(3,5-dibromophenyl)-1,4-oxazepane

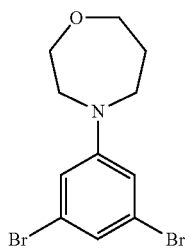 [SMILES: Brc1cc(Br)cc(N2CCCOCC2)c1]

The title compound (365 mg, 42%) was prepared in a manner similar to that in Example A59 step 1 from 1,3-dibromo-5-iodobenzene and 1,4-oxazepane. LC-MS (M+H)$^+$=335.9.

Step 2: 3-(3-bromo-5-(1,4-oxazepan-4-yl)phenyl)tetrahydrofuran-3-ol

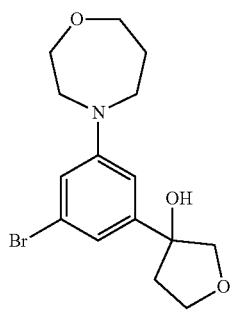 [SMILES: OC1(c2cc(Br)cc(N3CCCOCC3)c2)CCOC1]

The title compound (83 mg, 50%) was prepared in a manner similar to that Example A54 step 1 from 4-(3,5-dibromophenyl)-1,4-oxazepane and dihydrofuran-3-one. LC-MS (M+H)$^+$=342.0.

Step 3: 3-(3-(5-amino-6-((1-(1-methylpiperidin-4-yl)-1H-pyrazol-4-yl)oxy)pyrazin-2-yl)-5-(1,4-oxazepan-4-yl)phenyl)tetrahydrofuran-3-ol Example A98 (27 mg, 22%) was prepared in a manner similar to that in Example A83 step 4 from 3-(3-bromo-5-(1,4-oxazepan-4-yl)phenyl)tetrahydrofuran-3-ol and 3-((1-(1-methylpiperidin-4-yl)-1H-pyrazol-4-yl)oxy)-5-(4,4,5,5-tetramethyl-1,3,2-dioxaborolan-2-yl)pyrazin-2-amine. $^1$H NMR (400 MHz, DMSO-d6) δ 8.22 (s, 1H), 8.07 (s, 1H), 7.59 (s, 1H), 7.19 (s, 1H), 7.05 (s, 1H), 6.81 (s, 1H), 6.65 (s, 2H), 5.29 (s, 1H), 4.14-3.95 (m, 3H), 3.82-3.73 (m, 2H), 3.76-3.69 (m, 2H), 3.65-3.53 (m, 6H), 2.89-2.82 (m, 2H), 2.35-2.23 (m, 1H), 2.20 (s, 3H), 2.14-1.86 (m, 10H). LC-MS (M+H)=536.4.

Example B1

5-(2-(diethylamino)-6-((methylamino)methyl)pyridin-4-yl)-3-((1-(1-methylpiperidin-4-yl)-1H-pyrazol-4-yl)oxy)pyrazin-2-amine

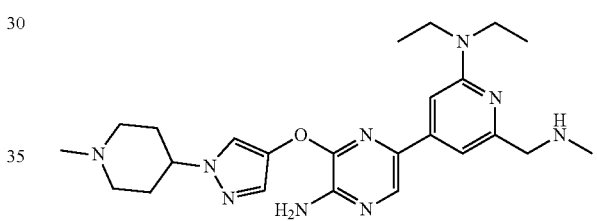

Step 1: methyl 4-chloro-6-(diethylamino) picolinate

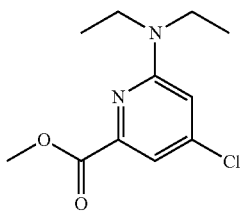 [SMILES: CCN(CC)c1cc(Cl)cc(C(=O)OC)n1]

To a solution of methyl 4,6-dichloropyridine-2-carboxylate (4.0 g, 18.4 mmol) in toluene (25 mL) was added diethylamine (11.4 g, 148 mmol), Pd(OAc)$_2$ (218 mg, 0.922 mmol), XPhos (1481 mg, 2.95 mmol) and K$_2$CO$_3$ (4025 mg, 27.7 mmol) at room temperature. The mixture was stirred for overnight at 100° C. under nitrogen. The mixture was cooled to room temperature and concentrated under reduced pressure. The residue was purified by silica gel chromatography (EtOAc:hexanes=1:4) to give the title compound (2.1 g, 47%). LC-MS (M+H)$^+$=243.2.

Step 2:
(4-chloro-6-(diethylamino)pyridin-2-yl)methanol

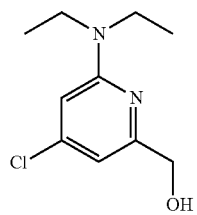

To a solution of methyl 4-chloro-6-(diethylamino) picolinate (2.20 g, 8.36 mmol) in THF (20 mL) was added BH₃ in THF (1 M, 28.7 mL, 28.7 mmol) dropwise over 5 min at 0° C. The mixture was heated to 70° C. under nitrogen. After 2 h, the mixture was cooled 0° C., was then MeOH (5 mL) was carefully added. The mixture was concentrated under reduced pressure and the residue was purified by silica gel chromatography (EtOAc:hexanes=1:4) to give the title compound (1.47 g, 82%). LC-MS (M+H)$^+$=215.2.

Step 3: 4-chloro-6-(diethylamino) picolinaldehyde

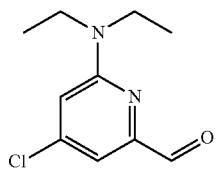

To a solution of (4-chloro-6-(diethylamino)pyridin-2-yl) methanol (1.50 g, 6.24 mmol) in DCM (20 mL) was added Dess-Martin periodinane (7.96 g, 17.8 mmol) at room temperature. After 2 h, saturated NaHCO₃(10 mL) and saturated Na₂S₂O₃ (10 mL) was added at 0° C. The mixture was extracted with EtOAc (30 mL×3). The combined organic layer was washed with brine (30 mL), dried over Na₂SO₄ and filtered. The filtrate was concentrated under reduced pressure to give the title compound (1.24 g, 93%). LC-MS (M+H)$^+$=213.2.

Step 4: 4-chloro-N,N-diethyl-6-((methylamino) methyl)pyridin-2-amine

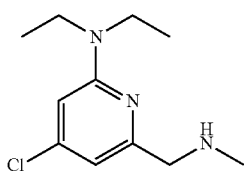

To a stirred solution of 4-chloro-6-(diethylamino) picolinaldehyde (1.16 g, 5.437 mmol) and methylamine in THF (2 M, 3.9 mL, 7.8 mmol) in MeOH (15 mL) was added HOAc (1 mL) at room temperature. After 15 min, the solution was cooled to 0° C., and NaBH₃CN (0.58 g, 8.8 mmol) was added in portions. The mixture was warmed to room temperature and stirred for 1 h, then cooled back to 0° C. Water (50 mL) was added and the mixture was extracted with EtOAc (30 mL×3). The combined organic layers were washed with brine (10 mL×3), dried over anhydrous Na₂SO₄ and filtered. The filtrate was concentrated under reduced pressure to give the title compound (1.1 g, 88%). LC-MS (M+H)$^+$=228.3.

Step 5: tert-butyl ((4-chloro-6-(diethylamino)pyridin-2-yl)methyl)methyl)carbamate

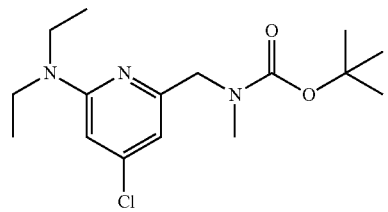 [SMILES: CCN(CC)c1cc(Cl)cc(CN(C)C(=O)OC(C)(C)C)n1]

The title compound (400 mg, 88%) was prepared in a manner similar to that in Example A20 step 1 from 4-chloro-N,N-diethyl-6-((methylamino)methyl)pyridin-2-amine. LC-MS (M+H)$^+$=328.3.

Step 6: tert-butyl ((6-(diethylamino)-4-(4,4,5,5-tetramethyl-1,3,2-dioxaborolan-2-yl)pyridin-2-yl) methy)(methyl)carbamate

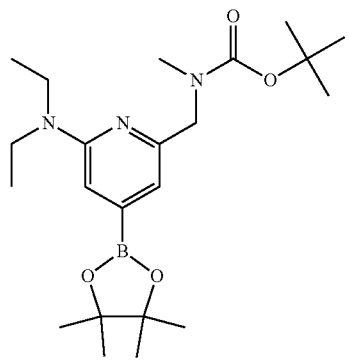 [SMILES: CCN(CC)c1cc(B2OC(C)(C)C(C)(C)O2)cc(CN(C)C(=O)OC(C)(C)C)n1]

The title compound (249 mg, 52%) was prepared in a manner similar to that in Example A1 step 6 from tert-butyl ((4-chloro-6-(diethylamino)pyridin-2-yl)methyl)(methyl) carbamate and BPD. LC-MS (M+H)$^+$=420.4.

Step 7: tert-butyl ((4-(5-amino-6-((1-(1-methylpiperidin-4-yl)-1H-pyrazol-4-yl)oxy)pyrazin-2-yl)-6-(diethylamino)pyridin-2-yl)methyl)(methyl)carbamate

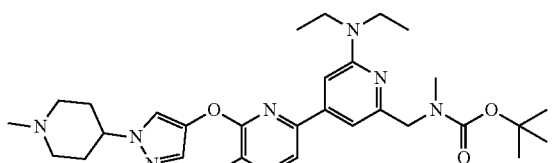

The title compound (35 mg, 34%) was prepared in a manner similar to that in Example A1 step 7 from 5-bromo-3-((1-(1-methylpiperidin-4-yl)-1H-pyrazol-4-yl)oxy)pyrazin-2-amine and tert-butyl ((6-(diethylamino)-4-(4,4,5,5-tetramethyl-1,3,2-dioxaborolan-2-yl)pyridin-2-yl)methyl)(methyl)carbamate. LC-MS (M+H)$^+$=566.5.

Step 2: 5-(2-(diethylamino)-6-((methylamino)methyl)pyridin-4-yl)-3-((1-(1-methylpiperidin-4-yl)-1H-pyrazol-4-yl)oxy)pyrazin-2-amine Example B1 (3 mg, 11%) was prepared in a manner similar to that in Example A20 step 4 from tert-butyl ((4-(5-amino-6-((1-(1-methylpiperidin-4-yl)-1H-pyrazol-4-yl)oxy)pyrazin-2-yl)-6-(diethylamino)pyridin-2-yl)methyl)(methyl)carbamate. $^1$H NMR (400 MHz, DMSO-d6) δ 8.30 (s, 1H), 8.06 (s, 1H), 7.61 (s, 1H), 6.98 (s, 1H), 6.90 (s, 2H), 6.80 (s, 1H), 4.14-4.03 (m, 1H), 3.57 (s, 2H), 3.55-3.45 (m, 4H), 2.90-2.82 (m, 2H), 2.33 (s, 3H), 2.20 (s, 3H), 2.09-1.90 (m, 6H), 1.10 (t, J=6.9 Hz, 6H). LC-MS (M+H)$^+$=466.3.

Example B2

(R)-5-(2-((methylamino)methyl)-6-(2-methylpyrrolidin-1-yl)pyridin-4-yl)-3-((1-(1-methylpiperidin-4-yl)-1H-pyrazol-4-yl)oxy)pyrazin-2-amine

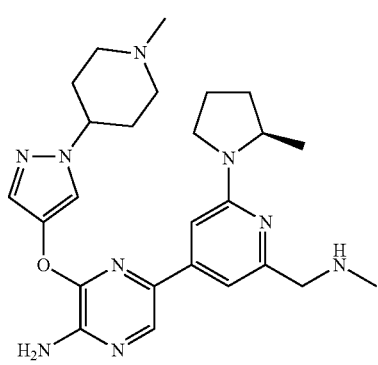 [SMILES: CNCc1cc(-c2cnc(N)c(Oc3cnn(C4CCN(C)CC4)c3)n2)cc(N2CCC[C@H]2C)n1]

Step 1: methyl (R)-4-chloro-6-(2-methylpyrrolidin-1-yl) picolinate

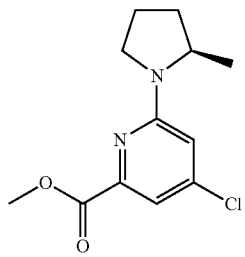

The title compound (1.8 g, 31%) was prepared in a manner similar to that in Example B1 step 1 from methyl 4,6-dichloropyridine-2-carboxylate and (2R)-2-methylpyrrolidine. LC-MS (M+H)=255.2.

Step 2: (R)-(4-chloro-6-(2-methylpyrrolidin-1-yl)pyridin-2-yl)methanol

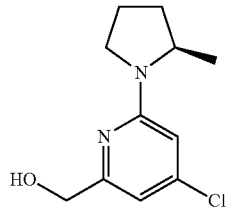

The title compound (1.1 g, 68%) was prepared in a manner similar to that in Example B1 step 2 from methyl (R)-4-chloro-6-(2-methylpyrrolidin-1-yl) picolinate. LC-MS (M+H)$^+$=227.2.

Step 3: (R)-4-chloro-6-(2-methylpyrrolidin-1-yl) picolinaldehyde

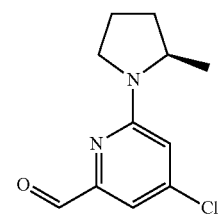

The title compound (864 mg, 85%) was prepared in a manner similar to that in Example B1 step 3 from (R)-(4-chloro-6-(2-methylpyrrolidin-1-yl)pyridin-2-yl)methanol. LC-MS (M+H)$^+$=225.2.

Step 4: (R)-1-(4-chloro-6-(2-methylpyrrolidin-1-yl)pyridin-2-yl)-N-methylmethanamine

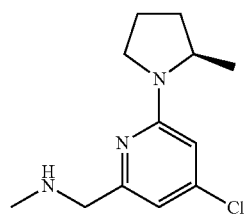

The title compound (864 mg, 85%) was prepared in a manner similar to that in Example B1 step 4 from (R)-4-chloro-6-(2-methylpyrrolidin-1-yl)picolinaldehyde. LC-MS (M+H)$^+$=240.2.

Step 5: tert-butyl (R)-((4-chloro-6-(2-methylpyrrolidin-1-yl)pyridin-2-yl)methyl)(methyl)carbamate

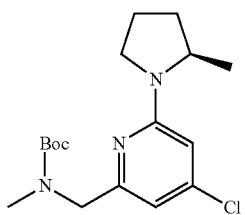

The title compound (1.05 g, 86%) was prepared in a manner similar to that in Example A20 step 1 from (R)-1-(4-chloro-6-(2-methylpyrrolidin-1-yl)pyridin-2-yl)-N-methylmethanamine. LC-MS (M+H)$^+$=340.2.

Step 6: tert-butyl (R)-methyl((6-(2-methylpyrrolidin-1-yl)-4-(4,4,5,5-tetramethyl-1,3,2-dioxaborolan-2-yl)pyridin-2-yl)methyl)carbamate

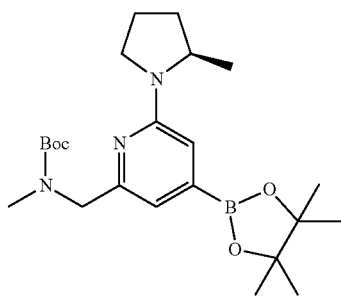

The title compound (473 mg, 87%) was prepared in a manner similar to that in Example A1 step 6 from tert-butyl (R)-((4-chloro-6-(2-methylpyrrolidin-1-yl)pyridin-2-yl)methyl)(methyl)carbamate and BPD. LC-MS (M-pin)$^+$=350.3.

Step 7: tert-butyl (R)-((4-(5-amino-6-((1-(1-methylpiperidin-4-yl)-1H-pyrazol-4-yl)oxy)pyrazin-2-yl)-6-(2-methylpyrrolidin-1-yl)pyridin-2-yl)methyl)(methyl)carbamate

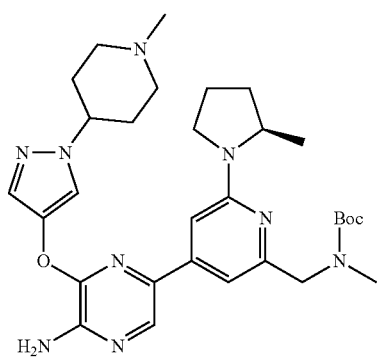 [SMILES: C[C@@H]1CCCN1c1cc(-c2cnc(N)c(Oc3cnn(C4CCN(C)CC4)c3)n2)cc(CN(C)C(=O)OC(C)(C)C)n1]

The title compound (94 mg, 46%) was prepared in a manner similar to that in Example A1 step 7 from tert-butyl (R)-methyl((6-(2-methylpyrrolidin-1-yl)-4-(4,4,5,5-tetramethyl-1,3,2-dioxaborolan-2-yl)pyridin-2-yl)methyl)carbamate and 5-bromo-3-((1-(1-methylpiperidin-4-yl)-1H-pyrazol-4-yl)oxy)pyrazin-2-amine. LC-MS (M+H)$^+$=578.4.

Step 8: (R)-5-(2-((methylamino)methyl)-6-(2-methylpyrrolidin-1-yl)pyridin-4-yl)-3-((1-(1-methylpiperidin-4-yl)-1H-pyrazol-4-yl)oxy)pyrazin-2-amine Example B2 (6 mg, 7%) was prepared in a manner similar to that in Example A20 step 4 from tert-butyl (R)-((4-(5-amino-6-((1-(1-methylpiperidin-4-yl)-1H-pyrazol-4-yl)oxy)pyrazin-2-yl)-6-(2-methylpyrrolidin-1-yl)pyridin-2-yl)methyl)(methyl)carbamate. $^1$H NMR (400 MHz, DMSO-d$_6$) δ 8.31 (s, 1H), 8.11 (s, 1H), 7.73 (s, 1H), 6.99 (s, 1H), 6.94 (s, 2H), 6.84 (s, 1H), 4.45-4.37 (m, 2H), 3.58 (s, 3H), 3.55-3.47 (m, 4H), 3.10 (t, J=6.4 Hz, 2H), 2.34 (s, 3H), 1.12 (t, J=7.0 Hz, 6H). LC-MS (M+H)$^+$=478.4.

Example B3

(R)-2-(4-(5-amino-6-((1-(1-methylpiperidin-4-yl)-1H-pyrazol-4-yl)oxy)pyrazin-2-yl)-6-(3-methylmorpholino)pyridin-2-yl)propan-2-ol

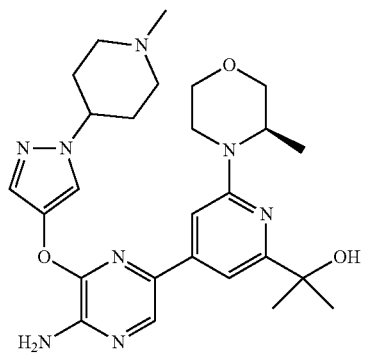 [SMILES: C[C@@H]1COCCN1c1cc(-c2cnc(N)c(Oc3cnn(C4CCN(C)CC4)c3)n2)cc(C(C)(C)O)n1]

Step 1: methyl 4-chloro-6-fluoropicolinate

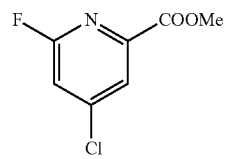

To a solution of methyl 4-chloropyridine-2-carboxylate (5.0 g, 27.7 mmol) in acetonitrile (120 mL) was added AgF (5.55 g, 41.5 mmol) at room temperature under nitrogen. After 24 h, mixture was concentrated under vacuum. The residue was purified by silica gel chromatography, eluting with EtOAc in PE (0% to 50% gradient) to give the title compound (4.17 g, 80%). LC-MS (M+H)$^+$=189.9.

Step 2: (R)-methyl 4-chloro-6-(3-methylmorpholino) picolinate

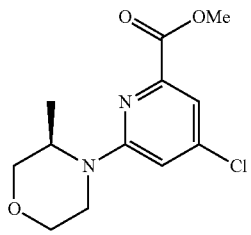 [SMILES: COC(=O)c1cc(Cl)cc(N2CCOC[C@H]2C)n1]

A mixture of methyl 4-chloro-6-fluoropyridine-2-carboxylate (1.36 g, 7.2 mmol), DIPEA (2.63 mL, 14.3 mmol) and (3R)-3-methylmorpholine (840 mg, 7.9 mmol) in DMSO (20 mL) was stirred at 50° C. under nitrogen. The mixture was cooled to room temperature, diluted with brine (30 mL), and successively extracted with EtOAc (30 mL×2). The combined organic layer was dried over $Na_2SO_4$, filtered and the filtrate was concentrated under reduced pressure. The residue was purified by reverse flash chromatography to give the title compound (864 mg, 44%). LC-MS $(M+H)^+$= 270.9.

Step 3: (R)-2-(4-chloro-6-(3-methylmorpholino) pyridin-2-yl)propan-2-ol

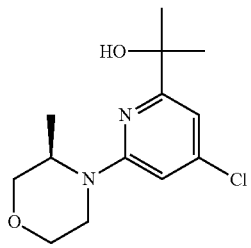 [SMILES: C[C@@H]1COCCN1c1cc(Cl)cc(C(C)(C)O)n1]

At 0° C., to a solution of (R)-methyl 4-chloro-6-(3-methylmorpholino) picolinate (700 mg, 2.48 mmol) in ethyl ether (10 mL) was added MeMgBr in ethyl ether (3.0 M, 2.2 mL, 6.6 mmol) dropwise under nitrogen. The mixture was stirred for 2 h at 0° C. The mixture was quenched with sat. $NH_4Cl$ (10 mL). The aqueous layer was extracted with EtOAc (20 mL×3). The combined organic layer was concentrated under reduced pressure. The residue was purified by silica gel chromatography, eluting with EtOAc in PE (0% to 50% gradient) to give the title compound (500 mg, 74%). LC-MS $(M+H)^+$=271.0.

Step 4: (R)-2-(6-(3-methylmorpholino)-4-(4,4,5,5-tetramethyl-1,3,2-dioxaborolan-2-yl)pyridin-2-yl)propan-2-ol

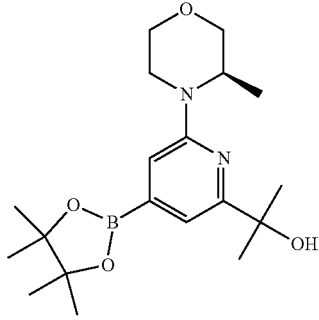 [SMILES: C[C@@H]1COCCN1c1cc(B2OC(C)(C)C(C)(C)O2)cc(C(C)(C)O)n1]

The title compound (276 mg, 69%) was prepared in a manner similar to that in Example A1 step 6 from (R)-2-(4-chloro-6-(3-methylmorpholino)pyridin-2-yl)propan-2-ol and BPD. LC-MS $(M+H)^+$=362.2.

Step 5: (R)-2-(4-(5-amino-6-((1-(1-methylpiperidin-4-yl)-1H-pyrazol-4-yl)oxy)pyrazin-2-yl)-6-(3-methylmorpholino)pyridin-2-yl)propan-2-ol Example B3 (32 mg, 22%) was prepared in a manner similar to that in Example A1 step 7 from 5-bromo-3-((1-(1-methylpiperidin-4-yl)-1H-pyrazol-4-yl)oxy)pyrazin-2-amine and (R)-2-(6-(3-methylmorpholino)-4-(4,4,5,5-tetramethyl-1,3,2-dioxaborolan-2-yl)pyridin-2-yl)propan-2-ol. $^1$H NMR (400 MHz, DMSO-$d_6$) δ 8.35 (s, 1H), 8.15 (s, 1H), 7.59 (s, 1H), 7.38 (s, 1H), 7.00-6.88 (m, 3H), 5.07 (s, 1H), 4.42-4.34 (m, 1H), 4.16-4.06 (m, 1H), 3.99-3.82 (m, 2H), 3.78-3.60 (m, 2H), 3.58-3.46 (m, 1H), 3.14-3.01 (m, 1H), 2.92-2.82 (m, 2H), 2.22 (s, 3H), 2.12-1.90 (m, 6H), 1.42 (s, 6H), 1.11 (d, J=6.5 Hz, 3H). LC-MS $(M+H)^+$=509.4.

Example B4

(R)-3-(4-(5-amino-6-(1-(1-methylpiperidin-4-yl)-1H-pyrazol-4-yloxy)pyrazin-2-yl)-6-(3-methylmorpholino)pyridin-2-yl)oxetan-3-ol

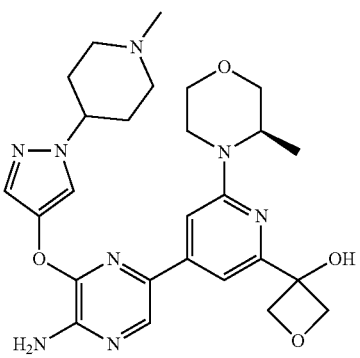 [SMILES: C[C@@H]1COCCN1c1cc(-c2cnc(N)c(Oc3cnn(C4CCN(C)CC4)c3)n2)cc(C2(O)COC2)n1]

Step 1: (R)-4-(6-bromo-4-chloropyridin-2-yl)-3-methylmorpholine

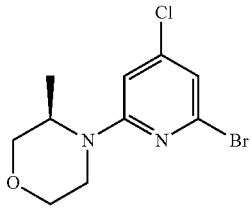

The title compound (2.4 g, 59%) was prepared in a manner similar to that in B1 step 1 from 2,6-dibromo-4-chloropyridine and (3R)-3-methylmorpholine. LC-MS (M+H)$^+$=291.0.

Step 2: (R)-3-(4-chloro-6-(3-methylmorpholino)pyridin-2-yl)oxetan-3-ol

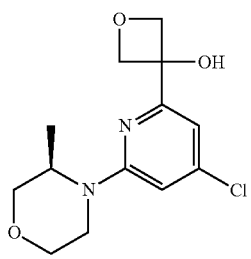 [SMILES: C[C@@H]1COCCN1c1cc(Cl)cc(C2(O)COC2)n1]

The title compound (280 mg, 48%) was prepared in a manner similar to that in Example A54 step 1 from (R)-4-(6-bromo-4-chloropyridin-2-yl)-3-methylmorpholine and 3-oxetanone. LC-MS (M+H)$^+$=285.1.

Step 3: (R)-3-(6-(3-methylmorpholino)-4-(4,4,5,5-tetramethyl-1,3,2-dioxaborolan-2-yl)pyridin-2-yl)oxetan-3-ol

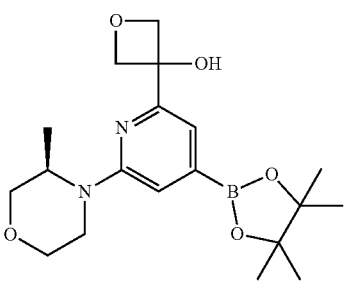 [SMILES: C[C@@H]1COCCN1c1cc(B2OC(C)(C)C(C)(C)O2)cc(C2(O)COC2)n1]

The title compound (90 mg, 69%) was prepared in a manner similar to that in Example A1 step 6 from (R)-3-(4-chloro-6-(3-methylmorpholino)pyridin-2-yl)oxetan-3-ol and BPD. LC-MS (M+H)$^+$=295.2.

Step 4: (R)-3-(4-(5-amino-6-(1-(1-methylpiperidin-4-yl)-1H-pyrazol-4-yloxy)pyrazin-2-yl)-6-(3-methylmorpholino)pyridin-2-yl)oxetan-3-ol (Compound 4, 005-2468-0)

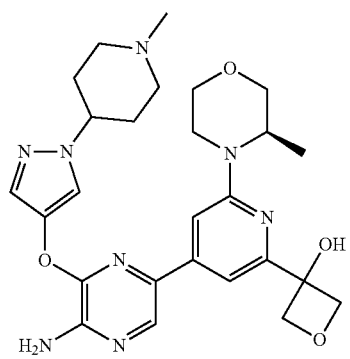 [SMILES: C[C@@H]1COCCN1c1cc(-c2cnc(N)c(Oc3cnn(C4CCN(C)CC4)c3)n2)cc(C2(O)COC2)n1]

Example B4 (26 mg, 22%) was prepared in a manner similar to that in Example A1 step 7 from 5-bromo-3-((1-(1-methylpiperidin-4-yl)-1H-pyrazol-4-yl)oxy)pyrazin-2-amine and (R)-3-(6-(3-methylmorpholino)-4-(4,4,5,5-tetramethyl-1,3,2-dioxaborolan-2-yl)pyridin-2-yl)oxetan-3-ol. $^1$H NMR (300 MHz, DMSO-d$_6$) δ 8.36 (s, 1H), 8.10 (s, 1H), 7.56 (s, 1H), 7.33 (s, 1H), 7.05 (s, 1H), 6.96 (s, 2H), 6.30 (s, 1H), 4.94-4.86 (m, 2H), 4.62-4.54 (m, 2H), 4.49-4.41 (m, 1H), 4.16-400 (m, 1H), 4.00-3.89 (m, 2H), 3.79-3.70 (m, 1H), 3.70-3.60 (m, 1H), 3.58-3.44 (m, 1H), 3.17-3.03 (m, 1H), 2.91-2.81 (m, 2H), 2.20 (s, 3H), 2.11-1.84 (m, 6H), 1.13 (d, J=6.6 Hz 3H). LC-MS (M+H)$^+$=523.4.

Biological Activity

HPK Kinase Activity Assay at 1 mM ATP

Compounds disclosed herein were tested for inhibition of HPK1 kinase (aa1-346. Life Technologies) activity in assays based on the time-resolved fluorescence-resonance energy transfer (TR-FRET) methodology. The assays were carried out in 384-well low volume black plates in a reaction mixture containing HPK1 kinase (40 nM), 1 mM ATP, 0.5 µM STK1 substrate and 0-10 µM compound in buffer containing 50 mM HEPES, 0.01% BSA, 0.1 mM Orthovanadate, 10 mM MgCl$_2$, 1 mM DTT, pH=7.0, 0.005% Tween-20. The kinase was incubated with the compounds disclosed herein or DMSO for 60 minutes at room temperature and the reaction was initiated by the addition of ATP and STK1 substrate. After reaction at room temperature for 120 minutes, an equal volume of stop/detection solution was added according to the manufacture's instruction (CisBio). The stop/detection solution contained STY, Antibody-Cryptate and XL005-conjugated streptavidin in Detection Buffer. The TR-FRET signals (ratio of fluorescence emission at 665 nm over emission at 620 nm with excitation at 337 nm wavelength) were recorded on a PHERAstar FS plate reader (BMG Labtech). Phosphorylation of STK1 substrate led to the binding of STK Antibody-Cryptate to the biotinylated STK1 substrate, which places fluorescent donor (Eu$^{3+}$ crypate) in close proximity to the accepter (Streptavidin-XL665), thus resulting in a high degree of fluorescence resonance energy transfer. The inhibition of HPK1 in presence of increasing concentrations of compounds was calculated based on the ratio of fluorescence at 665 nm to that at 620 nm. IC$_{50}$ determination was performed by fitting the curve of percent inhibition versus the log of the inhibitor concentration using Dotmatics. The compounds disclosed herein showed the enzymatic activity values as in Table 1.

TABLE 1

Enzymatic activity $IC_{50}$(nM) for the compounds disclosed herein

| Example | Enzymatic activity $IC_{50}$ (nM) | Example | Enzymatic activity $IC_{50}$ (nM) |
|---|---|---|---|
| A1 | 47 | A2 | 14 |
| A3 | 110 | A4 | 25 |
| A5 | 35 | A6 | 44 |
| A7 | 20 | A8 | 8 |
| A9 | 46 | A10 | 44 |
| A11 | 9 | A12 | 127 |
| A13 | 139 | A14 | 45 |
| A15 | 83 | A16 | 18 |
| A17 | 59 | A18 | 100 |
| A19 | 44 | A20 | 70 |
| A21 | 104 | A22 | 14 |
| A23 | 6 | A24 | 104 |
| A25 | 14 | A26 | 30 |
| A27 | 57 | A28 | 50 |
| A29 | 21 | A30 | 111 |
| A31 | 34 | A32 | 30 |
| A33 | 67 | A34 | 65 |
| A35 | 47 | A36 | 22 |
| A37 | 17 | A38 | 37 |
| A39 | 35 | A40 | 33 |
| A4 | 11 | A42 | 19 |
| A43 | 6 | A44 | 9 |
| A45 | 51 | A46 | 51 |
| A47 | 68 | A48 | 50 |
| A49 | 11 | A50 | 18 |
| A51 | 46 | A52 | 70 |
| A53 | 16 | A54 | 10 |
| A55 | 34 | A56 | 53 |
| A57 | 24 | A58 | 29 |
| A59 | 8.2 | A60 | 40 |
| A61A | 253 | A61B | 10 |
| A62 | 48 | A63 | 39 |
| A64 | 16 | A65 | 18 |
| A66 | 36 | A67 | 17 |
| A68 | 51 | A69 | 57 |
| A70 | 6.7 | A71 | 26 |
| A72 | 5.6 | A73 | 11 |
| A74A | 46 | A74B | 10 |
| A75 | 29 | A76 | 5.8 |
| A77 | 38 | A78 | 5.5 |
| A79 | 12 | A80A | 29 |
| A80B | 5.4 | A81 | 37 |
| A82 | 37 | A83 | 17 |
| A84 | 58 | A85 | 3.7 |
| A86 | 40 | A87 | 56 |
| A88 | 34 | A89 | 11 |
| A90A | 82 | A90B | 7.1 |
| A91 | 11 | A92 | 7.0 |
| A93 | 37 | A94 | 15 |
| A95A | 44 | A95B | 4.5 |
| A96 | 36 | A97A | 18 |
| A97B | 30 | A98 | 9.2 |
| B1 | 26 | B2 | 12 |
| B3 | 11 | B4 | 31 |

Cellular pSLP76(S376) HTRF Assay

Jurkat cell line was used in this study. Cells were maintained in RPMI 1640 supplemented with heat-inactivated 10% fetal bovine serum (Thermo Fisher), 50 units/mL penicillin and streptomycin (Thermo Fisher) and kept at 37° C. in a humidified atmosphere of 5% $CO_2$ in air. Cells were reinstated from frozen stocks that were laid down within 30 passages from the original cells purchased. After cell starvation in the assay buffer (RPMI 1640 supplemented with heat-inactivated 0.1% fetal bovine serum) for 18 hours, cells were seeded into a round bottom 96-well plate at 150,000 cells per well density. Cells were treated with a 9-point dilution series of test compounds. The final compound concentration is from 0 to 2 μM. After 2 h compound treatment, cells were stimulated with 0.05 μg/mL anti-human CD3 (OKT3, Bioxcell) for 30 min at 37° C. Then the cells were lysed, and the pSLP76(S376) level in the cell lysates was detected by HTRF kit (Cisbio). A total of 16 μL of cell lysate from each well of a 96-well plate was transferred to a 384-well small volume white assay plate. Lysate from each well was incubated with 2 μL of $E^{3+}$-cryptate (donor) labeled anti-phospho-SLP76 and 2 μL of D2 (acceptor) labeled anti-phospho-SLP76 antibodies (Cisbio) overnight in dark at room temperature. FRET signals (655 nm) were measured using a PHERAstar FSX reader (BMG Labtech). $IC_{50}$ determination was performed by fitting the curve of percent inhibition versus the log of the inhibitor concentration using Dotmatics. The compounds disclosed herein showed the cellular activity values as in Table 2.

TABLE 2

Cellular activity $IC_{50}$(nM) for the compounds disclosed herein

| Example | Cellular activity $IC_{50}$ (nM) | Example | Cellular activity $IC_{50}$ (nM) |
|---|---|---|---|
| A1 | 93 | A2 | 34 |
| A3 | 150 | A4 | 91 |
| A5 | 70 | A6 | 35 |
| A7 | 62 | A8 | 30 |
| A9 | 99 | A10 | 117 |
| A11 | 54 | A12 | 119 |
| A13 | 120 | A14 | 59 |
| A15 | 157 | A16 | 80 |
| A17 | 194 | A18 | 47 |
| A19 | 46 | A20 | 97 |
| A21 | 188 | A22 | 38 |
| A23 | 35 | A24 | 175 |
| A25 | 62 | A26 | 82 |
| A27 | 81 | A28 | 97 |
| A29 | 97 | A30 | 330 |
| A31 | 77 | A32 | 81 |
| A33 | 102 | A34 | 155 |
| A35 | 123 | A36 | 54 |
| A37 | 98 | A38 | 125 |
| A39 | 176 | A40 | 125 |
| A41 | 101 | A42 | 82 |
| A43 | 26 | A44 | 61 |
| A45 | 119 | A46 | 98 |
| A47 | 183 | A48 | 183 |
| A49 | 82 | A50 | 95 |
| A51 | 101 | A52 | 118 |
| A53 | 63 | A54 | 33 |
| A55 | 111 | A56 | 85 |
| A57 | 76 | A58 | 69 |
| A59 | 51 | A60 | 91 |
| A61B | 44 | A62 | 79 |
| A63 | 102 | A64 | 45 |
| A65 | 84 | A66 | 132 |
| A67 | 76 | A68 | 157 |
| A69 | 84 | A70 | 76 |
| A71 | 39 | A72 | 59 |
| A73 | 59 | A74A | 85 |
| A74B | 41 | A75 | 129 |
| A76 | 62 | A77 | 91 |
| A78 | 51 | A79 | 71 |
| A80A | 194 | A80B | 48 |
| A81 | 72 | A82 | 125 |
| A83 | 105 | A84 | 83 |
| A85 | 28 | A86 | 130 |
| A87 | 89 | A88 | 85 |
| A89 | 64 | A90B | 100 |
| A91 | 199 | A92 | 156 |
| A93 | 164 | A94 | 119 |
| A95A | 124 | A95B | 68 |
| A96 | 117 | A97A | 78 |
| A97B | 154 | A98 | 73 |
| B1 | 181 | B2 | 121 |
| B3 | 229 | B4 | 102 |

It is to be understood that, if any prior art publication is referred to herein; such reference does not constitute an admission that the publication forms a part of the common general knowledge in the art in any country.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and Examples should not be construed as limiting the scope of the invention.

What is claimed is:

1. A compound selected from:

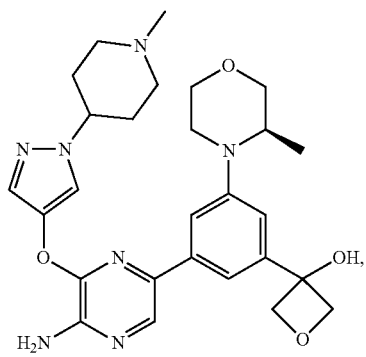

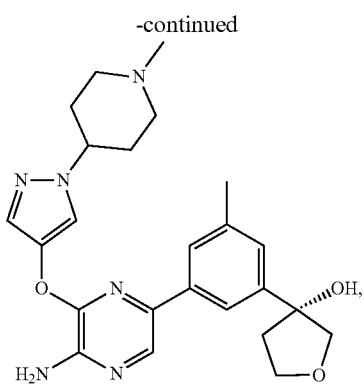

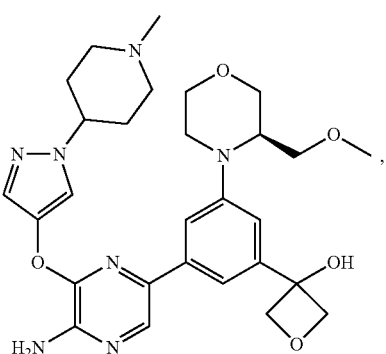

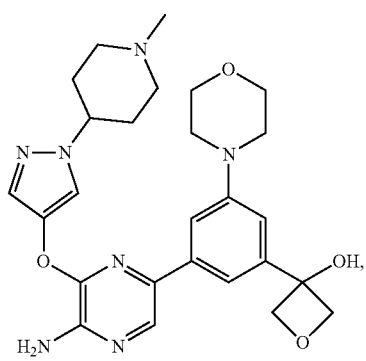

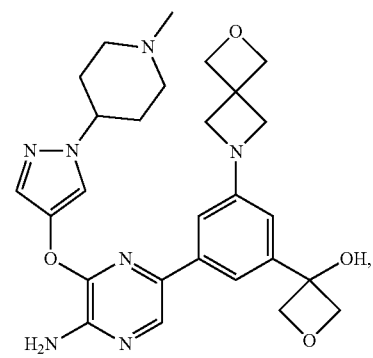

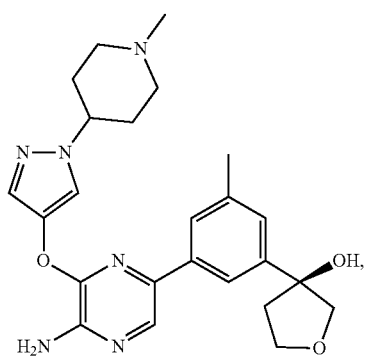

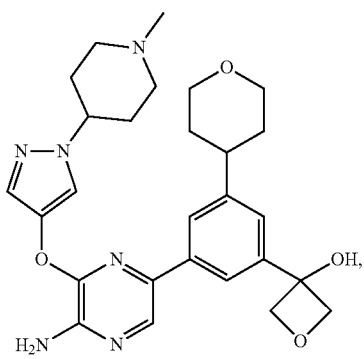

245
-continued
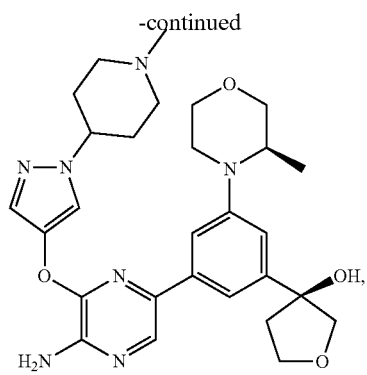
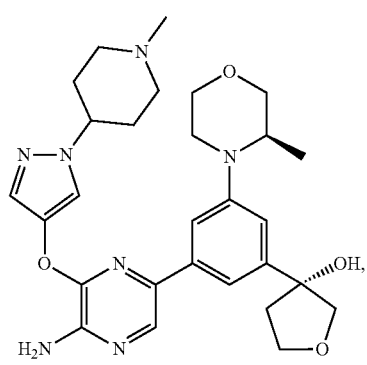
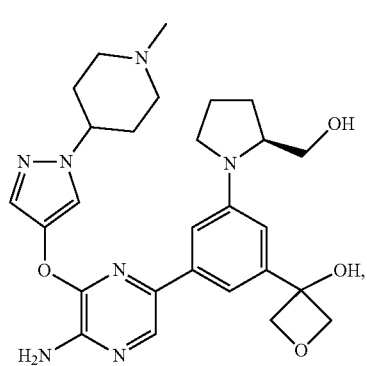
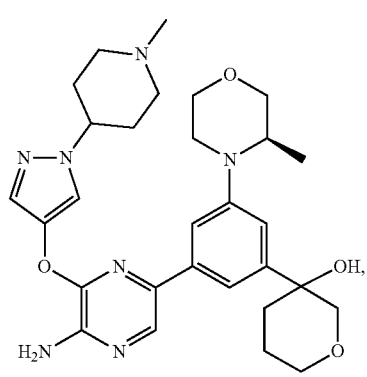
246
-continued
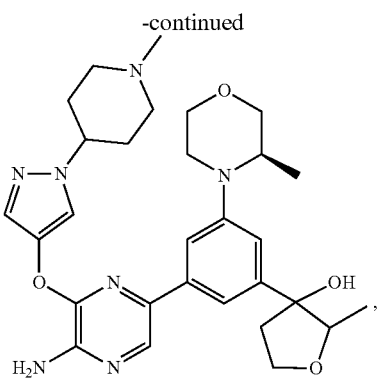
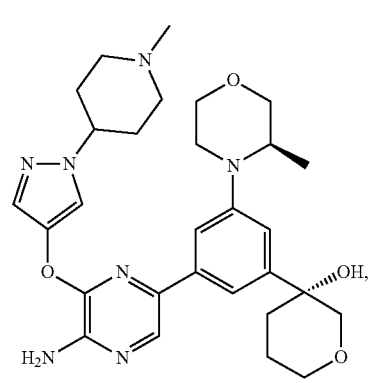
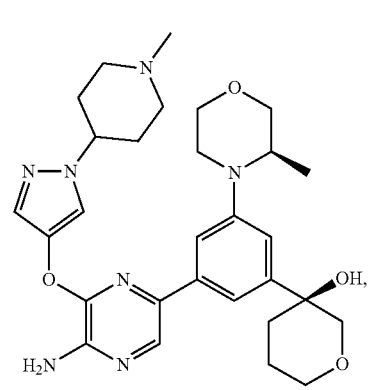
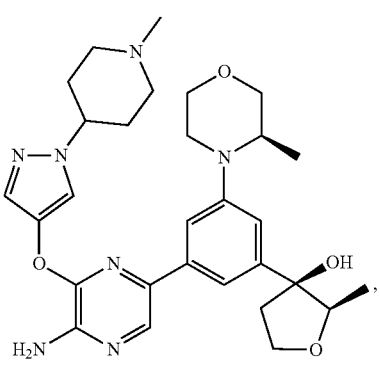
and

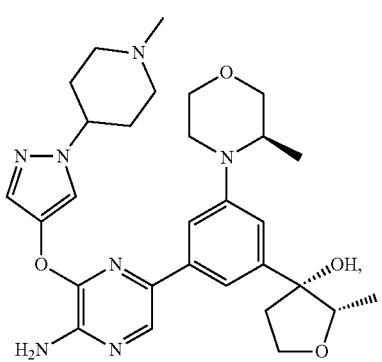 [SMILES: C[C@@H]1COCCN1c1cc(-c2cnc(N)c(Oc3cnn(C4CCN(C)CC4)c3)n2)cc([C@]2(O)CCO[C@H]2C)c1]

or a pharmaceutically acceptable salt thereof.

2. A pharmaceutical composition comprising the compound of claim 1, or a pharmaceutically acceptable salt thereof, and a pharmaceutically acceptable excipient.

3. A method of treating cancer caused by HPK1 overexpression in a subject in need thereof, comprising administering to the subject the compound of claim 1, or a pharmaceutically acceptable salt thereof.

4. The compound of claim 1, wherein the compound is

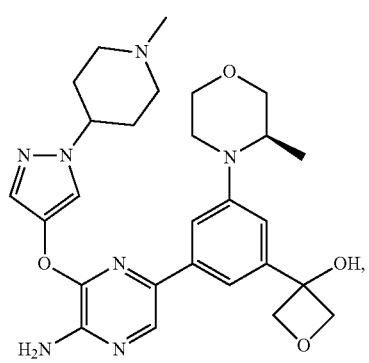 [SMILES: C[C@@H]1COCCN1c1cc(-c2cnc(N)c(Oc3cnn(C4CCN(C)CC4)c3)n2)cc(C2(O)COC2)c1]

or a pharmaceutically acceptable salt thereof.

5. The compound of claim 1, wherein the compound is

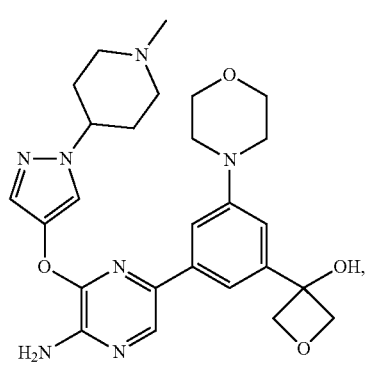 [SMILES: CN1CCC(n2cc(Oc3nc(-c4cc(N5CCOCC5)cc(C5(O)COC5)c4)cnc3N)cn2)CC1]

or a pharmaceutically acceptable salt thereof.

6. The compound of claim 1, wherein the compound is

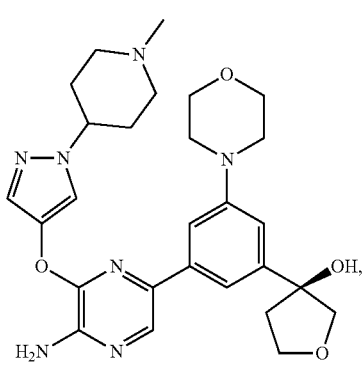 [SMILES: CN1CCC(n2cc(Oc3nc(-c4cc(N5CCOCC5)cc([C@@]5(O)CCOC5)c4)cnc3N)cn2)CC1]

or a pharmaceutically acceptable salt thereof.

7. The compound of claim 1, wherein the compound is

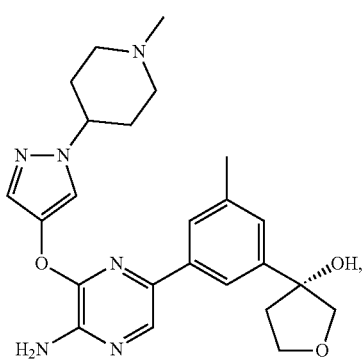 [SMILES: Cc1cc(-c2cnc(N)c(Oc3cnn(C4CCN(C)CC4)c3)n2)cc([C@]2(O)CCOC2)c1]

or a pharmaceutically acceptable salt thereof.

8. The compound of claim 1, wherein the compound is

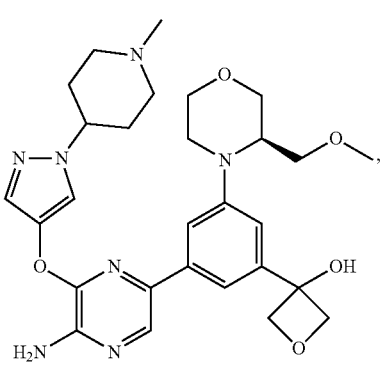 [SMILES: COC[C@@H]1COCCN1c1cc(-c2cnc(N)c(Oc3cnn(C4CCN(C)CC4)c3)n2)cc(C2(O)COC2)c1]

or a pharmaceutically acceptable salt thereof.

9. The compound of claim 1, wherein the compound is

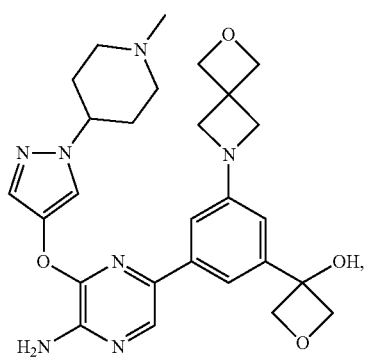 [SMILES: CN1CCC(n2cc(Oc3nc(-c4cc(N5CC6(COC6)C5)cc(C5(O)COC5)c4)cnc3N)cn2)CC1]

or a pharmaceutically acceptable salt thereof.

10. The compound of claim 1, wherein the compound is

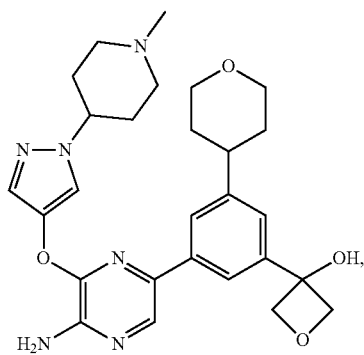

or a pharmaceutically acceptable salt thereof.

11. The compound of claim 1, wherein the compound is

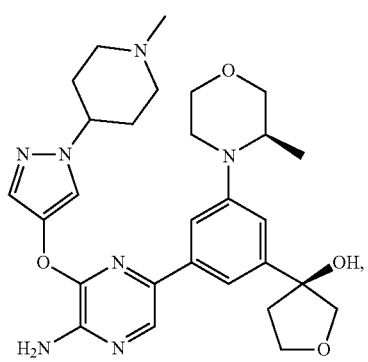 [SMILES: C[C@@H]1COCCN1c1cc(-c2cnc(N)c(Oc3cnn(C4CCN(C)CC4)c3)n2)cc([C@@]2(O)CCOC2)c1]

or a pharmaceutically acceptable salt thereof.

12. The compound of claim 1, wherein the compound is

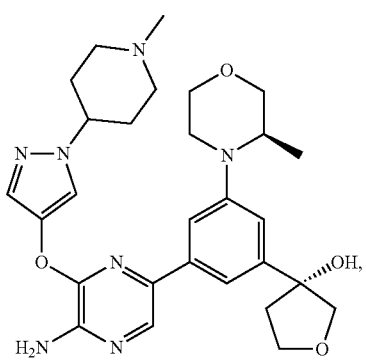 [SMILES: C[C@@H]1COCCN1c1cc(-c2cnc(N)c(Oc3cnn(C4CCN(C)CC4)c3)n2)cc([C@]2(O)CCOC2)c1]

or a pharmaceutically acceptable salt thereof.

13. The compound of claim 1, wherein the compound is

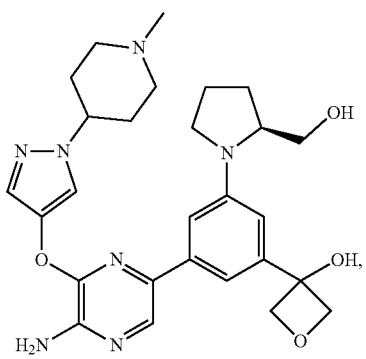 [SMILES: CN1CCC(n2cc(Oc3nc(-c4cc(N5CCC[C@H]5CO)cc(C5(O)COC5)c4)cnc3N)cn2)CC1]

or a pharmaceutically acceptable salt thereof.

14. The compound of claim 1, wherein the compound is

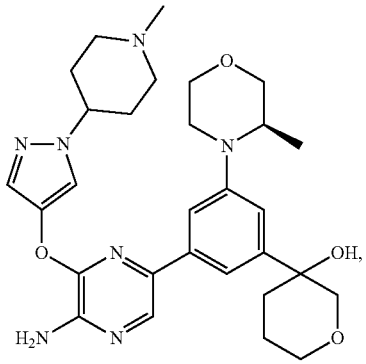 [SMILES: C[C@@H]1COCCN1c1cc(-c2cnc(N)c(Oc3cnn(C4CCN(C)CC4)c3)n2)cc(C2(O)CCCOC2)c1]

or a pharmaceutically acceptable salt thereof.

15. The compound of claim 1, wherein the compound is
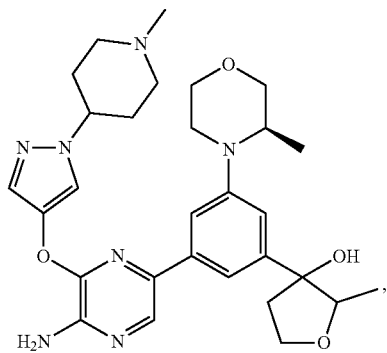
or a pharmaceutically acceptable salt thereof.
16. The compound of claim 1, wherein the compound is
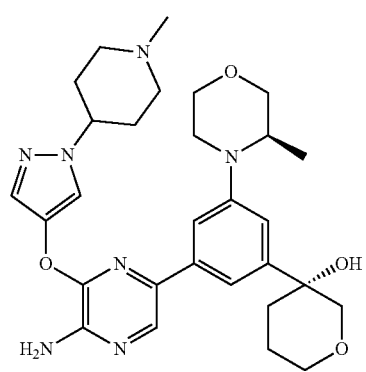 [SMILES: C[C@@H]1COCCN1c1cc(-c2cnc(N)c(Oc3cnn(C4CCN(C)CC4)c3)n2)cc([C@]2(O)CCCOC2)c1]
or
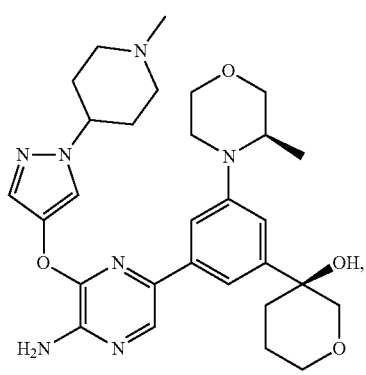 [SMILES: C[C@@H]1COCCN1c1cc(-c2cnc(N)c(Oc3cnn(C4CCN(C)CC4)c3)n2)cc([C@@]2(O)CCCOC2)c1]
or a pharmaceutically acceptable salt thereof.
17. The compound of claim 1, wherein the compound is
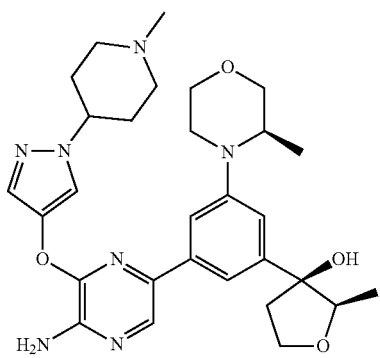 [SMILES: C[C@@H]1COCCN1c1cc(-c2cnc(N)c(Oc3cnn(C4CCN(C)CC4)c3)n2)cc([C@@]2(O)CCO[C@@H]2C)c1]
or
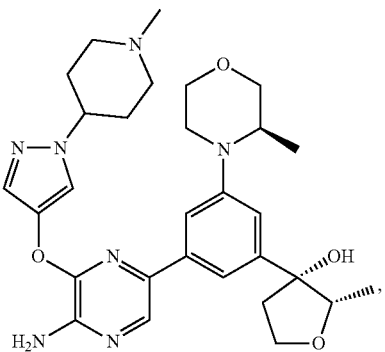 [SMILES: C[C@@H]1COCCN1c1cc(-c2cnc(N)c(Oc3cnn(C4CCN(C)CC4)c3)n2)cc([C@]2(O)CCO[C@H]2C)c1]
or a pharmaceutically acceptable salt thereof.
\* \* \* \* \*

UNITED STATES PATENT AND TRADEMARK OFFICE
CERTIFICATE OF CORRECTION

| | | |
|---|---|---|
| PATENT NO. | : 12,195,449 B2 | |
| APPLICATION NO. | : 18/650207 | |
| DATED | : January 14, 2025 | |
| INVENTOR(S) | : Sanjia Xu, Jing Li and Zhiwei Wang | |

Page 1 of 1

It is certified that error appears in the above-identified patent and that said Letters Patent is hereby corrected as shown below:

On the Title Page

Item (54) and in the Specification, Column 1, Lines 1-3:
"3-[(1H-PYRAZOL-R-YL)OXY]PYRAZIN-2-AMINE COMPOUNDS AS HPK1 INHIBITOR AND USE THEREOF"

Should read:
--3-[(1H-PYRAZOL-4-YL)OXY]PYRAZIN-2-AMINE COMPOUNDS AS HPK1 INHIBITOR AND USE THEREOF--.

Signed and Sealed this
Eleventh Day of March, 2025

Coke Morgan Stewart
*Acting Director of the United States Patent and Trademark Office*